(12) United States Patent
Fay et al.

(10) Patent No.: US 8,044,052 B2
(45) Date of Patent: Oct. 25, 2011

(54) BIARYL ETHER UREA COMPOUNDS

(75) Inventors: Lorraine Kathleen Fay, Kent (GB); Douglas S. Johnson, Mystic, CT (US); Suzanne Ross Kesten, Ann Arbor, MI (US); Scott E. Lazerwith, San Francisco, CA (US); Mark Anthony Morris, Arlington, MA (US); Cory Michael Stiff, Salem, CT (US); Marvin Jay Meyers, Wentzville, MO (US); Lijuan Jane Wang, Wildwood, MO (US)

(73) Assignee: Pfizer Inc., New York, NY (US)

( * ) Notice: Subject to any disclaimer, the term of this patent is extended or adjusted under 35 U.S.C. 154(b) by 651 days.

(21) Appl. No.: 11/874,577

(22) Filed: Oct. 18, 2007

(65) Prior Publication Data

US 2008/0261941 A1  Oct. 23, 2008

Related U.S. Application Data

(60) Provisional application No. 60/829,966, filed on Oct. 18, 2006, provisional application No. 60/965,210, filed on Aug. 17, 2007.

(51) Int. Cl.
*C07D 401/12* (2006.01)
*A61K 31/501* (2006.01)

(52) U.S. Cl. .................................. 514/252.03; 544/238

(58) Field of Classification Search .................. 544/237, 544/238; 514/252.02, 252.03, 252.04
See application file for complete search history.

(56) References Cited

U.S. PATENT DOCUMENTS

| | | | |
|---|---|---|---|
| 3,576,810 A | 4/1971 | Duncan et al. | |
| 4,116,665 A | 9/1978 | Krumkalns | |
| 4,730,047 A | 3/1988 | Boyle | |
| 6,271,015 B1 | 8/2001 | Gilula et al. | |
| 7,678,796 B2* | 3/2010 | Wallberg et al. | 514/252.05 |
| 7,737,143 B2* | 6/2010 | Burns et al. | 514/236.5 |
| 7,750,011 B2* | 7/2010 | Peters et al. | 514/252.02 |
| 7,750,151 B2* | 7/2010 | Bilodeau et al. | 544/127 |
| 2001/0032615 A1 | 10/2001 | Yonezawa et al. | |
| 2002/0091116 A1 | 7/2002 | Zhu et al. | |
| 2003/0036655 A1 | 2/2003 | Bley et al. | |
| 2003/0084948 A1 | 5/2003 | Tanaka et al. | |
| 2004/0034101 A1 | 2/2004 | Rao et al. | |
| 2004/0063726 A1 | 4/2004 | Artman | 514/255.06 |
| 2004/0087646 A1 | 5/2004 | Differding et al. | |
| 2004/0186148 A1 | 9/2004 | Shankar et al. | |
| 2004/0204477 A1 | 10/2004 | Moll et al. | |
| 2005/0075345 A1 | 4/2005 | Heymans et al. | 514/254.02 |
| 2005/0171099 A1 | 8/2005 | Carson et al. | |
| 2006/0106029 A1 | 5/2006 | Ohkubo et al. | |
| 2006/0167044 A1 | 7/2006 | Arnaiz et al. | |
| 2006/0173184 A1 | 8/2006 | Apodaka et al. | |
| 2007/0004741 A1 | 1/2007 | Apodaca et al. | |
| 2008/0103209 A1 | 5/2008 | Piomelli et al. | 514/627 |

FOREIGN PATENT DOCUMENTS

| | | |
|---|---|---|
| CA | 2129374 | 6/1995 |
| DE | 102004045796 | 9/2004 |
| EP | 1227090 | 7/2002 |
| EP | 1308443 | 7/2003 |
| EP | 1655297 | 10/2006 |
| EP | 1813606 | 1/2007 |
| EP | 2065369 | 6/2009 |
| FR | 2442839 | 6/1980 |
| GB | 138405 | 1/1969 |
| GB | 1138405 | 1/1969 |
| GB | 1260886 | 1/1972 |
| GB | 1295447 | 11/1972 |
| GB | 1310235 | 3/1973 |
| GB | 2167407 | 11/1984 |
| WO | WO91/11172 | 8/1991 |
| WO | WO93/12107 | 6/1993 |
| WO | WO94/02518 | 2/1994 |
| WO | WO95/06037 | 3/1995 |
| WO | WO9621648 | 7/1996 |
| WO | WO97/24328 | 7/1997 |
| WO | WO97/28141 | 8/1997 |
| WO | WO98/55148 | 2/1998 |
| WO | WO9856771 | 12/1998 |

(Continued)

OTHER PUBLICATIONS

Almarsson & Zaworotko; 2004; Chemical Communication; Crystal engineering of the composition of pharmaceutical phases. ; vol. 17; pp. 1889-1896.

Amuro, et al.; 1990;Isolation and characterization of the two distinct genes for human glutamate dehydrogenase; Biochimica et Biophysica Acta; 1049(2); 216-218.

Amuro, et al.; 1988; Molecular Cloning and Nucleotide Sequence of the cDNA for Human Liver Glutamate Dehydrogenase Precursor; Biochimica Res. Commun.; 152(3); 1395-1400.

Arreaza, et al.; 1997; Deletion of a proline-rich region and a transmembrane domain in fatty acid amide hydrolase1;FEBS Letters; 454; 57-60.

(Continued)

*Primary Examiner* — James O. Wilson
*Assistant Examiner* — Cecilia M Jaisle
(74) *Attorney, Agent, or Firm* — Jennifer A. Kispert; Linda S. Li; Robert T. Ronau

(57) ABSTRACT

The present invention relates to compounds of Formula (I)

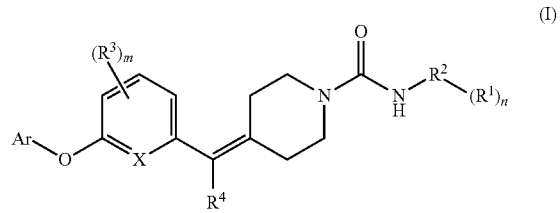

or a pharmaceutically acceptable salt thereof; processes for the preparation of the compounds; intermediates used in the preparation of the compounds; compositions containing the compounds; and uses of the compounds in treating diseases or conditions associated with fatty acid amide hydrolase (FAAH) activity.

10 Claims, No Drawings

FOREIGN PATENT DOCUMENTS

| | | |
|---|---|---|
| WO | WO99/50262 | 10/1999 |
| WO | WO00/58295 | 10/2000 |
| WO | WO00/59477 | 10/2000 |
| WO | WO01/32615 | 5/2001 |
| WO | WO01/53263 | 7/2001 |
| WO | WO01/58891 | 8/2001 |
| WO | WO01/66543 | 9/2001 |
| WO | WO01/95856 | 12/2001 |
| WO | WO0240466 | 5/2002 |
| WO | WO02062963 | 8/2002 |
| WO | WO03037271 | 5/2003 |
| WO | WO03076400 | 9/2003 |
| WO | WO03/084948 | 10/2003 |
| WO | WO03080060 | 10/2003 |
| WO | WO03/099787 | 12/2003 |
| WO | WO2004/037371 | 5/2004 |
| WO | WO2004/087646 | 10/2004 |
| WO | WO2004/100952 | 11/2004 |
| WO | WO2004/101521 | 11/2004 |
| WO | WO2005/007647 | 1/2005 |
| WO | WO2005/044797 | 5/2005 |
| WO | WO2005/051390 | 6/2005 |
| WO | WO2005/115987 | 12/2005 |
| WO | WO2005/121121 | 12/2005 |
| WO | WO2005115370 | 12/2005 |
| WO | WO2006034341 | 3/2006 |
| WO | WO2006/035303 | 4/2006 |
| WO | WO2006/048248 | 5/2006 |
| WO | WO2006/018280 | 6/2006 |
| WO | WO2006/067401 | 6/2006 |
| WO | WO2006/067531 | 6/2006 |
| WO | WO2006/074025 | 7/2006 |
| WO | WO2006/085196 | 8/2006 |
| WO | WO2006/088075 | 8/2006 |
| WO | WO2006116703 | 11/2006 |
| WO | WO2006/129842 | 12/2006 |
| WO | WO2006/137465 | 12/2006 |
| WO | WO2006129199 | 12/2006 |
| WO | WO2007/003962 | 1/2007 |
| WO | WO2007/005510 | 1/2007 |
| WO | WO2007/023882 | 1/2007 |
| WO | WO2007/027352 | 3/2007 |
| WO | WO2007079180 | 7/2007 |
| WO | WO2007/103456 | 9/2007 |
| WO | WO2008005368 | 1/2008 |
| WO | WO2008020866 | 2/2008 |
| WO | WO2008021625 | 2/2008 |
| WO | WO2008022976 | 2/2008 |
| WO | WO2008024139 | 2/2008 |
| WO | WO2008030752 | 3/2008 |
| WO | WO2008153752 | 3/2008 |
| WO | WO2008042892 | 4/2008 |
| WO | WO2008047229 | 4/2008 |
| WO | WO2008/063300 | 5/2008 |
| WO | WO2008063714 | 5/2008 |
| WO | WO2008075978 | 6/2008 |

OTHER PUBLICATIONS

Austen, et al.; 1977; Nocotinamide Adenine Dinucleotide-specific Glutamate Dehydrogenase of Neurospora; Journal of Biological Chemistry; 252; 22; 8142-8149.

Banner, et al.; 1987; Isolation of a Human Brain cDNA for Glutamate Dehydrogenase; Journal of Neurochemistry; 49; 1; 246-252.

Batra,et al.;1989Ident . . . of Histidyl Peptide labeled by 2-(4-Bromo-2,3-dioxobutylthio) adenosine5'-Mono . . . in an ADP Reg . . . Site of Glut . . . Dehy . . . ;Ar.of Bioch.&Biop.270;1;277-85.

Berge, et al.; 1977; Pharmaceutical Salts; Journal of Pharmaceutical Sciences; 66; 1; 1-19.

Bracey, et al; Structural Adaptations in a membrane Enzyme That Terminates Endocannabinoid Signaling; Science; 298; 1793-1796, 2002.

Collins, F.S.; 2002; Induction of neurite outgrowth by a conditioned-medium factor bound to the culture substratum; PNAS; vol. 99 No. 26; 5210-5213.

Cravatt, et al; 1996; Molecular characterization of an enzyme that degrades neuromodulatory fatty-acid amides; Letters to Nature; vol. 384; 83-87.

Day, et al.; 1999; Role of Fatty acid Amide Hydrolase in the Transport of Endogenous Cannabinoid Anandamide; Molecular Pharmacology; 59; 1369-1375.

DeBank, et al.; 2005; A spectrophotometric assay for fatty acid amide hydrolase suitable for high-throughput screening; Biochemical Pharmacology; 69; 1187-1193.

Deloukas,et al.;1993;Three Human Glutamate Dehydrogenase Genes(GLUD1,GLUDP2, andGLUDP3) Are Located on Chromosome 10q, but Are Not Closely Physically Linked;Genomics;1;676-681.

Deutsch, et al.; 2002; The fatty acid amide hydrolase (FAAH); Prostaglandins, Leukotrienes ad Essential Fatty Acids; 66;(2&3);201-210.

Falck, et al.; 2001; Bromo-Boronolactonization of Olefins; Journal of Organic Chemistry; 66; 7148-7150.

Fang, et al; 2002; Expression, purification and characterizationof human glutamate dehydrogenase (GDH) allosteric regulatory mutations; Biochemical Journal; 363(Pt.1); 81-87.

Finnin, et al.; 1999; Transdermal Penetration Enhancers: Applications, Limitations and Potential; J. of Pharmaceutical Sciences; 88, 10; 955-958.

Finnin and Morgan; 1999; Transdermal Penetration Enhancers:Applications, Limitations and Potential; Journal of Pharmaceutical Sciences; 88(10); 955-958.

Fujioka,et al.; 2001;Mole . . . characterisation of glutamate dehydrogenase gene defects in Japanese patients w/ congenital hyperinsulinism/hyperammonaemia;E.J.ofHum.Gen.9;931-937.

Giang, et al.; 1997; Molecular characterization of human and mouse fatty acid amide hydrolases; PNAS; 94; 2238-2242.

Giang & Cravatt;1997; Molecular characterization of human and mouse fatty acid amide hydrolases; PNAS; vol. 94; 2238-2242.

Haberland, et al.; 1980; Nicotinamide Adenine dinucleotide-specific Glutamate Dehydrogenase of Neurospora crassa; Journal of Biological Chemistry; 255; 16; 7984-7992.

Haleblian, J.K.; 1975;Characterization of Habits and Crystalline Modification of Solids and Their Pharmaceutical Applications; Journal of Pharmaceutical Science;64 8;1269-1288.

Hochstrasser, et al.; 1992; Human liver protein map:A reference database established by microsequencing and gel comparison; Electrophoresis; 13; 992-1001.

Houge & Mersfelder; 2002; Pathophysiology and First-Line Treatment of Osteoarthritis; Annals of Pharmacotherapy; vol. 36; 679-686.

Ishiyama, et al.;1995; Palladium(0)-Catalyzed Cross-Coupling Reaction of Alkoxydiboron with Haloarenes: A Direct Proccedure . . . ;Journal of Organic Chemistry; 60; 7508-7510.

Jayamanne, A. et al.; 2006; Actions of the FAAH inhibitor URB597 inneuropathic and inflammatory chronic pain models; British Journal of Pharmacology; vol. 147; 281-288.

Julliard, et al.;1979; Partial Amino Acid Seq . . . of the Glutamate Dehydrogenase of Hum. Liver and a Revision ofthe Seq.of the Bovine Enzyme; J.of Bio. Chem.;254;9;3427-3438.

Jung, et al.; 1989;Assignment of the GDH Loci to Human Chromosomes 10q23 and Xq24 by in Situ Hybridization; Annals of Genetics; 32(2); 109-110.

Kaltwasser, et al.; 1966; NADH-Dependent Coupled Enzyme Assay for Urease and Other Ammonia-Producing Systems; Analytical Biochemistry 16; 132-138.

Kapoor, et al.; 1993; NAD+-specific glutamate dehydrogenase of Neurospora crassa:cloning, complete nucleotide sequence, and gene map . . . Biochem. and Cell Biology 71(3-4);205-219.

Kathuria, S. et al.;2003; Modulation of anxiety through blockade of anandamide hydrolysis; Nature Medicine; vol. 9; pp. 76-81.

Kim, et al.;2003; Molecular Gene Cloning, Expression, and characterization of bovine Brain Glutamate Dehyudrogenase; J. of Biochem. and Molecular Biology; 36(6); 545-551.

Labahn, et al; 2003; An Alternative Mechanism for Amidase Signature Enzymes; J. of Molecular Biology; 322; 1053-1064.

Lancien, et al.; 2000;Enzyme Redundancy and the importance of 2-Oxoglutarate in Higher Plant Ammonium Assimilation; Plant Physiology; 123; 817-824.

Levitzki, et al.; 1970;Determination of Submicro Quasntities of Ammonia; Analytical Biochemistry; 33; 335-340.

Li, et al.;2004;High Stereoselective Preparation of O-Protected 2-Trifluoromethyl 3-Bromoallylic alcohols from 1, 1-Dibromo-1-alkenes; Organic Letters; vol. 6; pp. 4467-4470.

Liang and Chen; 2001; Fast-dissolving intraoral drug delivery systgems; Expert Opinion on Therapeutic Patents; vol. 11(6); pp. 981-988.

Lichtman, A.H. et al.; 2004; Reversible Inhibitors of Fatty Acid Amide Hydrolase That Promote Analgesia:Evidence.;J. of Pharmacological Experiments; 2004; vol. 311; 441-448.

McCarthy, et al.; 1994; Chapter 20; Osteoarthritis; Textbook of Pain; ed. Wall and Melzack; 387-395.

MacCarrone, et al.; 1998; Anandamide Hydrolysis by Human Cells in Culture and Brain; J. of Biological Chemistry; 273, 48; 32332-32339.

Malakhov, et al.; 2004; SUMO fusions and SUMO-specific protease for efficient expression and purification of proteins; J. of Structural and Function Genomics; 5; 75-86.

Meissner, et al., 1999; Congenital Hyperinsulinism: Molecular Basis of a Heterogeneous Disease; Human Mutation; 13(5); 351-361.

Meyer, et al.; 1994; Chapter 1; Peripheral neural mechanisms of nociception; Textbook of Pain; ed Wall and Melzack; 13-44.

Miki, et al.; 2000; Novel missense mutations in the glutamate dehydrogenase gene in the congenital hyperinsulinism-hyperammonemia syndrome;Journal of Pediatrics; 136(1); 69-72.

Millan; 1999; The Induction of Pain: An Integrative Review; Progress in Neurobiology; vol. 57; 1-164.

Miyaura, et al.;1995; Palladium-Catalyzed Cross-Couplng Reactins of Organoboron Compounds; Chemical Review; 95;2457-2483.

Moon, et al.; 1973;Sequence of Bovine Liver Glutamate Dehydrogenase; J. Biological Chemistry; 248(9); 3082-3088.

Nakatani, et al.; 1987;Comparison of Human Brain and Liver Glutamate Dehydrogenase cDNAS; BBRC; 149(2); 405-410.

Nakatani, et al.; 1988; Complete nucleotide sequence of human glutamate dehydrogenase BcDNA; Nucleic Acids Res.; 16(13); 6237.

Patricelli, et al.; 1998; Comparative Characterization of a Wild Type and Transmembrane Domain-Deleted Fatty Acid Amide Hydrolase:Ident. OligomerBiochemistry; 37; 15177-15187.

Patricelli, et al,;1999;Chemical & Mutagenic Investigations of Fatty Acid Amide Hydrolase: Evidence for a Family of Serine Hydrolases with Distinct.Biochemistry; 38; 9804-9812.

Piomelli, D. et al.; Antidepressant-like activity and modulation of brain monoaminergic transmission by blockade of anandamide hydro . . . PNAS, USA; 2005; vol. 102; pp. 18620-1862.

Plaitakis et al; 1982;Abnormal glutamate Metabolism in an Adult-onset Degenerative Neurological Disorder; Science 216(4542); 193-196.

Plaitakis; 1982; Abnormal glutamate Metabolism in an Adult-Onset Degenerative Neurological Disorder; Science; 216 (9); 193-196.

Rasched et al.; 1974;Studies of Glutamate Dehydrogenase:Identification of an Amino Group Involved in the Substrate Binding; European Journal of Biochemistry;41(3)603-606.

Santer, et al.; 2001; Novel Misense mutations outside the allosteric domain of glutamate dehydrogenase are prevalent in European patients with . . . Human Genetics; 108(1); 66-71.

Sipe, et al; 2002;A missense mutation in human fatty acid amide hydrolase associated with problem drug use; PNAS; 99(12); 8394-8399.

Smith, et al; 2001; Structures of Bovine Glutamate Dehydrogenase Complexes Elucidate the Mechanism of Purine Regulation; Journal of Molecular Biology; 307(3); 707-720.

Stanley, et al.; 1998;Hyperinsulinism & Hyperammonemia in Infants with Regulatory Mutations of the Glutamate Dehydrogenase . . . New England Journal of Medicine; 338(19); 1352-1357.

Strausberg et al., 2002;Generation and initial analysis of more than 15,000 full-length human and mouse cDNA sequences; PNAS; 99(26); 16899-16903.

Tanizawa, et al.; 2002;Unregulated Elevation of Glutamate Dehydrogenase Activity Induces Glutamine-Stimulated Insulin Secretion; Diabetes; 5193); 712-717.

Thavonekham, B.;1997; A Practical Synthesis of Ureass from Phenyl Carbamates; Synthesis; 1189-1194.

Tzimagiorgis et al.;1993;Structure and expression analysis of a member of the human glutamate dehydrogenase(GLUD)gene family mapped to chrom.10p;Human Genetics; 91(5); 433-438.

Ueda, et al.,; 2000; The fatty acid amide hydrolase (FAAH); Chemistry and Physics of Lipids; 108; 107-121.

Verma, et al.; 2001; Current Status of Drug Delivery Technologies and Future Directions; Pharmaceutical Technology On-Line; 25; 1-14.

Vierula et al.; 1989; NAD-specific Glutamate Dehydrogenase of *Neurospora crassa*; Journal of Biological Chemistry; 264;No. 2;1108-1114.

Waleh, et al.; 2002; Transcriptional regulation of the mouse fatty acid amide hydrolase gene; Gene; 291; 203-210.

Wan, et al.; 1998;Conserved Chromosomal Location and Genomic Structure of Human and Mouse Fatty-Acid Amide Hydrolase Genes and Evaluation of clasper . . . Genomics; 54(3); 408-414.

Witzemann, et al.;1974;Studies of Glutamate Dehydrogenase:Chemical Modification and Quantitative Determination of Tryptophan . . . European Journal of Biochemistry; 43(2); 319-325.

Woolf & Decosterd; 1999; Implications of recent advances in the understanding of pain pathophysiology for the assessment of pain in patients; Pain Supplement; 6; S141-S147.

Woolf & Mannion, et al.; 1999; Neuropathic pain: aetiology, symptoms, mechanisms, and management; Lancet; 353 9168; 1959-1964.

Woolf & Salter; 2000; Neuronal Plasticity: Increasing the Gain in Pain; Science; 288;1765-1768.

Yoon, et al.; 2002;Cassette Mutagenesis and Photoaffinity Labeling of Adenine Binding Domain of ADP REgulatory Site within Human Glutamate Dehydrogenase; Biochem.;41;6817-6823.

Yoon,et al.; Importance of Glutamate 279 for the Coenzyme Binding of Human Glutamate Dehydrogenase; Journal of Biological Chemistry; 277 No. 44;47448-41454, 2002.

Zaganas,et al.; 2002; Single Amino Acid Substitution(G456A)in the Vicinity of the GTP Binding Domain of Human HousekeepingJournal of Biological Chemistry; 277(29); 26422-26428.

Zaganas, et al.; 2002; Substitution of Ser for Arg-443 in the Regulatory Domain of Human Housekeeping (GLUD1) Glutamate.; Journal of Biological Chemistry; 277(48); 46552-46558.

* cited by examiner

BIARYL ETHER UREA COMPOUNDS

This application claims priority to Provisional Application 60/829,966 filed Oct. 18, 2006 and Provisional Application 60/965,210 filed Aug. 17, 2007.

FIELD OF THE INVENTION

The present invention relates to biaryl ether urea compounds and the pharmaceutically acceptable salts of such compounds. The invention also relates to the processes for the preparation of the compounds, intermediates used in their preparation, compositions containing the compounds, and the uses of the compounds in treating diseases or conditions associated with fatty acid amide hydrolase (FAAH) activity.

BACKGROUND OF THE INVENTION

Fatty acid amides represent a family of bioactive lipids with diverse cellular and physiological effects. Fatty acid amides are hydrolyzed to their corresponding fatty acids by an enzyme known as fatty acid amide hydrolase (FAAH). FAAH is a mammalian integral membrane serine hydrolase responsible for the hydrolysis of a number of primary and secondary fatty acid amides, including the neuromodulatory compounds anandamide and oleamide. Anandamide (arachidonoyl ethanolamide) has been shown to possess cannabinoid-like analgesic properties and is released by stimulated neurons. The effects and endogenous levels of anandamide increase with pain stimulation, implying its role in suppressing pain neurotransmission and behavioral analgesia. Supporting this, FAAH inhibitors that elevate brain anandamide levels have demonstrated efficacy in animal models of pain, inflammation, anxiety, and depression. Lichtman, A. H. et al. (2004), *J. Pharmacol. Exp. Ther.* 311, 441-448; Jayamanne, A. et al. (2006), *Br. J. Pharmacol.* 147, 281-288; Kathuria, S. et al. (2003), *Nature Med.*, 9, 76-81; Piomelli D. et al. (2005), *Proc. Natl. Acad. Sci.* 102, 18620-18625.

The compounds of the present invention are inhibitors of FAAH and therefore are useful in the treatment of a wide range of disorders, particularly pain. Other conditions that may be treated with the compounds of the present invention urinary incontinence, overactive bladder, emesis, cognitive disorders, anxiety, depression, sleeping disorders, eating disorders, movement disorders, glaucoma, psoriasis, multiple sclerosis, cerebrovascular disorders, brain injury, gastrointestinal disorders, hypertension, or cardiovascular disease.

SUMMARY OF THE INVENTION

The present invention relates to compounds of the Formula I

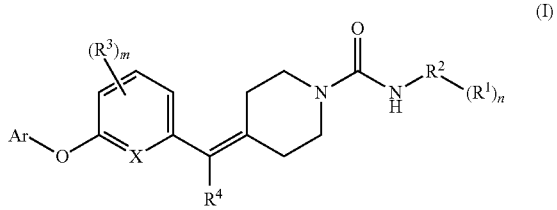

wherein:
each $R^1$ is independently hydrogen, —OH, halogen, haloalkyl, —$C_1$-$C_6$alkyl, —O—$C_1$-$C_6$alkyl, —S—$C_1$-$C_6$alkyl, aryl, heteroaryl, —O-aryl, —O-heteroaryl, —$NH_2$, —NHC(O)$C_1$-$C_6$alkyl, —$(CH_2)_{0-3}$—$C_3$-$C_6$cycloalkyl, —NHC(O)$C_3$-$C_6$cycloalkyl, —NHC$_1$-$C_6$alkyl, CN, —C(O)NR'R" or —C(O)$C_1$-$C_6$alkyl; with each $R^1$—$C_1$-$C_6$alkyl group being optionally substituted by an —O—$C_1$-$C_6$alkyl group or from 1 to 3 —OH substituents;

R' and R" are independently selected from H or $C_1$-$C_6$alkyl;

$R^2$ is aryl, heteroaryl, —C(O)-aryl, or —C(O)-heteroaryl;

each $R^3$ is independently hydrogen, halogen, haloalkyl, —$C_1$-$C_6$alkyl, —O—$C_1$-$C_6$alkyl, —S—$C_1$-$C_6$alkyl, —$(CH_2)_{0-3}$—$C_3$-$C_6$ cycloalkyl, —S—$C_3$-$C_6$cycloalkyl and —O—$C_3$-$C_6$cycloalkyl; said $R^3$—$C_1$-$C_6$alkyl, —O—$C_1$-$C_6$alkyl, —S—$C_1$-$C_6$alkyl, —$(CH_2)_{0-3}$—$C_3$-$C_6$ cycloalkyl, —S—$C_3$-$C_6$cycloalkyl and —O—$C_3$-$C_6$cycloalkyl, groups are optionally substituted with from 1 to 4 halogen, haloalkyl, —O-haloalkyl, —$C_1$-$C_6$alkyl, or —O($C_1$-$C_6$alkyl) substituents;

$R^4$ is hydrogen, —$C_1$-$C_6$alkyl, phenyl, —$(CH_2)_{0-3}$—$C_3$-$C_6$ cycloalkyl or halogen; said $R^4$—$C_1$-$C_6$alkyl, phenyl, and —$(CH_2)_{0-3}$—$C_3$-$C_6$ cycloalkyl groups being optionally substituted with from 1 to 4 halogen, —$C_1$-$C_6$alkyl, or —O($C_1$-$C_6$alkyl) substituents;

X is N, C, or CH;

m is 0, 1, 2, 3, or 4;

n is 0, 1, 2, 3 or 4; and

Ar is aryl, —$CH_2$-aryl, or heteroaryl, with said aryl, —$CH_2$-aryl and heteroaryl groups being optionally independently substituted with from 1 to 4 substituents selected from hydrogen, —$C_1$-$C_6$alkyl, —$C_2$-$C_6$alkenyl, —$C_2$-$C_6$alkynyl, —$(CH_2)_{0-3}$—$C_3$-$C_6$ cycloalkyl, halogen, haloalkyl, —O-haloalkyl, —C(O)$C_1$-$C_6$alkyl, —O—$C_1$-$C_6$alkyl, —S—$C_1$-$C_6$alkyl, —O—$C_2$-$C_6$alkenyl, —O—$C_2$-$C_6$alkynyl, CN, aryl, heterocyclyl or heteroaryl; said —$C_1$-$C_6$alkyl, —$(CH_2)_{0-3}$—$C_3$-$C_6$cycloalkyl, —C(O)$C_1$-$C_6$alkyl, —O($C_1$-$C_6$alkyl), —S—$C_1$-$C_6$alkyl, aryl, —$CH_2$-aryl, heterocyclyl and heteroaryl substituents on Ar are optionally independently substituted with from 1 to 4 —$C_1$-$C_6$alkyl, —$C_1$-$C_6$alkoxy, —OH, or halogen substituents;

or a pharmaceutically acceptable salt thereof.

Also provided are separate groups of compounds, each compound defined by Formula I wherein Ar is selected from the group of pyridine, pyrimidine, phenyl, benzyl, quinazoline, pyrido[2,3-d]pyrimidine, quinoxaline, benzothiazole, or thiadiazole, each optionally substituted as defined above, and $R^1$, $R^2$, $R^3$, $R^4$, X, m and n are as defined above. Within each of these groups are subgroups of compounds, and pharmaceutically acceptable salt forms thereof, wherein $R^2$ is selected from the group of pyridine, isoxazole, pyrazine, pyridazine, benzisoxazole, phenyl, pyrrolo[2,3-b]pyridine, benzotriazole, pyrazole, triazole, thiadiazole or thiazole, each optionally substituted as defined above for Formula I.

One group of compounds are those defined by Formula I in which Ar is phenyl, pyrimidinyl, pyridyl, benzothiazole; and $R^2$ is isoxazole, pyridyl, pyrazinyl, or pyridazinyl; m is 0, 1 or 2; n is 0 to 2; and X is C or CH; or a pharmaceutically acceptable salt thereof. Within this group are compounds in which Ar is substituted by from 1 to 3 groups selected from haloalkyl, —O-haloalkyl, —$C_1$-$C_6$alkyl, —$C_2$-$C_6$alkenyl, —$C_2$-$C_6$alkynyl, —$(CH_2)_{0-3}$—$C_3$-$C_6$ cycloalkyl, halogen or CN, or a pharmaceutically acceptable salt thereof.

The invention is also directed, in part, to pharmaceutical compositions comprising a therapeutically effective amount of a compound herein, and the pharmaceutically acceptable salts thereof. Reference to one or more compounds herein is understood to include those described and/or specifically named herein, including the compounds following within Formula I and Formula II and the specifically named compounds herein.

The invention is also directed, in part, to methods of treating FAAH-mediated diseases or conditions including acute pain, chronic pain, neuropathic pain, nociceptive pain, inflammatory pain urinary incontinence, overactive bladder, emesis, cognitive disorders, anxiety, depression, sleeping disorders, eating disorders, movement disorders, glaucoma, psoriasis, multiple sclerosis, cerebrovascular disorders, brain injury, gastrointestinal disorders, hypertension, or cardiovascular disease in a subject by administering to a subject in need thereof a therapeutically effective amount of one or more of the compounds herein, and the pharmaceutically acceptable salts thereof.

DETAILED DESCRIPTION

Definitions and Abbreviations

This disclosure uses the definitions provided below. Some of the chemical formulae may include a dash ("-") to indicate a bond between atoms or indicate a point of attachment.

"Substituted" groups are those in which one or more hydrogen atoms have been replaced with one or more non-hydrogen atoms or groups.

"Alkyl" refers to straight chain or branched chain saturated hydrocarbon groups, generally having a specified number of carbon atoms (i.e., $C_1$-$C_6$alkyl). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain or branched chain hydrocarbon groups having one or more unsaturated carbon-carbon double bond, and having a specified number of carbon atoms (i.e., $C_2$-$C_6$alkenyl). Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched chain hydrocarbon groups having one or more carbon-carbon triple bond, and having a specified number of carbon atoms (i.e., $C_2$-$C_6$alkenyl). Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Alkanoyl" refers to alkyl-C(O)—, where alkyl is defined above. Examples of alkanoyl groups include formyl, acetyl, propionyl, butyryl, pentanoyl, hexanoyl, and the like.

"Alkoxy" refers to alkyl-O— groups wherein the alkyl portions, which may be straight chain or branched, have from 1 to 6 carbon atoms. Examples of alkoxy groups include methoxy, ethoxy, n-propoxy, i-propoxy, n-butoxy, s-butoxy, t-butoxy, n-pentoxy, s-pentoxy, and the like. "Alkenyloxy" and "alkynyloxy" refer, respectively, to alkenyl-O—, and alkynyl-O— wherein the alkenyl and alkynyl portions have from 2 to 6 carbon atoms and each of which may be straight or branched.

"Alkoxycarbonyl" refers to alkyl-O—C(O)—, alkenyl-O—C(O)—, alkynyl-O—C(O)—, where alkyl, alkenyl, and alkynyl are defined above. Examples of alkoxycarbonyl groups include methoxycarbonyl, ethoxycarbonyl, n-propoxycarbonyl, i-propoxycarbonyl, n-butoxycarbonyl, s-butoxycarbonyl, t-butoxycarbonyl, n-pentoxycarbonyl, s-pentoxycarbonyl, and the like.

"Halo," or "halogen" may be used interchangeably, and are fluoro, chloro, bromo, and iodo. The terms "haloalkyl" or "—O-haloalkyl" refer, respectively, to $C_1$-$C_6$ alkyl or $C_1$-$C_6$ alkoxy groups substituted by one or more halogens. Examples include —$CF_3$, —$CH_2$—$CF_3$, —$CF_2$—$CF_3$, —O—$CF_3$, and —$OCH_2$—$CF_3$.

"Cycloalkyl" refers to saturated monocyclic and bicyclic hydrocarbon rings, generally having a specified number of carbon atoms that comprise the ring (i.e. $C_3$-$C_7$cycloalkyl). The cycloalkyl groups may include one or more substituents. Useful substituents include alkyl, alkenyl, alkynyl, haloalkyl, haloalkenyl, haloalkynyl, alkoxy, alkoxycarbonyl, alkanoyl, and halo, as defined above, and hydroxy, mercapto, nitro, and amino. Examples of monocyclic cycloalkyl groups include cyclopropyl, cyclobutyl, cyclopentyl, cyclohexyl, and the like. Examples of bicyclic cycloalkyl groups include bicyclo[1.1.0]butyl, bicyclo[1.1.1]pentyl, bicyclo[2.1.0]pentyl, bicyclo[2.1.1]hexyl, bicyclo[3.1.0]hexyl, bicyclo[2.2.1]heptyl, bicyclo[3.2.0]heptyl, bicyclo[3.1.1]heptyl, bicyclo[4.1.0]heptyl, bicyclo[2.2.2]octyl, bicyclo[3.2.1]octyl, bicyclo[4.1.1]octyl, bicyclo[3.3.0]octyl, bicyclo[4.2.0]octyl, bicyclo[3.3.1]nonyl, bicyclo[4.2.1]nonyl, bicyclo[4.3.0]nonyl, bicyclo[3.3.2]decyl, bicyclo[4.2.2]decyl, bicyclo[4.3.1]decyl, bicyclo[4.4.0]decyl, bicyclo[3.3.3]undecyl, bicyclo[4.3.2]undecyl, bicyclo[4.3.3]dodecyl, and the like.

"Cycloalkenyl" refers monocyclic and bicyclic hydrocarbon rings having one or more carbon-carbon double bonds, generally having a specified number of carbon atoms that comprise the ring (i.e., $C_3$-$C_7$cycloalkyl). Useful substituents include alkyl, alkenyl, alkynyl, haloalkyl, haloalkenyl, haloalkynyl, alkoxy, alkoxycarbonyl, alkanoyl, and halo, as defined above, and hydroxy, mercapto, nitro, and amino and the like.

"Cycloalkanoyl" and "cycloalkenoyl" refer to cycloalkyl-C(O)— and cycloalkenyl-C(O)—, respectively. Examples of cycloalkanoyl groups include cyclopropanoyl, cyclobutanoyl, cyclopentanoyl, cyclohexanoyl, cycloheptanoyl, 1-cyclobutenoyl, 2-cyclobutenoyl, 1-cyclopentenoyl, 2-cyclopentenoyl, 3-cyclopentenoyl, 1-cyclohexenoyl, 2-cyclohexenoyl, 3-cyclohexenoyl, and the like.

"Cycloalkoxy" and "cycloalkoxycarbonyl" refer, respectively, to cycloalkyl-O— and cycloalkenyl-O and to cycloalkyl-O—C(O)— and cycloalkenyl-O—C(O)—, where cycloalkyl and cycloalkenyl are defined above. References to cycloalkoxy and cycloalkoxycarbonyl generally include a specified number of carbon atoms, excluding the carbonyl carbon. Examples of cycloalkoxy groups include cyclopropoxy, cyclobutoxy, cyclopentoxy, cyclohexoxy, 1-cyclobutenoxy, 2-cyclobutenoxy, 1-cyclopentenoxy, 2-cyclopentenoxy, 3-cyclopentenoxy, 1-cyclohexenoxy, 2-cyclohexenoxy, 3-cyclohexenoxy, and the like. Examples of cycloalkoxycarbonyl groups include cyclopropoxycarbonyl, cyclobutoxycarbonyl, cyclopentoxycarbonyl, cyclohexoxycarbonyl, 1-cyclobutenoxycarbonyl, 2-cyclobutenoxycarbonyl, 1-cyclopentenoxycarbonyl, 2-cyclopentenoxycarbonyl, 3-cyclopentenoxycarbonyl, 1-cyclohexenoxycarbonyl, 2-cyclohexenoxycarbonyl, 3-cyclohexenoxycarbonyl, and the like.

"Aryl" and "arylene" refer to monocyclic or bicyclic monovalent and divalent aromatic carbocyclic groups, such as phenyl, biphenyl or naphthyl groups.

"Heteroaryl" and "heteroarylene" refer to monovalent or divalent aromatic groups, respectively, containing from 1 to 4 ring heteroatoms selected from O, S or N. Examples of monocyclic (and monovalent) aryl groups include pyrrolyl, furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, and the like. The groups defined by —CH$_2$-aryl include benzyl and —CH$_2$-naphthyl.

Heteroaryl and heteroarylene groups also include bicyclic groups, tricyclic groups, including fused ring systems wherein at least one ring is aromatic. Examples of multicyclic (and monovalent) aryl groups include pyrenyl, carbazolyl, benzofuranyl, benzothiopheneyl, indolyl, benzoxazolyl, benzodioxazolyl, benzimidazolyl, indazolyl, benzotriazolyl, benzothiofuranyl, benzothiazolyl, benzotriazolyl, benzotetrazolyl, benzoisoxazolyl, benzoisothiazolyl, benzoimidazolinyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolizinyl, imidazo[1,2-a]pyridinyl, imidazo[1,5-a]pyridinyl, pyrazolo[1,5-a]pyridinyl, pyrrolo[1,2-b]pyridinyl, and imidazo[1,2-c]pyridinyl. Other examples include quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, phenanthridinyl, phenanthrolinyl, phenazinyl, phenothiazinyl, phenoxathiinyl, phenoxazinyl, acridinyl, azocinyl, 4aH-carbazolyl, chromanyl, chromenyl, indolenyl, indolinyl, 3H-indolyl, isobenzofuranyl, isochromanyl, isoindazolyl, isoindolinyl, pyrimidinyl, pteridinyl, phthalazinyl, purinyl, pyridazinyl, pyrazinyl, pyridooxazole, pyridoimidazole, pyridothiazole, pyridyl, pyridopyrimidinyl, quinoxalinyl, quinazolinyl, thianthrenyl, xanthenyl, and the like.

Aryl, arylene, heteroaryl and heteroarylene groups may include one or more substituents. Useful substituents include alkyl, alkenyl, alkynyl, haloalkyl, haloalkenyl, haloalkynyl, cycloalkyl, cycloalkenyl, alkoxy, cycloalkoxy, alkanoyl, cycloalkanoyl, cycloalkenoyl, alkoxycarbonyl, cycloalkoxycarbonyl, and halo, as defined above, and hydroxy, mercapto, nitro, amino, alkylamino, and the like.

"Heterocycle" and "heterocyclyl" refer to saturated or partially unsaturated or bicyclic rings having from 3 to 7 or from 7 to 11 ring members, respectively. These groups have ring members made up of carbon atoms and from 1 to 4 heteroatoms that are each independently selected from nitrogen, oxygen or sulfur, and may include any bicyclic group in which any of the above-defined monocyclic heterocycles are fused to a benzene ring. The nitrogen and sulfur heteroatoms may optionally be oxidized. Useful substituents include alkyl, alkenyl, alkynyl, haloalkyl, haloalkenyl, haloalkynyl, cycloalkyl, cycloalkenyl, alkoxy, cycloalkoxy, alkanoyl, cycloalkanoyl, cycloalkenoyl, alkoxycarbonyl, cycloalkoxycarbonyl, and halo, as defined above, and hydroxy, mercapto, nitro, amino, alkylamino, and the like.

Examples of heterocycles include oxiranyl, thiaranyl, aziridinyl, oxetanyl, thiatanyl, azetidinyl, tetrahydrothiopheneyl, tetrahydropyran, tetrahydrothiopyran, 1,4-dioxanyl, 1,4-oxathianyl, 1,4-dithianyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 5,6-dihydro-2H-pyranyl, 2H-pyranyl, 1,2,3,4-tetrahydropyridinyl, 1,2,5,6-tetrahydropyridinyl, carbolinyl, decahydroquinolinyl, 2H,6H-1,5,2-dithiazinyl, dihydrofuro[2,3-b]tetrahydrofuranyl, furazanyl, imidazolidinyl, imidazolinyl, morpholinyl, octahydroisoquinolinyl, oxazolidinyl, oxazolidinyl, isoxazolidinyl, piperazinyl, piperidinyl, pyranyl, pyrazolidinyl, pyrazolinyl, pyrrolidinyl, pyrrolinyl, 2H-pyrrolyl, 4H-quinolizinyl, quinuclidinyl, tetrahydrofuranyl, tetrahydroisoquinolinyl, tetrahydroquinolinyl, 6H-1,2,5-thiadiazinyl, thiadiazolyl, thienothiazolyl, thienooxazolyl, thienoimidazolyl, triazinyl, 1,2,4-triazolyl, and 1,2,5-triazolyl.

"Heteroaryl" and "heteroarylene" refer, respectively, to monovalent and divalent heterocycles or heterocyclyl groups, as defined above, which are aromatic. Heteroaryl and heteroarylene groups represent a subset of aryl and arylene groups, respectively.

"Arylcarbonyl" and "heteroarylcarbonyl" refer, respectively, to aryl-C(O)— and heteroaryl-C(O), where aryl and heteroaryl are defined above. Examples include phenylcarbonyl, imidazol-2-yl-methylcarbonyl, and the like.

"Subject" refers to a mammal, including humans. "Treating" refers to reversing, alleviating, inhibiting the progress of, or preventing a disorder or condition to which such term applies, or to reversing, alleviating, inhibiting the progress of, or preventing one or more symptoms of such disorder or condition. "Therapeutically effective amount" refers to the quantity of a compound that may be used for treating a subject, which amount may depend on the weight and age of the subject and the route of administration, among other things. "Excipient" or "adjuvant" refers to any substance in a pharmaceutical formulation that is not an active pharmaceutical ingredient (API). "Pharmaceutical composition" refers to the combination of one or more drug substances and one or more excipients. "Drug product," "pharmaceutical dosage form," "dosage form," "final dosage form" and the like, refer to a pharmaceutical composition that is administered to a subject in need of treatment and generally may be in the form of tablets, capsules, liquid solutions or suspensions, patches, films, and the like.

TABLE 1

List of Abbreviations

| Abbreviation | Description |
| --- | --- |
| ACN | Acetonitrile |
| ADP | Adenosine diphosphate |
| API | active pharmaceutical ingredient |
| Boc | tert-butyloxycarbonyl |
| DCM | Dichloromethane |
| DMF | Dimethylformamide |
| DMSO | Dimethylsulfoxide |
| EDTA | ethylenediaminetetraacetic acid |
| Et | Ethyl |
| EtOAc | ethyl acetate |
| EtOH | ethyl alcohol |
| h | hour(s) |
| $K_i$ | equilibrium dissociation constant for enzyme inhibition |
| $k_{inact}$ | first-order rate constant of enzyme inactivation at infinite inhibitor concentration |
| $k_{inact}/K_i$ | second-order rate constant ($M^{-1}s^{-1}$) that is a measure of inhibitory potency for an irreversible inhibitor |
| Me | Methyl |
| MeOH | methyl alcohol |
| min | minute(s) |
| NMP | N-methylpyrrolidinone |
| PG | protecting group |
| PGLA | poly(DL-lactic-coglycolic)acid |

TABLE 1-continued

List of Abbreviations

| Abbreviation | Description |
| --- | --- |
| PPTS | pyridinium p-tolunesulfonate |
| RT | room temperature (approximately 20° C. to 25° C.) |
| s | second(s) |
| TBS | tert-butyldimethysilyl |
| TBDPS | tert-butyldiphenylsilyl |
| THF | Tetrahydrofuran |
| THP | Tetrahydropyranyl |
| TIPS | triisopropylsilyl |
| wt % | weight (mass) percent |

The present invention relates to compounds of Formula I, Formula II and Formula III, compounds specifically named below, and their pharmaceutically acceptable salts, which are effective for inhibiting the activity of FAAH. The invention also concerns materials and methods for preparing the compounds, pharmaceutically acceptable salts, pharmaceutical compositions containing them, and their use for treating a variety of disorders such as pain, depression, or anxiety.

Also provided are compounds of Formula II:

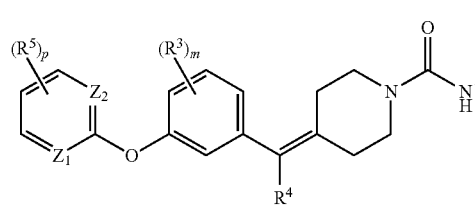

II wherein:
$R^2$ is a 5- or 6-membered heterocycle containing a nitrogen ring heteroatom and optionally having a second ring heteroatom selected from O or N;
each $R^1$ is independently hydrogen, halogen, haloalkyl, —$C_1$-$C_6$alkyl, —O—$C_1$-$C_6$alkyl, —S—$C_1$-$C_6$alkyl, aryl, heteroaryl, —$NH_2$, —NHC(O)$C_1$-$C_6$alkyl, —NHC(O)$C_3$-$C_6$cycloalkyl, —NHC$_1$-$C_6$alkyl, CN, or —C(O)$C_1$-$C_6$alkyl;
each $R^3$ is independently hydrogen, halogen, haloalkyl, —$C_1$-$C_6$alkyl, —O—$C_1$-$C_6$alkyl, —S—$C_1$-$C_6$alkyl, —$(CH_2)_{0-3}$—$C_3$-$C_6$ cycloalkyl, —S—$C_3$-$C_6$cycloalkyl and —O—$C_3$-$C_6$cycloalkyl; said —$C_1$-$C_6$alkyl, —O—$C_1$-$C_6$alkyl, —S—$C_1$-$C_6$alkyl, —$(CH_2)_{0-3}$—$C_3$-$C_6$ cycloalkyl, —S—$C_3$-$C_6$cycloalkyl and —C—$C_3$-$C_6$cycloalkyl, groups are optionally substituted with from 1 to 4 halogen, haloalkyl, —O-haloalkyl, —$C_1$-$C_6$alkyl, or —O($C_1$-$C_6$alkyl) substituents;
$R^4$ is hydrogen, —$C_1$-$C_6$alkyl, phenyl, —$(CH_2)_{0-3}$—$C_3$-$C_6$ cycloalkyl or halogen; said —$C_1$-$C_6$alkyl, phenyl, and —$(CH_2)_{0-3}$—$C_3$-$C_6$ cycloalkyl groups being optionally substituted with from 1 to 4 halogen, —$C_1$-$C_6$alkyl, or —O($C_1$-$C_6$alkyl) substituents;
each $R^5$ is independently hydrogen, halogen, haloalkyl, —O-haloalkyl, —$C_1$-$C_6$alkyl, —C(O)$C_1$-$C_6$alkyl, —O—$C_1$-$C_6$alkyl, —S—$C_1$-$C_6$alkyl, —$(CH_2)_{0-3}$—$C_3$-$C_6$cycloalkyl, CN, aryl, and heteroaryl; said —$C_1$-$C_6$alkyl, —O($C_1$-$C_6$alkyl), —$C_3$-$C_6$cycloalkyl, aryl, and heteroaryl groups are optionally independently substituted with from 1 to 4-$C_1$-$C_6$alkyl, —OH, or halogen substituents;

m is 0, 1, 2, 3, or 4;
n is 0, 1, 2, 3 or 4;
p is 0, 1, 2, 3, or 4 and
$Z_1$ and $Z_2$ are independently selected from N, C, or CH;
or a pharmaceutically acceptable salt thereof.

Within Formula II are separate groups of compounds, and the pharmaceutically acceptable salts thereof, wherein $R^2$ is selected from pyridine, pyrimidine, pyridazine, pyrazine, pyrazole and isoxazole. $R^1$, $R^3$, $R^4$, $R^5$, $Z^1$, $Z^2$, m, n, and p are as defined for Formula II in each of these groups designated by the definition of $R^2$. Within each of these groups are subgroups wherein the 6-membered ring defined by $Z_1$ and $Z_2$ and optionally substituted by $(R^5)_p$ is selected from phenyl, pyridine or pyrimidine. Within each of these groups and subgroups within the definitions of Formula II are further subgroups of compounds wherein $R^4$ is H or —$C_1$-$C_6$alkyl; and $R^3$ is H or —$C_1$-$C_6$alkyl; or a pharmaceutically acceptable salt thereof.

Further provided are compounds of Formula III:

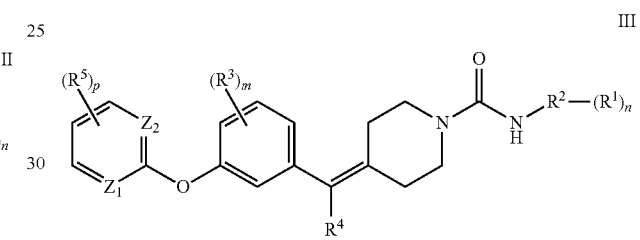

III wherein:
each $R^1$ is independently hydrogen, —$C_1$-$C_6$alkyl, or —O($C_1$-$C_6$alkyl);
$R^2$ is an isoxazole ring or a 6-membered aromatic heterocycle containing 1 or 2 nitrogen ring heteroatoms;
each $R^3$ is independently hydrogen, halogen, —$C_1$-$C_6$alkyl, —$(CH_2)_{0-3}$—$C_3$-$C_6$ cycloalkyl, or —O—$C_1$-$C_6$alkyl;
$R^4$ is hydrogen, —$C_1$-$C_6$alkyl, phenyl, or halogen;
each $R^5$ is independently hydrogen, halogen, haloalkyl, —O-haloalkyl, —$C_1$-$C_6$alkyl, —C(O)$C_1$-$C_6$alkyl, —O—$C_1$-$C_6$alkyl, —S—$C_1$-$C_6$alkyl, —$(CH_2)_{0-3}$—$C_3$-$C_6$cycloalkyl, CN, aryl, and heteroaryl; said —$C_1$-$C_6$alkyl, —O($C_1$-$C_6$alkyl), —$(CH_2)_{0-3}$—$C_3$-$C_6$cycloalkyl, aryl, and heteroaryl groups are optionally independently substituted with from 1 to 4-$C_1$-$C_6$alkyl, —OH, or halogen substituents;
m is 0, 1, 2, 3, or 4;
n is 0, 1, 2, 3 or 4;
p is 0, 1, 2, 3, or 4 and
$Z_1$ and $Z_2$ are independently selected from N, C, or CH;
or a pharmaceutically acceptable salt thereof.

Examples of 6-membered aromatic heterocycles represented by $R^2$ in the compounds of Formula III are pyridine, pyrazine, pyridazine and pyrimidine groups. Compounds of Formula III include those in which $Z_1$ is N; $Z_2$ is CH; p is 1; $R^5$ is $CF_3$; $R^1$ is hydrogen; and $R^2$ is selected from pyridine, pyridazine, pyrazine and pyrimidine; or a pharmaceutically acceptable salt thereof.

Also provided are compounds of Formula IV:

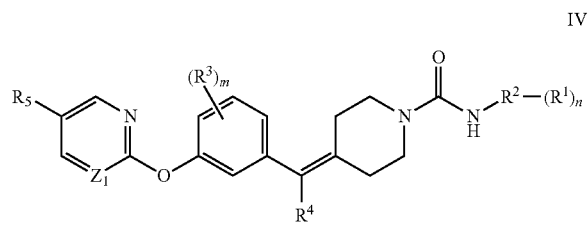

IV wherein:
each $R^1$ is independently hydrogen, —$C_1$-$C_6$alkyl, or —O($C_1$-$C_6$alkyl);
$R^2$ is pyridine, pyrazine, pyridazine or pyrimidine;
each $R^3$ is independently hydrogen, halogen, —$C_1$-$C_6$alkyl, —$(CH_2)_{0-3}$—$C_3$-$C_6$ cycloalkyl, or —O—$C_1$-$C_6$alkyl;
$R^4$ is hydrogen, —$C_1$-$C_6$alkyl, phenyl, or halogen;
$R^5$ is hydrogen, halogen, haloalkyl, —$C_1$-$C_6$alkyl, or —$(CH_2)_{0-3}$—$C_3$-$C_6$cycloalkyl; and said —$C_1$-$C_6$alkyl is optionally substituted with from 1 to 4 —OH substituents and —$(CH_2)_{0-3}$—$C_3$-$C_6$cycloalkyl is optionally substituted by from 1 to 4 halogen or —OH substituents;
m is 0, 1 or 2;
n is 0, 1, 2, 3 or 4;
$Z_1$ is selected from N or CH;
or a pharmaceutically acceptable salt thereof.

The compounds of Formula IV include those wherein $R^5$ is selected from hydrogen, halogen, —$C_1$-$C_6$alkyl, —$CF_3$ or —$C_3$-$C_6$ cycloalkyl; or a pharmaceutically acceptable salt thereof. Also included are those wherein $R^5$ is selected from hydrogen, halogen, —$C_1$-$C_6$alkyl, —$CF_3$ or cyclopropyl; or a pharmaceutically acceptable salt thereof.

The compounds herein and the pharmaceutically acceptable salts thereof, which includes those of Formula I and Formula II, may be used to treat pain (including neuropathic pain, nociceptive pain, and inflammatory pain); urinary incontinence; overactive bladder; emesis; movement disorders; glaucoma; psoriasis; multiple sclerosis; cerebrovascular disorders; brain injury; gastrointestinal disorders; hypertension; cardiovascular disease; and central nervous system disorders including anxiety, depression, sleeping disorders, and eating disorders.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan, 1999, Prog. Neurobiol., 57, 1-164 for a review). These sensory fibers are known as nociceptors and are characteristically small diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibers. Myelinated A-delta fibers transmit rapidly and are responsible for sharp and stabbing pain sensations, while unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumor related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact etiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple etiologies and thus can be classified in more than one area, e.g. back pain and cancer pain have both nociceptive and neuropathic components.

Other types of pain include:

Pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardical infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

As described above, the compounds herein, and the pharmaceutically acceptable salts thereof, may be used to treat CNS disorders, including schizophrenia and other psychotic disorders, mood disorders, anxiety disorders, sleep disorders, and cognitive disorders, such as delirium, dementia, and amnestic disorders. The standards for diagnosis of these disorders may be found in the American Psychiatric Association's *Diagnostic and Statistical Manual of Mental Disorders* (4th ed., 2000), which is commonly referred to as the *DSM Manual*.

For the purposes of this disclosure, schizophrenia and other psychotic disorders include schizophreniform disorder, schizoaffective disorder, delusional disorder, brief psychotic disorder, shared psychotic disorder, psychotic disorder due to general medical condition, and substance-induced psychotic disorder, as well as medication-induced movement disorders, such as neuroleptic-induced Parkinsonism, neuroleptic malignant syndrome, neuroleptic-induced acute dystonia, neuroleptic-induced acute akathisia, neuroleptic-induced tardive dyskinesia, and medication-induced postural tremor.

Mood disorders include depressive disorders, such as major depressive disorder, dysthymic disorder, premenstrual dysphoric disorder, minor depressive disorder, recurrent brief depressive disorder, postpsychotic depressive disorder of schizophrenia, and major depressive episode with schizophrenia; bipolar disorders, such as bipolar I disorder, bipolar II disorder, cyclothymia, and bipolar disorder with schizophrenia; mood disorders due to general medical condition; and substance-induced mood disorders.

Anxiety disorders include panic attack, agoraphobia, panic disorder without agoraphobia, agoraphobia without history of panic disorder, specific phobia, social phobia (social anxiety disorder), obsessive-compulsive disorder, posttraumatic stress disorder, acute stress disorder, generalized anxiety disorder, anxiety disorder due to general medical condition, substance-induced anxiety disorder, and mixed anxiety-depressive disorder.

Sleep disorders include primary sleep disorders, such as dyssomnias (primary insomnia, primary hypersomnia, narcolepsy, breathing-related sleep disorder, circadian rhythm sleep disorder, sleep deprivation, restless legs syndrome, and periodic limb movements) and parasomnias (nightmare disorder, sleep terror disorder, sleepwalking disorder, rapid eye movement sleep behavior disorder, and sleep paralysis); sleep disorders related to another mental disorder, including insomnia related to schizophrenia, depressive disorders, or anxiety disorders, or hypersomnia associated with bipolar disorders;

sleep disorders due to a general medical condition; and substance-induced sleep disorders, Delirium, dementia, and amnestic and other cognitive disorders, includes delirium due to a general medical condition, substance-induced delirium, and delirium due to multiple etiologies; dementia of the Alzheimer's type, vascular dementia, dementia due to general medical conditions, dementia due to human immunodeficiency virus disease, dementia due to head trauma, dementia due to Parkinson's disease, dementia due to Huntington's disease, dementia due to Pick's disease, dementia due to Creutzfeldt-Jakob disease, dementia due to other general medical conditions, substance-induced persisting dementia, dementia due to multiple etiologies; amnestic disorders due to a general medical condition, and substance-induced persisting amnestic disorder.

Substance-induced disorders refer to those resulting from the using, abusing, dependence on, or withdrawal from, one or more drugs or toxins, including alcohol, amphetamines or similarly acting sympathomimetics, caffeine, cannabis, cocaine, hallucinogens, inhalants, nicotine, opioids, phencyclidine or similarly acting arylcyclohexylamines, and sedatives, hypnotics, or anxiolytics, among others.

Urinary incontinence includes the involuntary or accidental loss of urine due to the inability to restrain or control urinary voiding. Urinary incontinence includes mixed urinary incontinence, nocturnal enuresis, overflow incontinence, stress incontinence, transient urinary incontinence, and urge incontinence.

Compounds of Formula I, which include compounds represented by Formula II, and compounds specifically named above, may form pharmaceutically acceptable complexes, salts, solvates and hydrates. The salts include acid addition salts (including di-acids) and base salts.

Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride, chloride, hydrobromide, bromide, hydroiodide, iodide, isethionate, lactate, malate, maleate, malonate, mesylate, methylsulfate, naphthylate, 2-napsylate, nicotinate, nitrate, orotate, oxalate, almitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium ($Na^+$), potassium ($K^+$), magnesium ($Mg^{2+}$), calcium ($Ca^{2+}$), zinc ($Zn^{2+}$), and aluminum ($Al^{3+}$). Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., "Pharmaceutical Salts," 66 *J. Pharm. Sci.*, 1-19 (1977); see also Stahl and Wermuth, *Handbook of Pharmaceutical Salts: Properties, Selection, and Use* (2002).

Pharmaceutically acceptable salts may be prepared using various methods. For example, one may react a compound with an appropriate acid or base to give the desired salt. One may also react a precursor of the compound with an acid or base to remove an acid- or base-labile protecting group or to open a lactone or lactam group of the precursor. Additionally, one may convert a salt of the compound to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

The compounds herein, and the pharmaceutically acceptable salts thereof, may exist in a continuum of solid states ranging from fully amorphous to fully crystalline. They may also exist in unsolvated and solvated forms. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, $d_6$-acetone, $d_6$-DMSO).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will be the norm.

The compounds herein, and the pharmaceutically acceptable salts thereof, may also exist as multi-component complexes (other than salts and solvates) in which the compound and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, Chem. Commun., 17:1889-1896 (2004). For a general review of multi-component complexes, see J. K. Haleblian, *J. Pharm. Sci.* 64(8):1269-88 (1975).

"Prodrugs" refer to compounds that when metabolized in vivo, undergo conversion to compounds having the desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula I, Formula II, compounds specifically named above, and the pharmaceutically acceptable salts. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula I, Formula II, compounds specifically named above, and the pharmaceutically acceptable salts thereof having methyl, alkoxy, tertiary amino, secondary amino, phenyl, and amide groups, respectively.

Geometrical (cis/trans) isomers may be separated by conventional techniques such as chromatography and fractional crystallization.

"Tautomers" refer to structural isomers that are interconvertible via a low energy barrier. Tautomeric isomerism (tautomerism) may take the form of proton tautomerism in which the compound contains, for example, an imino, keto, or oxime group, or valence tautomerism in which the compound contains an aromatic moiety.

Compounds described herein also include all pharmaceutically acceptable isotopic variations, in which at least one atom is replaced by an atom having the same atomic number, but an atomic mass different from the atomic mass usually found in nature. Isotopes suitable for inclusion in the compounds herein, and the pharmaceutically acceptable salts thereof include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds herein, and the pharmaceutically acceptable salts thereof, can be administered as crystalline or amorphous forms, prodrugs, metabolites, hydrates, solvates, complexes, and tautomers thereof, as well as all isotopically-labeled compounds thereof. They may be administered alone or in combination with one another or with one or more pharmacologically active compounds which are different than the compounds described or specifically named herein, and the pharmaceutically acceptable salts thereof. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

The compounds herein, and the pharmaceutically acceptable salts thereof, may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches.

Liquid formulations include suspensions, solutions, syrups and elixirs. Such formulations may be employed as fillers in soft or hard capsules (made, for example, from gelatin or hydroxypropyl methylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

The compounds herein, and the pharmaceutically acceptable salts thereof, may also be used in fast-dissolving, fast-disintegrating dosage forms such as those described in Liang and Chen, *Expert Opinion in Therapeutic Patents*, 11 (6):981-986 (2001).

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet. Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology, Vol.* 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include antioxidants, colorants, flavorants and flavor enhancers, preservatives, salivary stimulating agents, cooling agents, co-solvents (including oils), emollients, bulking agents, antifoaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14. Compounds of Formula I, Formula II, compounds specifically named above, and the pharmaceutically acceptable salts thereof may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula I, Formula II, compounds specifically named above, and the pharmaceutically acceptable salts thereof may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula I, Formula II, compounds specifically named above, and the pharmaceutically acceptable salts thereof may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

The compounds herein, and the pharmaceutically acceptable salts thereof, may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10):955-958 (1999).

Other means of topical administration include delivery by electroporation, iontophoresis, phonophoresis, sonophoresis and microneedle or needle-free injection. Formulations for topical administration may be formulated to be immediate or modified release as described above.

The compounds herein, and the pharmaceutically acceptable salts thereof, may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 μg to about 20 mg of the API per actuation and the actuation volume may vary from about 1 μL to about 100 μL. A typical formulation may comprise one or more compounds of Formula I, Formula II, compounds specifically named above, and the pharmaceutically acceptable salts thereof, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 μg to about 1000 μg of the API. The overall daily dose will typically range from about 100 μg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

The compounds herein, and the pharmaceutically acceptable salts thereof, and the pharmaceutically acceptable salts thereof may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

As noted above, the compounds herein, and the pharmaceutically acceptable salts thereof, and their pharmaceutically active complexes, solvates and hydrates, may be combined with one another or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula I; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

The claimed and disclosed compounds may be combined with one or more other pharmacologically active compounds for the treatment of one or more related disorders, the pharmacologically active compounds can be selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. acetaminophen, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazocin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiramate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, meclinertant, Miraxion® or sarizotan;

a vanilloid receptor (VR1; also known as transient receptor potential channel, TRPV1) agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine, or a nicotine partial agonist such as varenicline;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid receptor (CB1, CB2) ligand, either agonist or antagonist such as rimonabant;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazapine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy- 1-(5-thiazolyl)butyl]thio]-4-chlorobenzonitrile, (2S, 4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504);

a sodium channel blocker, such as lidocaine;

a 5-HT3 antagonist, such as ondensetron; or anti-nerve growth factor (NGF) antibodies.

The compounds herein, and the pharmaceutically acceptable salts thereof, may be generally prepared using the techniques described below. Starting materials and reagents may be obtained from commercial sources or may be prepared using literature methods unless otherwise specified.

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and the like, see T. W. Greene and P. G. Wuts, *Protecting Groups in Organic Chemistry* (1999) and P. Kocienski, *Protective Groups* (2000).

Generally, the chemical reactions described throughout the specification may be carried out using substantially stoichiometric amounts of reactants, though certain reactions may benefit from using an excess of one or more of the reactants. Additionally, many of the reactions disclosed throughout the specification may be carried out at about room temperature and ambient pressure, but depending on reaction kinetics, yields, and the like, some reactions may be run at elevated pressures or employ higher (e.g., reflux conditions) or lower (e.g., −70° C. to 0° C.) temperatures. Any reference in the disclosure to a stoichiometric range, a temperature range, a pH range, etc., whether or not expressly using the word "range," also includes the indicated endpoints.

Many of the chemical reactions may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

The compounds of this invention may be prepared as described below. In the reaction schemes and discussion that follow, Ar, X, m, n, p, $R^1$, $R^2$, $R^3$, $R^4$ and $R^5$ are defined as above.

Scheme A

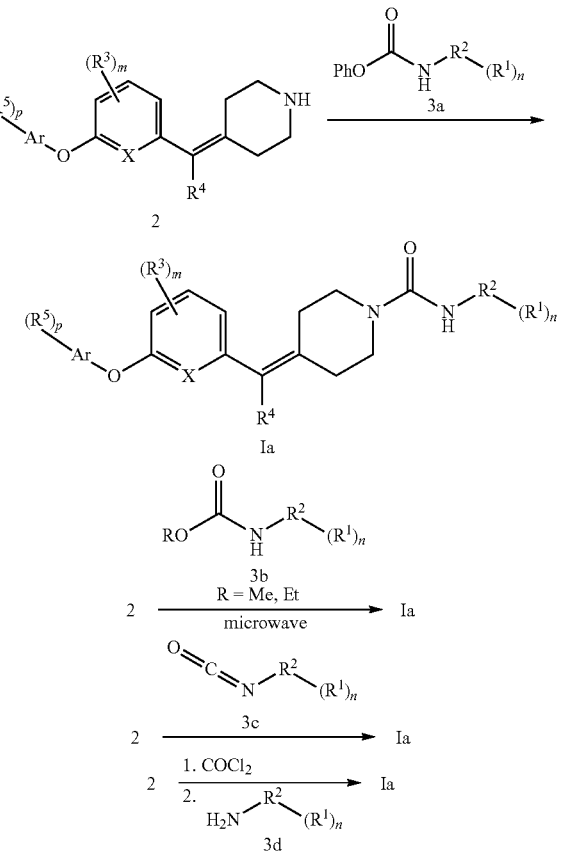

Compounds of Formula Ia can be prepared according to Scheme A. The reaction of a compound of formula 2 with a phenyl carbamate of formula 3a provides compounds of the Formula Ia. The reaction can be conducted in a polar aprotic solvent such as dimethylsulfoxide (DMSO) or acetonitrile. The temperature of the reaction may vary from about ambient temperature to about 60° C. The reaction can also be conducted using a trifluoroacetic acid or hydrochloride salt of the compound of formula 2 in the presence of a base such as triethylamine or diisopropylethyl amine. Alternatively, the reaction of a compound of formula 2 with a carbamate of formula 3b (R=Me or Et) under microwave irradiation provides compounds of the Formula Ia. The reaction can be conducted in a solvent such as acetonitrile. The reaction can also be conducted using a trifluoroacetic acid or hydrochloride salt of the compound of formula 2 in the presence of a base such as triethylamine or diisopropylethyl amine. Furthermore, compounds of the Formula Ia can be prepared by reacting compounds of formula 2 with an isocyanate of formula 3c. The reaction is typically conducted in a solvent such as methylene chloride at ambient temperature. The reaction can also be conducted using a trifluoroacetic acid or hydrochloride salt of the compound of formula 2 in the presence of a base such as triethylamine or diisopropylethyl amine. Alternatively, compounds of formula 2 can be reacted with phosgene in the presence of a base such as triethylamine or diisopropylethylamine and a solvent such as dichloromethane at 0° C. to generate the chloroformate derivative of formula 2 which can be isolated as a crude material and reacted with amines of formula 3d in the presence of a base such as triethylamine or diisopropylethylamine and a catalyst such as 4-(dimethylamino)-pyridine in a suitable solvent such as acetonitrile, dichloromethane, and dichloroethane. The reaction temperature may vary from about ambient temperature to about 70° C.

Scheme B

Compounds of formula 2 can be prepared according to Scheme B. The synthesis begins with a nucleophilic aromatic substitution of a phenol of formula 6 with an electron deficient aryl halide of the formula ArZ (where Z is F, Cl) to form the biaryl ether of formula 7 or 8. This reaction is preferably run in the presence of a base such as potassium carbonate, sodium carbonate, cesium carbonate, triethylamine or diisopropylethylamine. The solvent used may be dimethylformamide (DMF), N-methylpyrrolidinone (NMP), dimethylsulfoxide (DMSO), acetonitrile, tetrahydrofuran, dioxane or a combination of two or more of these solvents. The hydroxy group of the compound of formula 7 is converted into a leaving group (L) using conventional methods (for example, using thionyl chloride) to provide the corresponding compound of formula 9 wherein L is a halogen such as bromide, iodide or chloride. Alternatively, compounds of formula 8 can be brominated at the benzylic position (N-bromosuccinimide, benzoyl peroxide, CCl$_4$) to give compounds of formula 9 where L=Br. The resulting compounds of formula 9 are then reacted with triethyl phosphite to give the corresponding phosphonates of formula 10. The reaction can be conducted neat or in a solvent such as toluene, xylene, or chlorobenzene. The temperature of the reaction may vary from about ambient temperature to about the reflux temperature of the solvent used. The reaction is preferably conducted with a compound of formula 9 where L=Cl or Br in refluxing triethyl phosphite. Horner-Wadsworth-Emmons olefination of a compound of formula 10 with 1-Boc-4-piperidone in the presence of a base provides the compound of formula 11. This reaction is conducted in the presence of a base such as potassium tert-butoxide, sodium tert-butoxide, sodium hydride, potassium hydride, lithium diisopropylamide, lithium bis(trimethylsilyl)amide, potassium bis(trimethylsilyl)amide, sodium bis(trimethylsilyl)amide, or butyllithium. The reaction can be conducted in a solvent such as tetrahydrofuran (THF), 2-methyltetrahydrofuran, dioxane, ethylene glycol dimethyl-ether, dimethylformamide (DMF) or N-methylpyrrolidinone (NMP), and the temperature of the reaction may vary from about ambient temperature to about the reflux temperature of the solvent used. An additive such as 15-crown-5 can also be used to help promote the reaction. The compound of formula 11 is deprotected using conventional methods (for example, using HCl in dioxane, acetyl chloride in ethanol or trifluoroacetic acid) to provide the corresponding compound of formula 2 which can be isolated as the free base or as the corresponding salt (hydrochloride or trifluoroacetate).

Scheme C

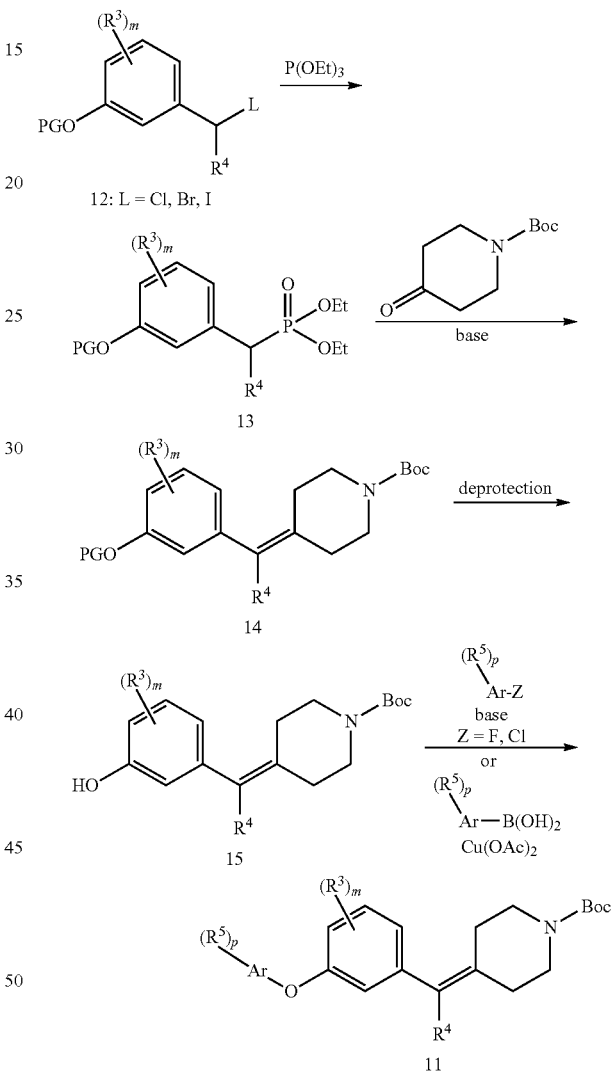

Scheme C illustrates a method for preparing compounds of formula 11. Compounds of formula 12, where PG is tetrahydropyranyl (THP), benzyl (Bn), p-methoxybenzyl, tert-butyldimethysilyl (TBS), triisopropylsilyl (TIPS) or tert-butyldiphenylsilyl (TBDPS), are reacted with triethyl phosphite to give the phosphonate of formula 13 as described in Scheme B. Horner-Wadsworth-Emmons olefination of a compound of the formula 13 with N-Boc-4-piperidone in the presence of a base provides the compound of formula 14 as described in Scheme B. Compounds of formula 14 wherein PG is tert-butyldimethysilyl, triisopropylsilyl (TIPS) or tert-butyldiphenylsilyl can be deprotected using conventional methods such as treatment with tetrabutylammonium fluoride in tetrahydrofuran to yield compounds of formula 15. Compounds of formula 14 where PG is tetrahydropyranyl (THP) can be deprotected using conventional methods such as treatment with PPTS (pyridinium p-toluenesulfonate) or p-toluenesulfonic acid in ethanol to give the corresponding compounds of formula 15. Nucleophilic aromatic substitution of a phenol of the formula 15 with an electron deficient aryl halide of the formula ArZ (where Z is F, Cl) provides the biaryl ether of formula 11 as described in Scheme B. Alternatively, copper (II)-promoted coupling of a phenol of formula 15 with a boronic acid of the formula ArB(OH)$_2$ provided the biaryl ether of formula 11. Preferably the reaction is conducted with one (1) equivalent of copper(II) acetate and 5-10 equivalents of triethylamine in a solvent such as methylene chloride with 4 Å molecular sieves at ambient temperature (*Tetrahedron Let.* 1998, 39, 2937).

tion of a phenol of formula 17 with an electron deficient aryl halide of the formula ArZ (where Z is F, Cl) provided the biaryl ether of the Formula Ia under similar conditions as described in Scheme B. Alternatively, copper(II)-promoted coupling of a phenol of formula 17 with a boronic acid of the formula ArB(OH)$_2$ provided the biaryl ether of the Formula Ia under similar conditions as described in Scheme C.

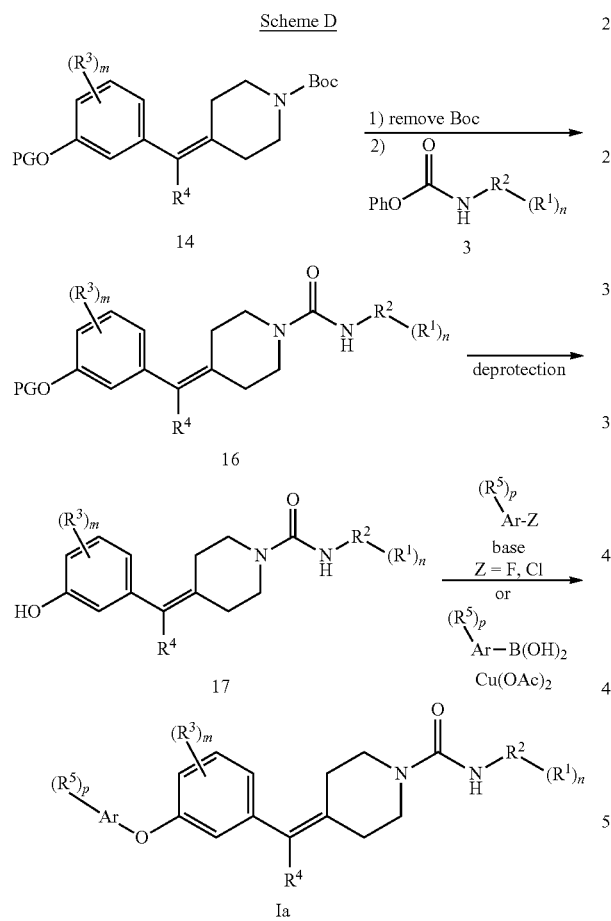

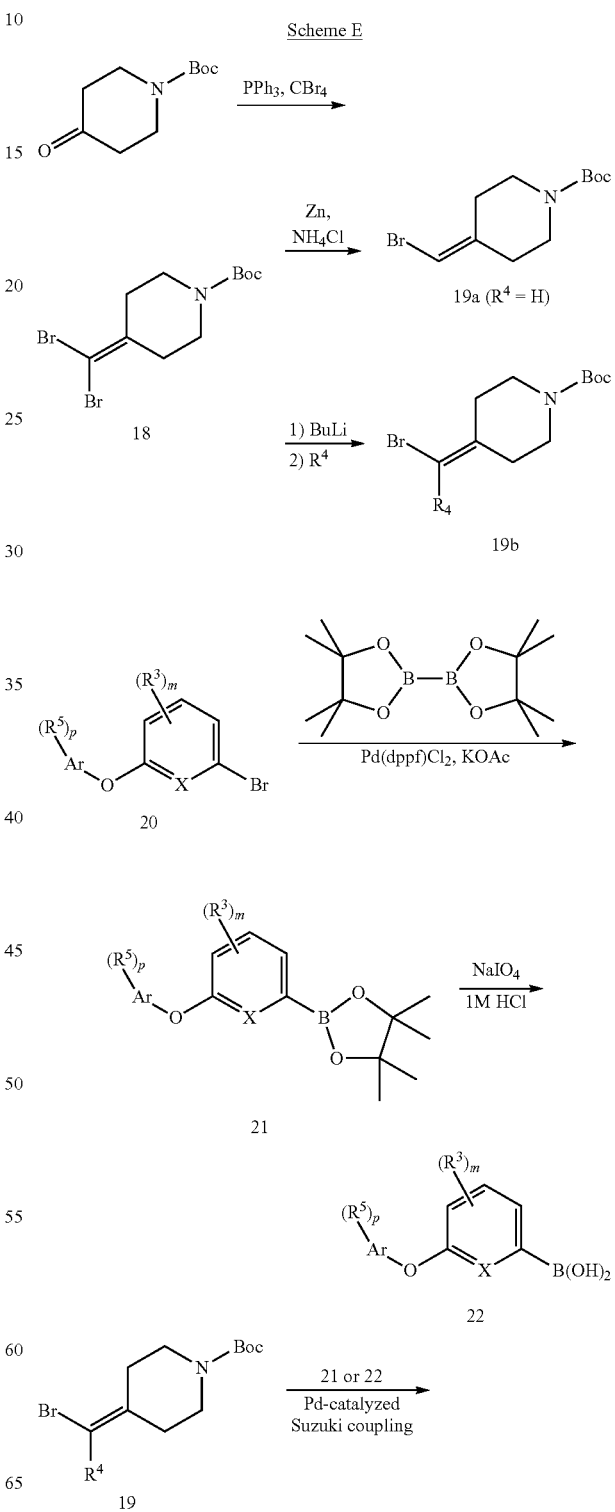

Compounds of the Formula Ia can also be prepared according to Scheme D. The Boc protecting group of a compound of formula 14 can be removed using conventional methods (for example, using HCl in dioxane, acetyl chloride in ethanol or trifluoroacetic acid) to provide the corresponding piperidine which is treated with a compound of formula 3 to give a urea of formula 16 under the conditions described in Scheme A. Compounds of formula 16 wherein PG is tert-butyldimethysilyl, triisopropylsilyl or tert-butyldiphenylsilyl can be deprotected using conventional methods such as treatment with tetrabutylammonium fluoride in tetrahydrofuran to yield compounds of formula 17. Nucleophilic aromatic substitu-

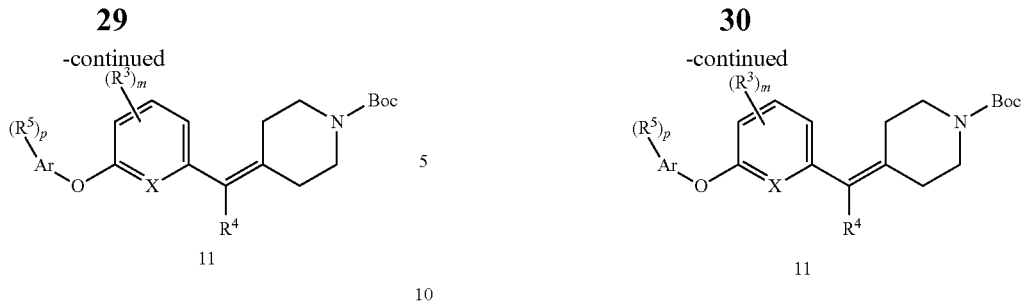

11

Scheme E illustrates another method for preparing compounds of formula 11. The requisite intermediates can be prepared as follows. Treatment of N-Boc-4-piperidone with carbon tetrabromide and triphenylphosphine gives the dibromoalkene compound of the formula 18. Selective reduction of one of the bromides provides the bromoalkene compound of the formula 19a. Metallation of a compound of the formula 18 with n-butyllithium followed by quenching with an alkylhalide of the formula $R^4$—I provides compounds of the formula 19b (*Org. Lett.* 2004, 6, 4467). The intermediate boronic ester of the formula 21 can be prepared by the palladium-catalyzed cross-coupling reaction of the pinacol ester of diboronic acid with compounds of the formula 20 (*J. Org. Chem.* 1995, 60, 7508). The intermediate boronic acid of the formula 22 can be prepared by treatment of compounds of the formula 21 with sodium periodate and aqueous HCl (*J. Org. Chem.* 2001, 66, 7148).

Compounds of formula 19 can be reacted with a boronic ester of formula 21 or a boronic acid of formula 22 under palladium-catalyzed Suzuki cross-coupling conditions (*Chem. Rev.* 1995, 95, 2457), to give the corresponding compounds of formula 11. For example, the coupling can be conducted using a catalytic amount of tetrakis(triphenylphosphine)-palladium(0) in the presence of a base such as aqueous sodium carbonate, sodium hydroxide, or sodium ethoxide, in a solvent such as THF, dioxane, ethylene glycol dimethylether, ethanol or benzene. The temperature of the reaction may vary from about ambient temperature to about the reflux temperature of the solvent used.

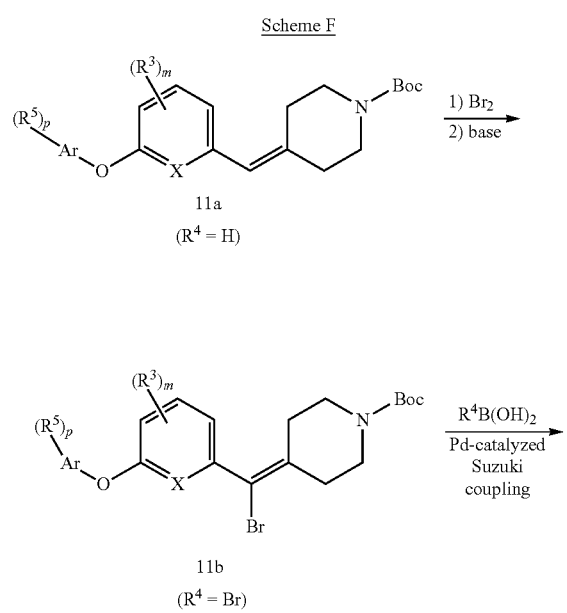

Alternatively, compounds of formula 11 can be prepared according to Scheme F. Bromination of a compound of formula 11a followed by treatment with a base such as potassium tert-butoxide or sodium hydroxide provides a compound of formula 11b. Compounds of formula 11b can be reacted with a boronic acid of the formula $R^4B(OH)_2$ under palladium-catalyzed Suzuki cross-coupling conditions to give the corresponding compounds of formula 11 under conditions similar to that described in Scheme E.

EXAMPLES

The following examples are intended to illustrate particular embodiments of the invention and are not intended to limit the scope of the claims.

$^1$H Nuclear magnetic resonance (NMR) spectra were obtained for the compounds in the following examples. Characteristic chemical shifts (δ) are given in parts-per-million downfield from tetramethylsilane using conventional abbreviations for designation of major peaks, including s (singlet), d (doublet), t (triplet), q (quartet); m (multiplet), and br (broad). The mass spectra were recorded using electrospray (ES) or atmospheric pressure chemical ionization (APCI). The following abbreviations are used for common solvents: $CDCl_3$ (deuterochloroform), $DMSO-d_6$ (deuterodimethylsulfoxide), $CD_3OD$ (deuteromethanol), and $THF-d_8$ (deuterotetrahydrofuran).

Example 1a

Synthesis of N-pyridin-3-yl-4-(3-{[5-(trifluoromethyl)pyridin-2-yl]oxy}benzylidene)piperidine-1-carboxamide Phenyl pyridin-3-ylcarbamate To a stirred solution of 3-aminopyridine (51.7 g, 0.549 moles) in THF (900 mL) at −10° C. was added pyridine (52.1 g, 0.659 moles) in a stream over a 10 min period, followed by the dropwise addition of phenyl chloroformate (90 g, 0.575 moles) over a 20 min period. The reaction temperature increased to 5° C. A precipitate formed during the addition. The resulting suspension was stirred at temperatures reaching ambient temperature over the next 3 h. The reaction mixture was partitioned between water (2 L) and EtOAc (1.5 L). The aqueous portion was extracted with EtOAc (1 L). The combined organic portions were dried ($MgSO_4$) and concentrated in vacuo to a damp solid residue. This was suspended in EtOAc:ether (1:1, 600 mL). The resulting suspension was stirred at −10° C. for 2 h and filtered. The solid was rinsed with EtOAc:ether (1:1, 100 mL) and pressed dry under suction. Further drying in vacuo at 35° C. for 7 h provided 104 g (88%) of product. Analysis, Calcd for $C_{12}H_{10}N_2O_2$: C, 67.28; H, 4.71; N, 13.08. Found: C, 67.15; H, 4.76; N, 12.87.

Step 1

[3-(5-Trifluoromethyl-pyridin-2-yloxy)-phenyl]-methanol

3-Hydroxymethyl-phenol (5.00 g, 40.3 mmol, from Lancaster Synthesis), 2-chloro-5-trifluoromethyl-pyridine (7.31 g, 40.3 mmol, from TCI America) and potassium carbonate (6.96 g, 50.3 mmol) were suspended in dimethylformamide (80 mL) and heated to 95° C. After stirring for 16 h, the solvent was distilled off in vacuo at 65° C., and a residue was partitioned between water and heptane/ethyl acetate (1:1). The organic layer was separated and the aqueous was extracted again with heptane/ethyl acetate (1:1). The combined organic layer was dried over sodium sulfate, filtered and concentrated to give a residue. The residue was purified by silica gel chromatography (10-60%, EtOAc:heptane) to afford the desired product (5.70 g, 53% yield) as a light yellow oil. $^1$H NMR (400 MHz, CDCl$_3$) δ ppm 4.73 (s, 2H) 7.02 (dt, J=8.66, 0.57 Hz, 1H) 7.04-7.11 (m, J=8.06, 2.40, 0.50, 0.50 Hz, 1H) 7.15-7.19 (m, 1H) 7.25 (ddd, J=8.39, 1.60, 0.80 Hz, 1H) 7.42 (t, J=7.87 Hz, 1H) 7.90 (ddd, J=8.67, 2.55, 0.50 Hz, 1H) 8.43 (td, J=1.68, 0.84 Hz, 1H).

Step 2

2-(3-Chloromethyl-phenoxy)-5-trifluoromethyl-pyridine

[3-(5-Trifluoromethyl-pyridin-2-yloxy)-phenyl]-methanol from Step 1 (4.68 g, 17.4 mmol), in dichloromethane (46 mL), was cooled to 0° C., and treated dropwise with thionyl chloride (1.40 mL, 19.1 mmol). The reaction mixture was allowed to warm to ambient temperature and was stirred for 30 min. Toluene (10 mL) was added and the mixture was concentrated by evaporation to form a residue. The residue was evaporated again from toluene and dried under high vacuum to afford the desired product (4.88 g, 98% yield) as an oil. $^1$H NMR (400 MHz, CDCl$_3$) δ ppm 4.60 (s, 2H) 7.03 (d, J=8.70 Hz, 1H) 7.11 (ddd, J=8.09, 2.35, 0.94 Hz, 1H) 7.20 (t, J=2.03 Hz, 1H) 7.26-7.31 (m, 1H) 7.42 (t, J=7.88 Hz, 1H) 7.91 (dd, J=8.67, 2.53 Hz, 1H) 8.44 (dd, J=1.51, 0.90 Hz, 1H).

Step 3

[3-(5-Trifluoromethyl-pyridin-2-yloxy)-benzyl]-phosphonic acid diethyl ester 2-(3-Chloromethyl-phenoxy)-5-trifluoromethyl-pyridine (4.88 g, 17.0 mmol) from Step 2 was treated neat with triethylphosphite (4.36 mL, 25.4 mmol) and heated to 150° C. After 6 h, the reaction mixture was cooled, treated with an additional 0.5 mL triethylphosphite (2.9 mmol) and reheated to 150° C. After 6 h, the reaction mixture was removed from the heat and slowly treated with heptane (about 60 mL) while stirring to afford a white solid. The solid was collected by filtration, washed with heptane and dried in a vacuum oven for 16 h at 45° C. to afford a white powder (5.99 g, 91% yield). MS (APCI) M+1=390.1; $^1$H NMR (400 MHz, CDCl$_3$) δ ppm 1.26 (t, J=7.02 Hz, 6H) 3.18 (d, J=21.83 Hz, 2H) 3.99-4.10 (m, 4H) 7.01 (d, J=8.58 Hz, 1H) 7.03-7.08 (m, 1H) 7.12 (q, J=2.21 Hz, 1H) 7.19-7.24 (m, 1H) 7.38 (t, J=7.90 Hz, 1H) 7.90 (dd, J=8.58, 2.53 Hz, 1H) 8.43 (dd, J=1.66, 0.88 Hz, 1H).

Step 4

4-[3-(5-Trifluoromethyl-pyridin-2-yloxy)-benzylidene]-piperidine-1-carboxylic acid tert-butyl ester

[3-(5-Trifluoromethyl-pyridin-2-yloxy)-benzyl]-phosphonic acid diethyl ester (2.3 g, 6.0 mmol) from Step 3 and 1,4,7,10,13-pentaoxacyclopentadecane (15-Crown-5, 0.03 mL, 0.15 mmol) were combined in THF (10 mL). The mixture was cooled to 0° C. and sodium hydride (240 mg, 60% dispersion in mineral oil, 6.0 mmol) was added. The reaction was warmed to room temperature, stirred for 30 minutes and then cooled back to 0° C. A solution of 4-oxo-piperidine-1-carboxylic acid tert-butyl ester (1.2 g, 6.0 mmol) in THF (6 mL) was added and the reaction was warmed to room temperature. After 16 hours, water was added and the layers were separated. The aqueous layer was extracted with EtOAc (2×200 mL) and the combined organic layer was dried over anhydrous sodium sulfate, filtered and concentrated to a thick oil. Treatment of the oil with hot isopropyl ether (45 mL) provided the title compound as a white solid (1.88 g). $^1$H NMR (400 MHz, CD$_3$OD) δ ppm 1.46 (s, 9H) 2.34 (td, J=5.85, 1.18 Hz, 2H) 2.46 (td, J=5.87, 1.07 Hz, 2H) 3.37-3.44 (m, 2H) 3.45-3.57 (m, 2H) 6.41 (s, 1H) 6.92-7.04 (m, 2H) 7.06-7.17 (m, 2H) 7.31-7.54 (m, 1H) 8.08 (ddd, J=8.74, 2.59, 0.56 Hz, 1H) 8.42 (td, J=1.73, 0.90 Hz, 1H).

Step 5

2-(3-Piperidin-4-ylidenemethyl-phenoxy)-5-trifluoromethyl-pyridine hydrochloride 4-[3-(5-Trifluoromethyl-pyridin-2-yloxy)-benzylidene]-piperidine-1-carboxylic acid tert-butyl ester (1.35 g, 3.11 mmol) from Step 4 was dissolved in CH$_2$Cl$_2$ (30 mL) and treated with HCl in diethyl ether (10 mL, 2.0 M, 20 mmol). After 16 hours the reaction was concentrated in vacuo to form a residue and the residue was suspended in acetonitrile (10 mL) to yield a solid. Filtration of the solid provided the title compound as a white solid (1.1 g). $^1$H NMR (400 MHz, CD$_3$OD) δ ppm 2.62 (td, J=6.11, 0.91 Hz, 2H) 2.67-2.81 (m, 2H) 3.14-3.21 (m, 2H) 3.22-3.29 (m, 2H) 6.56 (s, 1H) 6.99-7.09 (m, 2H) 7.10-7.18 (m, 2H) 7.42 (t, J=7.91 Hz, 1H) 8.09 (ddd, J=8.74, 2.60, 0.33 Hz, 1H) 8.41 (td, J=1.63, 0.74 Hz, 1H).

Step 6

2-(3-Piperidin-4-ylidenemethyl-phenoxy)-5-trifluoromethyl-pyridine hydrochloride (800 mg, 2.16 mmol, from Step 5), phenyl pyridin-3-ylcarbamate (508 mg, 2.37 mmol) and diisopropylethylamine (0.75 mL, 4.52 mmol) were combined in acetonitrile (10 mL) and stirred at room temperature. After 16 hours, the reaction was concentrated forming a residue and the residue was partitioned between EtOAc and water. The organic layer was separated, washed with 5% NaOH (aq), dried over anhydrous sodium sulfate, filtered and concentrated. Treatment of the residue with hot isopropyl ether and purified from isopropyl ether/methanol provided the title compound as a white solid (574 mg). MS (APCI 10V) AP+ 455.3, 376.2, 335.2, AP− 453.2; $^1$H NMR (400 MHz, CD$_3$OD) δ ppm 2.46 (td, J=5.86, 0.97 Hz, 2H) 2.58 (td, J=5.82, 1.16 Hz, 2H) 3.51-3.60 (m, 2H) 3.61-3.70 (m, 2H) 6.46 (s, 1H) 6.98-7.07 (m, 2H) 7.09-7.19 (m, 2H) 7.34 (ddd, J=8.41, 4.81, 0.65 Hz, 1H) 7.40 (td, J=7.69, 0.74 Hz, 1H) 7.91 (ddd, J=8.38, 2.58, 1.44 Hz, 1H) 8.08 (ddd, J=8.73, 2.61, 0.55 Hz, 1H) 8.16 (dd, J=4.84, 1.06 Hz, 1H) 8.43 (td, J=1.74, 0.91 Hz, 1H) 8.58 (d, J=1.88 Hz, 1H).

Example 1b

Large scale synthesis of N-pyridin-3-yl-4-(3-{[5-(trifluoromethyl)pyridin-2-yl]oxy}benzylidene)piperidine-1-carboxamide Step 1: Preparation of [3-(5-Trifluoromethyl-pyridin-2-yloxy)-phenyl]-methanol To a solution of 5-trifluoromethyl-2-chloro-pyridine (150.0 g, 0.826 mol) in DMF (1.9 L) was added 3-hydroxyphenyl-methanol (112.5 g, 0.906 mol) and of potassium carbonate (171.0 g, 1.237 mol). The solids were washed into the flask with 100 mL of DMF. The stirred mixture was heated to 95-105° C. for 5 h. It was cooled to ambient temperature and then poured into 5 L of stirred ice-water. The mixture was extracted with ether:hexane (2:1, 1.5 L, 1.0 L). The combined organic layers were dried over magnesium sulfate and concentrated in vacuo to dryness to give the product (222.5 g, 100%).

Step 2: Preparation of 2-(3-chloromethyl-phenoxy)-5-trifluoromethylpyridine

To a solution of [3-(5-trifluoromethyl-pyridin-2-yloxy)-phenyl]-methanol (281.0 g, 1.044 moles) in dichloromethane (2.0 L) at −5° C. was added dropwise over a 25 min period thionyl chloride (136.6 g, 1.148 mol). A few minutes into the addition, a white substance separated but this went into solution several minutes later. The reaction was stirred at ambient temperature for 1 h and then was concentrated in vacuo to near dryness (357 g). 200 mL of toluene was added to the residue and the solution was again concentrated in vacuo to near dryness. 200 mL of toluene was added and some solid (~8 g) was filtered off. The filtrate was concentrated in vacuo to ~390 g of dark yellow liquid.

Step 3: Preparation of [3-(5-trifluoromethyl-pyridin-2-yloxy)-benzyl]-phosphonic acid diethyl ester A solution of 2-(3-chloromethyl-phenoxy)-5-trifluoromethylpyridine (~298 g, ~1.036 mol) containing some toluene in triethyl phosphite (267.0 g, 1.551 mol) was heated to 135° C.-140° C. for 7 h. Boiling began at ~110° C. and continued throughout the reaction. The solution was left standing at ambient temperature overnight and it solidified. The solid was suspended in ether:hexane (1:2, 450 mL), and the suspension was stirred at ambient temperature for 3 h and filtered. The solid was rinsed with ether:hexane (1:2, 150 mL) and pressed dry under suction. Further drying in vacuo at 32° C. for 7 h provided 286.3 g (71%–2 steps from crude chloride) of product. The filtrate was concentrated in vacuo to remove the low boiling solvents. Triethyl phosphite (36.0 g, 0.217 mol) was added and the solution was heated to 130° C. for 2 h. The reaction was cooled to 100° C. and 300 mL of heptane was added slowly. A solid separated. As the temperature decreased to ~30° C., 150 mL of ether was added. The resulting suspension was left standing at ambient temperature overnight and was filtered. The solid was rinsed with ether:heptane (1:2, 75 mL) and pressed dry under suction. Further drying in vacuo at 32° C. for 7 h afforded and additional 35.7 g (9%) of product. Total yield=322 g (80%). Anal. Calcd for C17H19F3NO4P (389.31): C, 52.45; H, 4.92; N, 3.60; F, 14.64; P, 7.96. Found: C, 52.73; H, 5.04; N, 3.58; F, 14.35; P, 7.74; chloride, <0.10%.

Step 4: Preparation of 4-[3-(5-trifluoromethyl-pyridin-2-yloxy)-benzylidene]-piperidine-1-carboxylic acid tert-butyl ester To a stirred mixture of [3-(5-trifluoromethyl-pyridin-2-yloxy)-benzyl]-phosphonic acid diethyl ester (155.7 g, 0.40 mol) in tetrahydrofuran (800 mL) at −10° C. was added dropwise over a 5 min period 1.0 M tBuOK in tetrahydrofuran (420.0 mL, 0.42 mol). The temperature rose to −3° C. during the addition. The resulting red mixture was stirred between −6° C. and −10° C. for 2.5 h. A solution of tert-butyl 4-oxopiperidine-1-carboxylate (79.7 g, 0.40 mol) in tetrahydrofuran (300 mL) was added dropwise over a 5 min period. The temperature rose to 2° C. The resulting red mixture was stirred at temperatures reaching 21° C. over the next 16 h. TLC showed product with no phosphonate present. The mixture was poured into 3.5 L of stirred ice-water. The resulting suspension was stirred at ambient temperature for 2.5 h and then was extracted with successive 1.0 L and 0.6 L portions of dichloromethane. The combined extracts were washed with 500 mL of brine, dried over magnesium sulfate and concentrated in vacuo to a thick semi solid residue. 250 mL of methyl t-butyl ether was added. The suspension was stirred at −10° C. for 2 h and filtered. Drying in vacuo at 25° C. for 66 h provided 85 g (49%) of product. The filtrate was concentrated in vacuo to a damp solid residue. This was taken up in 100 mL of methyl t-butyl ether. To the stirred suspension was added 300 mL of heptane and the resulting suspension was stirred at −10° C. for 2 h. The solid was filtered off, rinsed with 50 mL of methyl t-butyl ether:heptane (1:3) and pressed dry under suction. Further drying in vacuo at 34° C. for 6 h provided an additional 34.2 g (19.5%) of product. Total yield=119.2 g (68.5%).

Step 5: Preparation of 2-(3-piperidin-4-ylidenemethyl-phenoxy)-5-trifluoromethyl-pyridine, hydrochloride To a mixture of 4-[3-(5-trifluoromethyl-pyridin-2-yloxy)-benzylidene]-piperidine-1-carboxylic acid tert-butyl ester (312 g, 0.718 mol) in ethyl acetate (2.8 L) at 0° C. to −5° C. was added streamwise over a 20 min period, 4.0 M hydrogen chloride in dioxane (800 mL, 3.2 mol). No significant temperature change was noted. The resulting suspension was stirred at temperatures reaching 22° C. over the next 17 h. The suspension was filtered. The solid was washed with EtOAc (500 mL) and pressed as dry as possible under suction. The damp solid was dried in vacuo at 33° C. for 7 h to afford 225 g (84%) of product.

Step 6: Preparation of N-pyridin-3-yl-4-(3-{[5-(trifluoromethyl)pyridin-2-yl]oxy}benzylidene)piperidine-1-carboxamide To a mixture of 2-(3-piperidin-4-ylidenemethyl-phenoxy)-5-trifluoromethyl-pyridine (80.0 g, 0.216 mol) and phenyl pyridin-3-ylcarbamate (48.6 g, 0.227 mol) in acetonitrile (650 mL) was added dropwise diisopropylethyl amine (55.8 g, 0.432 mol). A solution formed after ~45 min of stirring. The slightly turbid solution was stirred at ambient temperature for 18 h. TLC showed a prominent product spot with traces of both starting materials and two other fast moving spots. The solution was concentrated in vacuo to a viscous oil. This was partitioned between dichloromethane (600 mL) and water (500 mL). The aqueous layer was extracted with 200 mL of dichloromethane. The combined organic layers were washed with successive portions of 500 mL of 5% sodium hydroxide, and 200 mL of water, then dried over magnesium sulfate and concentrated in vacuo to 139.5 g of a viscous oil. This was dissolved in 350 mL of warm (50° C.) methyl t-butyl ether. Soon after a solution formed, solid began separating. The crystallizing mixture was kept at −10° C. for 4 h and filtered. The solid was rinsed with 60 mL of methyl t-butyl ether and pressed dry under suction. Further drying in vacuo at 28° C. for 16 h and then at 35° C. for 6 h provided 93.2 g (95%) of product.

Example 2

Synthesis of N-(3,4-dimethylisoxazol-5-yl)-4-(3-{[5-(trifluoromethyl)pyridin-2-yl]oxy}benzylidene)piperidine-1-carboxamide Following the procedure in Example 1, Step 6, 2-(3-piperidin-4-ylidenemethyl-phenoxy)-5-trifluoromethyl-pyridine hydrochloride (150 mg, 0.40 mmol, from Example 1, Step 5) and phenyl 3,4-dimethylisoxazol-5-ylcarbamate (94 mg, 0.40 mmol, prepared according to the procedure described in *Synthesis*, 1997, 1189-1194 from 5-amino-3,4-dimethylisoxazole) were used to provide the title compound (187 mg). MS (APCI 10V) AP+ 473.3, AP– 471.2; $^1$H NMR (400 MHz, CD$_3$OD) δ ppm 1.83 (s, 3H) 2.18 (s, 3H) 2.41-2.49 (m, 2H) 2.53-2.62 (m, 2H) 3.49-3.57 (m, 2H) 3.58-3.66 (m, 2H) 6.46 (s, 1H) 6.97-7.05 (m, 2H) 7.10-7.20 (m, 2H) 7.40 (tt, J=7.64, 0.76 Hz, 1H) 8.08 (dd, J=8.65, 2.51 Hz, 1H) 8.33-8.51 (m, J=2.31, 1.33, 0.88, 0.74 Hz, 1H).

Example 3

Synthesis of N-(6-methylpyridin-3-yl)-4-(3-{[5-(trifluoromethyl)pyridin-2-yl]oxy}benzylidene)piperidine-1-carboxamide Following the procedure in Example 1, Step 6, 2-(3-piperidin-4-ylidenemethyl-phenoxy)-5-trifluoromethyl-pyridine hydrochloride (150 mg, 0.40 mmol, from Example 1, Step 5) and phenyl 6-methylpyridin-3-ylcarbamate (92 mg, 0.40 mmol, prepared according to the procedure described in *Synthesis*, 1997, 1189-1194 from 3-amino-6-methylpyridine, 3B Medical Systems, Inc.) were used to provide the title compound (184 mg). MS (APCI 10V) AP+ 469.3, AP– 467.2, 448.2; $^1$H NMR (400 MHz, CD$_3$OD) δ ppm 2.41-2.44 (m, 2H) 2.46 (s, 3H) 2.58 (td, J=5.80, 0.83 Hz, 2H) 3.51-3.57 (m, 2H) 3.60-3.67 (m, 2H) 6.45 (s, 1H) 6.97-7.05 (m, 2H) 7.09-7.17 (m, 2H) 7.20 (d, J=8.50 Hz, 1H) 7.40 (td, J=7.70, 0.78 Hz, 1H) 7.77 (dd, J=8.37, 2.52 Hz, 1H) 8.08 (ddd, J=8.71, 2.56, 0.50 Hz, 1H) 8.42 (d, J=0.54 Hz, 1H) 8.43 (s, 1H).

Example 4

Synthesis of N-pyrazin-2-yl-4-(3-{[5-(trifluoromethyl)pyridin-2-yl]oxy}benzylidene)piperidine-1-carboxamide Following the procedure in Example 1, Step 6, 2-(3-piperidin-4-ylidenemethyl-phenoxy)-5-trifluoromethyl-pyridine hydrochloride (150 mg, 0.40 mmol, from Example 1, Step 5) and phenyl pyrazin-2-ylcarbamate (261 mg, 1.2 mmol, prepared according to the procedure described in *Synthesis*, 1997, 1189-1194 from aminopyrazine) were used to provide the title compound (24 mg). MS (APCI 10V) AP+ 456.2, 376.2, 335.2, AP– 454.2, 435.1; $^1$H NMR (400 MHz, CD$_3$OD) δ ppm 2.43-2.50 (m, 2H) 2.56-2.62 (m, 2H) 3.54-3.61 (m, 2H) 3.64-3.70 (m, 2H) 6.46 (s, 1H) 6.98-7.05 (m, 2H) 7.10-7.17 (m, 2H) 7.40 (td, J=7.72, 0.67 Hz, 1H) 8.06-8.11 (m, 1H) 8.16 (d, J=2.68 Hz, 1H) 8.28 (dd, J=2.68, 1.54 Hz, 1H) 8.43 (ddd, J=2.56, 1.71, 0.85 Hz, 1H) 9.04 (d, J=1.56 Hz, 1H).

Example 5a

Synthesis of N-pyridazin-3-yl-4-(3-{[5-(trifluoromethyl)pyridin-2-yl]oxy}benzylidene)piperidine-1-carboxamide 2-(3-Piperidin-4-ylidenemethyl-phenoxy)-5-trifluoromethyl-pyridine hydrochloride (500 mg, 1.35 mmol, from Example 1, Step 5), ethyl pyridazin-3-ylcarbamate (248 mg, 1.48 mmol, prepared according to the procedure described in *Synthesis*, 1997, 1189-1194 from 3-aminopyridazine) and triethylamine (0.376 mL, 2.7 mmol) were combined in acetonitrile (4.5 mL) and heated in a microwave at 180° C. for 40 minutes. The reaction mixture was cooled to rt and concentrated to form a residue. The residue was purified by silica gel chromatography (50-100% EtOAc in CH$_2$Cl$_2$) to provide the title compound (340 mg). MS (APCI 10V) AP+ 456.2, 376.2, 335.2; $^1$H NMR (400 MHz, CD$_3$OD) δ ppm 2.54 (dt, J=50.71, 5.84 Hz, 4H) 3.64 (dt, J=36.50, 5.84 Hz, 4H) 6.47 (s, 1H) 6.96-7.07 (m, 2H) 7.08-7.20 (m, 2H) 7.40 (td, J=7.72, 0.52 Hz, 1H) 7.59 (dd, J=9.13, 4.62 Hz, 1H) 8.08 (dd, J=8.67, 2.68 Hz, 1H) 8.13 (d, J=8.92 Hz, 1H) 8.43 (dt, J=1.79, 0.81 Hz, 1H) 8.79 (d, J=4.19 Hz, 1H).

Example 5b

Large scale synthesis of N-pyridazin-3-yl-4-(3-{[5-(trifluoromethyl)pyridin-2-yl]oxy}benzylidene)piperidine-1-carboxamide To a mixture of 2-(3-piperidin-4-ylidenemethyl-phenoxy)-5-trifluoromethyl-pyridine, hydrochloride (37.1 g, 0.10 mol, see Example 1b, step 5) and phenyl pyridazin-3-ylcarbamate (21.5 g, 0.10 mol, see Example 39, steps 1 and 2) in acetonitrile (400 mL) was added dropwise diisopropylethyl amine (25.8 g, 0.20 mol). A solution formed after 2 h of stirring. The slightly turbid solution was stirred at ambient temperature for 17 h. It was poured into 2.5 L of stirred ice-water. The resulting mixture was stirred for 1 h. The solid was filtered off, rinsed with 300 mL of water and pressed dry under suction. This was dissolved in 400 mL of dichloromethane. Water was removed using a sep funnel and then the solution was dried over magnesium sulfate and concentrated in vacuo to ~50 mL. The viscous solution was diluted with 65 mL of ethyl acetate and then with 85 mL of methyl t-butyl ether. A solution formed, and then a solid began separating. The crystallizing mixture was kept at –10° C. for 2 h and filtered. The solid was rinsed with EtOAc:MTBE (40 mL) and pressed dry under suction. Further drying in vacuo at 40° C. for 7 h provided 30.3 g (66%) of product. The mother liquor was concentrated in vacuo to 19 g of a viscous oil. This was dissolved in 15 mL of ethyl acetate. The solution was diluted with 60 mL of methyl t-butyl ether, seeded and kept at 5° C. for 18 h. The solid which crystallized was filtered off, rinsed with 10 mL of methyl t-butyl ether, and pressed dry under suction. 9.0 g (20%) of additional product was obtained. Total yield=39.3 g (86%).

Example 6

Synthesis of N-2,1-benzisoxazol-3-yl-4-(3-{[5-(trifluoromethyl)pyridin-2-yl]oxy}benzylidene)piperidine-1-carboxamide Following the procedure in Example 1, Step 6, 2-(3-piperidin-4-ylidenemethyl-phenoxy)-5-trifluoromethyl-pyridine hydrochloride (150 mg, 0.40 mmol, from Example 1, Step 5) and phenyl benzo[c]isoxazol-3-ylcarbamate (113 mg, 0.40 mmol, prepared according to the procedure described in *Synthesis*, 1997, 1189-1194 from 3-amino-2,1-benzisoxazole) were combined to provide the title compound (168 mg). MS (APCI 10V) AP+ 495.2, 376.2, 335.2; $^1$H NMR (400 MHz, CD$_3$OD) δ ppm 2.56 (dt, J=50.88, 5.69 Hz, 4H) 3.66 (dt, J=37.31, 5.71 Hz, 4H) 6.48 (s, 1H) 6.98-7.07 (m, 2H) 7.13 (ddd, J=8.75, 0.68, 0.56 Hz, 1H) 7.16 (d, J=7.77 Hz, 1H) 7.30

(ddd, J=8.05, 6.80, 1.16 Hz, 1H) 7.41 (t, J=7.99 Hz, 1H) 7.49-7.66 (m, 2H) 7.85 (dt, J=8.13, 1.03 Hz, 1H) 8.09 (ddd, J=8.72, 2.67, 0.38 Hz, 1H) 8.43 (td, J=1.82, 0.93 Hz, 1H).

Example 7

Synthesis of N-(5-methylpyridin-3-yl)-4-(3-{[5-(trifluoromethyl)pyridin-2-yl]oxy}benzylidene)piperidine-1-carboxamide A solution of 2-(3-piperidin-4-ylidenemethyl-phenoxy)-5-trifluoromethyl-pyridine hydrochloride (0.371 g, 1.00 mmol) (from Example 1, Step 5) and phenyl 5-methylpyridin-3-ylcarbamate (0.274 g, 1.2 mmol, prepared according to the procedure described in *Synthesis*, 1997, 1189-1194 from 3-amino-5-methylpyridine) in DMSO (2.5 mL) was treated with diisopropylethylamine (0.155 g, 1.2 mmol) and the mixture was heated to 60° C. After 4 h, the reaction mixture was partitioned between water and ethyl acetate. The organic layer was separated and the aqueous layer was extracted again with ethyl acetate. The organic layers were combined and were washed with brine and dried over sodium sulfate, filtered and concentrated to form a residue. The residue was purified by silica gel chromatography (10% of the 1N $NH_3$ in MeOH, in dichloromethane) to afford the title compound as a white foam (300 mg, 64%). MS (APCI 10V) AP+ 458.16; $^1$H NMR (400 MHz, DMSO) δ ppm 2.34 (t, J=5.46 Hz, 2H) 2.46 (t, J=5.46 Hz, 2H) 3.29 (s, 3H) 3.46 (t, J=5.46 Hz, 2H) 3.54 (t, J=5.46 Hz, 2H) 6.38 (s, 1H) 7.03 (m, 2H) 7.13 (d, J=7.80 Hz, 1H) 7.21 (d, J=8.58 Hz, 1H) 7.4 (dd, J=7.8 Hz, 2 Hz, 1H) 7.70 (s, 1H) 7.96 (d, J=2 Hz, 1H) 8.20 (dd, J=8.8 Hz, 2.5 Hz, 1H) 8.41 (d, J=2.2 Hz, 1H) 8.55 (s, 1H) 8.64 (s, 1H).

Example 8

Synthesis of N-(6-methoxypyridin-3-yl)-4-(3-{[5-(trifluoromethyl)pyridin-2-yl]oxy}benzylidene)piperidine-1-carboxamide Step 1

Phenyl 6-methoxypyridin-3-ylcarbamate

3-Amino-5-methoxy-pyridine (5.00 g, 40.3 mmol) was dissolved in THF (80 mL), cooled to 0° C., treated with pyridine (4.07 mL, 50.4 mmol) followed by phenylchloroformate (5.32 mL, 42.3 mmol). The reaction mixture was slowly warmed to RT over several hours and stirred an additional 12 h. The mixture was partitioned between water and EtOAc. The organic layer was separated and the aqueous layer was extracted again. The combined organic extracts were dried over sodium sulfate, filtered and concentrated to give the product as a reddish solid (9.45 g, 96%), which was used without purification.

Step 2

A solution of 2-(3-piperidin-4-ylidenemethyl-phenoxy)-5-trifluoromethyl-pyridine hydrochloride (0.371 g, 1.00 mmol) (from Example 1, Step 5) and phenyl 6-methoxypyridin-3-ylcarbamate (0.244 g, 1.00 mmol, from Step 1) in DMSO (2.5 mL) was treated with diisopropylethylamine (0.155 g, 1.2 mmol) and heated to 50° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was purified by silica gel chromatography (10% of the 1N $NH_3$ in MeOH, in dichloromethane) to afford the title compound (280 mg, 58%) as white crystals after trituration in diethyl ether. MS (APCI 10V) AP+ 485.30; $^1$H NMR (400 MHz, DMSO-$d_6$) δ ppm 2.34 (t, J=5.46 Hz, 2H) 2.46 (t, J=5.46 Hz, 2H) 3.46 (t, J=5.46 Hz, 2H) 3.54 (t, J=5.46 Hz, 2H) 3.76 (s, 3H) 6.38 (s, 1H) 6.69 (d, J=8.77 Hz, 1H) 7.03 (m, 2H) 7.12 (d, J=7.80 Hz, 1H) 7.21 (d, J=8.60 Hz, 1H) 7.4 (dd, J=8.5 Hz, 1 Hz, 1H) 7.73 (dd, J=8.9 Hz, 2.7 Hz, 1H) 8.14 (d, J=2.5 Hz, 1H) 8.20 (dd, J=8.77 Hz, 2.5 Hz, 1H) 8.49 (s, 1H) 8.55 (d, J=2.5 Hz, 1H).

Example 9

Synthesis of N-(pyridin-2-yl)-4-(3-{[5-(trifluoromethyl)pyridin-2-yl]oxy}benzylidene piperidine-1-carboxamide A solution of 2-(3-piperidin-4-ylidenemethyl-phenoxy)-5-trifluoromethyl-pyridine hydrochloride (0.371 g, 1.00 mmol, from Example 1, Step 5) and phenyl pyridin-2-ylcarbamate (0.254 g, 1.2 mmol, prepared according to the procedure described in *Synthesis*, 1997, 1189-1194 from 2-aminopyridine) in DMSO (2.5 mL) was treated with diisopropylethylamine (0.155 g, 1.2 mmol) and heated to 60° C. After 4 h, the reaction mixture was partitioned between water and ethyl acetate. The organic layer was separated and the aqueous layer was extracted again with ethyl acetate. The combined organic layer was washed with brine, dried over sodium sulfate, filtered and concentrated to a white solid. Trituration with diethyl ether provided the title compound as a white solid (280 mg, 58%). MS (APCI 10V) AP+ 455.21; $^1$H NMR (400 MHz, DMSO-$d_6$) δ ppm 2.34 (t, J=5.46 Hz, 2H) 2.45 (t, J=5.46 Hz, 2H) 3.46 (t, J=5.46 Hz, 2H) 3.54 (t, J=5.46 Hz, 2H) 6.37 (s, 1H) 6.92 (dq, J=5.07 Hz, 1.1 Hz, 1H) 7.03 (m, 2H) 7.11 (d, J=7.60 Hz, 1H) 7.2 (d, J=8.77 Hz, 1H) 7.39 (dt, J=7.6 Hz, 2 Hz, 1H) 7.64 (dt, J=7.22 Hz, 1.7 Hz, 1H) 7.70 (d, J=1.7 Hz, 1H) 8.20 (m, 2H) 8.55 (s, 1H) 9.14 (s, 1H).

Example 10

Synthesis of N-phenyl-4-(3-{[5-(trifluoromethyl)pyridin-2-yl]oxy}benzylidene)piperidine-1-carboxamide A solution of 2-(3-piperidin-4-ylidenemethyl-phenoxy)-5-trifluoromethyl-pyridine hydrochloride (0.371 g, 1.00 mmol) (from Example 1, Step 5) and phenylisocyanate (0.143 g, 1.2 mmol) in dichloromethane (20 mL) was treated with diisopropylethylamine (0.155 g, 1.2 mmol) and stirred at RT for 18 h. The reaction mixture was stirred with 10% $K_2CO_3$ for 1 h and then partitioned after diluting with additional dichloromethane (200 mL). The combined organic layer was washed with brine and dried over sodium sulfate, filtered and concentrated. The residue was purified by silica gel chromatography (1% of the 1N $NH_3$ in MeOH, in dichloromethane) to afford the title compound (100 mg, 22%) as a white solid after trituration with diethyl ether. MS (APCI 10V) AP+ 454.28; $^1$H NMR (400 MHz, DMSO-$d_6$) δ ppm 2.34 (t, J=5.46 Hz, 2H) 2.46 (t, J=5.46 Hz, 2H) 3.29 (s, 3H) 3.46 (t, J=5.46 Hz, 2H) 3.54 (t, J=5.46 Hz, 2H) 6.37 (s, 1H) 6.89 (t, J=8.60 Hz, 1H) 7.03 (m, 2H) 7.12 (d, J=7.60 Hz, 1H) 7.19-

7.22 (m, 3H) 7.38 (d, J=7.8 Hz, 1H) 7.41 (d, J=8.77 Hz, 2H) 8.20 (dd, J=8.8 Hz, 2.8 Hz, 1H) 8.50 (s, 1H) 8.55 (s, 1H).

Example 11

Synthesis of N-(6-cyanopyridin-3-yl)-4-(3-{[5-(trifluoromethyl)pyridin-2-yl]oxy}benzylidene)piperidine-1-carboxamide hydrochloride A solution of 2-(3-piperidin-4-ylidenemethyl-phenoxy)-5-trifluoromethyl-pyridine hydrochloride (0.371 g, 1.00 mmol) (from Example 1, Step 5) and phenyl 6-cyanopyridin-3-yl-carbamate (0.286 g, 1.00 mmol, prepared according to the procedure described in *Synthesis*, 1997, 1189-1194 from 3-amino-6-cyanopyridine) in DMSO (2.5 mL) was treated with diisopropylethylamine (0.155 g, 1.2 mmol) and was heated to 50° C. After 3 h, the reaction mixture was partitioned between water and ethyl acetate. The organic layer was separated and the aqueous layer was extracted again with ethyl acetate. The combined organic layer was washed with brine and dried over sodium sulfate, filtered and concentrated to form a residue. The residue was purified by silica gel chromatography (10% of the 1N $NH_3$ in MeOH, in dichloromethane) to provide an oil upon concentration of the pure fractions. This oil was dissolved in 20 mL of diethyl ether and treated with 1 mL of 1N HCl in diethyl ether. The resulting solid was collected by filtration to provide the title compound (270 mg, 56%). MS (APCI 10V) AP+ 480.20; $^1$H NMR (400 MHz, DMSO-$d_6$) δ ppm 2.36 (t, J=5.46 Hz, 2H) 2.46 (t, J=5.46 Hz, 2H+DMSO) 3.49 (t, J=5.46 Hz, 2H) 3.56 (t, J=5.46 Hz, 2H) 6.39 (s, 1H) 7.03 (m, 2H) 7.12 (d, J=7.80 Hz, 1H) 7.21 (d, J=8.80 Hz, 1H) 7.4 (dd, J=8.5 Hz, 1 Hz, 1H) 7.84 (d, J=8.75 Hz, 1H) 8.10 (dd, J=8.57 Hz, 2.2 Hz, 1H) 8.20 (dd, J=9.24 Hz, 3 Hz, 1H) 8.55 (s, 1H) 8.8 (d, J=2.3 Hz, 1H) 9.29 (s, 1H).

Example 12

Synthesis of N-(5-methoxypyrazin-2-yl)-4-(3-{[5-(trifluoromethyl)pyridin-2-yl]oxy}benzylidene)piperidine-1-carboxamide A solution of 2-(3-piperidin-4-ylidenemethyl-phenoxy)-5-trifluoromethyl-pyridine hydrochloride (0.371 g, 1.00 mmol) (from Example 1, Step 5) and phenyl 5-methoxypyrazin-2-ylcarbamate (0.254 g, 1.2 mmol, prepared according to the procedure described in *Synthesis*, 1997, 1189-1194 from 2-amino-5-methoxypyrazine) in DMSO (2.5 mL) was treated with diisopropylethylamine (0.155 g, 1.2 mmol) and was heated to 60° C. After 4 h, the reaction mixture was partitioned between water and ethyl acetate. The organic layer was separated and the aqueous layer was extracted again with ethyl acetate. The combined organic layer was washed with brine and dried over sodium sulfate, filtered and concentrated to a white solid. Trituration with diethyl ether provided the title compound as a white solid (365 mg, 75%). MS (APCI 10V) AP+ 486.25; $^1$H NMR (400 MHz, DMSO-$d_6$) δ ppm 2.32 (t, J=5.46 Hz, 2H) 2.44 (t, J=5.46 Hz, 2H) 3.47 (t, J=5.46 Hz, 2H) 3.54 (t, J=5.46 Hz, 2H) 3.83 (s, 3H) 6.37 (s, 1H) 7.02-7.05 (m, 2H) 7.11 (d, J=7.8 Hz, 1H) 7.21 (d, J=8.57 Hz, 1H) 7.39 (dt, J=7.6 Hz, 2 Hz, 1H) 7.99 (d, J=1.6 Hz, 1H) 8.21 (dd, J=9.2 Hz, 2.7 Hz, 1H) 8.53 (m, 2H) 9.18 (s, 1H).

Example 13

Synthesis of N-1H-pyrrolo[2,3-b]pyridin-6-yl-4-(3-{[5-(trifluoromethyl)pyridin-2-yl]oxy}benzylidene)piperidine-1-carboxamide Step 1

Phenyl 1H-pyrrolo[2,3-b]pyridin-5-ylcarbamate

To a solution of 1H-pyrrolo[2,3-b]pyridin-5-ylamine (0.50 g, 3.7 mmol, see *Synthesis*, 2005, No. 15, 2503-2506) in THF (4 mL) and $CH_3CN$ (6 mL) was added pyridine (0.36 mL, 4.4 mmol) followed by phenyl chloroformate (0.49 mL, 3.8 mmol) slowly. The reaction was stirred overnight. The mixture was partitioned between water and EtOAc. The aqueous layer was extracted again with EtOAc. The combined organic layer was dried over sodium sulfate, filtered and concentrated. Purification by chromatography (0-100% EtOAc/hexane) provided the desired product as a white solid (0.213 g, 23%). MS M+1: 254.15.

Step 2

To a solution of phenyl 1H-pyrrolo[2,3-b]pyridin-5-ylcarbamate (0.150 g, 0.60 mmol, from Step 1) in DMSO (5 mL) was added 2-(3-piperidin-4-ylidenemethyl-phenoxy)-5-trifluoromethyl-pyridine hydrochloride (0.22 g, 0.60 mmol) (from Example 1, Step 5), followed by the addition of triethylamine (0.17 mL, 1.2 mmol). The reaction mixture was stirred at 60° C. overnight. The reaction mixture was cooled down and EtOAc (30 mL) was added. The organic layer was washed with water, saturated $NH_4Cl$, and brine, dried over $Na_2SO_4$, filtered and concentrated. Purification by column chromatography (0-5% MeOH/$CH_2Cl_2$) gave a foam. Diethyl ether was added and a precipitate formed which was collected by filtration to give the title compound (208 mg). MS (M+1): 494.19; $^1$H NMR (400 MHz, DMSO-$d_6$) δ ppm 11.38-11.40 (m, 1H) 8.54-8.56 (m, 1H) 8.46-8.49 (m, 1H) 8.20 (dd, 1H) 8.15 (d, 1H) 7.92-7.94 (m, 1H) 7.34-7.42 (m, 2H) 7.21 (d, 1H) 7.11-7.15 (m, 1H) 7.02-7.06 (m, 2H) 6.37-6.40 (m, 1H) 6.31-6.34 (m, 1H) 3.55 (t, 2H) 3.47 (t, 2H) 3.28-3.30 (m, 1H) 2.50-2.51 (m, 1H) 2.34 (t, 2H).

Example 14

Synthesis of N-1H-1,2,3-benzotriazol-6-yl-4-(3-{[5-(trifluoromethyl)pyridin-2-yl]oxy}benzylidene)piperidine-1-carboxamide Step 1

Phenyl 1H-benzo[d][1,2,3]triazol-5-ylcarbamate

To a solution of 1H-benzo[d][1,2,3]triazol-5-amine (1.85 g, 13.8 mmol, Alfa Aesar) in THF (10 mL) and $CH_3CN$ (8 mL) was added pyridine (1.34 mL, 16.6 mmol) followed by phenyl chloroformate (2.27 mL, 14.5 mmol) slowly. The reaction was stirred overnight. The reaction was concentrated to give an oil, which was partitioned between $CH_2Cl_2$ and water. The organic layer was dried using a SPE phase separator and concentrated to give a solid. This was taken up in $CH_2Cl_2$ and the precipitate was filtered to give the desired product (2.0 g, 57%) which was used without purification. MS M+1: 256.06.

Step 2

To a solution of phenyl 1H-benzo[d][1,2,3]triazol-5-ylcarbamate (0.15 g, 0.62 mmol, from Step 1) in DMSO (5 mL)

was added 2-(3-piperidin-4-ylidenemethyl-phenoxy)-5-trifluoromethyl-pyridine hydrochloride (0.23 g, 0.62 mmol) (from Example 1, Step 5), followed by triethylamine (0.16 mL, 1.2 mmol). The reaction was stirred at 60° C. overnight. The reaction was cooled down and EtOAc (30 mL) was added. The organic layer was washed with water, saturated $NH_4Cl$, and brine, dried over anhydrous $Na_2SO_4$, filtered and concentrated. Purification by column chromatography (0-5% MeOH/$CH_2Cl_2$) gave the desired compound as a foam (144 mg). MS (M+1): 495.1; $^1H$ NMR (400 MHz, DMSO-$d_6$) δ ppm 8.76-8.80 (m, 1H) 8.54-8.56 (m, 1H) 8.20 (dd, 1H) 8.01-8.04 (m, 1H) 7.76-7.82 (m, 1H) 7.37-7.42 (m, 2H) 7.21 (d, 1H) 7.13 (d, 1H) 7.02-7.05 (m, 2H) 6.37-6.40 (m, 1H) 3.56 (t, 2H) 3.48 (t, 2H) 3.28-3.30 (m, 1H) 2.50-2.51 (m, 1H) 2.33-2.38 (m, 2H).

Example 15

Synthesis of N-{[4-(3-{[5-(trifluoromethyl)pyridin-2-yl]oxy}benzylidene)piperidin-1-yl]carbonyl}pyridine-2-carboxamide Step 1

Phenyl picolinoylcarbamate

Picolinamide (0.500 g, 16 mmol) was dissolved in THF (25 mL) and cooled to −10° C. To the solution, lithium diisopropyl amide (5.1 mL, 2.0 M in heptane/THF/ethyl benzene, 10 mmol) was added dropwise. The resulting mixture was stirred at −10° C. for 15 minutes then treated with phenyl chloroformate (1.69 mL, 12.3 mmol) in THF (5 mL). After 20 minutes the reaction was warmed to room temperature and stirred for 3 hours at which time the reaction was quenched with saturated aqueous ammonium chloride. The mixture was extracted with EtOAc and the combined organic layer was dried over anhydrous sodium sulfate, filtered and concentrated. The residue was purified by silica gel chromatography (20-50% EtOAc in heptane) to provide the desired product (0.504 g). $^1H$ NMR (400 MHz, $CDCl_3$) δ ppm 7.18-7.26 (m, 3H) 7.34-7.41 (m, 2H) 7.54 (ddd, J=7.63, 4.78, 1.23 Hz, 1H) 7.92 (td, J=7.74, 1.70 Hz, 1H) 8.28 (dt, J=7.82, 1.09 Hz, 1H) 8.62 (ddd, J=4.77, 1.67, 0.93 Hz, 1H) 10.47 (s, 1H).

Step 2

Phenyl picolinoylcarbamate (145 mg, 0.599 mmol, from Step 1), 2-(3-piperidin-4-ylidenemethyl-phenoxy)-5-trifluoromethyl-pyridine hydrochloride (175 mg, 0.472 mmol) (from Example 1, Step 5), and diisopropylethyl amine (0.16 mL, 0.92 mmol) were combined in acetonitrile (5 mL) and warmed to 50° C. After 3 hours the mixture was cooled to room temperature and concentrated to form a residue. The residue was purified by silica gel chromatography (20-75% EtOAc in $CH_2Cl_2$) to provide the title compound (0.152 g). MS APCI M+ 483.1, 376.1, 335.1; M− 481.1; $^1H$ NMR (400 MHz, $CD_3OD$) δ ppm 2.45-2.72 (m, 4H) 3.64 (m, 4H) 6.47 (s, 1H) 6.96-7.06 (m, 2H) 7.08-7.20 (m, 2H) 7.40 (td, J=7.65, 0.91 Hz, 1H) 7.63 (ddd, J=7.63, 4.76, 1.23 Hz, 1H) 8.02 (td, J=7.75, 1.69 Hz, 1H) 8.08 (ddd, J=8.71, 2.55, 0.61 Hz, 1H) 8.18 (dt, J=7.86, 1.08 Hz, 1H) 8.42 (td, J=1.72, 0.80 Hz, 1H) 8.67 (ddd, J=4.76, 1.69, 0.95 Hz, 1H).

Example 16

Synthesis of 6-methyl-N-{[4-(3-{[5-(trifluoromethyl)pyridin-2-yl]oxy}benzylidene)piperidin-1-yl]carbonyl}pyridine-2-carboxamide Phenyl 2-methylpicolinoylcarbamate (150 mg, 0.585 mmol, prepared according to the procedure in Example 15, Step 1 from 6-methyl-pyridine-2-carboxamide), 2-(3-piperidin-4-ylidenemethyl-phenoxy)-5-trifluoromethyl-pyridine hydrochloride (175 mg, 0.472 mmol) (from Example 1, Step 5), and diisopropylethyl amine (0.16 mL, 0.92 mmol) were combined in acetonitrile (5 mL) and warmed to 50° C. After 3 hours the mixture was cooled to room temperature and concentrated. The residue was purified by silica gel chromatography (10-75% EtOAc in $CH_2Cl_2$) to provide the title compound (0.197 g). MS APCI M+ 497.2, 376.12, 335.12; $^1H$ NMR (400 MHz, $CD_3OD$) δ ppm 2.61 (s, 3H) 2.46-2.70 (m, 4H) 3.64 (m, 4H) 6.47 (s, 1H) 6.96-7.06 (m, 2H) 7.08-7.19 (m, 2H) 7.40 (td, J=7.69, 0.73 Hz, 1H) 7.50 (dd, J=7.80, 0.46 Hz, 1H) 7.88 (t, J=7.71 Hz, 1H) 7.98 (ddd, J=7.74, 0.99, 0.50 Hz, 1H) 8.08 (ddd, J=8.73, 2.48, 0.66 Hz, 1H) 8.42 (td, J=1.75, 0.87 Hz, 1H).

Example 17

Synthesis of 4-[3-(benzyloxy)benzylidene]-N-pyridin-3-ylpiperidine-1-carboxamide Step 1

(3-Benzyloxy-benzyl)-phosphonic acid diethyl ester

1-Benzyloxy-3-bromomethyl-benzene (4.95 g, 17.9 mmol) was treated with triethyl phosphite (3.2 mL, 18.7 mmol) and heated to 150° C. After 3 hours the reaction was cooled to room temperature and concentrated to give the title compound which was used without further purification (5.9 g).

Step 2

4-(3-Benzyloxy-benzylidene)-piperidine-1-carboxylic acid tert-butyl ester

Following the procedure in Example 1, Step 4, (3-benzyloxy-benzyl)-phosphonic acid diethyl ester (1.0 g, 3.0 mmol, from Step 1) and 4-oxo-piperidine-1-carboxylic acid tert-butyl ester (500 mg, 2.5 mmol) were used to give the title compound (534 mg).

Step 3

4-(3-Benzyloxy-benzylidene)-piperidine trifluoroacetate 4-(3-Benzyloxy-benzylidene)-piperidine-1-carboxylic acid tert-butyl ester (534 mg, 1.4 mmol) from Step 2 was dissolved in $CH_2Cl_2$ (5 mL) and treated with trifluoroacetic acid (1.05 mL, 14.1 mmol). After 2 hours, the solution was concentrated to provide the title compound which was used without further purification (550 mg).

Step 4

Following the procedure in Example 1, Step 6, 4-(3-benzyloxy-benzylidene)-piperidine trifluoroacetate (550 mg, 1.4 mmol, from Step 3) and phenyl pyridin-3-ylcarbamate (331 mg, 1.55 mmol) were used to provide the title compound (530 mg). MS (APCI 10 V) AP+ 400.2; $^1H$ NMR (400 MHz, $CD_3OD$) δ ppm 2.40-2.46 (m, 2H) 2.46-2.52 (m, 2H) 3.48-3.54 (m, 2H) 3.60-3.66 (m, 2H) 5.08 (s, 2H) 6.40 (s, 1H) 6.76-6.89 (m, 3H) 7.22 (t, J=8.09 Hz, 1H) 7.26-7.46 (m, 5H)

7.86-7.95 (m, J=8.36, 2.48, 1.45, 0.89 Hz, 1H) 8.16 (dd, J=4.81, 1.40 Hz, 1H) 8.58 (d, J=2.53 Hz, 1H).

Example 18

Synthesis of N-2,1-benzisoxazol-3-yl-4-[3-(4-fluorophenoxy)benzylidene]piperidine-1-carboxamide Step 1

[3-(4-Fluoro-phenoxy)-benzyl]-phosphonic acid diethyl ester

Following the procedure in Example 17, Step 1, starting from 3-(4-fluorophenoxy)benzyl bromide (1.0 g, 3.6 mmol) yielded the title compound (1.2 g).

Step 2

4-[3-(4-Fluoro-phenoxy)-benzylidene]-piperidine-1-carboxylic acid tert-butyl ester Following the procedure in Example 1, Step 4, using [3-(4-fluoro-phenoxy)-benzyl]-phosphonic acid diethyl ester (1.2 g, 3.5 mmol) (Step 1) and 4-oxo-piperidine-1-carboxylic acid tert-butyl ester (707 mg, 3.55 mmol) yielded the title compound (1.05 g).

Step 3

4-[3-(4-Fluoro-phenoxy)-benzylidene]-piperidine hydrochloride

4-[3-(4-Fluoro-phenoxy)-benzylidene]-piperidine-1-carboxylic acid tert-butyl ester (1.05 g, 2.74 mmol) (Step 2) was dissolved in $CH_2Cl_2$ (20 mL) and treated with HCl in diethyl ether (8.2 mL, 16.4 mmol). After 16 hours the solution was concentrated and the residue suspended in diethyl ether. The resulting solid was filtered to provide the title compound as the hydrochloride salt (774 mg).

Step 4

Following the procedure in Example 1, Step 6, 4-[3-(4-fluoro-phenoxy)-benzylidene]-piperidine hydrochloride (200 mg, 0.625 mmol) (Step 3) and phenyl benzo[c]isoxazol-3-ylcarbamate (175 mg, 0.688 mmol) were used to provide the title compound (275 mg). MS (APCI 10V) AP+ 444.2, 284.2, AP− 442.2; $^1$H NMR (400 MHz, $CDCl_3$) δ ppm 2.46-2.52 (m, 2H) 2.57-2.63 (m, 2H) 3.56-3.62 (m, 2H) 3.66-3.72 (m, 2H) 6.39 (s, 1H) 6.78-6.87 (m, 2H) 6.91-6.96 (m, J=7.93, 1.25, 0.68, 0.57 Hz, 1H) 6.97-7.07 (m, 4H) 7.25-7.31 (m, 2H) 7.47 (dt, J=8.41, 0.77 Hz, 1H) 7.50-7.55 (m, 1H) 7.71 (s, 1H) 8.09 (d, J=7.90 Hz, 1H).

Example 19

Synthesis of N-(3,4-dimethylisoxazol-5-yl)-4-[3-(4-fluorophenoxy)benzylidene]piperidine-1-carboxamide Following the procedure in Example 1, Step 6, 4-[3-(4-fluoro-phenoxy)-benzylidene]-piperidine hydrochloride (200 mg, 0.625 mmol, from Example 18, Step 3) and phenyl 3,4-dimethylisoxazol-5-ylcarbamate (160 mg, 0.40 mmol) were used to provide the title compound (196 mg). MS (APCI 10 V) AP+ 422.2, 284.2, AP− 420.2; $^1$H NMR (400 MHz, $CD_3OD$) δ ppm 1.83 (s, 3H) 2.18 (s, 3H) 2.42 (td, J=5.76, 1.10 Hz, 2H) 2.51 (td, J=5.88, 1.13 Hz, 2H) 3.47-3.52 (m, 2H) 3.57-3.63 (m, 2H) 6.40 (s, 1H) 6.77-6.84 (m, 2H) 6.94-6.98 (m, J=7.78, 1.45, 0.77, 0.77 Hz, 1H) 6.98-7.03 (m, 2H) 7.05-7.13 (m, 2H) 7.29 (t, J=7.85 Hz, 1H).

Example 20

Synthesis of 4-[3-(4-fluorophenoxy)benzylidene]-N-pyridin-3-ylpiperidine-1-carboxamide Following the procedure in Example 1, step 6, 4-[3-(4-fluoro-phenoxy)-benzylidene]-piperidine hydrochloride (200 mg, 0.625 mmol, from Example 18, Step 3) and phenyl pyridin-3-ylcarbamate (147 mg, 0.688 mmol) were used to provide the title compound (238 mg). MS (APCI 10 V) AP+ 404.3, AP− 402.1; $^1$H NMR (400 MHz, $CD_3OD$) δ ppm 2.43 (td, J=5.79, 1.10 Hz, 2H) 2.52 (td, J=5.89, 1.01 Hz, 2H) 3.51-3.55 (m, 2H) 3.60-3.66 (m, 2H) 6.40 (s, 1H) 6.78-6.84 (m, 2H) 6.95-6.98 (m, J=7.67, 1.53, 0.75, 0.75 Hz, 1H) 6.98-7.04 (m, 2H) 7.05-7.15 (m, 2H) 7.30 (t, J=7.77 Hz, 1H) 7.34 (ddd, J=8.41, 4.84, 0.76 Hz, 1H) 7.91 (ddd, J=8.38, 2.60, 1.45 Hz, 1H) 8.16 (dd, J=4.85, 1.46 Hz, 1H) 8.58 (dd, J=2.62, 0.67 Hz, 1H).

Example 21

Synthesis of N-(5-phenyl-pyrazin-2-yl)-4-(3-{[5-(trifluoromethyl)pyridin-2-yl]oxy}benzylidene)piperidine-1-carboxamide A solution of 2-(3-piperidin-4-ylidenemethyl-phenoxy)-5-trifluoromethyl-pyridine hydrochloride (0.371 g, 1.00 mmol) (from Example 1, Step 5) and phenyl 5-phenylpyrazin-2-ylcarbamate (0.291 g, 1.00 mmol) in DMSO (2.5 mL) was treated with diisopropylethylamine (0.155 g, 1.2 mmol) and heated to 60° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was purified by silica gel chromatography (10% of the 1N $NH_3$ in MeOH, in dichloromethane) to afford the title compound (200 mg, 37%) as white crystals after trituration in diethyl ether. MS (APCI 10V) AP+ 532.25; $^1$H NMR (400 MHz, DMSO-$d_6$) δ ppm 2.34 (t, J=5.46 Hz, 2H) 2.46 (t, J=5.46 Hz, 2H) 3.46 (t, J=5.46 Hz, 2H) 3.50 (t, J=5.46 Hz, 2H) 6.37 (s, 1H) 6.69 (d, J=8.77 Hz, 1H) 7.01-7.03 (m, 2H) 7.10 (d, J=7.81 Hz, 1H) 7.19 (d, J=8.59, Hz, 1H) 7.35-7.39 (m, 2H) 7.43-7.47 (m, 2H) 8.02 (dd, J=7.03 Hz, 1.95 Hz, 2H) 8.17 (dd, J=8.78 Hz, 2.15 Hz, 1H) 8.53 (d, J=2.5 Hz, 1H) 8.85 (s, 1H) 9.04 (s, 1H) 9.63 (s, 1H).

Example 22

Synthesis of N-(5-methyl-pyrazin-2-yl l)-4-(3-{[5-(trifluoromethyl)pyridin-2-yl]oxy}benzylidene)piperidine-1-carboxamide Step 1

Phenyl 5-methylpyrazin-2-ylcarbamate

2-Amino-5-methyl-pyrazine (2.00 g, 21.25 mmol) was dissolved in THF (80 mL), cooled to 0° C., and treated with pyridine (1.77 g, 22.3 mmol) followed by the dropwise addition of phenylchloroformate (3.49 g, 22.3 mmol) in THF (30 mL). After stirring for 3 h, 100 mL of MeCN was added and the reaction mixture was reduced to a volume of 100 mL in vacuo. The title compound as white crystals was collected by filtration (2.5 g, 55%) and was used without further purification.

Step 2

A solution of 2-(3-piperidin-4-ylidenemethyl-phenoxy)-5-trifluoromethyl-pyridine hydrochloride (0.371 g, 1.00 mmol) (from Example 1, Step 5) and phenyl 5-methylpyrazin-2-ylcarbamate (0.214 g, 1.00 mmol, from Step 1) in DMSO (2.5 mL) was treated with diisopropylethylamine (0.155 g, 1.2 mmol) and heated to 60° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was purified by silica gel chromatography (5% of 1N $NH_3$ in MeOH, in dichloromethane) to afford the title compound (200 mg, 37%) as white crystals after trituration in diethyl ether. MS (APCI 10V) AP+ 470.22; $^1$H NMR (400 MHz, DMSO-$d_6$) δ ppm 2.33 (t, J=5.46 Hz, 2H) 2.37 (s, 3H) 2.44 (t, J=5.46 Hz, 2H) 3.48 (t, J=5.46 Hz, 2H) 3.55 (t, J=5.46 Hz, 2H) 6.37 (s, 1H) 7.02-7.04 (m, 2H) 7.11 (d, J=7.81 Hz, 1H) 7.21 (d, J=8.57, Hz, 1H) 7.39 (t, J=8.77 Hz, 1H) 8.15 (s, 1H) 8.19 (dd, J=8.58 Hz, 2.14 Hz, 1H) 8.54 (s, 1H) 8.89 (s, 1H) 9.04 (s, 1H) 9.36 (s, 1H).

Example 23

Synthesis of N-(6-methoxypyrazin-2-yl)-4-(3-{[5-(trifluoromethyl)pyridin-2-yl]oxy}benzylidene)piperidine-1-carboxamide Step 1

Phenyl 6-methoxypyrazin-2-ylcarbamate

2-Amino-6-methoxy-pyrazine (1.00 g, 8 mmol) was dissolved in a mix of 1:2 THF:MeCN (30 mL), cooled to 0° C., and treated with pyridine (0.664 g, 8.3 mmol) followed by the dropwise addition of phenylchloroformate (1.3 g, 8.3 mmol) in THF (10 mL). After stirring for 18 h, the resulting white solid was collected by filtration (1.3 g, 68%) and was used without further purification.

Step 2

A solution of 2-(3-piperidin-4-ylidene-methyl-phenoxy)-5-trifluoromethyl-pyridine hydrochloride (0.371 g, 1.00 mmol) (from Example 1, Step 5) and phenyl 6-methoxypyrazin-2-ylcarbamate (0.245 g, 1.00 mmol, from Step 1) in DMSO (2.5 mL) was treated with diisopropylethylamine (0.155 g, 1.2 mmol) and heated to 60° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was crystallized in a 1:1 mix of hexanes and ethyl ether to afford the title compound (310 mg, 69%) as white crystals. MS (APCI 10 V) AP+ 486.20; $^1$H NMR (400 MHz, DMSO-$d_6$) δ ppm 2.33 (t, J=5.46 Hz, 2H) 2.44 (t, J=5.46 Hz, 2H) 3.46 (t, J=5.46 Hz, 2H) 3.55 (t, J=5.46 Hz, 2H) 3.86 (s, 3H) 6.37 (s, 1H) 7.02-7.04 (m, 2H) 7.10 (d, J=7.62 Hz, 1H) 7.20 (d, J=8.60, Hz, 1H) 7.38 (t, J=8.77 Hz, 1H) 7.81 (s, 1H) 8.20 (dd, J=8.59 Hz, 2.14 Hz, 1H) 8.55 (s, 1H) 8.58 (s, 1H) 9.25 (s, 1H).

Example 24

Synthesis of N-(3-methylpyrazin-2-yl)-4-(3-{[5-(trifluoromethyl)pyridin-2-yl]oxy}benzylidene)piperidine-1-carboxamide Step 1

Phenyl 3-methylpyrazin-2-ylcarbamate

A solution of 2-amino-3-methyl-pyrazine (1.50 g, 1.37 mmol) in a mix of 1:2 THF:MeCN (30 mL), and pyridine (0.664 g, 1.44 mmol) was treated dropwise with phenylchloroformate (1.3 g, 1.44 mmol) in THF (10 mL). After stirring for 18 h, the reaction mixture was concentrated in vacuo to a solid and was used without further purification.

Step 2

A solution of 2-(3-piperidin-4-ylidene-methyl-phenoxy)-5-trifluoromethyl-pyridine hydrochloride (0.510 g, 1.37 mmol) (from Example 1, Step 5) and phenyl 3-methylpyrazin-2-ylcarbamate (0.315 g, 1.37 mmol, from Step 1) in DMSO (2.5 mL) was treated with diisopropylethylamine (0.170 g, 1.6 mmol) and heated to 60° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was purified by silica gel chromatography (10% of 1N $NH_3$ in MeOH, in dichloromethane) to afford the title compound (100 mg, 15%) as white crystals after trituration in diethyl ether. MS (APCI 10 V) AP+ 470.22; $^1$H NMR (400 MHz, DMSO-$d_6$) δ ppm 2.32 (s, 3H) 2.34 (t, J=5.46 Hz, 2H) 2.45 (t, J=5.46 Hz, 2H) 3.46 (t, J=5.46 Hz, 2H) 3.54 (t, J=5.46 Hz, 2H) 6.39 (s, 1H) 7.02-7.04 (m, 2H) 7.12 (d, J=7.60 Hz, 1H) 7.21 (d, J=8.20, Hz, 1H) 7.39 (t, J=8.01 Hz, 1H) 8.20 (dd, J=5.28 Hz, 2.74 Hz, 2H) 8.22 (d, J=2.54, Hz, 1H) 8.54 (s, 1H) 9.12 (s, 1H).

Example 25

Synthesis of N-(pyridazin-4-yl)-4-(3-{[5-(trifluoromethyl)pyridin-2-yl]oxy}benzylidene)piperidine-1-carboxamide Step 1

Phenyl pyridazin-4-ylcarbamate

A solution of 4-aminopyridazine (2.5 g, 26.3 mmol) in a mix of 1:1 THF:MeCN (20 mL), and pyridine (2.18, 27.6 mmol) was treated dropwise with phenylchloroformate (1.3 g, 27.6 mmol) in THF (10 mL). After stirring for 18 h, the resulting solid was collected and dried to provide the title compound (2 g, 37%).

Step 2

A solution of 2-(3-piperidin-4-ylidene-methyl-phenoxy)-5-trifluoromethyl-pyridine hydrochloride (0.371 g, 1.00 mmol) (from Example 1, Step 5) and phenyl pyridazin-4-ylcarbamate (0.215 g, 1.00 mmol, from Step 1) in DMSO (2.5 mL) was treated with diisopropylethylamine (0.155 g, 1.2 mmol) and heated to 60° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was crystallized in a 1:1 mix of hexanes and ethyl ether to afford the title compound (335 mg, 73%) as white crystals. MS (APCI 10V) AP+ 456.16; $^1$H NMR (400 MHz, DMSO-$d_6$) δ ppm 2.36 (t, J=5.46 Hz, 2H) 2.44 (t, J=5.46 Hz, 2H+DMSO) 3.49 (t, J=5.46 Hz, 2H) 3.56 (t, J=5.46 Hz, 2H) 6.39 (s, 1H) 7.03-7.04 (m, 2H) 7.12 (d, J=7.81 Hz, 1H) 7.21 (d, J=8.79 Hz, 1H) 7.39 (t, J=8.77 Hz, 1H) 7.74 (dd, J=5.86 Hz, 2.73 Hz, 1H) 8.20 (dd, J=8.60 Hz, 2.15 Hz, 1H) 8.54 (s, 1H) 8.58 (s, 1H) 8.85 (d, J=5.86 Hz, 1H) 9.20 (s, 1H) 9.25 (d, J=2.93 Hz, 1H).

Example 26

Synthesis of N-(6-methoxypyridazin-3-yl)-4-(3-{[5-(trifluoromethyl)pyridin-2-yl]oxy}benzylidene)piperidine-1-carboxamide Step 1

Phenyl 6-methoxypyridazin-3-ylcarbamate

A solution of 3-amino-6-methoxypyridazine (1.25 g, 10.0 mmol) in a mix of 1:1 THF:MeCN (20 mL), and pyridine (0.83 g, 1.5 mmol) was treated dropwise with phenylchloroformate (1.65 g, 10.5 mmol) in THF (10 mL). After stirring for 3 h, the resulting solid was collected and dried to provide the title compound (2 g, 81%).

Step 2

A solution of 2-(3-piperidin-4-ylidene-methyl-phenoxy)-5-trifluoromethyl-pyridine hydrochloride (0.371 g, 1.00 mmol) (from Example 1, Step 5) and phenyl 6-methoxypyridazin-3-ylcarbamate (0.215 g, 1.00 mmol, from Step 1) in DMSO (2.5 mL) was treated with diisopropylethylamine (0.155 g, 1.2 mmol) and heated to 60° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was crystallized in a 1:1 mix of hexanes and ethyl ether to afford the title compound (365 mg, 75%) as white crystals. MS (APCI 10V) AP+ 486.19; $^1$H NMR (400 MHz, DMSO-$d_6$) δ ppm 2.33 (t, J=5.46 Hz, 2H) 2.44 (t, J=5.46 Hz, 2H+DMSO) 3.48 (t, J=5.46 Hz, 2H) 3.55 (t, J=5.46 Hz, 2H) 3.93 (s, 3H) 6.37 (s, 1H) 7.02-7.04 (m, 2H) 7.11 (d, J=9.37 Hz, 2H) 7.21 (d, J=8.79 Hz, 1H) 7.39 (t, J=8.77 Hz, 1H) 7.86 (d, J=9.57 Hz, 1H) 8.19 (dd, J=8.59 Hz, 2.54 Hz, 1H) 8.54 (s, 1H) 9.60 (s, 1H).

Example 27

Synthesis of N-(6-chloropyrazin-2-yl)-4-(3-{[5-(trifluoromethyl)pyridin-2-yl]oxy}benzylidene)piperidine-1-carboxamide Step 1

Phenyl 6-chloropyrazin-2-ylcarbamate

A solution of 2-amino-6-chloropyrazine (2.0 g, 15.44 mmol) in a mix of 1:1 THF:MeCN (20 mL), and pyridine (1.28, 16.2 mmol) was treated dropwise with phenylchloroformate (2.54 g, 16.2 mmol) in THF (10 mL). After stirring for 18 h, the resulting solid was collected and dried to provide the title compound (2 g, 53%).

Step 2

A solution of 2-(3-piperidin-4-ylidene-methyl-phenoxy)-5-trifluoromethyl-pyridine hydrochloride (0.370 g, 1.00 mmol) (from Example 1, Step 5) and phenyl 6-chloropyrazin-2-ylcarbamate (0.262 g, 1.00 mmol, from Step 1) in DMSO (2.5 mL) was treated with diisopropylethylamine (0.170 g, 1.6 mmol) and heated to 60° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was purified by silica gel chromatography (5% of 1N $NH_3$ in MeOH, in dichloromethane) to afford the title compound (175 mg, 36%) as white crystals after trituration in diethyl ether. MS (APCI 10V) AP+ 490.13; $^1$H NMR (400 MHz, DMSO-$d_6$) δ ppm 2.32 (s, 3H) 2.34 (t, J=5.46 Hz, 2H) 2.45 (t, J=5.46 Hz, 2H) 3.46 (t, J=5.46 Hz, 2H) 3.54 (t, J=5.46 Hz, 2H) 6.39 (s, 1H) 7.02-7.04 (m, 2H) 7.12 (d, J=7.60 Hz, 1H) 7.21 (d, J=8.20, Hz, 1H) 7.39 (t, J=8.01 Hz, 1H) 8.20 (dd, J=5.28 Hz, 2.74 Hz, 2H) 8.25 (s, 1H) 9.0 (s, 1H) 9.90 (s, 1H).

Example 28

Synthesis of 4-(3-(5-(trifluoromethyl)pyridin-2-yloxy)benzylidene)-N-(6-bromopyridin-3-yl)piperidine-1-carboxamide Step 1

Phenyl 6-bromopyridin-3-ylcarbamate

To a solution of 2-bromo-5-aminopyridine (3.0 g, 17.3 mmol) in THF (44 mL) cooled to 0° C. was added pyridine (1.8 mL, 21.7 mmol) followed by phenylchloroformate (2.3 mL, 18.2 mmol). A precipitate formed and the reaction was stirred at 0° C. for 1 h. The reaction was stirred at RT overnight and quenched with 1N HCl. The mixture was extracted with EtOAc. The organic layer was washed with water, saturated aqueous $NaHCO_3$ and brine, dried over $Na_2SO_4$ and concentrated to give the title compound as a biege solid (4.81 g, 94% yield).

Step 2

To a solution of phenyl 6-bromopyridin-3-ylcarbamate (1.03 g, 3.5 mmol) in DMSO (5 mL) was added 2-(3-(piperidin-4-ylidenemethyl)phenoxy)-5-(trifluoromethyl)pyridine (1.3 g, 3.51 mmol) followed by triethylamine (0.98 mL, 7.01 mmol). The reaction was stirred at 60° C. overnight and then allowed to cool to RT. The reaction mixture was partitioned between EtOAc and water. The organic layer was washed with brine, dried over $MgSO_4$ and concentrated. Purification by silica gel column chromatography (0-5% MeOH/$CH_2Cl_2$) afforded the title compound as an oil, which foamed up on the pump (1.76 g, 94% yield). MS (APCI 10V) AP+2 535.08; $^1$H NMR (400 MHz, $CDCl_3$) δ ppm 2.46 (t, 2H) 2.59 (t, 2H) 3.50 (t, 2H) 3.59 (t, 2H) 6.40 (s, 1H) 6.47 (br. s., 1H) 6.97-7.03 (m, 3H) 7.08 (d, 1H) 7.36-7.41 (m, 2H) 7.87-7.92 (m, 2H) 8.20 (d, 1H) 8.43 (d, 1H).

Example 29

Synthesis of 4-(3-(5-(trifluoromethyl)pyridin-2-yloxy)benzylidene)-N-(2-fluorophenyl)piperidine-1-carboxamide (PF-04551858)

To a solution of 2-(3-(piperidin-4-ylidenemethyl)phenoxy)-5-(trifluoromethyl)pyridine hydrochloride (0.150 g) and triethylamine (0.124 mL, 2.20 equiv) in dichloromethane (2 mL, 0.2 M) was added 4-fluorophenyl isocyanate (0.050 mL, 1.1 equiv). The reaction was stirred at room temperature for 18 h. Water was added and the mixture was extracted with dichloromethane (2×). The combined organic extracts was washed with water and brine, dried over magnesium sulfate, filtered and concentrated. The residue was purified by silica gel chromatography (0-10% ethyl acetate/dichloromethane) to give the title compound as a white solid (0.172 g, 90% yield). $^1$H NMR (400 MHz, CDCl$_3$) δ ppm 2.47 (2H, t, J=6.0 Hz), 2.61 (2H, t, J=5.6 Hz), 3.52 (2H, t, J=6.0 Hz), 3.61 (2H, t, J=5.8 Hz), 6.41 (1H, s), 6.64 (1H, d, J=3.5 Hz), 6.94-7.05 (5H, m), 7.07-7.12 (2H, m), 7.39 (1H, t, J=7.8 Hz), 7.90 (1H, dd, J=8.8, 2.5 Hz), 8.10 (1H, td, J=8.2, 1.7 Hz), 8.44 (1H, dd, J=1.6, 0.8 Hz).

Example 30

Synthesis of 4-(3-(5-cyanopyridin-2-yloxy)benzylidene)-N-(pyridin-3-yl)piperidine-1-carboxamide A solution of 2-(3-piperidin-4-ylidene-methyl-phenoxy)-5-cyanopyridine trifluoroacetate (0.280 g, 0.72 mmol) and phenyl pyridin-3-ylcarbamate (0.154 g, 0.72 mmol) in DMSO (2.0 mL) was treated with diisopropylethylamine (0.170 g, 1.6 mmol) and heated to 60° C. After 3 h, the reaction mixture was partitioned between water and ethyl acetate. The organic layer was separated and the aqueous layer was extracted again with ethyl acetate. The combined organic layers were washed with brine and dried over sodium sulfate, filtered and concentrated. The residue was purified by silica gel chromatography (5% of 1N NH$_3$ in MeOH, in dichloromethane) to afford the title compound (155 mg, 52%) as white crystals after trituration in diethyl ether. MS (APCI 10V) AP+ 412.16; $^1$H NMR (400 MHz, DMSO-d$_6$) δ ppm 2.34 (t, J=5.46 Hz, 2H) 2.45 (t, J=5.46 Hz, 2H) 3.46 (t, J=5.46 Hz, 2H) 3.54 (t, J=5.46 Hz, 2H) 6.39 (s, 1H) 7.02-7.04 (m, 2H) 7.12 (d, J=7.60 Hz, 1H) 7.21 (d, J=8.20, Hz, 1H) 7.25-7.27 (m, 1H) 7.39 (t, J=8.01 Hz, 1H) 7.83 (dd, J=5.28 Hz, 2.74 Hz, 2H) 8.10 (d, J=2.86 Hz, 1H) 8.25 (s, 1H) 8.30 (s, 1H) 8.8 (m, 1H) 8.75 (s, 1H).

Example 31

Synthesis of N-(pyridin-3-yl)-4-(3-[{phenyl-2-yl}oxy}benzylidene)piperidine-1-carboxamide

Step 1

2-(3-Piperidin-4-ylidene-methyl-phenoxy)-benzene

A slurry of tert-butyl 4-(3-hydroxybenzylidene)piperidine-1-carboxylate (500 mg, 1.73 mmol), phenylboronic acid (418 mg, 3.43 mmol), cupric acetate (314 mg, 1.73 mmol), triethyl amine (1.21 mL 1.8 mmol), and 4 Å powdered sieves (300 mg) in dichloromethane (15 mL) was stirred 18 h at ambient temperature. The reaction mixture was diluted with additional solvent and filtered to remove solid material, washed successively with 1N NaOH and brine, and dried over Na$_2$SO$_4$ to provide a brown oil. This material was purified by column chromatography (1:4 ethyl acetate:heptane) to provide the intermediate Boc-protected material (190 mg, 33%). This material was dissolved in dichloromethane (20 mL) and stirred with trifluoroacetic acid (1 mL) for 3 d at ambient temperature. The reaction was concentrated to a foam that was dissolved in toluene and re-evaporated to give the title compound which was used in the next reaction.

Step 2

A solution of 2-(3-piperidin-4-ylidene-methyl-phenoxy)-benzene (0.068 g, 0.26 mmol, from step 1) and phenyl pyridin-3-ylcarbamate (0.100 g, 0.47 mmol) in DMSO (2.0 mL) was treated with diisopropylethylamine (0.170 g, 1.6 mmol) and heated to 60° C. After 3 h, the reaction mixture was partitioned between water and ethyl acetate. The organic layer was separated and the aqueous layer was extracted again with ethyl acetate. The combined organic layers were washed with 1N NaOH and brine, dried over sodium sulfate, filtered and concentrated. The residue was purified by silica gel chromatography (10% methanol in ethyl acetate) to afford the title compound (40 mg, 40%) as white crystals after trituration in diethyl ether. MS (APCI 10V) AP+ 386.11; $^1$H NMR (400 MHz, DMSO-d$_6$) δ ppm 2.32 (t, J=5.46 Hz, 2H) 2.41 (t, J=5.46 Hz, 2H) 3.43 (t, J=5.46 Hz, 2H) 3.53 (t, J=5.46 Hz, 2H) 6.35 (s, 1H) 6.80 (s, 1H) 6.83 (dd, J=8.19 Hz, 2.14 Hz, 1H) 7.00 (m, 3H) 7.12 (t, J=7.39 Hz, 1H) 7.23 (dd, J=8.38 Hz, 4.68 Hz, 2H) 7.31-7.39 (m, 4H) 7.84 (dd, J=8.39 Hz, 3.9 Hz, 1H) 8.10 (d, J=4.67 Hz, 1H) 8.60 (s, 1H) 8.70 (s, 1H).

Example 32

Synthesis of N-(pyridazin-3-yl)-4-(3-{[phenyl-2-yl]oxy}benzylidene)piperidine-1-carboxamide A solution of 2-(3-piperidin-4-ylidene-methyl-phenoxy)-benzene (0.068 g, 0.26 mmol, from step 1) and phenyl pyridazin-3-ylcarbamate (0.100 g, 0.47 mmol) in DMSO (2.0 mL) was treated with diisopropylethylamine (0.170 g, 1.6 mmol) and heated to 60° C. After 3 h, the reaction mixture was partitioned between water and ethyl acetate. The organic layer was separated and the aqueous layer was extracted again with ethyl acetate. The combined organic layers were washed with 1N NaOH and brine, dried over sodium sulfate, filtered and concentrated. The residue was purified by silica gel chromatography (10% methanol in ethyl acetate) to afford the title compound (45 mg, 50%) as white crystals after trituration in diethyl ether. MS (APCI 10V) AP+ 387.11; $^1$H NMR (400 MHz, DMSO-d$_6$) δ ppm 2.32 (t, J=5.46 Hz, 2H) 2.41 (t, J=5.46 Hz, 2H) 3.43 (t, J=5.46 Hz, 2H) 3.53 (t, J=5.46 Hz, 2H) 6.34 (s, 1H) 6.79 (d, J=1.76 Hz, 1H) 6.83 (dd, J=7.41 Hz, 2.54 Hz, 1H) 7.00 (m, 3H) 7.12 (t, J=2.14 Hz, 1H) 7.31-7.39 (m, 4H) 7.52 (dd, J=8.97 Hz, 4.68 Hz, 1H) 7.96 (d, J=9.16 Hz, 1H) 8.80 (d, J=4.72 Hz, 1H) 9.84 (s, 1H).

Example 33

Synthesis of 4-{3-[(5-bromopyridin-2-yl)oxy]benzylidene}-N-pyridin-3-ylpiperidine-1-carboxamide

Step 1

3-(5-Bromopyridin-2-yloxy)phenyl)methanol

3-Hydroxymethyl-phenol (3.205 g, 25.82 mmol), 5-bromo-2-fluoropyridine (5.00 g, 28.4 mmol) and cesium carbonate (9.26 g, 28.4 mmol) were suspended in DMSO (40 mL) and heated to 100° C. After stirring for 16 h, the reaction mixture was partitioned between water (400 mL) and ethyl acetate (400 mL). The organic layer was separated and the aqueous layer was extracted again with ethyl acetate. The combined organic layers were dried over sodium sulfate, filtered and concentrated. The residue was purified by flash chromatography on silica (10-60%, EtOAc:heptane) to afford the desired product (5.71 g, 79% yield) as a clear oil. MS (APCI) M+1=280.0; $^1$H NMR (400 MHz, CDCl$_3$) δ ppm 1.82 (s, 1H) 4.70 (s, 2H) 6.84 (dd, J=8.58, 0.58 Hz, 1H) 7.00-7.06 (m, 1H) 7.13 (t, J=1.75 Hz, 1H) 7.17-7.23 (m, 1H) 7.38 (t, J=7.80 Hz, 1H) 7.76 (dd, J=8.77, 2.53 Hz, 1H) 8.20 (dd, J=2.63, 0.49 Hz, 1H).

Step 2

5-Bromo-2-(3-(chloromethyl)phenoxy)pyridine 3-(5-Bromopyridin-2-yloxy)phenyl)methanol (3.00 g, 10.7 mmol), in dichloromethane (30 mL), was cooled to 0° C., and treated dropwise with thionyl chloride (0.86 mL, 11.8 mmol). The reaction mixture was allowed to warm to ambient temperature and was stirred for 1 h. Toluene (5 mL) was added and the mixture was concentrated by evaporation. The residue was evaporated again from toluene and dried under high vacuum to afford the desired product (3.09 g, 97% yield) as a white semi-solid. MS (APCI) M+1=300.0; $^1$H NMR (400 MHz, CD$_3$OD) δ ppm 4.64 (s, 2H) 6.93 (dd, J=8.68, 0.68 Hz, 1H) 7.07 (ddd, J=8.19, 1.17, 0.97 Hz, 1H) 7.15-7.21 (m, 1H) 7.24-7.30 (m, 1H) 7.40 (t, J=7.90 Hz, 1H) 7.94 (dd, J=8.77, 2.53 Hz, 1H) 8.19 (dd, J=2.53, 0.58 Hz, 1H).

Step 3

Diethyl 3-(5-bromopyridin-2-yloxy)benzylphosphonate

5-Bromo-2-(3-(chloromethyl)phenoxy)pyridine (3.08 g, 10.3 mmol) from Step 2 was treated neat with triethylphosphite (2.65 mL, 15.5 mmol) and heated to 150° C. After 5 h, the reaction mixture was removed from the heating bath and treated slowly with heptane until an oil precipitated out of solution. Ethyl acetate was added until mixture became homogenous. Heptane was slowly added again (at a cooler temperature) until a white precipitate formed. After the addition of more heptane and stirring for 15 min, the precipitate was filtered to afford a white solid (3.35 g, 81% yield). MS (APCI) M+1=400.0; $^1$H NMR (400 MHz, CDCl$_3$) δ ppm 1.26 (t, J=7.02 Hz, 6H) 3.17 (d, J=21.64 Hz, 2H) 3.98-4.08 (m, 4H) 6.84 (d, J=8.77 Hz, 1H) 7.00-7.05 (m, 1H) 7.08 (q, J=2.21 Hz, 1H) 7.15-7.20 (m, 1H) 7.35 (t, J=7.90 Hz, 1H) 7.77 (dd, J=8.58, 2.53 Hz, 1H) 8.21 (d, J=2.73 Hz, 1H).

Step 4 tert-Butyl 4-(3-(5-bromopyridin-2-yloxy)benzylidene)piperidine-1-carboxylate

Diethyl 3-(5-bromopyridin-2-yloxy)benzylphosphonate (2.00 g, 5.00 mmol) from Step 3 and 1,4,7,10,13-pentaoxacyclopentadecane (15-Crown-5, 0.025 mL, 0.13 mmol) were combined in THF (7 mL). The mixture was cooled to 0° C. and sodium hydride (210 mg, 60% dispersion in mineral oil, 5.25 mmol) was added. The reaction was warmed to room temperature, stirred for 30 min and then cooled back to 0° C. A solution of 4-oxo-piperidine-1-carboxylic acid tert-butyl ester (1.05 g, 5.25 mmol) in THF (4 mL) was added and the reaction was warmed to room temperature. After 16 h, an additional amount of sodium hydride (spatula tip) was added and the mixture was stirred an additional 6 h. Water was added and the mixture was extracted twice with ethyl acetate. The combined organic layers were dried over anhydrous sodium sulfate, filtered and concentrated to a yellow oil. This material was crystallized from hot isopropyl ether/heptane. The supernatant was decanted and the solid was washed with heptane and dried in vacuo to afford the title compound (1.37 g, 62% yield) as an off-white solid. MS (APCI) M−100=345.0; $^1$H NMR (400 MHz, CDCl$_3$) δ ppm 1.48 (s, 9H) 2.30-2.37 (m, 2H) 2.44-2.50 (m, 2H) 3.38-3.44 (m, 2H) 3.48-3.54 (m, 2H) 6.35 (s, 1H) 6.85 (dd, J=8.77, 0.58 Hz, 1H) 6.94-7.00 (m, 2H) 7.03-7.07 (m, 1H) 7.35 (t, J=7.80 Hz, 1H) 7.78 (dd, J=8.67, 2.63 Hz, 1H) 8.23 (dd, J=2.53, 0.58 Hz, 1H).

Step 5

5-Bromo-2-(3-(piperidin-4-ylidenemethyl)phenoxy)pyridine trifluoroacetate tert-Butyl 4-(3-(5-bromopyridin-2-yloxy)benzylidene)piperidine-1-carboxylate (1.36 g, 3.05 mmol) from Step 4 was dissolved in CH$_2$Cl$_2$ (15 mL) and treated with trifluoroacetic acid (6 mL). After 2 h, toluene was added and the reaction was concentrated in vacuo. After evaporating again from toluene, the residue was dried in vacuo to afford the title compound (2.08 g, quantitative yield based on 3 eq trifluoroacetic acid) as an orange oil. This material was dissolved in acetonitrile (0.33 mmol/mL) and used in the next step.

Step 6

5-Bromo-2-(3-(piperidin-4-ylidenemethyl)phenoxy)pyridine trifluoroacetate (1 mmol, from Step 5) in acetonitrile (3 mL) was treated with phenyl pyridin-3-ylcarbamate (236 mg, 1.10 mmol) and diisopropylethylamine (0.52 mL, 3.00 mmol) and stirred at room temperature. After 2 h, the reaction was concentrated and the residue was purified by flash chromatography on silica gel (0-7% ethanol (containing 11% aq NH$_4$OH):dichloromethane) to afford the title compound (0.340 g, 73%) as a white foam. MS (APCI) M+1=465.0; $^1$H NMR (400 MHz, CDCl$_3$) δ ppm 2.07 (br. s, 1H) 2.44-2.50 (m, 2H) 2.57-2.63 (m, 2H) 3.50-3.56 (m, 2H) 3.60-3.66 (m, 2H) 6.40 (s, 1H) 6.78 (s, 1H) 6.86 (dd J=8.77, 0.58 Hz, 1H) 6.96-7.02 (m, 2H) 7.04-7.09 (m, 1H) 7.23-7.27 (m, 1H) 7.37 (t, J=7.90 Hz, 1H) 7.78 (dd, J=8.58, 2.53 Hz, 1H) 8.02-8.07 (m, 1H) 8.23 (dd, J=2.63, 0.68 Hz, 1H) 8.27 (dd, J=4.68, 1.36 Hz, 1H) 8.49 (d, J=2.34 Hz, 1H).

Example 34

Synthesis of 4-(3-(5-bromopyridin-2-yloxy)benzylidene)-N-(pyridazin-3-yl)piperidine-1-carboxamide 5-Bromo-2-(3-(piperidin-4-ylidenemethyl)phenoxy)pyridine trifluoroacetate (1 mmol, from Step 5), in acetonitrile (3 mL) was treated with ethyl pyridazin-3-ylcarbamate (184 mg, 1.10 mmol) and diisopropylethylamine (0.52 mL, 3.00 mmol) and was heated to 180° C. in a microwave for 40 min. The reaction mixture was concentrated and the residue was purified by flash chromatography on silica gel (0-6% ethanol (containing 11% aq NH$_4$OH):dichloromethane) to afford a light yellow foam (168 mg, 36% yield). MS (APCI) M+1=466.0; $^1$H NMR (400 MHz, CDCl$_3$) δ ppm 2.48 (t, J=5.46 Hz, 2H) 2.58-2.65 (m, 2H) 3.60 (t, J=5.75 Hz, 2H) 3.65-3.74 (m, 2H) 6.42 (s, 1H) 6.86 (dd, J=8.67, 0.49 Hz, 1H) 6.96-7.03 (m, 2H) 7.07 (d, J=7.60 Hz, 1H) 7.38 (t, J=7.80 Hz, 1H) 7.44 (dd, J=9.16, 4.48 Hz, 1H) 7.79 (dd, J=8.77, 2.53 Hz, 1H) 8.24 (dd, J=2.53, 0.39 Hz, 1H) 8.26-8.37 (m, 1H) 8.79 (br. s, 1H).

Example 35

Synthesis of 4-(3-(5-bromopyridin-2-yloxy)benzylidene)-N-(3,4-dimethylisoxazol-5-yl)piperidine-1-carboxamide 5-Bromo-2-(3-(piperidin-4-ylidenemethyl)phenoxy)pyridine trifluoroacetate (0.584 mmol, from Step 5), in acetonitrile (1.75 mL) was treated with phenyl 3,4-dimethylisoxazol-5-ylcarbamate (100 mg, 0.467 mmol, prepared according to the procedure described in Synthesis, 1997, 1189-1194 from 3,4-dimethylisoxazol-5-amine) and diisopropylethylamine (0.305 mL, 1.75 mmol) and stirred at room temperature. After 2 h, the reaction was concentrated and the residue was purified by flash chromatography on silica gel (0-6% ethanol (containing 11% aq NH$_4$OH):dichloromethane) to afford a clear oil which was evaporated from isopropyl ether/dichloromethane and evaporated again from diethyl ether/dichloromethane to give the title compound (0.200 g, 96% yield) as a white foam. MS (APCI) M+1=483.1; $^1$H NMR (400 MHz, CDCl$_3$) δ ppm 1.89 (s, 3H) 2.20 (s, 3H) 2.43-2.49 (m, 2H) 2.56-2.62 (m, 2H) 3.45-3.52 (m, 2H) 3.56-3.62 (m, 2H) 6.41 (br. s, 1H) 6.61 (br. s, 1H) 6.86 (dd, J=8.68, 0.49 Hz, 1H) 6.95-7.02 (m, 2H) 7.04-7.09 (m, 1H) 7.37 (t, J=7.90 Hz, 1H) 7.79 (dd, J=8.58, 2.53 Hz, 1H) 8.22-8.24 (m, 1H).

Example 36

Synthesis of 4-(3-(5-bromopyrimidin-2-yloxy)benzylidene)-N-(pyridin-3-yl)piperidine-1-carboxamide Step 1

(3-(5-Bromopyrimidin-2-yloxy)phenyl)methanol

3-Hydroxybenzyl alcohol (1.50 g, 12.1 mmol) and 2-chloro-5-bromopyrimidine (2.57 g, 13.3 mmol) were suspended in DMSO (20 mL), treated with cesium carbonate (4.35 g, 13.4 mmol) and heated to 110° C. After 16 h, the reaction mixture was cooled and partitioned between water (200 mL) and heptane:ethyl acetate (1:1, 200 mL). The organic layer was separated and the aqueous was extracted again with heptane:ethyl acetate. The combined organic layers were dried over sodium sulfate, filtered and concentrated. The residue was purified by flash chromatography on silica (20-70% EtOAc:heptane) to afford the title compound (0.790 g, 23% yield) as a light yellow oil. MS (APCI) M+1=281.0; $^1$H NMR (400 MHz, CDCl$_3$) δ ppm 4.74 (s, 2H) 7.08-7.14 (m, 1H) 7.20-7.23 (m, 1H) 7.25-7.30 (m, 1H) 7.43 (t, J=7.80 Hz, 1H) 8.57 (s, 2H).

Step 2

5-Bromo-2-(3-(chloromethyl)phenoxy)pyrimidine (3-(5-Bromopyrimidin-2-yloxy)phenyl)methanol (0.790 g, 2.81 mmol) in dichloromethane (9 mL) was cooled to 0° C. and treated dropwise with thionyl chloride (0.215 mL, 2.95 mmol). The reaction mixture was allowed to warm to ambient temperature and stirred for 1 h. Toluene (5 mL) was added and the mixture was concentrated to give the title compound (0.815 g, 97% yield) as a semi-solid. MS (APCI) M+1=299.0.

Step 3

Diethyl 3-(5-bromopyrimidin-2-yloxy)benzylphosphonate

5-Bromo-2-(3-(chloromethyl)phenoxy)pyrimidine (810 mg, 2.70 mmol) was treated with triethyl phosphite (1 mL, 2.2 mmol), and heated to 150° C. After 16 h, the reaction mixture was removed from the heat and ethyl acetate (about 3 mL) followed by heptane were added. As the reaction mixture cooled an oily precipitate formed. The mixture was made homogenous by addition of ethyl acetate. Heptane was added dropwise until a white solid precipitated. Additional heptane was added and the solid was filtered, washed with heptane and dried in vacuo to afford the title compound (0.737 g, 68% yield) as a white solid. MS (APCI) M+1=401; $^1$H NMR (400 MHz, CDCl$_3$) δ ppm 1.26 (t, J=6.92 Hz, 6H) 3.18 (d, J=21.64 Hz, 2H) 3.98-4.10 (m, 4H) 7.06-7.11 (m, 1H) 7.15 (q, J=2.01 Hz, 1H) 7.20-7.26 (m, 1H) 7.35-7.42 (m, 1H) 8.56 (s, 2H).

Step 4 tert-Butyl 4-(3-(5-bromopyrimidin-2-yloxy)benzylidene)piperidine-1-carboxylate

Diethyl 3-(5-bromopyrimidin-2-yloxy)benzylphosphonate (0.700 g, 1.74 mmol) from Step 3 and 1,4,7,10,13-pentaoxacyclopentadecane (15-Crown-5, 0.017 mL, 0.087 mmol) were suspended in THF (2 mL). The mixture was cooled to 0° C. and sodium hydride (84 mg, 60% dispersion in mineral oil, 2.1 mmol) was added. The reaction was warmed to room temperature, stirred for 30 min and then cooled back to 0° C. A solution of 4-oxo-piperidine-1-carboxylic acid tert-butyl ester (0.452 g, 2.27 mmol) in THF (1.5 mL) was added and the reaction was warmed to room temperature. After 40 h, water was added and the mixture was extracted twice with ethyl acetate. The combined organic layers were washed with water, brine, dried over anhydrous sodium sulfate, filtered and concentrated to an orange oil (about 1 g). This material was purified by flash chromatography on silica (10-40% EtOAc:heptane) to afford the title compound (0.285 g, 37% yield). MS (APCI) M−100=346; $^1$H NMR (400 MHz, CDCl$_3$) δ ppm 1.48 (s, 9H) 2.30-2.37 (m, 2H) 2.43-2.52 (m, 2H) 3.37-3.45 (m, 2H) 3.48-3.55 (m, 2H) 6.36 (s, 1H) 6.99-7.07 (m, 2H) 7.11 (d, J=7.80 Hz, 1H) 7.39 (t, J=7.90 Hz, 1H) 8.58 (s, 2H).

Step 5

5-Bromo-2-(3-(piperidin-4-ylidenemethyl)phenoxy)pyrimidine trifluoroacetate tert-Butyl 4-(3-(5-bromopyrimidin-2-yloxy)benzylidene)piperidine-1-carboxylate (0.285 g, 0.629 mmol) was suspended in dichloromethane (4 mL) and treated with trifluoroacetic acid (2 mL). The reaction mixture was stirred at ambient temperature for 3 h. Toluene was added and the reaction was concentrated in vacuo. After evaporating again from toluene, the residue was dried in vacuo to afford the title compound (0.385 g, quantitative yield based on 2.3 eq trifluoroacetic acid) as an orange oil. This material was dissolved in acetonitrile (3 mL) and used in the next step.

Step 6

5-Bromo-2-(3-(piperidin-4-ylidenemethyl)phenoxy)pyrimidine trifluoroacetate (0.315 mmol, from Step 5), in acetonitrile (1.5 mL) was treated with phenyl pyridin-3-ylcarbamate (75 mg, 0.35 mmol, prepared according to the procedure described in *Synthesis*, 1997, 1189-1194 from 3-aminopyridine) and diisopropylethylamine (0.192 mL, 1.10 mmol) and stirred at room temperature. After 72 h, the reaction was concentrated and the residue was purified by flash chromatography on silica gel (0-10% ethanol (containing 11% aq NH$_4$OH):dichloromethane) to afford the title compound (0.114 g, 78% yield) as a white foam. MS (APCI) M+1=466; $^1$H NMR (400 MHz, CDCl$_3$) δ ppm 2.48 (t, J=5.36 Hz, 2H) 2.61 (t, J=5.36 Hz, 2H) 3.55-3.63 (m, 2H) 3.66-3.73 (m, 2H) 6.41 (s, 1H) 7.01-7.09 (m, 2H) 7.12 (d, J=7.80 Hz, 1H) 7.40 (t, J=7.80 Hz, 1H) 7.43-7.48 (m, 1H) 7.89 (br. s., 1H) 8.21 (d, J=4.29 Hz, 1H) 8.48 (d, J=8.97 Hz, 1H) 8.58 (s, 2H) 8.88 (br. s, 1H).

Example 37

Synthesis of 4-(3-(5-bromopyrimidin-2-yloxy)benzylidene)-N-(pyridazin-3-yl)piperidine-1-carboxamide 5-Bromo-2-(3-(piperidin-4-ylidenemethyl)phenoxy)pyrimidine trifluoroacetate (0.315 mmol, from Step 5), in acetonitrile (1.5 mL) was treated with phenyl pyridazin-3-ylcarbamate (75 mg, 0.35 mmol) and diisopropylethylamine (0.192 mL, 1.10 mmol) and stirred at ambient temperature for 72 h. The reaction mixture was concentrated and the residue was purified by flash chromatography on silica gel (0-10% ethanol (containing 11% aq NH$_4$OH):dichloromethane) to afford the title compound (0.099 g, 67% yield) as a white foam. MS (APCI) M=466.0; $^1$H NMR (400 MHz, CDCl$_3$) δ ppm 2.50 (t, J=5.56 Hz, 2H) 2.63 (t, J=5.65 Hz, 2H) 3.59-3.67 (m, 2H) 3.73 (t, J=4.39 Hz, 2H) 6.44 (s, 1H) 7.02-7.09 (m, 2H) 7.12 (d, J=7.60 Hz, 1H) 7.41 (t, J=7.90 Hz, 1H) 7.49 (dd, J=9.06, 4.58 Hz, 1H) 8.41-8.50 (m, 1H) 8.59 (s, 2H) 8.78 (br. s, 1H).

Example 38

Synthesis of 4-(3-(5-cyclopropylpyridin-2-yloxy) benzylidene)-N-(pyridin-3-yl)piperidine-1-carboxamide

Step 1 tert-Butyl 4-(3-(5-cyclopropylpyridin-2-yloxy)benzylidene)piperidine-1-carboxylate To a solution of tert-butyl 4-(3-(5-bromopyridin-2-yloxy)benzylidene)piperidine-1-carboxylate (Example 33, step 4) (1.64 g, 3.68 mmol) in toluene (12 mL) and water (0.6 mL) under a N$_2$ atmosphere was added cyclopropyl boronic acid (410 mg, 4.77 mmol), potassium phosphate (2.24 g, 12.9 mmol), tricyclohexyl phosphine (103 mg, 0.367 mmol) and palladium acetate (41.2 mg, 0.184 mmol). The mixture was heated at 80° C. overnight. The reaction was cooled to RT and water was added. The mixture was extracted with ethyl acetate and the organic layer was washed with brine, dried over MgSO$_4$ and concentrated. Purification by silica gel column chromatography (0-50% EtOAc/hexane) gave the title compound as an oil that solidified on the vacuum pump (1.3 g, 87% yield).

Step 2

5-Cyclopropyl-2-(3-(piperidin-4-ylidenemethyl)phenoxy)pyridine trifluoroacetate To a solution of tert-butyl 4-(3-(5-cyclopropylpyridin-2-yloxy)benzylidene)piperidine-1-carboxylate (350 mg, 0.861 mmol) in CH$_2$Cl$_2$ (10 mL) was added trifluoroacetic acid (2 mL, 25.8 mmol). The reaction was stirred at RT overnight. The reaction was concentrated to give an oil. CH$_2$Cl$_2$ was added and the mixture was concentrated again to give the title compound as an oil (253 mg, 70% yield).

Step 3

To a solution of 5-cyclopropyl-2-(3-(piperidin-4-ylidenemethyl)phenoxy)pyridine trifluoroacetate (125 mg, 0.408 mmol) in DMSO (5 mL) was added phenyl pyridin-3-ylcarbamate (87.4 mg, 0.408 mmol) followed by triethylamine (0.12 mL, 0.82 mmol). The reaction was heated to 60° C. overnight and then allowed to cool to RT. The reaction mixture was partitioned between EtOAc and water. The organic layer was dried and concentrated. Purification by silica gel column chromatography (0-5% MeOH/CH$_2$Cl$_2$) afforded the title compound as a white foam (101 mg, 58% yield). MS (APCI 10V) AP+2 427.07; $^1$H NMR (400 MHz, CDCl$_3$) δ ppm 0.61-0.66 (m, 2H) 0.93-0.99 (m, 2H) 1.55 (s, 1H) 1.81-1.89 (m, 1H) 2.45 (t, 2H) 2.58 (t, 2H) 3.50 (t, 2H) 3.60 (t, 2H) 6.38 (s, 1H) 6.44 (s, 1H) 6.80 (d, 1H) 6.94 (br. s., 1H) 6.96-7.01 (m, 2H) 7.20-7.23 (m, 1H) 7.29-7.35 (m, 2H) 7.99-8.01 (m, 1H) 8.26 (d, 1H) 8.42 (d, 1H).

Example 39

Synthesis of 4-(3-(5-cyclopropylpyridin-2-yloxy) benzylidene)-N-(pyridazin-3-yl)piperidine-1-carboxamide

Step 1

Pyridazin-3-amine

To a solution of 6-chloropyridazin-3-amine (19.2 g, 148 mmol) in EtOH (500 mL) was added 10% Pd catalyst on 1940 carbon (unreduced, 55% water). Triethylamine (50 mL) was added and the mixture was hydrogenated under 500 psi/mole for 1.9 h. The reaction was filtered and the ethanol was washed with aqueous NH$_4$Cl. The organic layer was concentrated to give the title compound as a white solid (11 g, 78% yield). MS (APCI 10V) AP+1 96.2.

Step 2

Phenyl pyridazin-3-ylcarbamate

To a suspension of pyridazin-3-amine (5 g, 50 mmol) in THF (50 mL) and CH$_3$CN (70 mL) was added pyridine (5.10 mL, 63.1 mmol) followed by phenyl chloroformate (6.95 mL, 55.2 mmol) slowly. The reaction was stirred overnight. The reaction was filtered to remove the precipitate. The filtrate was concentrated and then taken up in CH$_2$Cl$_2$ which was washed with water. The organic layer was dried using SPE phase separators and concentrated. The residue was purified by silica gel column chromatography (0-5% MeOH/CH$_2$Cl$_2$). An undesired side product eluted first followed by the title compound which was concentrated to give a white solid (7.5 g, 70% yield). MS (APCI 10 V) AP+1 216.12; $^1$H NMR (400 MHz, DMSO-d$_6$) δ ppm 7.20-7.24 (m, 2H) 7.25-7.28 (m, 1H) 7.39-7.44 (m, 2H) 7.64-7.69 (m, 1H) 8.05 (dd, 1H) 8.94 (dd, 1H) 11.34 (s, 1H).

Step 3

To a solution of 5-cyclopropyl-2-(3-(piperidin-4-ylidenemethyl)phenoxy)pyridine trifluoroacetate (0.972 g, 3.17 mmol) in CH$_3$CN (10 mL) was added phenyl pyridazin-3-ylcarbamate (0.751 g, 3.49 mmol) followed by diisopropylethylamine (2.76 mL, 15.9 mmol). The reaction was stirred at room temperature for 3 d. The reaction mixture was concentrated and the residue was purified by silica gel column chromatography (0-15% EtOH/CH$_2$Cl$_2$) to afford the title compound as a white foam (1.19 g). Recrystallization from hot diisopropyl ether with a few drops of methanol afforded the title compound as an off-white solid (0.857 g, 63% yield). MS (APCI 10V) AP+2 428.09; $^1$H NMR (400 MHz, CDCl$_3$) δ ppm 0.61-0.67 (m, 2H) 0.93-0.99 (m, 2H) 1.82-1.90 (m, 1H) 2.45 (t, 2H) 2.59 (t, 2H) 3.54 (t, 2H) 3.64 (t, 2H) 6.39 (s, 1H) 6.79-6.82 (m, 1H) 6.92-6.96 (m, 1H) 6.96-7.01 (m, 2H) 7.30-7.35 (m, 2H) 7.38-7.42 (m, 1H) 7.73 (br. s., 1H) 8.01 (d, 1H) 8.29 (d, 1H) 8.82 (d, 1H).

Example 40

Synthesis of 4-(3-(6-methylpyridin-2-yloxy)benzylidene)-N-(pyridin-3-yl)piperidine-1-carboxamide Step 1

(3-(6-Methylpyridin-2-yloxy)phenyl)methanol

3-Hydroxymethyl-phenol (3.69 g, 29.7 mmol), 2-fluoro-6-methyl-pyridine (3.00 g, 27 mmol,) and cesium carbonate (9.68 g, 29.7 mmol) were suspended in dimethylsulfoxide (25 mL) and heated to 110° C. After stirring for 16 h, the reaction was partitioned between water (250 mL) and ethyl acetate (250 mL). The organic layer was separated and the aqueous was extracted again with ethyl acetate. The combined organic layer was dried over sodium sulfate, filtered and concentrated. The residue was purified by silica gel chromatography (10-50%, EtOAc:heptane) to afford the title compound (3.72 g, 64% yield) as an off-white solid.

Step 2

2-(3-(Chloromethyl)phenoxy)-6-methylpyridine (3-(6-Methylpyridin-2-yloxy)phenyl)methanol from Step 1 (3.7 g, 17 mmol), in dichloromethane (50 mL), was cooled to 0° C., and treated dropwise with thionyl chloride (1.50 mL, 20.6 mmol). The reaction mixture was allowed to warm to ambient temperature and was stirred for 3 h. Saturated aqueous sodium bicarbonate (20 mL) was added and the mixture was stirred at RT for 5 min. The organic layer was separated, dried over sodium sulfate, filtered and concentrated by evaporation to afford the title compound (4.0 g, 99% yield) as an oil.

Step 3

Diethyl 3-(6-methylpyridin-2-yloxy)benzylphosphonate 2-(3-(Chloromethyl)phenoxy)-6-methylpyridine (4.0 g, 17 mmol) from Step 2 was treated neat with triethylphosphite (3.67 mL, 21.4 mmol) and heated to 150° C. After 16 h, the reaction mixture was cooled to room temperature and partioned between water and ethyl acetate. The organic layer was separated and the aqueous was extracted again with ethyl acetate. The combined organic layer was dried over sodium sulfate, filtered and concentrated. The residue was purified by silica gel chromatography (30-60%, EtOAc:CH$_2$Cl$_2$) to afford the title compound (4.7 g, 82% yield) as a thick oil.

Step 4 tert-Butyl 4-(3-(6-methylpyridin-2-yloxy)benzylidene)piperidine-1-carboxylate

Diethyl 3-(6-methylpyridin-2-yloxy)benzylphosphonate (4.7 g, 14 mmol) from Step 3 and 1,4,7,10,13-pentaoxacyclopentadecane (15-Crown-5, 0.05 mL, 0.28 mmol) were combined in THF (150 mL). Sodium hydride (617 mg, 60% dispersion in mineral oil, 15.4 mmol) was added. The reaction was stirred for 30 min and then a solution of 4-oxo-piperidine-1-carboxylic acid tert-butyl ester (3.07 g, 15.4 mmol) in THF (15 mL) was added. After 16 h, water was added and the layers were separated. The aqueous layer was extracted with EtOAc (2×200 mL) and the combined organic layer was dried over anhydrous sodium sulfate, filtered and concentrated. The residue was purified by silica gel chromatography (10-30%, EtOAc:heptane) to afford the title compound (4.4 g, 83% yield) as a thick oil.

Step 5

2-Methyl-6-(3-(piperidin-4-ylidenemethyl)phenoxy) pyridine hydrochloride tert-Butyl 4-(3-(6-methylpyridin-2-yloxy)benzylidene)piperidine-1-carboxylate (4.3 g, 11 mmol) from Step 4 was dissolved in CH$_2$Cl$_2$ (50 mL) and treated with HCl in dioxane (20 mL, 4.0 M, 80 mmol). After 16 h the reaction was concentrated in vacuo to provide the title compound as a white solid (4.0 g).

Step 6

2-Methyl-6-(3-(piperidin-4-ylidenemethyl)phenoxy)pyridine hydrochloride (500 mg, 1.42 mmol, from Step 5), phenyl pyridin-3-ylcarbamate (333 mg, 1.56 mmol) and triethylamine (0.79 mL, 5.66 mmol) were combined in acetonitrile (10 mL) and stirred at room temperature. After 16 h, the reaction was concentrated forming a residue and the residue was partitioned between EtOAc and water. The organic layer was separated, dried over anhydrous sodium sulfate, filtered and concentrated. The residue was purified by silica gel chromatography (0-5%, (8:1 EtOH:conc. NH$_4$OH):CH$_2$Cl$_2$) to afford the title compound (399 mg) as a foamy white solid. MS (APCI 10V) AP+ 401.5, 281.2 $^1$H NMR (400 MHz, CD$_3$OD) d ppm 2.42 (s, 3H) 2.45 (td, J=5.74, 1.04 Hz, 2H) 2.56 (td, J=5.80, 1.15 Hz, 2H) 3.51-3.58 (m, 2H) 3.61-3.67 (m, 2H) 6.44 (s, 1H) 6.64 (d, J=8.24 Hz, 1H) 6.91-6.97 (m, 2H) 6.99 (d, J=7.19 Hz, 1H) 7.07 (d, J=7.65 Hz, 1H) 7.29-7.40 (m, 2H) 7.63-7.74 (m, 1H) 7.90 (ddd, J=8.38, 2.53, 1.39 Hz, 1H) 8.16 (dd, J=4.79, 1.40 Hz, 1H) 8.58 (d, J=2.31 Hz, 1H).

Example 41

Synthesis of 4-(3-(6-methylpyridin-2-yloxy)benzylidene)-N-(pyridazin-3-yl)piperidine-1-carboxamide 2-Methyl-6-(3-(piperidin-4-ylidenemethyl)phenoxy)pyridine hydrochloride (500 mg, 1.42 mmol, from Example 40, Step 5), phenyl pyridazin-3-ylcarbamate (335 mg, 1.56 mmol) and triethylamine (0.79 mL, 5.66 mmol) were combined in acetonitrile (10 mL) and stirred at room temperature. After 16 h, the reaction was concentrated forming a residue and the residue was partitioned between EtOAc and water. The organic layer was separated, dried over anhydrous sodium sulfate, filtered and concentrated. The residue was purified by silica gel chromatography (0-5%, (8:1 EtOH: conc. NH$_4$OH):CH$_2$Cl$_2$) to afford the title compound (336 mg) as a foamy white solid. MS (APCI 10V) AP+ 402.0, 281.1; $^1$H NMR (400 MHz, CD$_3$OD) δ ppm 2.42 (s, 3H) 2.46 (td, J=5.84, 0.80 Hz, 2H) 2.58 (td, J=5.78, 1.13 Hz, 2H) 3.52-3.63 (m, 2H) 3.63-3.72 (m, 2H) 6.45 (s, 1H) 6.65 (dt, J=8.21, 0.69 Hz, 1H) 6.90-6.97 (m, 2H) 6.99 (dt, J=7.16, 0.48 Hz, 1H) 7.04-7.11 (m, J=8.10, 1.21, 0.84, 0.63 Hz, 1H) 7.36 (dd, J=8.86, 7.71 Hz, 1H) 7.59 (dd, J=9.11, 4.65 Hz, 1H) 7.68 (dd, J=8.08, 7.52 Hz, 1H) 8.12 (d, J=8.87 Hz, 1H) 8.79 (d, J=3.90 Hz, 1H).

Example 42

Synthesis of 4-(3-(3-methylpyridin-2-yloxy)benzylidene)-N-(pyridin-3-yl)piperidine-1-carboxamide Step 1

(3-(3-Methylpyridin-2-yloxy)phenyl)methanol

3-Hydroxymethyl-phenol (3.69 g, 29.7 mmol), 2-fluoro-3-methyl-pyridine (3.00 g, 27 mmol) and cesium carbonate (9.68 g, 29.7 mmol) were suspended in dimethylsulfoxide (25 mL) and heated to 110° C. After stirring for 16 h, the reaction was partitioned between water (250 mL) and ethyl acetate (250 mL). The organic layer was separated and the aqueous was extracted again with ethyl acetate. The combined organic layer was dried over sodium sulfate, filtered and concentrated. The residue was purified by silica gel chromatography (10-50%, EtOAc:heptane) to afford the title compound (3.33 g, 57% yield) as a thick oil.

Step 2

2-(3-(Chloromethyl)phenoxy)-3-methylpyridine (3-(3-Methylpyridin-2-yloxy)phenyl)methanol from Step 1 (3.3 g, 15 mmol), in dichloromethane (50 mL), was cooled to 0° C., and treated dropwise with thionyl chloride (1.34 mL, 18.4 mmol). The reaction mixture was allowed to warm to ambient temperature and was stirred for 3 h. Saturated aqueous sodium bicarbonate (20 mL) was added and the mixture was stirred at RT for 5 min. The organic layer was separated, dried over sodium sulfate, filtered and concentrated by evaporation to afford the title compound (3.6 g, 99% yield) as an oil.

Step 3

Diethyl 3-(3-methylpyridin-2-yloxy)benzylphosphonate 2-(3-(Chloromethyl)phenoxy)-3-methylpyridine (3.6 g, 15 mmol) from Step 2 was treated neat with triethylphosphite (3.3 mL, 19.3 mmol) and heated to 150° C. After 16 h, the reaction mixture was cooled to room temperature and partioned between water and ethyl acetate. The organic layer was separated and the aqueous was extracted again with ethyl acetate. The combined organic layer was dried over sodium sulfate, filtered and concentrated. The residue was purified by silica gel chromatography (30-60%, EtOAc:CH$_2$Cl$_2$) to afford the title compound (4.3 g, 83% yield) as a thick oil.

Step 4 tert-Butyl 4-(3-(3-methylpyridin-2-yloxy)benzylidene)piperidine-1-carboxylate

Diethyl 3-(3-methylpyridin-2-yloxy)benzylphosphonate (4.3 g, 13 mmol) from Step 3 and 1,4,7,10,13-pentaoxacyclopentadecane (15-Crown-5, 0.05 mL, 0.28 mmol) were combined in THF (150 mL). Sodium hydride (564 mg, 60% dispersion in mineral oil, 14.1 mmol) was added. The reaction was stirred for 30 min and then a solution of 4-oxo-piperidine-1-carboxylic acid tert-butyl ester (1.81 g, 14.1 mmol) in THF (15 mL) was added. After 16 h, water was added and the layers were separated. The aqueous layer was extracted with EtOAc (2×200 mL) and the combined organic layer was dried over anhydrous sodium sulfate, filtered and concentrated. The residue was purified by silica gel chromatography (10-30%, EtOAc:heptane) to afford the title compound (3.9 g, 80% yield) as a thick oil.

Step 5

3-Methyl-2-(3-(piperidin-4-ylidenemethyl)phenoxy)pyridine hydrochloride tert-Butyl 4-(3-(3-methylpyridin-2-yloxy)benzylidene)piperidine-1-carboxylate (3.9 g, 10 mmol) from Step 4 was dissolved in CH$_2$Cl$_2$ (50 mL) and treated with HCl in dioxane (20 mL, 4.0 M, 80 mmol). After 16 h the reaction was concentrated in vacuo to provide the title compound as a white solid (3.6 g).

Step 6

3-Methyl-2-(3-(piperidin-4-ylidenemethyl)phenoxy)pyridine hydrochloride (500 mg, 1.42 mmol, from Step 5), phenyl pyridin-3-ylcarbamate (333 mg, 1.56 mmol) and triethylamine (0.79 mL, 5.66 mmol) were combined in acetonitrile (10 mL) and stirred at room temperature. After 16 h, the reaction was concentrated forming a residue and the residue was partitioned between EtOAc and water. The organic layer was separated, dried over anhydrous sodium sulfate, filtered and concentrated. The residue was purified by silica gel chromatography (0-5%, (8:1 EtOH:conc. NH$_4$OH):CH$_2$Cl$_2$) to afford the title compound (445 mg) as a foamy white solid. MS (APCI 10V) AP+ 401.4, 281.2; $^1$H NMR (400 MHz, CD$_3$OD) δ ppm 2.33 (s, 3H) 2.44 (td, J=5.81, 1.29 Hz, 2H) 2.57 (td, J=5.92, 1.22 Hz, 2H) 3.50-3.57 (m, 2H) 3.61-3.68 (m, 2H) 6.44 (s, 1H) 6.83-6.94 (m, 2H) 7.00-7.09 (m, 2H) 7.28-7.41 (m, 2H) 7.64-7.74 (m, J=7.28, 2.03, 1.07, 1.07 Hz, 1H) 7.87-7.96 (m, 2H) 8.16 (dd, J=4.80, 1.44 Hz, 1H) 8.58 (dd, J=2.60, 0.72 Hz, 1H).

Example 43

Synthesis of 4-(3-(3-methylpyridin-2-yloxy)benzylidene)-N-(pyridazin-3-yl)piperidine-1-carboxamide 3-Methyl-2-(3-(piperidin-4-ylidenemethyl)phenoxy)pyridine hydrochloride (500 mg, 1.42 mmol, from Example 42, Step 5), phenyl pyridazin-3-ylcarbamate (335 mg, 1.56 mmol) and triethylamine (0.79 mL, 5.66 mmol) were combined in acetonitrile (10 mL) and stirred at room temperature.

After 16 h, the reaction was concentrated forming a residue and the residue was partitioned between EtOAc and water. The organic layer was separated, dried over anhydrous sodium sulfate, filtered and concentrated. The residue was purified by silica gel chromatography (0-5%, (8:1 EtOH: conc. NH$_4$CH):CH$_2$Cl$_2$) to afford the title compound (380 mg) as a white foam. MS (APCI 10V) AP+ 402.0, 281.1; $^1$H NMR (400 MHz, CD$_3$OD) δ ppm 2.33 (s, 3H) 2.46 (td, J=5.86, 0.80 Hz, 2H) 2.59 (td, J=5.71, 0.82 Hz, 2H) 3.52-3.62 (m, 2H) 3.64-3.71 (m, 2H) 6.44 (s, 1H) 6.84-6.94 (m, 2H) 7.03 (d, J=7.24 Hz, 1H) 7.05 (d, J=7.33 Hz, 1H) 7.34 (dd, J=8.78, 7.66 Hz, 1H) 7.59 (dd, J=9.15, 4.67 Hz, 1H) 7.66-7.73 (m, 1H) 7.87-7.96 (m, J=4.96, 1.22, 0.55, 0.55 Hz, 1H) 8.12 (d, J=8.97 Hz, 1H) 8.78 (d, J=4.26 Hz, 1H).

Example 44

Synthesis of 4-(3-(5-methylpyridin-2-yloxy)benzylidene)-N-pyridin-3-yl)piperidine-1-carboxamide Step 1

(3-(5-Methylpyridin-2-yloxy)phenyl)methanol

3-Hydroxymethyl-phenol (5.04 g, 40.6 mmol), 2-fluoro-5-methyl-pyridine (4.1 g, 37 mmol,) and cesium carbonate (15.0 g, 46.1 mmol) were suspended in dimethylsulfoxide (50 mL) and heated to 110° C. After stirring for 16 h, the reaction was partitioned between water (500 mL) and ethyl acetate (500 mL). The organic layer was separated and the aqueous was extracted again with ethyl acetate. The combined organic layer was dried over sodium sulfate, filtered and concentrated. The residue was purified by silica gel chromatography (10-20%, EtOAc:heptane) to afford the title compound (4.2 g, 53% yield) as a thick oil.

Step 2

2-(3-(Chloromethyl)phenoxy)-5-methylpyridine (3-(5-Methylpyridin-2-yloxy)phenyl)methanol from Step 1 (1.9 g, 8.8 mmol), in dichloromethane (25 mL), was cooled to 0° C., and treated dropwise with thionyl chloride (0.773 mL, 10.6 mmol). The reaction mixture was allowed to warm to ambient temperature and was stirred for 3 h. Saturated aqueous sodium bicarbonate (20 mL) was added and the mixture was stirred at RT for 5 min. The organic layer was separated, dried over sodium sulfate, filtered and concentrated by evaporation to afford the title compound (2.1 g, 99% yield) as an oil.

Step 3

Diethyl 3-(5-methylpyridin-2-yloxy)benzylphosphonate 2-(3-(Chloromethyl)phenoxy)-5-methylpyridine (2.0 g, 8.8 mmol) was treated neat with triethylphosphite (1.89 mL, 11 mmol) and heated to 150° C. After 16 h, the reaction mixture was cooled to room temperature and partioned between water and ethyl acetate. The organic layer was separated and the aqueous was extracted again with ethyl acetate. The combined organic layer was dried over sodium sulfate, filtered and concentrated to give a residue. The residue was purified by silica gel chromatography (10-75%, EtOAc:CH$_2$Cl$_2$) to afford the title compound (1.75 g, 59% yield) as a thick oil.

Step 4 tert-Butyl 4-(3-(5-methylpyridin-2-yloxy)benzylidene)piperidine-1-carboxylate

Diethyl 3-(5-methylpyridin-2-yloxy)benzylphosphonate (1.75 g, 5.22 mmol) from Step 3 and 1,4,7,10,13-pentaoxacyclopentadecane (15-Crown-5, 0.02 mL, 0.10 mmol) were combined in THF (5 mL). Sodium hydride (230 mg, 60% dispersion in mineral oil, 5.74 mmol) was added. The reaction was stirred for 30 min and then a solution of 4-oxo-piperidine-1-carboxylic acid tert-butyl ester (1.14 g, 5.74 mmol) in THF (5 mL) was added. After 16 h, water was added and the layers were separated. The aqueous layer was extracted with EtOAc (2×200 mL) and the combined organic layer was dried over anhydrous sodium sulfate, filtered and concentrated. The residue was purified by silica gel chromatography (0-30%, EtOAc:heptane) to afford the title compound (1.24 g, 62% yield) as a thick oil.

Step 5

5-Methyl-2-(3-(piperidin-4-ylidenemethyl)phenoxy)pyridine hydrochloride tert-Butyl 4-(3-(5-methylpyridin-2-yloxy)benzylidene)piperidine-1-carboxylate (1.24 g, 3.26 mmol) from Step 4 was dissolved in CH$_2$Cl$_2$ (10 mL) and treated with HCl in dioxane (3.26 mL, 4.0 M, 13 mmol). After 16 h the reaction was concentrated in vacuo to provide the title compound as a white solid (1.48 g).

Step 6

5-Methyl-2-(3-(piperidin-4-ylidenemethyl)phenoxy)pyridine hydrochloride (150 mg, 0.473 mmol, from Step 5), phenyl pyridin-3-ylcarbamate (101 mg, 0.473 mmol) and diisopropylethylamine (0.20 mL, 1.15 mmol) were combined in acetonitrile (5 mL) and stirred at room temperature. After 16 h, the reaction was concentrated and the residue was purified by silica gel chromatography (50-100% EtOAc:CH$_2$Cl$_2$) to afford the title compound (86 mg) as a foamy white solid. MS APCI M+ 401.2, 281.2 M− 399.2; $^1$H NMR (400 MHz, CD$_3$OD) δ ppm 2.29 (s, 3H) 2.45 (td, J=5.89, 1.17 Hz, 2H) 2.56 (td, J=5.78, 1.23 Hz, 2H) 3.51-3.57 (m, 2H) 3.61-3.67 (m, 2H) 6.43 (s, 1H) 6.83-6.87 (m, 1H) 6.90-6.95 (m, J=5.12, 2.53, 1.32, 1.32 Hz, 2H) 7.04-7.10 (m, 1H) 7.30-7.39 (m, 2H) 7.66 (ddd, J=8.41, 2.49, 0.66 Hz, 1H) 7.91 (ddd, J=8.38, 2.60, 1.44 Hz, 1H) 7.97 (td, J=1.63, 0.78 Hz, 1H) 8.16 (dd, J=4.82, 1.43 Hz, 1H) 8.58 (dd, J=2.55, 0.65 Hz, 1H).

Example 45

Synthesis of 4-(3-(5-methylpyridin-2-yloxy)benzylidene)-N-(pyridazin-3-yl)piperidine-1-carboxamide 5-Methyl-2-(3-(piperidin-4-ylidenemethyl)phenoxy)pyridine hydrochloride (507 mg, 1.6 mmol, from Example 44, Step 5), phenyl pyridazin-3-ylcarbamate (430 mg, 2.0 mmol) and triethylamine (0.892 mL, 6.4 mmol) were combined in acetonitrile (10 mL) and stirred at room temperature. After 16 h, the reaction was concentrated and the residue was partitioned between EtOAc and water. The organic layer was separated, dried over anhydrous sodium sulfate, filtered and concentrated. The residue was purified by silica gel chromatography (0-10%, MeOH:CH$_2$Cl$_2$) to afford the title compound (526 mg) as a foamy white solid. MS APCI M+ 402.1, 281.2 M– 400.1; ¹H NMR (400 MHz, CD₃OD) δ ppm 2.29 (s, 3H) 2.46 (td, J=5.71, 0.93 Hz, 2H) 2.58 (td, J=5.74, 1.06 Hz, 2H) 3.52-3.61 (m, 2H) 3.65-3.71 (m, 2H) 6.44 (s, 1H) 6.85 (dd, J=8.41, 0.33 Hz, 1H) 6.89-6.96 (m, J=4.21, 4.21, 2.47, 1.01 Hz, 2H) 7.04-7.11 (m, J=7.63, 1.41, 1.04, 0.83 Hz, 1H) 7.31-7.42 (m, 1H) 7.59 (dd, J=9.09, 4.70 Hz, 1H) 7.66 (ddd, J=8.39, 2.49, 0.66 Hz, 1H) 7.97 (td, J=1.63, 0.77 Hz, 1H) 8.12 (d, J=9.32 Hz, 1H) 8.79 (d, J=4.37 Hz, 1H).

Example 46

Synthesis of 4-(3-(5-methylpyridin-2-yloxy)benzylidene)-N-(3,4-dimethylisoxazol-5-yl)piperidine-1-carboxamide 5-Methyl-2-(3-(piperidin-4-ylidenemethyl)phenoxy)pyridine hydrochloride (150 mg, 0.473 mmol, from Example 44, Step 5), phenyl 3,4-dimethylisoxazol-5-ylcarbamate (110 mg, 0.473 mmol, prepared according to the procedure described in *Synthesis,* 1997, 1189-1194 from 5-amino-3,4-dimethylisoxazole) and diisopropylethylamine (0.20 mL, 1.15 mmol) were combined in acetonitrile (5 mL) and stirred at room temperature. After 16 h, the reaction was concentrated and the residue was purified by silica gel chromatography (0-30% EtOAc:CH₂Cl₂) to afford the title compound (86 mg) as a foamy white solid. MS APCI M+ 419.3, 378.2, 281.3; ¹H NMR (400 MHz, CD₃OD) δ ppm 1.83 (s, 3H) 2.18 (s, 3H) 2.29 (s, 3H) 2.43 (td, J=5.86, 1.16 Hz, 2H) 2.55 (td, J=5.73, 1.20 Hz, 2H) 3.48-3.54 (m, 2H) 3.57-3.65 (m, 2H) 6.44 (s, 1H) 6.82-6.87 (m, 1H) 6.89-6.96 (m, 2H) 7.02-7.11 (m, J=7.60, 1.50, 1.06, 0.74 Hz, 1H) 7.35 (dd, J=8.77, 7.65 Hz, 1H) 7.61-7.69 (m, J=8.38, 2.46, 1.15, 0.45 Hz, 1H) 7.96 (td, J=1.60, 0.72 Hz, 1H).

Example 47

Synthesis of 4-(3-(5-ethoxypyridin-2-yloxy)benzylidene)-N-(pyridin-3-yl)piperidine-1-carboxamide Step 1 tert-Butyl 4-(3-(5-(4,4,5,5-tetramethyl-1,3,2-dioxaborolan-2-yl)pyridin-2-yloxy)benzylidene)piperidine-1-carboxylate tert-Butyl 4-(3-(5-bromopyridin-2-yloxy)benzylidene)piperidine-1-carboxylate (3.5 g, 7.85 mmol, from Example 33, Step 4) was dissolved in toluene (20 mL) and dioxane (20 mL) under inert atmosphere. Bis(pinacolato)diboron (2.9 g, 11.7 mmol) and potassium phosphate (3.3 g, 15.7 mmol) were added and the reaction mixture was degassed for 30 min. PdCl₂(dppf)₂ was added and the reaction mixture was refluxed for 24 h at 110° C. The reaction mixture was concentrated and 15 mL of distilled water was added. The mixture was extracted with ethyl acetate (20 mL×3 times) and the organic layer was washed with brine, dried over Na₂SO₄ and concentrated to dryness. The residue was purified by silica gel column chromatography (2:5 ethyl acetate:hexane) to give the title compound (3.45 g, 91%). ¹H NMR (500 MHz, CDCl₃): δ 8.57 (s, 1H), 8.04 (d, J=7.5 Hz, 1H), 7.32 (t, J=8 Hz, 1H), 6.99 (m, 2H), 6.96 (s, 1H), 6.84 (s, 1H), 6.33 (s, 1H), 3.49 (m, 2H), 3.39 (m, 2H), 2.46 (m, 2H), 2.31 (m, 2H), 1.47 (s, 9H), 1.33 (s, 12H); m/z (493.3, M⁺ H⁺).

Step 2 tert-Butyl 4-(3-(5-hydroxypyridin-2-yloxy)benzylidene)piperidine-1-carboxylate

To a solution of tert-butyl 4-(3-(5-(4,4,5,5-tetramethyl-1,3,2-dioxaborolan-2-yl)pyridin-2-yloxy)benzylidene)piperidine-1-carboxylate (3.45 g, 7 mmol) in THF (15 mL) was added AcOOH (4.6 mL, 60.67 mmol) at 0° C. The temperature was allowed to warm to RT and the reaction was stirred for 3 h. The reaction was quenched with Na₂SO₃ solution at 0° C. and the pH of the solution was adjusted to 7-7.5. Then the mixture was extracted with ethyl acetate and the organic layer was dried over Na₂SO₄ and concentrated to dryness. The residue was purified by silica gel column chromatography (1:3 acetone:hexane) to give the title compound (2.02 g, 75%). ¹H NMR (500 MHz, DMSO-d₆): δ 9.67 (s, 1H), 7.72 (s, 1H), 7.28 (m, 2H), 6.98 (d, J=7.2 Hz, 1H), 6.89 (d, J=8.5 Hz, 1H), 6.85 (d, J=7.5 Hz), 6.83 (s, 1H), 6.35 (s, 1H), 3.41 (m, 2H), 3.31 (m, 2H), 2.38 (m, 2H), 2.27 (m, 2H), 1.41 (s, 9H); m/z (383.1, M⁺ H⁺).

Step 3 tert-Butyl 4-(3-(5-ethoxypyridin-2-yloxy)benzylidene)piperidine-1-carboxylate

To a stirred solution of tert-butyl 4-(3-(5-hydroxypyridin-2-yloxy)benzylidene)piperidine-1-carboxylate (0.6 g, 1.56 mmol) in acetone (5 mL) was added ethyl iodide (0.304 g, 1.96 mmol), K₂CO₃ (0.431 g, 3.12 mmol) and 18-crown-6 (0.824 g, 3.12 mmol) at 0° C. The reaction mixture was stirred at RT overnight. The reaction mixture was diluted with water (10 mL) and extracted with ethyl acetate three times. The organic layer was washed with fresh water and brine solution, dried over Na₂SO₄ and concentrated to dryness under reduced pressure. The residue was purified by silica gel column chromatography (1:19 acetone:hexanes) to give the title compound (610 mg, 95%). ¹H NMR (500 MHz, CDCl₃): δ 7.86 (d, J=2.5 Hz, 1H), 7.27 (m, 2H), 6.96 (d, J=7.5 Hz, 1H), 6.90 (m, 2H), 6.85 (d, J=9 Hz, 1H), 6.32 (s, 1H), 4.02 (q, 2H, J=6.8), 3.49 (s, 2H), 3.38 (s, 2H), 2.45 (s, 2H), 2.30 (s, 2H), 1.47 (s 9H) 1.40 (t, J=6.92 Hz, 3H); m/z (411.51, M⁺ H⁺).

Step 4

5-Ethoxy-2-(3-(piperidin-4-ylidenemethyl)phenoxy)pyridine

To a solution of tert-butyl 4-(3-(5-ethoxypyridin-2-yloxy)benzylidene)piperidine-1-carboxylate (0.6 g, 1.46 mmol) in CH₂Cl₂ (5 mL) cooled to 0° C. under a N₂ atmosphere was added TFA (1.1 mL, 14.6 mmol). The resulting mixture was stirred for 1 h at RT. The solution was concentrated and then quenched with saturated NaHCO₃ solution. The mixture was extracted with CH₂Cl₂ and the organic layer was dried over Na₂SO₄, and concentrated under reduced pressure to give the title compound (0.45 g, 99%); m/z (311.5, M⁺ H⁺).

Step 5

To a solution of 5-ethoxy-2-(3-(piperidin-4-ylidenemethyl)phenoxy)pyridine (0.22 g, 0.708 mmol) in DMSO (4 mL) was added phenyl pyridin-3-ylcarbamate (0.151 g, 0.708 mmol) followed by triethylamine (0.265 mL, 2.12 mmol). The resulting mixture was stirred at RT for 12 h. The reaction mixture was diluted with water and extracted with EtOAc.

The organic extract was dried over Na₂SO₄ and concentrated under reduced pressure. The residue was purified by silica gel column chromatography (38% acetone, 62% hexane) to give the title compound (0.17 g, 55%). $^1$H NMR (500 MHz, CDCl$_3$): δ 8.44 (d, J=1.8 Hz, 1H), 8.25 (d, J=4 Hz, 1H), 8.0 (s, 1H), 7.86 (d, J=2.8 Hz, 1H), 7.23 (m, 3H), 6.97 (d, J=4.05 Hz, 3H), 692 (d, J=4 Hz, 2H), 6.86 (d, J=8.8 Hz, 1H), 6.38 (s, 1H), 4.03 (t, J=6.95, 2H), 3.59 (t, J=5.6 Hz, 2H), 3.49 (t, J=5.6 Hz, 2H), 2.56 (t, J=5.7 Hz 2H), 2.43 (t, J=5.1 Hz, 2H), 1.40 (t, J=8.25 Hz, 3H). $^{13}$C NMR (125 MHz, CDCl$_3$): δ 157.32, 155.27, 154.5, 151.85, 143.96, 141.15, 128.78, 137.64, 136.16, 133.59, 129.42, 127.40, 126.82, 124.83, 124.57, 123.58, 120.54, 118.31, 112.54, 64.62, 53.43, 45.71, 44.71, 41.01, 35.73, 29.14, 14.82; m/z (431.2, M$^+$ H$^+$); HPLC: 98.8%.

Example 48

Synthesis of 4-(3-(5-ethoxypyridin-2-yloxy)benzylidene)-N-(pyridazin-3-yl)piperidine-1-carboxamide To a solution of 5-ethoxy-2-(3-(piperidin-4-ylidenemethyl)phenoxy)pyridine (0.22 g, 0.708 mmol) in DMSO (4 mL) was added phenyl pyridazin-3-ylcarbamate (0.152 g, 0.708 mmol) followed by triethylamine (0.265 mL, 2.12 mmol). The resulting mixture was stirred at RT for 12 h. The reaction mixture was diluted with water and extracted with EtOAc. The organic extract was dried over Na₂SO₄ and concentrated under reduced pressure. The residue was purified by silica gel column chromatography (38% acetone, 62% hexane) to give the title compound (0.225 g, 73% yield). $^1$H NMR (500 MHz, CDCl$_3$): δ 8.80 (s, 1H), 8.29 (s, 1H), 7.87 (d, J=3.0 Hz, 1H), 7.41 (d, J=4.0 Hz, 1H), 7.34-7.23 (m, 1H), 6.99-6.93 (m, 3H), 6.86 (d, J=9.0 Hz, 1H), 6.39 (s, 1H), 4.02 (q, J=7.0 Hz, 2H), 3.67 (s, 2H), 3.57 (s, 2H), 2.6-2.5 (m, 2H), 2.47 (m, 2H), 1.40 (t, J=7.0 Hz, 3H). $^{13}$C NMR (125 MHz, CDCl$_3$): δ 157.32, 156.79, 155.24, 151.82, 147.4, 138.74, 137.55, 133.57, 129.40, 127.97, 126.82, 124.89, 124.56, 120.55, 118.91, 112.52, 64.61, 45.66, 44.66, 35.78, 29.14, 14.82; m/z (432.1, M$^+$ H$^+$); HPLC: 98.76%.

Example 49

Synthesis of 4-(3-(5-(2,2,2-trifluoroethoxy)pyridin-2-yloxy)benzylidene)-N-(pyridin-3-yl)piperidine-1-carboxamide Step 1 tert-Butyl 4-(3-(5-(2,2,2-trifluoroethoxy)pyridin-2-yloxy)benzylidene)piperidine-1-carboxylate To a stirred solution of tert-butyl 4-(3-(5-hydroxypyridin-2-yloxy)benzylidene)piperidine-1-carboxylate (0.8 g, 2.09 mmol) in DMF (5 mL) cooled to 0° C. was added trifluoromethyliodide (548.9 mg, 2.614 mmol) and Cs₂CO₃ (1.3 gm, 4.18 mmol). The reaction mixture was stirred at 80° C. overnight. The reaction mixture was diluted with water (10 mL) and extracted with ethyl acetate three times. The organic layer was washed with water and brine solution, dried over Na₂SO₄ and concentrated to dryness under reduced pressure. The residue was purified by silica gel column chromatography (1:19 acetone:hexane) to give the title compound (360 mg, 37%). $^1$H NMR (500 MHz, CDCl$_3$): δ 7.91 (d, J=2.8 Hz, 1H), 7.31 (m, 2H), 7.0 (d, J=7.75 Hz, 1H), 6.89 (m, 3H), 6.33 (s, 1H), 4.33 (q, J=8 Hz, 2H), 3.49 (m, 2H), 3.39 (m, 2H), 2.45 (m, 2H), 2.31 (m, 2H), 1.47 (s, 9H); m/z (465.1, M$^+$ H$^+$).

Step 2

2-(3-(Piperidin-4-ylidenemethyl)phenoxy)-5-(2,2,2-trifluoroethoxy)pyridine

To a solution of tert-butyl 4-(3-(5-(2,2,2-trifluoroethoxy)pyridin-2-yloxy)benzylidene)piperidine-1-carboxylate (0.36 g, 0.77 mmol) in CH₂Cl₂ (3 mL) cooled to 0° C. under a N₂ atmosphere was added TFA (0.46 mL, 5.97 mmol). The resulting mixture was stirred for 2 h at RT. The solution was concentrated and then quenched with saturated NaHCO₃ solution. The mixture was extracted with CH₂Cl₂ and the organic extract was dried over Na₂SO₄, and concentrated under reduced pressure to give the title compound (0.282 g, 99%). m/z (365.1, M$^+$ H$^+$).

Step 3

To a solution of 2-(3-(piperidin-4-ylidenemethyl)phenoxy)-5-(2,2,2-trifluoroethoxy)pyridine (0.14 g, 0.38 mmol) in DMSO (3 mL) was added phenyl pyridin-3-ylcarbamate (0.082 g, 0.38 mmol) followed by triethylamine (0.235 mL, 1.692 mmol). The resulting mixture was stirred at RT for 12 h. The reaction mixture was diluted with water and extracted with EtOAc. The organic extract was dried over Na₂SO₄ and concentrated under reduced pressure. The residue was purified by silica gel column chromatography (30% acetone, 70% hexane) to give the title compound (0.13 g, 70%). $^1$H NMR (500 MHz, CDCl$_3$): δ 8.74 (s, 1H), 8.30 (d, J=7.2 Hz, 1H), 8.22 (d, J=4.4 Hz, 1H), 7.91 (d, J=8.2 Hz, 1H), 7.32 (m, 4H), 7.02 (d, J=7.5 Hz, 1H), 6.95 (d, J=9 Hz, 1H), 6.95 (s, 1H), 6.90 (d, J=8.8 Hz, 1H), 6.39 (s, 1H), 4.33 (q, J=7.8 Hz, 2H), 3.65 (m, 2H), 3.55 (m, 2H), 2.60 (m, 2H), 2.47 (m, 2H). $^{13}$C NMR (125 MHz, CDCl$_3$): δ 158.96, 154.56, 154.45, 150.43, 143.12, 140.48, 138.89, 137.80, 136.56, 134.41, 129.49, 127.96, 125.08, 124.74, 123.80, 121.02, 118.77, 112.57, 67.33, 67.05, 45.75, 44.70, 35.74, 29.16; m/z (485.1, M$^+$ H$^+$); HPLC: 93.6%.

Example 50

Synthesis of 4-(3-(5-(2,2,2-trifluoroethoxy)pyridin-2-yloxy)benzylidene)-N-(pyridazin-3-yl)piperidine-1-carboxamide To a solution of 2-(3-(piperidin-4-ylidenemethyl)phenoxy)-5-(2,2,2-trifluoroethoxy)pyridine (0.2 g, 0.54 mmol) in DMSO (3 mL) was added phenyl pyridazin-3-ylcarbamate (0.118 g, 0.54 mmol) followed by triethylamine (0.235 mL, 1.692 mmol). The resulting mixture was stirred at RT for 12 h. The reaction mixture was diluted with water and extracted with EtOAc. The organic extract was dried over Na₂SO₄, and concentrated under reduced pressure. The residue was purified by silica gel column chromatography (30% acetone, 70% hexane) to give the title compound (0.141 g, 55%). $^1$H NMR (500 MHz, CDCl$_3$): δ 8.75 (s, 1H), 8.6 (s, 1H), 7.92 (d, J=2.6 Hz, 1H), 7.54 (s, 1H), 7.33 (m, 2H), 7.01 (d, J=7.5 Hz, 1H), 6.91 (m, 3H), 6.41 (s, 1H), 4.35 (q, J=8 Hz, 2H), 3.74 (m, 2H), 3.65 (m, 2H), 2.62 (m, 2H), 2.48 (m, 2H). $^{13}$C NMR (125 MHz, CDCl$_3$): δ 158.95, 156.57, 154.55, 150.42, 138.82, 137.61, 134.35, 129.50, 128.19, 127.97, 125.07, 124.87, 124.15, 121.03, 118.80, 112.57, 67.60, 67.31, 67.03, 66.74, 45.65, 44.63, 35.75, 29.14; m/z (486.1, M$^+$ H$^+$); HPLC: 93.7%.

Example 51

Synthesis of 4-(3-(5-isopropoxypyridin-2-yloxy)benzylidene)-N-(pyridin-3-yl)piperidine-1-carboxamide

Step 1 tert-Butyl 4-(3-(5-isopropoxypyridin-2-yloxy)benzylidene)piperidine-1-carboxylate To a stirred solution of tert-butyl 4-(3-(5-hydroxypyridin-2-yloxy)benzylidene)piperidine-1-carboxylate (0.6 g, 1.56 mmol) in acetone (5 mL) cooled to 0° C. was added isopropyliodide (0.33 g, 1.96 mmol) and $K_2CO_3$ (0.43 g, 3.12 mmol). The reaction mixture was stirred at 80° C. overnight. The reaction mixture was evaporated to dryness and water (10 mL) was added and the mixture was extracted with ethyl acetate three times. The organic layer was washed with water and brine, dried over $Na_2SO_4$ and concentrated to dryness under reduced pressure. The residue was purified by silica gel column chromatography (1:19 acetone:hexane) to give the title compound (0.5 g, 75%). $^1$H NMR (500 MHz, $CDCl_3$): δ 7.86 (d, J=3.3 Hz, 1H), 7.28 (m, 2H), 6.96 (d, J=7.5 Hz, 1H), 6.91 (m, 2H), 6.84 (d, J=8.5 Hz, 1H), 6.32 (s, 1H), 4.45 (m, 1H), 3.49 (m, 2H), 3.38 (m, 2H), 2.45 (m, 2H), 2.31 (m, 2H), 1.47 (s, 9H), 1.33 (d, J=6 Hz, 6H); m/z (425.2, $M^+$ $H^+$).

Step 2

5-Isopropoxy-2-(3-(piperidin-4-ylidenemethyl)phenoxy)pyridine

To a solution of tert-butyl 4-(3-(5-isopropoxypyridin-2-yloxy)benzylidene)piperidine-1-carboxylate (0.5 g, 1.17 mmol) in $CH_2Cl_2$ (3 mL) cooled to 0° C. under a $N_2$ atmosphere was added TFA (0.46 mL, 5.97 mmol). The resulting mixture was stirred for 2 h at RT. The solution was concentrated and then quenched with saturated $NaHCO_3$ solution. The mixture was extracted with $CH_2Cl_2$ and the organic layer was dried over $Na_2SO_4$ and concentrated under reduced pressure to give the title compound (0.38 g, 99%). $^1$H NMR (500 MHz, $CDCl_3$): δ 8.94 (m, 2H), 7.35 (m, 2H), 7.0 (m, 2H), 6.90 (s, 1H), 6.47 (s, 1H), 4.53 (m, 1H), 3.50 (m, 2H), 3.32 (m, 2H), 2.76 (m, 2H), 2.65 (m, 2H), 1.35 (d, J=6 Hz, 6H).

Step 3

To a solution of 5-isopropoxy-2-(3-(piperidin-4-ylidenemethyl)phenoxy)pyridine (0.18 g, 0.55 mmol) in DMSO (3 mL) was added phenyl pyridin-3-ylcarbamate (0.118 g, 0.55 mmol) followed by triethylamine (0.235 mL, 1.692 mmol). The resulting mixture was stirred at RT for 12 h. The reaction mixture was diluted with water and extracted with EtOAc. The organic extract was dried over $Na_2SO_4$ and concentrated under reduced pressure. The residue was purified by silica gel column chromatography (30% acetone, 70% hexane) to give the title compound (0.22 g, 89.2%). $^1$H NMR (500 MHz, $CDCl_3$): δ 8.46 (s, 1H), 8.25 (d, J=3.5 Hz, 1H), 8.02 (d, J=8 Hz, 1H), 7.86 (d, J=3 Hz, 1H), 7.27 (m, 2H), 7.23 (m, 1H), 6.98 (d, J=7.5 Hz, 1H), 6.93 (m, 2H), 6.85 (d, J=9 Hz, 1H), 6.68 (s, 1H), 6.39 (s, 1H), 4.45 (m, 1H), 3.60 (m, 2H), 3.50 (m, 2H), 2.58 (m, 2H), 2.44 (m, 2H), 1.33 (d, J=6 Hz, 6H). $^{13}$C NMR (125 MHz, $CDCl_3$): δ 157.34, 155.19, 154.58, 150.73, 143.84, 141.11, 138.80, 137.68, 136.27, 135.56, 129.41, 128.34, 127.50, 124.80, 124.61, 123.60, 120.61, 118.36, 112.49, 71.68, 45.69, 44.71, 35.73, 29.15, 21.96; m/z (445.2, $M^+$ $H^+$); HPLC: 96.0%.

Example 52

Synthesis of 4-(3-(5-isopropoxypyridin-2-yloxy)benzylidene)-N-(pyridazin-3-yl)piperidine-1-carboxamide To a solution of 5-isopropoxy-2-(3-(piperidin-4-ylidenemethyl)phenoxy)pyridine (0.18 g, 0.55 mmol) in DMSO (3 mL) was added phenyl pyridazin-3-ylcarbamate (0.118 g, 0.55 mmol) followed by triethylamine (0.235 mL, 1.692 mmol). The resulting mixture was stirred at RT for 12 h. The reaction mixture was diluted with water and extracted with EtOAc. The organic extract was dried over $Na_2SO_4$ and concentrated under reduced pressure. The residue was purified by silica gel column chromatography (30% acetone, 70% hexane) to give the title compound (0.13 g, 52.6%). $^1$H NMR (500 MHz, $CDCl_3$): δ 8.80 (s, 1H), 8.30 (s, 1H), 7.86 (d, J=3 Hz, 1H), 7.40 (m, 1H), 7.31 (t, J=8 Hz, 1H), 7.28 (m, 1H), 6.93 (m, 3H), 6.86 (d, J=8.5 Hz, 1H), 6.40 (s, 1H), 4.45 (q, J=6 Hz, 1H), 3.67 (m, 2H), 3.57 (m, 2H), 2.6 (m, 2H), 2.46 (m, 2H), 1.33 (d, J=6 Hz, 6H). $^{13}$C NMR (125 MHz, $CDCl_3$): δ 157.33, 156.57, 155.18, 150.69, 138.70, 137.37, 135.54, 129.41, 128.33, 128.03, 125.0, 124.58, 120.63, 118.43, 112.45, 71.65, 45.64, 44.62, 35.75, 29.13, 21.96; m/z (446.2, $M^+$ $H^+$); HPLC: 98.5%.

Example 53

Synthesis of 4-(3-(4-(trifluoromethylphenoxy)benzylidene)-N-(pyridin-3-yl)piperidine-1-carboxamide

Step 1

(3-(4-(Trifluoromethyl)phenoxy)phenyl)methanol

3-Hydroxymethyl-phenol (1.0 g, 8.1 mmol), 4-fluorobenzotrifluoride (1.32 g, 8.1 mmol) and cesium carbonate (3.28 g, 10.1 mmol) were suspended in dimethylsulfoxide (15 mL) and heated to 110° C. After stirring for 16 h, the reaction was partitioned between water (150 mL) and ethyl acetate (150 mL). The organic layer was separated and the aqueous was extracted again with ethyl acetate. The combined organic layer was dried over sodium sulfate, filtered and concentrated. The residue was purified by silica gel chromatography (10-40%, EtOAc:heptane) to afford the title compound (1.32 g) as a thick oil.

Step 2

1-(Chloromethyl)-3-(4-(trifluoromethyl)phenoxy)benzene (3-(4-(Trifluoromethyl)phenoxy)phenyl)methanol from Step 1 (1.3 g, 4.85 mmol), in dichloromethane (10 mL), was cooled to 0° C., and treated dropwise with thionyl chloride (0.39 mL, 5.33 mmol). The reaction mixture was allowed to warm to ambient temperature and was stirred for 16 h. The reaction was concentrated by evaporation and the residue was purified by silica gel chromatography (0-20%, EtOAc:heptane) to afford the title compound (1.34 g) as a thick oil.

Step 3

Diethyl 3-(4-(trifluoromethyl)phenoxy)benzylphosphonate 1-(Chloromethyl)-3-(4-(trifluoromethyl)phenoxy)benzene (1.3 g, 4.5 mmol) was treated neat with triethylphosphite (1.2 mL, 6.8 mmol) and heated to 150° C. After 16 h, the reaction mixture was cooled to room temperature and concentrated to give a residue. The residue was purified by silica gel chromatography (0-30%, EtOAc:CH$_2$Cl$_2$) to afford the title compound (1.76 g) as a clear oil.

Step 4 tert-Butyl 4-(3-(4-(trifluoromethyl)phenoxy)benzylidene)piperidine-1-carboxylate Diethyl 3-(4-(trifluoromethyl)phenoxy)benzylphosphonate (1.7 g, 4.4 mmol) from Step 3 and 1,4,7,10,13-pentaoxacyclopentadecane (15-Crown-5, 0.02 mL, 0.10 mmol) were combined in THF (10 mL). Sodium hydride (195 mg, 60% dispersion in mineral oil, 4.9 mmol) was added. The reaction was stirred for 30 min and then a solution of 4-oxo-piperidine-1-carboxylic acid tert-butyl ester (875 mg, 4.9 mmol) in THF (5 mL) was added. After 16 h, water was added and the layers were separated. The aqueous layer was extracted with EtOAc (2×200 mL) and the combined organic layer was dried over anhydrous sodium sulfate, filtered and concentrated. The residue was purified by silica gel chromatography (10%, EtOAc:heptane) to afford the title compound (1.75 g, 92% yield) as a thick oil.

Step 5

4-(3-(4-(Trifluoromethyl)phenoxy)benzylidene)piperidine hydrochloride tert-Butyl 4-(3-(4-(trifluoromethyl)phenoxy)benzylidene)piperidine-1-carboxylate (1.75 g, 4.0 mmol) from Step 4 was dissolved in CH$_2$Cl$_2$ (15 mL) and treated with HCl in dioxane (7.0 mL, 4.0 M, 28 mmol). After 16 h the reaction was concentrated in vacuo to provide the title compound as a white solid (1.49 g).

Step 6

4-(3-(4-(Trifluoromethyl)phenoxy)benzylidene)piperidine hydrochloride (200 mg, 0.541 mmol, from Step 5), phenyl pyridin-3-ylcarbamate (116 mg, 0.541 mmol) and diisopropylethylamine (0.20 mL, 1.15 mmol) were combined in acetonitrile (5 mL) and stirred at room temperature. After 16 h, the reaction was concentrated and the residue was purified by silica gel chromatography (50-100% EtOAc:CH$_2$Cl$_2$) to afford the title compound (214 mg) as a white solid. MS APCI M+ 454.1, 375.1, 334.1 M− 452.1; $^1$H NMR (400 MHz, CD$_3$OD) δ ppm 2.45 (t, J=5.88 Hz, 2H) 2.52-2.59 (m, 2H) 3.51-3.58 (m, 2H) 3.60-3.67 (m, 2H) 6.44 (s, 1H) 6.90-6.98 (m, 2H) 7.06-7.13 (m, J=8.42 Hz, 3H) 7.34 (dd, J=8.36, 4.84 Hz, 1H) 7.36-7.42 (m, 1H) 7.63 (d, J=8.49 Hz, 2H) 7.91 (ddd, J=8.40, 2.59, 1.45 Hz, 1H) 8.16 (dd, J=4.61, 1.10 Hz, 1H) 8.58 (d, J=2.17 Hz, 1H).

Example 54

Synthesis of 4-(3-(4-(trifluoromethyl)phenoxy)benzylidene)-N-(pyridazin-3-yl)piperidine-1-carboxamide 4-(3-(4-(Trifluoromethyl)phenoxy)benzylidene)piperidine hydrochloride (200 mg, 0.541 mmol, from Example 53, Step 5), ethyl pyridazin-3-ylcarbamate (99 mg, 0.595 mmol) and triethylamine (0.15 mL, 1.08 mmol) were combined in acetonitrile (4.5 mL) and heated in a microwave at 180° C. for 40 min. The reaction mixture was cooled to RT and concentrated. The residue was purified by silica gel chromatography (50-100% EtOAc in CH$_2$Cl$_2$) to provide the title compound (156 mg). MS APCI M+ 455.2, 375.2, 334.2 M− 454.1; $^1$H NMR (400 MHz, CD$_3$OD) δ ppm 2.46 (td, J=5.81, 0.84 Hz, 2H) 2.56 (td, J=5.81, 0.84 Hz, 2H) 3.55-3.61 (m, 2H) 3.65-3.70 (m, 2H) 6.44 (s, 1H) 6.91-6.99 (m, 2H) 7.06-7.14 (m, J=8.32 Hz, 3H) 7.35-7.43 (m, 1H) 7.59 (dd, J=9.13, 4.68 Hz, 1H) 7.61-7.66 (m, J=9.08 Hz, 2H) 8.12 (d, J=9.30 Hz, 1H) 8.78 (d, J=4.68 Hz, 1H).

Example 55

Synthesis of 4-(3-(4-(trifluoromethyl)phenoxy)benzylidene)-N-(3,4-dimethylisoxazol-5-yl)piperidine-1-carboxamide 4-(3-(4-(Trifluoromethyl)phenoxy)benzylidene)piperidine hydrochloride (200 mg, 0.541 mmol, from Example 53, Step 5), phenyl 3,4-dimethylisoxazol-5-ylcarbamate (126 mg, 0.541 mmol, prepared according to the procedure described in *Synthesis*, 1997, 1189-1194 from 5-amino-3,4-dimethylisoxazole) and diisopropylethylamine (0.20 mL, 1.15 mmol) were combined in acetonitrile (5 mL) and stirred at room temperature. After 16 h, the reaction was concentrated and the residue was purified by silica gel chromatography (0-30% EtOAc:CH$_2$Cl$_2$) to afford the title compound (218 mg) as a white solid. MS APCI M+ 472.3, 431.2, 375.3, 334.2; $^1$H NMR (400 MHz, CD$_3$OD) δ ppm 1.83 (s, 3H) 2.18 (s, 3H) 2.44 (td, J=5.77, 1.07 Hz, 2H) 2.54 (td, J=5.81, 1.16 Hz, 2H) 3.49-3.54 (m, 2H) 3.59-3.63 (m, 2H) 6.44 (s, 1H) 6.90-6.98 (m, 2H) 7.05-7.14 (m, 3H) 7.35-7.44 (m, 1H) 7.59-7.67 (m, 2H).

Example 56

Synthesis of 4-(3-(4-(trifluoromethyl)phenoxy)benzylidene)-N-(6-methylpyridin-3-yl)piperidine-1-carboxamide 4-(3-(4-(Trifluoromethyl)phenoxy)benzylidene)piperidine hydrochloride (200 mg, 0.541 mmol, from Example 53, Step 5) and phenyl 6-methylpyridin-3-ylcarbamate (123 mg, 0.541 mmol, prepared according to the procedure described in *Synthesis*, 1997, 1189-1194 from 3-amino-6-methylpyridine) and diisopropylethylamine (0.20 mL, 1.15 mmol) were combined in acetonitrile (5 mL) and stirred at room temperature. After 16 h, the reaction was concentrated and the residue was purified by silica gel chromatography (50-100% EtOAc:CH$_2$Cl$_2$) to afford the title compound (220 mg) as a white solid. MS APCI M+ 468.2, 375.2, 334.1 M− 466.1; $^1$H NMR (400 MHz, CD$_3$OD) δ ppm 2.41-2.45 (m, 2H) 2.46 (s, 3H) 2.54 (td, J=5.90, 1.26 Hz, 2H) 3.50-3.55 (m, 2H) 3.58-3.65 (m, 2H) 6.43 (s, 1H) 6.91-6.96 (m, 2H) 7.06-7.12 (m, 3H)

7.20 (d, J=8.52 Hz, 1H) 7.35-7.42 (m, 1H) 7.59-7.68 (m, 2H) 7.77 (dd, J=8.45, 2.62 Hz, 1H) 8.43 (d, J=2.78 Hz, 1H).

Example 57

Synthesis of 4-(3-(6-(trifluoromethyl)pyridin-3-yloxy)benzylidene)-N-(pyridazin-3-yl)piperidine-1-carboxamide Step 1 tert-Butyl 4-(dibromomethylene)piperidine-1-carboxylate

To a stirred solution of triphenylphosphine (155.6 g, 0.59 mol) in dry dichloromethane (870 mL) at 0° C. was added carbon tetrabromide (100.86 g, 0.304 mol) portionwise. The mixture was stirred at RT for 30 min and then cooled to −78° C. A solution of tert-butyl 4-oxopiperidine-1-carboxylate (30 g, 0.15 mol) in $CH_2Cl_2$ (90 mL) was added dropwise and the reaction was stirred at −78° C. for 30 min and then at RT overnight. The mixture was filtered and the filtrate was evaporated to dryness. Diethyl ether was added and the mixture was filtered again. The filtrate was evaporated to dryness to give the title compound (64 g). $^1$H NMR (500 MHz, $CDCl_3$): δ 3.44 (m, 4H), 2.46 (m, 4H), 1.47 (s, 9H).

Step 2 tert-Butyl 4-(bromomethylene)piperidine-1-carboxylate tert-Butyl 4-(dibromomethylene)piperidine-1-carboxylate (64 g, 0.18 mol) was dissolved in methanol (438 mL) and THF (220 mL) and the solution was cooled to 0° C. Ammonium chloride (77.14 g, 1.44 mol) was added and the reaction was stirred for 30 min. Zinc dust (47.13 g, 0.72 mol) was added and the reaction mixture was stirred at RT for 2.5 h. The mixture was filtered and the filtrate was evaporated to dryness. The residue was purified by silica gel chromatography using 230-400 mesh silica gel (2% ethyl acetate in hexane) to give the title compound (33 g). $^1$H NMR (500 MHz, $CDCl_3$): δ 5.99 (s, 1H), 3.40 (m, 4H), 2.38 (m, 2H), 2.23 (m, 2H), 1.47 (s, 9H).

Step 3 tert-Butyl 4-(3-hydroxybenzylidene)piperidine-1-carboxylate

To a solution of tert-butyl 4-(bromomethylene)piperidine-1-carboxylate (38 g, 0.1376 mol) in dry THF (380 mL) was added 3-hydroxyphenyl boronic acid (22.77 g, 0.165 mol), potassium phosphate (88.2 g, 0.415 mol) and water (7.6 mL). The mixture was degassed with argon. 1,1'-Bis(diphenylphosphino)ferrocene palladium(II) dichloride dichloromethane complex (11.23 g, 0.01376 mol) was added and the mixture was degassed again. The reaction was heated at 50° C. for 1.5 h and then allowed to cool to RT. Water was added and the mixture was extracted with ethyl acetate (3×). The total organic extract was washed with brine, dried over sodium sulfate and evaporated to dryness. The residue was purified by silica gel chromatography using 100-200 mesh silica gel (8% ethyl acetate in hexane) to give the title compound (26.3 g, 66%). $^1$H NMR (500 MHz, $CDCl_3$): δ 7.16 (t, J=7.5 Hz, 1H), 6.74 (d, J=7.5 Hz, 1H), 6.68 (d, J=9 Hz, 1H), 6.68 (s, 1H), 6.30 (s, 1H), 5.37 (bs, 1H), 3.49 (m, 2H), 3.40 (m, 2H), 2.46 (m, 2H), 2.31 (m, 2H), 1.48 (s, 9H); $^{13}$C NMR (125 MHz, $CDCl_3$): δ 156.09, 155.09, 138.87, 138.15, 129.31, 124.58, 120.98, 115.74, 113.54, 80.10, 45.45, 44.57, 36.08, 29.23, 28.50.

Step 4 tert-Butyl 4-(3-(6-(trifluoromethyl)pyridin-3-yloxy)benzylidene)piperidine-1-carboxylate A mixture of tert-butyl 4-(3-hydroxybenzylidene)piperidine-1-carboxylate (0.200 g), 5-bromo-2-(trifluoromethyl)pyridine (0.156 g, 1.00 equiv), cesium carbonate (0.450 g, 2.00 equiv), and tetrakis(acetonitrile)copper(I) hexafluorophosphate (0.019 g, 0.074 equiv) in toluene (3 mL, 0.2 M) was heated to reflux for 12 h. Additional catalyst (0.02 g) and 5-bromo-2-(trifluoromethyl)pyridine (0.200 g) was added and the mixture was refluxed for an additional 6 h. The reaction was allowed to cool to room temperature and filtered through Celite washing with ethyl acetate. Water was added and the mixture was extracted with ethyl acetate (2×). The combined organic extract was washed with brine, dried over magnesium sulfate, filtered, and concentrated. The residue was purified by silica gel chromatography (10% ethyl acetate/dichloromethane) to give the title compound as a white solid (0.141 g, 47% yield). $^1$H NMR (400 MHz, $CDCl_3$) δ ppm 1.47 (9H, s), 2.32 (2H, t, J=5.6 Hz), 2.44 (2H, t, J=5.6 Hz), 3.41 (2H, t, J=5.8 Hz), 3.50 (2H, t, J=5.8 Hz), 6.32 (1H, s), 6.87-6.96 (2H, m), 7.06 (1H, d, J=7.6 Hz), 7.32-7.39 (2H, m), 7.62 (1H, d, J=8.6 Hz), 8.46 (1H, d, J=2.7 Hz).

Step 5

5-(3-(Piperidin-4-ylidenemethyl)phenoxy)-2-(trifluoromethyl)pyridine hydrochloride A solution of tert-butyl 4-(3-(6-(trifluoromethyl)pyridin-3-yloxy)benzylidene)piperidine-1-carboxylate (0.140 g) in dichloromethane (5 mL, 0.06 M) was treated with hydrogen chloride gas for 2 min. The reaction was allowed to stir for 2 h and then was concentrated to give the title compound as a white foam (0.100 g, 84% yield) which was used without purification. $^1$H NMR (400 MHz, DMSO-$d_6$) δ ppm 2.50 (2H, t, J=5.8 Hz), 2.59 (2H, t, J=5.8 Hz), 3.04 (2H, t, J=6.0 Hz), 3.10 (2H, t, J=6.0 Hz), 6.44 (1H, s), 7.01-7.09 (2H, m), 7.13 (1H, d, J=7.8 Hz), 7.43 (1H, t, J=7.8 Hz), 7.52 (1H, dd, J=8.6, 2.7 Hz), 7.88 (1H, d, J=8.6 Hz), 8.52 (1H, d, J=2.7 Hz), 8.98 (2H, br. s.).

Step 6

A solution of 5-(3-(piperidin-4-ylidenemethyl)phenoxy)-2-(trifluoromethyl)pyridine hydrochloride (0.100 g), phenyl pyridazin-3-ylcarbamate (0.070 g, 1.2 equiv), and triethylamine (0.083 mL, 2.2 equiv) in dimethyl sulfoxide (2 mL, 0.13 M) was heated to 65° C. for 2 h. The reaction was cooled to room temperature. Water was added and the mixture was extracted with ethyl acetate (3×). The combined organic extracts was washed with water and brine, dried over magnesium sulfate, filtered, and concentrated. The residue was purified by silica gel chromatography (0-100% ethyl acetate/dichloromethane) to give the title compound as a white foam (0.089 g, 72% yield). $^1$H NMR (400 MHz, $CDCl_3$) δ ppm 2.46 (2H, t, J=5.5 Hz), 2.56 (2H, t, J=5.6 Hz), 3.60 (2H, t, J=5.8 Hz), 3.69 (2H, t, J=5.8 Hz), 6.37 (1H, s), 6.92 (2H, m), 7.07

(1H, d, J=7.6 Hz), 7.30-7.46 (3H, m), 7.62 (1H, d, J=8.8 Hz), 8.25 (1H, d, J=8.2 Hz), 8.45 (1H, d, J=2.5 Hz), 8.76 (1H, d, J=1.9 Hz).

Example 58

Synthesis of 4-(3-ethoxy-5-(5-(trifluoromethyl)pyridin-2-yloxy)benzylidene)-N-(pyridin-3-yl)piperidine-1-carboxamide Step 1

3-(Hydroxymethyl)-5-(5-(trifluoromethyl)pyridin-2-yloxy)phenol 3,5-Dihydroxybenzyl alcohol (5.0 g, 40 mmol), 2-chloro-5-trifluoromethyl-pyridine (7.13 g, 39.2 mmol) and potassium carbonate (6.16 g, 44.6 mmol) were suspended in dimethylformamide (100 mL) and heated to 100° C. After stirring for 16 h, the reaction was cooled to room temperature and partitioned between water (500 mL) and ethyl acetate. The organic layer was separated and the aqueous was extracted again with ethyl acetate. The combined organic layer was dried over sodium sulfate, filtered and concentrated. The residue was purified by silica gel chromatography (10-75%, EtOAc:heptane) to afford the title compound (2.32 g, 20% yield) as a thick oil.

Step 2

(3-Ethoxy-5-(5-(trifluoromethyl)pyridin-2-yloxy)phenyl)methanol 3-(Hydroxymethyl)-5-(5-(trifluoromethyl)pyridin-2-yloxy)phenol from Step 1 (460 mg, 1.61 mmol), in acetone (10 mL), was treated with 1-iodoethane (0.143 mL, 1.77 mmol), potassium carbonate (279 mg, 2.02 mmol) and 18-crown-6 (85 mg, 0.323 mmol). The mixture was heated to reflux for 16 h, cooled to room temperature and concentrated in vacuo. The residue was purified by silica gel chromatography (0-30%, EtOAc:heptane) to afford the title compound (357 mg, 70% yield).

Step 3

2-(3-(Chloromethyl)-5-ethoxyphenoxy)-5-(trifluoromethyl)pyridine (3-Ethoxy-5-(5-(trifluoromethyl)pyridin-2-yloxy)phenyl)methanol from Step 2 (350 mg, 1.12 mmol), in dichloromethane (3 mL), was cooled to 0° C., and treated dropwise with thionyl chloride (0.122 mL, 1.68 mmol). The reaction mixture was allowed to warm to ambient temperature and was stirred for 3 h. The mixture was evaporated in vacuo to afford the desired product as an oil.

Step 4

Diethyl 3-ethoxy-5-(5-(trifluoromethyl)pyridin-2-yloxy)benzylphosphonate 2-(3-(Chloromethyl)-5-ethoxyphenoxy)-5-(trifluoromethyl)pyridine from Step 3 was treated neat with triethylphosphite (0.30 mL, 1.75 mmol) and heated to 150° C. After 16 h, the reaction mixture was cooled and purified by silica gel chromatography (0-50%, EtOAc:CH$_2$Cl$_2$) to afford the title compound (400 mg, 82% yield) as a thick oil.

Step 5 tert-Butyl 4-(3-ethoxy-5-(5-(trifluoromethyl)pyridin-2-yloxy)benzylidene)piperidine-1-carboxylate [3-(5-Trifluoromethyl-pyridin-2-yloxy)-benzyl]-phosphonic acid diethyl ester (395 mg, 0.911 mmol) from Step 4 and 1,4,7,10,13-pentaoxacyclopentadecane (15-Crown-5, 0.003 mL, 0.0182 mmol) were combined in THF (3 mL). Sodium hydride (40 mg, 60% dispersion in mineral oil, 1.0 mmol) was added and the mixture was stirred for 30 min. A solution of 4-oxo-piperidine-1-carboxylic acid tert-butyl ester (200 mg, 1.0 mmol) in THF (2 mL) was added and the reaction was stirred at room temperature. After 16 h, water was added and the layers were separated. The aqueous layer was extracted with EtOAc and the combined organic layer was dried over anhydrous sodium sulfate, filtered and concentrated to afford the title compound as a thick oil (436 mg).

Step 6

2-(3-Ethoxy-5-(piperidin-4-ylidenemethyl)phenoxy)-5-(trifluoromethyl)pyridine hydrochloride tert-Butyl 4-(3-ethoxy-5-(5-(trifluoromethyl)pyridin-2-yloxy)benzylidene)piperidine-1-carboxylate (436 mg, 0.91 mmol) from Step 5 was dissolved in CH$_2$Cl$_2$ (5 mL) and treated with HCl in dioxane (1.5 mL, 4.0 M, 3 mmol). After 16 h the reaction was concentrated in vacuo to provide the title compound as an oil (378 mg).

Step 7

2-(3-Ethoxy-5-(piperidin-4-ylidenemethyl)phenoxy)-5-(trifluoromethyl)pyridine hydrochloride (378 mg, 0.91 mmol, from Step 6), phenyl pyridin-3-ylcarbamate (215 mg, 1.0 mmol) and diisopropylethylamine (0.32 mL, 1.82 mmol) were combined in acetonitrile (5 mL) and stirred at room temperature. After 16 h, the reaction was concentrated forming a residue and the residue was purified by silica gel chromatography (0-5%, (8:1 EtOH:conc. NH$_4$OH):CH$_2$Cl$_2$) to afford the title compound (2.32 g, 20% yield) as a foamy white solid (307 mg). MS (APCI 10V) AP+ 499.2, 379.2; $^1$H NMR (400 MHz, CD$_3$OD) δ ppm 1.38 (t, J=6.98 Hz, 3H) 2.44 (td, J=5.75, 0.97 Hz, 2H) 2.58 (td, J=5.80, 1.00 Hz, 2H) 3.51-3.59 (m, 2H) 3.60-3.67 (m, 2H) 4.03 (q, J=7.00 Hz, 2H) 6.41 (s, 1H) 6.57-6.62 (m, 2H) 6.68 (t, J=1.58 Hz, 1H) 7.11 (dt, J=8.74, 0.67 Hz, 1H) 7.34 (ddd, J=8.37, 4.81, 0.76 Hz, 1H) 7.91 (ddd, J=8.37, 2.60, 1.46 Hz, 1H) 8.08 (ddd, J=8.73, 2.59, 0.57 Hz, 1H) 8.16 (dd, J=4.81, 1.45 Hz, 1H) 8.44 (td, J=1.73, 0.88 Hz, 1H) 8.58 (dd, J=2.58, 0.71 Hz, 1H).

Example 59

Synthesis of 4-(4-chloro-3-(5-(trifluoromethyl)pyridin-2-yloxy)benzylidene)-N-(pyridin-3-yl)piperidine 1-carboxamide Step 1

2-(5-Bromo-2-chlorophenoxy)-5-(trifluoromethyl)pyridine

To a solution of 5-bromo-2-chlorophenol (1.5 g, 7.23 mmol) in DMF (6 mL) was added potassium carbonate (2.5 g, 18.07 mmol) at RT followed by 2-chloro-5-(trifluoromethyl)

pyridine (1.3 g, 7.23 mmol) and the mixture was refluxed at 110° C. for 12 h. The reaction mixture was quenched with water and extracted with ethyl acetate three times. The total organic extract was washed with water and brine, dried over sodium sulfate and concentrated under reduced pressure to give the title compound (2.6 g, 100%). $^1$H NMR (500 MHz, CDCl$_3$): δ 8.38 (s, 1H), 7.95 (d, J=6.5 Hz, 1H), 7.65 (s, 1H), 7.47 (d, J=2 Hz, 1H), 7.12 (m, 2H).

Step 2

4-Chloro-3-(5-(trifluoromethyl)pyridin-2-yloxy) phenylboronic acid

To a solution of 2-(5-bromo-2-chlorophenoxy)-5-(trifluoromethyl)pyridine (2.6 g, 7.3 mmol) and triisopropylborate (2.0 mL, 8.76 mmol) in toluene (15 mL) and THF (7 mL) under a N$_2$ atmosphere was added n-BuLi (6.8 mL, 10.95 mmol) while maintaining the reaction at −70° C. The reaction was stirred for 1 h at −40° C. Gradually the temperature was increased to −20° C. and then 0° C. The reaction was quenched with 2N HCl and allowed to warm to RT. The reaction mixture was concentrated and extracted with EtOAc. The organic extract was dried over Na$_2$SO$_4$ and concentrated under reduced pressure to give the title compound (2.8 g). $^1$H NMR (500 MHz, DMSO-d$_6$): δ 8.56 (s, 1H), 8.29 (m, 3H), 7.94 (s, 1H), 7.81 (d, J=7.9 Hz, 1H), 7.36 (d, J=8.05 Hz, 2H); m/z (316.4, M$^−$ H$^−$).

Step 3 tert-Butyl 4-(4-chloro-3-(5-(trifluoromethyl)pyridin-2-yloxy)benzylidene)piperidine-1-carboxylate To a solution of 4-chloro-3-(5-(trifluoromethyl)pyridin-2-yloxy)phenylboronic acid (2.8 g, 8.82 mmol) and tert-butyl 4-(bromomethylene)piperidine-1-carboxylate (2.02 g, 7.32 mmol) in THF (10 mL) was added K$_3$PO$_4$ (4.7 g, 26.63 mmol). The air inside the flask was removed under vacuum and flushed with N$_2$ three times. Water (0.56 mL) was added and the system was flushed with N$_2$ again. PdCl$_2$(dppf) (720.3 mg, 0.882 mmol) was added and the system was flushed with N$_2$ two to three times again. The reaction mixture was refluxed at 50° C. for 1 h. The reaction mixture was concentrated, diluted with water and extracted with EtOAc. The organic extract was washed with brine, dried over Na$_2$SO$_4$, and concentrated under reduced pressure. The residue was purified by column chromatography (2.5% EtOAc-97.5% Hexane) to give the pure title compound (280 mg). $^1$H NMR (500 MHz, CDCl$_3$): δ 8.43 (s, 1H), 7.97 (d, J=8.65 Hz, 1H), 7.70 (d, J=1.9 Hz, 1H), 7.55 (d, J=8.35 Hz, 1H), 7.32 (d, J=8.35 Hz, 1H), 7.16 (d, J=8.7 Hz, 1H), 5.99 (s, 1H), 3.44 (m, 4H), 2.39 (m, 2H), 2.24 (m, 2H), 1.47 (s, 9H).

Step 4

2-(2-Chloro-5-(piperidin-4-ylidenemethyl)phenoxy)-5-(trifluoromethyl)pyridine

To a solution of tert-butyl 4-(4-chloro-3-(5-(trifluoromethyl)pyridin-2-yloxy)benzylidene)piperidine-1-carboxylate (280 mg, 0.597 mmol) in CH$_2$Cl$_2$ (3 mL) cooled to 0° C. was added TFA (0.46 mL, 5.97 mmol). The resulting mixture was stirred for 2 h at RT. The reaction was concentrated and then partitioned between saturated NaHCO$_3$ solution and CH$_2$Cl$_2$. The organic extract was dried over Na$_2$SO$_4$, and concentrated under reduced pressure to give the title compound (250 mg).

Step 5

To a solution of 2-(2-chloro-5-(piperidin-4-ylidenemethyl)phenoxy)-5-(trifluoromethyl)pyridine (250 mg, 0.677 mmol) in DMSO (3 mL) was added phenyl pyridin-3-ylcarbamate (137.9 mg, 0.643 mmol) followed by triethylamine (0.24 mL, 1.69 mmol). The resulting mixture was stirred at RT for 12 h. The reaction mixture was diluted with water and extracted with EtOAc. The organic extract was dried over Na$_2$SO$_4$ and concentrated under reduced pressure. The residue was purified by column chromatography (30% acetone-70% hexane) to give the pure title compound (180 mg, 54% yield). $^1$H NMR (500 MHz, CDCl$_3$): δ 8.51 (s, 1H), 8.41 (s, 1H), 8.27 (s, 1H), 8.08 (d, J=7.5 Hz, 1H), 7.95 (d, J=7 Hz, 1H), 7.33 (s, 1H), 7.18 (d, J=3.5 Hz, 2H), 7.12 (d, J=8 Hz, 1H), 6.72 (s, 1H), 6.37 (s, 1H), 3.64 (m, 2H), 3.56 (m, 2H), 2.62 (m, 2H), 2.49 (m, 2H); $^{13}$C NMR (125 MHz, CDCl$_3$): δ164.98, 154.54, 147.45, 145.35, 145.32, 143.84, 141.01, 138.68, 136.94, 136.22, 136.10, 130.79, 128.50, 127.62, 127.07, 126.69, 123.61, 123.45, 122.05, 121.78, 111.19, 45.68, 44.61, 40.91, 35.69, 29.14, 28.47; m/z (489.3, 491.1 M$^+$ H$^+$); HPLC: 96.8%.

Example 60

Synthesis of 4-(4-methyl-3-(5-(trifluoromethyl)pyridin-2-yloxy)benzylidene)-N-(pyridin-3-yl)piperidine-1-carboxamide Step 1

5-Bromo-2-methylphenol

5-Amino-2-methylphenol (5 g, 0.04 mol) was dissolved in HBr (20 mL) and H$_2$O (20 mL) was added dropwise maintaining a temperature below 0° C. The resulting mixture was stirred for 5 min and a solution of NaNO$_2$ (2.76 g, 0.04 mol) in H$_2$O (7.5 mL) was added dropwise. The mixture was stirred for 30 min below 0° C. Then a solution of cuprous bromide (5.73 g, 0.04 mol) in HBr (7.5 mL) cooled to 0° C. was added dropwise. The resulting mixture was warmed to RT and then refluxed for 2 h. The reaction was cooled and filtered through celite. The filtrate was diluted with water and extracted with EtOAc. The organic extract was dried over Na$_2$SO$_4$, and concentrated under reduced pressure. The residue was purified by column chromatography (2.5% EtOAc-97.5% Hexane) to give the pure title compound (1.57 g, 20%). $^1$H NMR (500 MHz, CDCl$_3$): δ 6.97 (s, 3H), 4.89 (s, 1H), 2.19 (s, 3H).

Step 2

2-(5-Bromo-2-methylphenoxy)-5-(trifluoromethyl) pyridine

To a solution of 5-bromo-2-methylphenol (1.0 g, 0.005 mol) in DMF (10 mL) was added K$_2$CO$_3$ (1.38 g, 0.01 mol) at RT. 2-Chloro-5-(trifluoromethyl)pyridine (908 mg, 0.005 mol) was added and the reaction was refluxed at 110° C. for 12 h. The reaction mixture was quenched with water and extracted with EtOAc three times. The organic extract was washed with water and brine, dried over sodium sulfate and concentrated under reduced pressure to give the title compound (1.5 g, 88%). $^1$H NMR (500 MHz, CDCl$_3$): δ 8.42 (s, 1H), 7.92 (d, J=2.15 Hz, 1H), 7.32 (t, J=6.45 1H), 7.23 (d, J=1.5 Hz, 1H), 7.17 (d, J=8.05 Hz, 1H), 7.03 (d, J=8.65 Hz, 1H), 2.12 (s, 3H).

Step 3

4-Methyl-3-(5-(trifluoromethyl)pyridin-2-yloxy) phenylboronic acid 2-(5-Bromo-2-methylphenoxy)-5-(trifluoromethyl)pyridine (1 g, 0.003 mol) and triisopropylborate (0.8 mL, 0.003 mol) were dissolved in toluene (20 mL) and THF (5 mL) and cooled to −78° C. under a N$_2$ atmosphere. n-BuLi (2.69 mL, 0.003 mol) was added while maintaining the reaction at −70° C. and then the reaction was stirred for 1 h at −40° C. Gradually the temperature was increased to −20-0° C. and then the reaction was quenched with 2N HCl. The reaction mixture was warmed to RT, concentrated and extracted with EtOAc. The organic extract was dried over Na$_2$SO$_4$ and concentrated under reduced pressure to give the title compound (1.13 g). m/z (296.4, 298.3, M⁻ H⁻).

Step 4 tert-Butyl 4-(4-methyl-3-(5-(trifluoromethyl)pyridin-2-yloxy)benzylidene)piperidine-1-carboxylate To a solution of 4-methyl-3-(5-(trifluoromethyl)pyridin-2-yloxy)phenylboronic acid (1.13 g, 0.0038 mol) and tert-butyl 4-(bromomethylene)piperidine-1-carboxylate (871 mg, 0.006 mol) in THF (10.5 mL) was added K$_3$PO$_4$ (2.43 g, 0.011 mol). The flask was put under vacuum and flushed with N$_2$ three times. Water (0.19 mL) was added and the system was flushed with N$_2$ again. PdCl$_2$(dppf) (310 mg, 0.0004 mol) was added and the system was flushed with N$_2$ two to three times again. The reaction mixture was refluxed at 50° C. for 1 h. The reaction mixture was concentrated, diluted with water and extracted with EtOAc. The organic extract was washed with brine, dried over Na$_2$SO$_4$, and concentrated under reduced pressure. The residue was purified by column chromatography (2.5% EtOAc-97.5% Hexane) to give the pure title compound (0.50 g). $^1$H NMR (500 MHz, CDCl$_3$): δ 8.42 (s, 1H), 7.90 (dd, J=2.25 Hz, J=8.75 Hz, 1H), 7.24 (d, J=8.0 Hz, 1H), 7.03-6.98 (m, 2H), 6.89 (s, 1H), 6.31 (s, 1H), 3.49 (t, J=5.0 Hz, 2H), 3.40 (t, J=5.5 Hz, 2H), 2.47 (t, J=5 Hz, 2H), 2.30 (s, 3H), 2.13 (s, 3H), 1.46 (s, 9H).

Step 5

2-(2-Methyl-5-(piperidin-4-ylidenemethyl)phenoxy)-5-(trifluoromethyl)pyridine

To a solution of tert-butyl 4-(4-methyl-3-(5-(trifluoromethyl)pyridin-2-yloxy)benzylidene)piperidine-1-carboxylate (0.50 g, 0.0011 mol) in CH$_2$Cl$_2$ (5 mL) cooled to 0° C. under a N$_2$ atmosphere was added TFA (0.85 mL, 0.011 mol) slowly. The resulting mixture was stirred for 2 h at RT. The reaction was concentrated under reduced pressure to give the title compound (440 mg).

Step 6

To a solution of 2-(2-methyl-5-(piperidin-4-ylidenemethyl)phenoxy)-5-(trifluoromethyl)pyridine (440 mg, 0.001 mol) in DMSO (5 mL) was added phenyl pyridin-3-ylcarbamate (278 mg, 0.001 mol) followed by triethylamine (0.4 mL, 0.003 mol). The resulting mixture was stirred at RT for 12 h. The reaction mixture was diluted with water and extracted with EtOAc. The organic extract was dried over Na$_2$SO$_4$ and concentrated under reduced pressure. The residue was purified by column chromatography (30% acetone-70% hexane) to give the pure title compound (0.310 g, 50%). $^1$H NMR (500 MHz, CDCl$_3$): δ 8.45-8.42 (m, 2H), 8.26 (d, J=4.5 Hz, 1H), 8.01 (d, J=7 Hz, 1H), 7.91 (d, J=9 Hz, 1H), 7.25-7.22 (m, 1H), 7.05-6.99 (m, 2H), 6.91 (s, 1H), 6.63 (s, 1H), 6.37 (s, 1H), 3.62 (t, J=5.5 Hz, 2H), 3.53 (t, J=11.5 Hz, 2H), 2.63-2.58 (m, 2H), 2.46 (t, J=5.5 Hz, 2H), 2.14 (s, 3H); $^{13}$C NMR (125 MHz, CDCl$_3$): δ 165.61, 154.45, 151.24, 145.65, 144.06, 141.14, 137.34, 136.77, 136.49, 136.05, 131.34, 128.95, 127.36, 126.42, 124.45, 123.59, 122.18, 110.76, 45.71, 44.60, 35.69, 29.14, 16.09; m/z (469.5, M⁺ H⁺); HPLC: 98.8%.

Example 61

Synthesis of 4-(3-methyl-5-(5-(trifluoromethyl)pyridin-2-yloxy)benzylidene)-N-(pyridin-3-yl)piperidine-1-carboxamide Step 1

2-(3-Bromo-5-methylphenoxy)-5-(trifluoromethyl) pyridine

To a solution of 3-bromo-5-methylphenol (2.0 g, 0.0106 mol) in DMF (15 mL) was added K$_2$CO$_3$ (2.93 g, 0.02 mol) at RT. 2-Chloro-5-(trifluoromethyl)pyridine (1.94 g, 0.0106 mol) was added and the reaction was refluxed at 110° C. for 12 h. The reaction mixture was quenched with water and extracted with EtOAc three times. The total organic extract was washed with water and brine, dried over sodium sulfate and concentrated under reduced pressure to give the title compound (3 g, 84.5%). $^1$H NMR (500 MHz, CDCl$_3$): δ 8.45 (s, 1H), 7.92 (d, J=8.6 Hz, 1H), 7.26 (d, J=14.95 Hz, 1H), 7.13 (s, 1H), 7.03 (d, J=10 Hz, 1H), 6.90 (s, 1H), 2.36 (s, 3H).

Step 2

3-Methyl-5-(5-(trifluoromethyl)pyridin-2-yloxy) phenylboronic acid 2-(3-Bromo-5-methylphenoxy)-5-(trifluoromethyl)pyridine (2 g, 0.006 mol) and triisopropylborate (1.66 mL, 0.0072 mol) were dissolved in toluene (40 mL) and THF (20 mL) and cooled to −78° C. n-BuLi (5.38 mL, 0.006 mol) was added while maintaining the reaction at −70° C. The reaction was stirred for 1 h at −40° C. Gradually the temperature was increased to −20-0° C. and the reaction was quenched with 2NHCl. The reaction mixture was warmed to RT, concentrated and extracted with EtOAc. The organic extract was dried over Na$_2$SO$_4$ and concentrated under reduced pressure to give the title compound (2.16 g).

Step 3 tert-Butyl 4-(3-methyl-5-(5-(trifluoromethyl)pyridin-2-yloxy)benzylidene)piperidine-1-carboxylate To a solution of 3-methyl-5-(5-(trifluoromethyl)pyridin-2-yloxy)phenylboronic acid (2.16 g, 0.007 mol) and tert-butyl 4-(bromomethylene)piperidine-1-carboxylate (1.67 g, 0.006 mol) in THF (20 mL) was added K$_3$PO$_4$ (4.48 g, 0.02 mol). The flask was put under vacuum and flushed with N$_2$ three times. Water (0.36 mL) was added and the system was flushed with N₂ again. PdCl₂(dppf) (571 mg, 0.0007 mol) was added and the system was flushed with N₂ two to three times again. The reaction mixture was refluxed at 50° C. for 1 h. The reaction mixture was concentrated, diluted with water and extracted with EtOAc. The organic extract was washed with brine, dried over Na₂SO₄ and concentrated under reduced pressure, The residue was purified by column chromatography (2.5% EtOAc-97.5% Hexane) to give the pure title compound (0.50 g). ¹H NMR (500 MHz, CDCl₃): δ 8.45 (s, 1H), 7.90 (dd, J=2.07 Hz, J=0.025 Hz, 1H), 7.00 (d, J=8.6 Hz, 1H), 6.90 (s, 1H), 6.81 (d, J=18.5 Hz, 2H), 6.31 (s, 1H), 3.50 (t, J=5.25 Hz, 2H), 3.40 (t, J=5.3 Hz, 2H), 2.47 (t, J=5 Hz, 2H), 2.36 (s, 3H), 2.31 (s, 2H), 1.47 (s, 9H).

Step 4

2-(3-Methyl-5-(piperidin-4-ylidenemethyl)phenoxy)-5-(trifluoromethyl)pyridine

To a solution of tert-butyl 4-(3-methyl-5-(5-(trifluoromethyl)pyridin-2-yloxy)benzylidene)piperidine-1-carboxylate (0.50 g, 0.0011 mol) in CH₂Cl₂ (5 mL) cooled to 0° C. under a N₂ atmosphere was added TFA (0.85 mL, 0.011 mol) slowly. The resulting mixture was stirred for 2 h at RT. The solution was concentrated under reduced pressure to give the title compound (445 mg).

Step 5

To a solution of 2-(3-methyl-5-(piperidin-4-ylidenemethyl)phenoxy)-5-(trifluoromethyl)pyridine (445 mg, 1.276 mmol) in DMSO (3 mL) was added phenyl pyridin-3-ylcarbamate (273 mg, 1.276 mmol) followed by triethylamine (0.53 mL, 3.83 mmol). The resulting mixture was stirred at RT for 12 h. The reaction mixture was diluted with water and extracted with EtOAc. The organic extract was dried over Na₂SO₄ and concentrated under reduced pressure. The residue was purified by column chromatography (30% acetone-70% hexane) to give the pure title compound (0.350 g, 58% yield). ¹H NMR (500 MHz, CDCl₃): δ 8.45 (m, 2H), 8.27 (s, 1H), 8.01 (m, 1H), 7.90 (m, 1H), 7.02 (m, 1H), 6.92 (s, 1H), 6.84 (d, J=20 Hz, 2H), 6.47 (s, 1H), 6.38 (s, 1H), 3.16 (s, 2H), 3.52 (s, 2H), 2.61 (s, 2H), 2.47 (s, 2H), 2.37 (s, 3H); ¹³C NMR (125 MHz, CDCl₃): δ 165.87, 154.81, 153.01, 145.50, 143.77, 141.29, 139.84, 138.79, 137.99, 136.71, 127.58, 126.93, 124.77, 123.58, 122.62, 121.62, 120.13, 118.82, 111.38, 45.72, 44.70, 35.78, 29.20, 21.45; m/z (469.5, M⁺H⁺); HPLC: 98.5%.

Example 62

Synthesis of 4-(3-bromo-5-(5-(trifluoromethyl)pyridin-2-yloxy)benzylidene)-N-(pyridin-3-yl)piperidine-1-carboxamide Step 1

(3-Bromo-5-(5-(trifluoromethyl)pyridin-2-yloxy)phenyl)methanol

To a solution of 3-bromo-5-(hydroxymethyl)phenol (3.0 g, 14.77 mmol) in DMF (15 mL) under a N₂ atmosphere was added potassium carbonate (4.08 g, 29.55 mmol) and the mixture was stirred for 20 min. 2-Chloro-5-(trifluoromethyl) pyridine (2.68 g, 14.77 mmol) was added at RT and then the reaction was refluxed at 110° C. overnight. The reaction mixture was cooled and water was added. The mixture was extracted with ethyl acetate three times. The organic layer was washed with brine, dried over Na₂SO₄ and evaporated to dryness to give the title compound (5.5 g) which was used in the next step without purification. ¹H NMR (500 MHz, CDCl₃): δ 8.44 (s, 1H), 7.92 (d, J=8.5 Hz, 1H), 7.41 (s, 1H), 7.24 (s, 1H), 7.19 (s, 1H), 7.04 (d, J=9 Hz, 1H), 4.71 (s, 2H); m/z (348, 349.9, M⁺H⁺).

Step 2

2-(3-Bromo-5-(chloromethyl)phenoxy)-5-(trifluoromethyl)pyridine

To a solution of (3-bromo-5-(5-(trifluoromethyl)pyridin-2-yloxy)phenyl)methanol (5.5 g, 15.8 mmol) in dry THF (30 mL) cooled to 0° C. was added thionyl chloride (3.22 mL, 44.3 mmol) dropwise. The reaction was warmed to RT and stirred for 2 h. The reaction mixture was then cooled and water was added. The mixture was extracted with ethyl acetate three times. The organic layer was washed with saturated NaHCO₃ solution and brine, dried over Na₂SO₄, and evaporated to dryness to give the title compound (4.7 g). ¹H NMR (500 MHz, CDCl₃): δ 8.44 (s, 1H), 7.93 (d, J=8.5 Hz, 1H), 7.43 (s, 1H), 7.29 (s, 1H), 7.15 (s, 1H), 7.05 (d, J=8.5 Hz, 1H), 4.54 (s, 2H).

Step 3

Diethyl 3-bromo-5-(5-(trifluoromethyl)pyridin-2-yloxy)benzylphosphonate 2-(3-Bromo-5-(chloromethyl)phenoxy)-5-(trifluoromethyl)pyridine (4.7 g, 12.82 mmol) was dissolved in triethylphosphite (18.7 mL, 107.7 mmol) and refluxed at 160° C. for 4 h. It was then purified by silica gel column chromatography (30-40% ethyl acetate/hexane) to give the title compound (3.8 g, 63%). ¹H NMR (500 MHz, CDCl₃): δ 8.42 (s, 1H), 7.91 (d, J=10.75 Hz, 1H), 7.33 (s, 1H), 7.24 (s, 1H), 7.07 (s, 1H), 7.02 (d, J=8.6 Hz, 1H), 4.04 (q, J=7.5 Hz, 4H), 3.14 (s, 1H), 3.10 (s, 1H), 1.25 (t, J=7 Hz, 6H); m/z (468.1, 470.1, M⁺ H⁺).

Step 4 tert-Butyl 4-(3-bromo-5-(5-(trifluoromethyl)pyridin-2-yloxy)benzylidene)piperidine-1-carboxylate To a suspension of sodium hydride (0.292 g, 12.17 mmol) in THF (10 mL) under inert atmosphere cooled to 0° C. was added diethyl 3-bromo-5-(5-(trifluoromethyl)pyridin-2-yloxy)benzylphosphonate (3.8 g, 8.11 mmol) as a solution in THF (10 mL) dropwise. The reaction was stirred for 30 min at 0° C. and tert-butyl 4-oxopiperidine-1-carboxylate (1.62 g, 8.11 mmol) was added as a solution in THF (10 mL). The reaction was stirred at RT for 5 h. The reaction mixture was cooled to 0° C. and quenched with saturated aqueous NH₄Cl. The mixture was extracted with ethyl acetate three times. The organic layer was washed with brine, dried over Na₂SO₄, and evaporated to dryness to give the title compound (4.22 g, 100%). ¹H NMR (500 MHz, CDCl₃): δ 8.44 (s, 1H), 7.92 (d, J=8.5 Hz, 1H), 7.22 (s, 1H), 7.18 (s, 1H), 7.03 (d, J=8.5 Hz, 1H), 6.91 (s, 1H), 6.28 (s, 1H), 3.49 (m, 2H), 3.40 (m, 2H), 2.44 (m, 2H), 2.32 (m, 2H), 1.47 (s, 9H); m/z (513.2, 515.2, M⁺ H⁺).

Step 5

2-(3-Bromo-5-(piperidin-4-ylidenemethyl)phenoxy)-5-(trifluoromethyl)pyridine To a solution of tert-butyl 4-(3-bromo-5-(5-(trifluoromethyl)pyridin-2-yloxy)benzylidene)piperidine-1-carboxylate (1.2 g, 2.33 mmol) in $CH_2Cl_2$ (5 mL) was added trifluoroacetic acid (1.79 mL, 23.37 mmol) at 0° C. The reaction mixture was stirred for 30 min at 0° C. and at RT for 1 h. The reaction mixture was quenched with saturated aqueous $NaHCO_3$ and extracted with $CH_2Cl_2$ three times. The organic layer was washed with brine, dried over $Na_2SO_4$, and evaporated to dryness to give the title compound (1.15 g, 100%). $^1H$ NMR (500 MHz, $CDCl_3$): δ 8.43 (s, 1H), 7.93 (d, J=6.75 Hz, 1H), 7.23 (s, 1H), 7.20 (s, 1H), 7.05 (d, J=8.45 Hz, 1H), 6.89 (s, 1H), 6.39 (s, 1H), 3.23 (m, 2H), 3.12 (m, 2H), 2.75 (m, 2H), 2.64 (m, 2H); m/z (413.2, 415.2, $M^+$ $H^+$).

Step 6

2-(3-Bromo-5-(piperidin-4-ylidenemethyl)phenoxy)-5-(trifluoromethyl)pyridine 2-(3-Bromo-5-(piperidin-4-ylidenemethyl)phenoxy)-5-(trifluoromethyl)pyridine (0.58 g, 1.4 mmol) and phenyl pyridin-3-ylcarbamate (0.3 g, 1.4 mmol) were dissolved in DMSO (3 mL). Triethylamine (0.59 mL, 4.21 mmol) was added and the reaction was stirred overnight. The reaction mixture was diluted with water and extracted with ethyl acetate three times. The organic layer was washed with brine, dried over $Na_2SO_4$, and evaporated to dryness. The residue was purified by silica gel column chromatography (35% acetone in hexane) to give the title compound (0.5 g, 67%). $^1H$ NMR (500 MHz, DMSO-$d_6$): δ 8.44 (s, 2H), 8.25 (d, J=4.4 Hz, 1H), 7.99 (d, J=7.8 Hz, 1H), 7.92 (d, J=10.45 Hz, 1H), 7.22 (m, 2H), 7.20 (s, 1H), 7.04 (d, J=8.6 Hz, 1H), 6.93 (s, 1H), 6.83 (s, 1H), 6.34 (s, 1H), 3.60 (m, 2H), 3.52 (m, 2H), 2.56 (m, 2H), 2.44 (m, 2H). $^{13}C$ NMR (125 MHz, $CDCl_3$): δ 165.16, 154.72, 153.51, 145.38, 143.81, 141.22, 140.33, 139.66, 136.99, 136.36, 128.85, 127.64, 123.63, 123.26, 122.83, 122.48, 120.73, 111.68, 45.59, 44.60, 35.71, 29.29, 29.17; m/z (533.2, 535.2, $M^+$ $H^+$); HPLC: 99.0%.

Example 63

Synthesis of 4-(3-bromo-5-(5-(trifluoromethyl)pyridin-2-yloxy)benzylidene)-N-(pyridazin-3-yl)piperidine-1-carboxamide 2-(3-Bromo-5-(piperidin-4-ylidenemethyl)phenoxy)-5-(trifluoromethyl)pyridine (0.57 g, 1.379 mmol) and phenyl pyridazin-3-ylcarbamate (0.296 g, 1.38 mmol) were dissolved in DMSO (4 mL). Triethylamine (0.57 mL, 4.13 mmol) was added and the reaction was stirred overnight. The reaction mixture was diluted with water and extracted with ethyl acetate three times. The organic layer was washed with brine, dried over $Na_2SO_4$, and evaporated to dryness. The residue was purified by silica gel column chromatography (37% acetone in hexane) to give the title compound (0.486 g, 66%). $^1H$ NMR (500 MHz, DMSO-$d_6$): δ 8.78 (s, 1H), 8.45 (s, 1H), 8.27 (s, 1H), 7.93 (d, J=8.5 Hz, 1H), 7.41 (dd, J=4.75 Hz, 1H), 7.24 (s, 1H), 7.20 (s, 1H), 7.04 (d, J=9 Hz, 1H), 6.94 (s, 1H), 6.35 (s, 1H), 3.69 (m, 2H), 3.60 (m, 2H), 2.58 (m, 2H), 2.17 (m, 2H). $^{13}C$ NMR (125 MHz, $CDCl_3$): δ 165.16, 156.80, 153.50, 145.43, 140.30, 139.57, 136.97, 128.86, 128.09, 124.66, 123.35, 122.86, 122.49, 122.24, 121.98, 120.73, 111.67, 45.55, 44.52, 35.74, 29.29, 29.18; m/z (534.1, 536.1, $M^+$ $H^+$); HPLC: 99.0%.

Example 64

Synthesis of 4-(3-cyclopropyl-5-(5-(trifluoromethyl)pyridin-2-yloxy)benzylidene)-N-(pyridazin-3-yl)piperidine-1-carboxamide

Step 1

Diethyl 3-cyclopropyl-5-(5-(trifluoromethyl)pyridin-2-yloxy)benzylphosphonate To a solution of diethyl 3-bromo-5-(5-(trifluoromethyl)pyridin-2-yloxy)benzylphosphonate (0.93 g, 1.99 mmol) and cyclopropylboronic acid (0.204 g, 2.38 mmol) in THF (5.6 mL) was added potassium phosphate (1.27 g, 5.99 mmol). The mixture was degassed by purging with argon. $PdCl_2$ ($dppf_2$ (162.2 mg, 0.198 mmol) and water (0.11 mL) were added to the reaction mixture and the mixture was degassed again. The reaction was heated at 50° C. for 1 h. The reaction mixture was concentrated and extracted with ethyl acetate three times. The organic layer was washed with brine, dried over $Na_2SO_4$ and evaporated to dryness. The residue was purified by silica gel column chromatography (20% ethyl acetate in hexane) to give the title compound (0.8 g, 94%). $^1H$ NMR (500 MHz, $CDCl_3$): δ 8.42 (s, 1H), 7.87 (d, J=8.5 Hz, 1H), 6.96 (d, J=9 Hz, 1H), 6.90 (s, 1H), 6.86 (s, 1H), 6.73 (s, 1H),), 4.02 (m, 4H), 3.14 (s, 1H), 3.10 (s, 1H), 1.87 (m, 1H), 1.24 (m, 6H), 0.96 (d, J=8.5 Hz, 2H), 0.69 (d, J=5 Hz, 2H); m/z (430.0, $M^+$ $H^+$).

Step 2 tert-Butyl 4-(3-cyclopropyl-5-(5-(trifluoromethyl)pyridin-2-yloxy)benzylidene)piperidine-1-carboxylate To a suspension of sodium hydride (0.11 g, 4.65 mmol) in dry THF (1.5 mL) under an inert atmosphere cooled to 0° C. was added diethyl 3-cyclopropyl-5-(5-(trifluoromethyl)pyridin-2-yloxy)benzylphosphonate (0.8 g, 1.86 mmol) as a solution in THF (6 mL). The mixture was stirred for 30 min at 0° C. N-Boc piperidone (0.37 g, 1.86 mmol) was added as a solution in THF (3 mL) and the mixture was stirred at RT for 5 h. The reaction was cooled to 0° C. and quenched with saturated aqueous ammonium chloride. The mixture was extracted with ethyl acetate three times. The organic layer was washed with brine, dried over $Na_2SO_4$ and evaporated to dryness. The residue was purified by silica gel column chromatography (10% ethyl acetate in hexane) to give the title compound (0.408 g, 46%). $^1H$ NMR (500 MHz, $CDCl_3$): δ 8.45 (s, 1H), 7.87 (d, J=8 Hz, 1H), 6.97 (d, J=8.5 Hz, 1H), 6.79 (s, 1H), 6.74 (s, 1H), 6.68 (s, 1H), 6.30 (s, 1H), 3.49 (m, 2H), 3.39 (m, 2H), 2.45 (m, 2H), 2.31 (m, 2H), 1.88 (m, 1H), 1.46 (s, 9H), 0.96 (d, J=8.5 Hz, 2H), 0.69 (d, J=4.5 Hz, 2H); m/z (475.1, $M^+$ $H^+$).

Step 3

2-(3-Cyclopropyl-5-(piperidin-4-ylidenemethyl)phenoxy)-5-(trifluoromethyl)pyridine To a solution of tert-butyl 4-(3-cyclopropyl-5-(5-(trifluoromethyl)pyridin-2-yloxy)benzylidene)piperidine-1-carboxylate (0.408 g, 0.859 mmol) in dry $CH_2Cl_2$ (5 mL) was added trifluoroacetic acid (1.0 mL, 13.05 mmol) at 0° C. The reaction mixture was stirred for 30 min at 0° C. and at RT for 1 h. The reaction mixture was quenched with saturated aqueous NaHCO$_3$ and extracted with CH$_2$Cl$_2$ three times. The organic layer was washed with brine, dried over Na$_2$SO$_4$ and evaporated to dryness to give the title compound (0.270 g, 84%) which was used in the next step.

Step 4

To a solution of 2-(3-cyclopropyl-5-(piperidin-4-ylidenemethyl)phenoxy)-5-(trifluoromethyl)pyridine (0.15 g, 0.401 mmol) and phenyl pyridin-3-ylcarbamate (85.8 mg, 0.4 mmol) in DMSO (1.5 mL) was added triethylamine (0.55 mL, 4.0 mmol) and the mixture was stirred overnight. The reaction mixture was diluted with water and extracted with ethyl acetate three times. The organic layer was washed with brine, dried over Na$_2$SO$_4$, and evaporated to dryness. The residue was purified by silica gel column chromatography (38% acetone in hexane) to give the title compound (0.13 g, 66%). $^1$H NMR (500 MHz, CDCl$_3$): δ 8.77 (s, 1H), 8.45 (s, 1H), 8.41 (s, 1H), 7.89 (d, J=8.5 Hz, 1H), 7.47 (t, J=4.5 Hz, 1H), 6.99 (d, J=8.5 Hz, 1H), 6.81 (s, 1H), 6.77 (s, 1H), 6.70 (s, 1H), 6.38 (s, 1H), 3.70 (m, 2H), 3.60 (m, 2H), 2.60 (m, 2H), 2.47 (d, 2H), 1.87 (m, 1H), 0.98 (d, J=8 Hz, 2H), 0.70 (d, J=4.5 Hz, 2H). $^{13}$C NMR (125 MHz, CDCl$_3$): δ 165.83, 156.60, 153.17, 146.31, 145.54, 138.65, 137.71, 136.70, 128.20, 124.83, 123.63, 118.77, 116.75, 111.30, 45.64, 44.62, 35.73, 29.21, 15.44, 9.51; m/z (496.2, M$^+$ H$^+$); HPLC: 98.6%.

Example 65

Synthesis of 4-(3-fluoro-5-(5-(trifluoromethyl)pyridin-2-yloxy)benzylidene)-N-(pyridin-3-yl)piperidine-1-carboxamide Step 1

1-Bromo-3-fluoro-5-methoxybenzene

To a solution of 1-bromo-3,5-difluorobenzene (10 g, 0.052 mol) in dry DMF (300 mL) cooled to 0-5° C. was added sodium methoxide (5.60 g, 0.1036 mol) and the reaction mixture was stirred at RT for 24 h. The reaction mixture was extracted with ethyl acetate three times. The organic layer was washed with brine, dried over Na$_2$SO$_4$ and evaporated to dryness to give the title compound (7.5 g, 71%).

Step 2

3-Bromo-5-fluorophenol

To a solution of 1-bromo-3-fluoro-5-methoxybenzene (3.0 g, 0.015 mol) in dry CH$_2$Cl$_2$ (80 mL) under an inert atmosphere and cooled to –30° C. was added 1 M BBr$_3$ (4.27 mL, 0.045 mol) in 21 mL of CH$_2$Cl$_2$ dropwise while maintaining temperature at –30° C. The reaction was stirred for 3 h at 0-5° C. and then the reaction mixture was quenched with aqueous saturated NaHCO$_3$. Water was added and the mixture was extracted with CH$_2$CO$_2$ three times. The organic layer was washed with brine, dried over Na$_2$SO$_4$ and evaporated to dryness to give the title compound (2.54 g, 91%).

Step 3

2-(3-Bromo-5-fluorophenoxy)-5-(trifluoromethyl) pyridine

To a solution of 3-bromo-5-fluorophenol (2.54 g, 0.013 mol) in DMF (12 mL) under a N$_2$ atmosphere was added potassium carbonate (3.59 g, 0.026 mol) and the reaction was stirred for 20 min at RT. 2-Chloro-5-trifluoromethylpyridine (2.4 g, 0.013 mol) was added and the reaction mixture was refluxed at 110° C. overnight. Water was added and the mixture was extracted with ethyl acetate three times. The organic layer was washed with brine, dried over Na$_2$SO$_4$ and evaporated to dryness. The residue was purified by silica gel column chromatography (10% ethyl acetate in hexane) to give the title compound (4.28 g, 96%). $^1$H NMR (500 MHz, CDCl$_3$): δ 8.45 (s, 1H), 7.96 (dd, J=2 Hz, J=8.5 Hz, 1H), 7.16-7.15 (m, 2H), 7.08 (d, J=8.5 Hz, 1H), 6.89-6.85 (m, 1H); m/z (337.9, M$^+$ H$^+$)

Step 4

3-Fluoro-5-(5-(trifluoromethyl)pyridin-2-yloxy)phenylboronic acid 2-(3-Bromo-5-fluorophenoxy)-5-(trifluoromethyl)pyridine (2 g, 0.005 mol) and tri-isopropyl borate (1.6 mL, 0.007 mol) were dissolved in dry THF (40 mL) and toluene (10 mL) under inert atmosphere and cooled to –78° C. n-BuLi (4.48 mL, 0.005 mol) was then added dropwise at –78° C. The reaction was warmed to –20° C. and 2N HCl (2 mL) was added and then the mixture was warmed to RT. The reaction mixture was concentrated and extracted with ethyl acetate three times. The organic layer was washed with brine, dried over Na$_2$SO$_4$ and evaporated to dryness to give the title compound (2.71 g, 70%); m/z (300.4, M$^-$ H$^-$).

Step 5 tert-Butyl 4-(3-fluoro-5-(5-(trifluoromethyl)pyridin-2-yloxy)benzylidene)piperidine-1-carboxylate To a solution of tert-butyl 4-(bromomethylene)piperidine-1-carboxylate (1.1 g, 0.0039 mol) in THF (13 mL) was added 3-fluoro-5-(5-(trifluoromethyl)pyridin-2-yloxy)phenylboronic acid (1.4 g, 4.7 mmol), potassium phosphate (2.5 g, 0.012 mol) and H$_2$O (0.23 mL) and the mixture was degassed using argon. PdCl$_2$(dppf)$_2$ (0.32 g, 0.4 mmol) was added and the mixture was degassed again. The reaction was heated at 50° C. for 1.5 h and then allowed to cool to RT. Water was added and the mixture was extracted with ethyl acetate three times. The organic layer was washed with brine, dried over Na$_2$SO$_4$ and evaporated to dryness. The residue was purified by silica gel column chromatography (2-4% ethyl acetate in hexane) to give the title compound (0.585 g, 19%). $^1$H NMR (500 MHz, CDCl$_3$): δ 8.45 (s, 1H), 7.94 (d, J=8.6 Hz, 1H), 7.05 (d, J=8.65 Hz, 1H), 6.81-6.75 (m, 3H), 6.30 (s, 1H), 3.51 (t, J=5.55 Hz, 2H), 3.42 (t, J=5.6 Hz, 2H), 2.47 (t, J=5.55 Hz, 2H), 2.33 (m, 2H), 1.47 (s, 9H).

Step 6

2-(3-Fluoro-5-(piperidin-4-ylidenemethyl)phenoxy)-5-(trifluoromethyl)pyridine

To a solution of tert-butyl 4-(3-fluoro-5-(5-(trifluoromethyl)pyridin-2-yloxy)benzylidene)piperidine-1-carboxylate (585 mg, 0.001 mol) in dry CH$_2$Cl$_2$ (7 mL) cooled to 0° C. was added trifluoroacetic acid (0.99 mL, 0.012 mol). The reaction mixture was stirred for 30 min at 0° C. and then for 1 h at RT. The reaction mixture was quenched with saturated aqueous NaHCO$_3$ and extracted with CH$_2$Cl$_2$ three times. The organic layer was washed with brine, dried over Na$_2$SO$_4$ and evaporated to dryness to give the title compound (469 mg, 100%). $^1$H NMR (500 MHz, CDCl$_3$): δ 9.82 (m, 1H), 8.43 (s, 1H), 7.95 (d, J=8 Hz, 1H), 7.07 (d, J=9 Hz, 1H), 6.83 (q, J=13.5 Hz, 2H), 6.43 (s, 1H), 3.29 (s, 1H), 3.17 (s, 1H), 2.85 (m, 1H), 2.72 (s, 1H).

Step 7

2-(3-Fluoro-5-(piperidin-4-ylidenemethyl)phenoxy)-5-(trifluoromethyl)pyridine (469 mg, 1.33 mmol) and phenyl pyridin-3-ylcarbamate (273 mg, 1.33 mmol) were dissolved in DMSO (4 mL) and triethylamine (0.53 mL, 3.83 mmol) was added. The reaction was stirred overnight. The reaction mixture was diluted with water and extracted with ethyl acetate three times. The organic layer was washed with brine, dried over Na$_2$SO$_4$ and evaporated to dryness. The residue was purified by silica gel column chromatography (35% acetone in hexane) to give the title compound (500 mg, 80%). $^1$H NMR (500 MHz, CDCl$_3$): δ 8.51 (s, 1H), 8.45 (s, 1H), 8.27 (d, J=4.5 Hz, 1H), 8.08 (d, J=8 Hz, 1H), 7.95 (d, J=9 Hz, 1H), 7.06 (d, J=8.5 Hz, 1H), 6.82 (m, 3H), 6.71 (s, 1H), 6.37 (s, 1H), 3.64 (t, J=5.5 Hz, 2H), 3.56 (t, J=5.5 Hz, 2H), 2.63 (m, 2H), 2.49 (m, 2H); $^{13}$C NMR (125 MHz, CDCl$_3$): δ 165.15, 163.96, 161.99, 154.67, 153.88, 153.79, 145.40, 143.56, 141.00, 140.15, 140.07, 139.38, 136.97, 136.44, 127.78, 124.64, 123.69, 122.49, 122.23, 121.97, 117.60, 112.87, 112.70, 111.71, 107.56, 107.37, 45.59, 44.54, 35.70, 29.18; m/z (473.4 M$^+$ H$^+$); HPLC: 96.6%.

Example 66

Synthesis of 4-(bromo(3-(5-(trifluoromethyl)pyridin-2-yloxy)phenyl)methylene)-N-(pyridin-3-yl)piperidine-1-carboxamide Step 1 tert-Butyl 4-bromo-4-(bromo(3-(5-(trifluoromethyl)pyridin-2-yloxy)phenyl)methyl)piperidine-1-carboxylate To a solution of tert-butyl 4-(3-(5-(trifluoromethyl)pyridin-2-yloxy)benzylidene)piperidine-1-carboxylate (example 1, step 4) (850 mg, 1.96 mmol) in dry CH$_2$Cl$_2$ (5 mL) was added potassium carbonate (136 mg, 0.98 mmol). To this mixture at 0° C., was added a solution of bromine (0.113 mL, 1.12 mmol) in CH$_2$Cl$_2$ (3 mL). After 1.5 h at RT, the reaction was filtered, concentrated and then diluted with EtOAc. The organic layer was washed with water, 0.5 M HCl and brine, dried over MgSO$_4$ and concentrated to give an oil. The residue was purified by silica gel column chromatography (0-5% MeOH/CH$_2$Cl$_2$) to afford the title compound (895 mg, 77% yield) as a white foam.

Step 2 tert-Butyl 4-(bromo(3-(5-(trifluoromethyl)pyridin-2-yloxy)phenyl)methylene)piperidine-1-carboxylate To a solution of tert-butyl 4-bromo-4-(bromo(3-(5-(trifluoromethyl)pyridin-2-yloxy)phenyl)methyl)piperidine-1-carboxylate (890 mg, 1.50 mmol) in MeOH (5 mL) was added 2N NaOH (3 mL). The reaction was stirred at 40° C. for 14 h. The reaction was concentrated and the residue was dissolved in ethyl acetate. Water was added and the pH was adjusted to 2 using concentrated HCl. The organic layer was concentrated and the residue was purified by silica gel column chromatography (0-5% MeOH/CH$_2$Cl$_2$) to afford the title compound (425 mg, 55% yield) as a white solid.

Step 3

2-(3-(Bromo(piperidin-4-ylidene)methyl)phenoxy)-5-(trifluoromethyl)pyridine trifluoroacetate To a solution of tert-butyl 4-(bromo(3-(5-(trifluoromethyl)pyridin-2-yloxy)phenyl)methylene)piperidine-1-carboxylate (0.42 g, 0.82 mmol) in CH$_2$Cl$_2$ (10 mL) was added TFA (3 mL). The pale yellow solution went to a darker yellow solution. The reaction was stirred at room temperature for 5 h. The reaction was concentrated to give the title compound as a solid (235 mg, 54% yield).

Step 4

4-(Bromo(3-(5-(trifluoromethyl)pyridin-2-yloxy)phenyl)methylene)-N-(pyridin-3-yl)piperidine-1-carboxamide A solution of 2-(3-(bromo(piperidin-4-ylidene)methyl)phenoxy)-5-(trifluoromethyl)pyridine trifluoroacetate (624 mg, 0.995 mmol) and phenyl pyridin-3-ylcarbamate (213 mg, 0.995 mmol) in DMSO (5 mL) was treated with triethyamine (0.28 mL, 201 mg, 1.99 mmol) and the mixture was heated to 60° C. After 4 h, the reaction mixture was partitioned between water and ethyl acetate. The organic layer was separated and the aqueous layer was extracted again with ethyl acetate. The combine organic layers were washed with brine and dried over magnesium sulfate, filtered and concentrated. The residue was purified by silica gel column chromatography (0-5% MeOH/CH$_2$Cl$_2$) to afford the title compound as a white foam (329 mg, 62% yield). MS (APCI 10V) AP+ 535.15; $^1$H NMR (400 MHz, DMSO-d$_6$) δ ppm 2.36 (2H) 2.65 (2H) 3.46 (2H) 3.63 (2H) 6.99 (d, J=8.38 Hz, 1H) 7.05 (2H) 7.12 (dd, 1H) 7.35 (1H) 7.62 (1H) 7.87 (dd, J=8.87, 2.05 Hz, 1H) 8.13 (1H) 8.41 (1H) 8.65 (1H) 8.93 (1H) 9.20 (1H)

Example 67

Synthesis of N-(pyridin-3-yl)-4-(1-(3-(5-(trifluoromethyl)pyridin-2-yloxy)phenyl)ethylidene)piperidine-1-carboxamide Step 1 tert-Butyl 4-(1-(3-(5-(trifluoromethyl)pyridin-2-yloxy)phenyl)ethylidene)piperidine-1-carboxylate To a solution of tert-butyl 4-(bromo(3-(5-(trifluoromethyl)pyridin-2-yloxy)phenyl)methylene)piperidine-1-carboxylate (Example 71, step 2) (420 mg, 0.818 mmol) in toluene (10 mL), under N$_2$ was added methyl boronic acid (54 mg, 0.900 mmol), dichloro[1,1'-bis(diphenylphosphino)ferrocene]palladium(II) (60 mg, 0.0818 mmol), potassium carbonate (226 mg, 1.64 mmol) and silver oxide (379 mg, 1.64 mmol). The reaction was heated to 85° C. overnight. The reaction was cooled down and filtered. The filtrate was washed with water and dried over MgSO$_4$. Purification by silica gel column chromatography (0-5% MeOH/CH$_2$Cl$_2$) gave the title compound (291 mg, 79% yield).

Step 2

2-(3-(1-(Piperidin-4-ylidene)ethyl)phenoxy)-5-(trifluoromethyl)pyridine trifluoroacetate To a solution of tert-butyl 4-(1-(3-(5-(trifluoromethyl)pyridin-2-yloxy)phenyl)ethylidene)piperidine-1-carboxylate (265 mg, 0.591 mmol) in $CH_2Cl_2$ (8 mL) was added TFA (2 mL). The reaction was stirred at RT overnight and concentrated to give an oil. This was redissolved in $CH_2Cl_2$ and concentrated to give the title compound as an oil (275 mg, 97% yield).

Step 3

N-(Pyridin-3-yl)-4-(1-(3-(5-(trifluoromethyl)pyridin-2-yloxy)phenyl)ethylidene)piperidine-1-carboxamide To a solution of phenyl pyridin-3-ylcarbamate (120 mg, 0.562 mmol) in DMSO (5 mL) was added 2-(3-(1-(piperidin-4-ylidene)ethyl)phenoxy)-5-(trifluoromethyl)pyridine trifluoroacetate (260 mg, 0.516 mmol), followed by triethylamine (0.16 mL, 1.12 mmol). The reaction was stirred at 60° C. overnight. Water was added and the mixture was extracted with EtOAc. The combined organic layers were washed with brine, dried over $MgSO_4$ and concentrated. The residue was purified by silica gel column chromatography (0-5% MeOH/$CH_2Cl_2$) to give the title compound (161 mg, 61% yield) as a clear oil which formed a foam under high vacuum. MS (APCI 10V) AP+ 469.18; $^1$H NMR (400 MHz, DMSO-$d_6$) δ ppm 1.99 (s, 3H) 2.31 (t, 2H) 2.50 (t, 2H) 3.40 (t, 2H) 3.61 (t, 2H) 6.63 (br. s., 1H) 6.89 (t, 1H) 6.97-7.04 (m, 3H) 7.17-7.22 (m, 1H) 7.37 (t, 1H) 7.89 (dd, 1H) 7.96 (dd, 1H) 8.23 (dd, 1H) 8.41 (dd, 2H).

Example 68

Synthesis of 4-(phenyl(3-(5-(trifluoromethyl)pyridin-2-yloxy)phenyl)methylene)-N-(pyridin-3-yl)piperidine-1-carboxamide Step 1 tert-Butyl 4-(phenyl(3-(5-(trifluoromethyl)pyridin-2-yloxy)phenyl)methylene)piperidine-1-carboxylate To a solution of tert-butyl 4-(bromo(3-(5-(trifluoromethyl)pyridin-2-yloxy)phenyl)methylene)piperidine-1-carboxylate (Example 71, Step 2) (91 mg, 0.18 mmol) in anhydrous toluene (3 mL) and ethanol (3 mL) was added phenyl boronic acid (43.7 mg, 0.358 mmol) and 2M $Na_2CO_3$ (0.53 mL, 1.08 mmol). This solution was degassed for 20 min and Pd(PPh$_3$)$_4$ (19 mg, 10 mol %) was added. The reaction was heated at 90° C. overnight. The reaction was cooled and extracted with EtOAc (3×). The organic layer was dried over $MgSO_4$ and concentrated. Purification by silica gel column chromatography (0-5% MeOH/$CH_2Cl_2$) gave the title compound as a foam (60 mg, 66% yield).

Step 2

2-(3-(Phenyl(piperidin-4-ylidene)methyl)phenoxy)-5-(trifluoromethyl)pyridine trifluoroacetate To a solution of tert-butyl 4-(phenyl(3-(5-(trifluoromethyl)pyridin-2-yloxy)phenyl)methylene)piperidine-1-carboxylate in $CH_2Cl_2$ (3 mL) was added trifluoroacetic acid (0.5 mL). The reaction was stirred overnight. The reaction was concentrated, redissolved in $CH_2Cl_2$ and concentrated again to give the title compound as an oil (33.7 mg, 70% yield).

Step 3

To a solution of phenyl pyridin-3-ylcarbamate (27.1 mg, 0.127 mmol) in DMSO (3 mL) was added 2-(3-(phenyl(piperidin-4-ylidene)methyl)phenoxy)-5-(trifluoromethyl)pyridine trifluoroacetate (52 mg, 0.13 mmol), followed by triethylamine (0.018 mL, 0.127 mmol). The reaction was stirred at 60° C. for 3 h and then cooled to RT. The reaction mixture was partitioned between water and ethyl acetate. The organic layer was washed with water and saturated aqueous $NH_4Cl$, dried and concentrated. Purification by silica gel column chromatography (0-5% MeOH/$CH_2Cl$) gave an oil. Diethyl ether was added followed by $CH_2Cl_2$ and the title compound crashed out as a solid (9.2 mg, 13% yield). MS (APCI 10V) AP+ 531.23; $^1$H NMR (400 MHz, CDCl$_3$) δ ppm 2.43 (t, 2H) 2.50 (t, 2H) 3.51-3.58 (m, 4H) 6.75 (s, 1H) 6.90-6.92 (m, 1H) 6.94-7.04 (m, 2H) 7.12 (dd, 2H) 7.17-7.23 (m, 3H) 7.26-7.37 (m, 3H) 7.86 (dd, 1H) 7.97 (dd, 1H) 8.23 (br. s., 1H) 8.42 (s, 2H).

Example 69

Synthesis of 4-(fluoro(3-(5-(trifluoromethyl)pyridin-2-yloxy)phenyl)methylene)-N-(pyridin-3-yl)piperidine-1-carboxamide Step 1

2-(3-Bromophenoxy)-5-(trifluoromethyl)pyridine

To a solution of 3-bromophenol (5 g, 27.54 mmol) and 2-chloro-5-(trifluoromethyl)pyridine (4.52 g, 26.16 mmol) in DMF (30 mL) was added $K_2CO_3$ and the mixture was refluxed at 110° C. overnight. Distilled water (30 mL) and diethyl ether (30 mL) were added and the mixture was stirred for 30 min. The ether layer was dried over $Na_2SO_4$ and concentrated to give pure pure title compound (8.0 g). $^1$H NMR (500 MHz, CDCl$_3$): δ 7.0 (d, 1H, J=10 Hz), 7.1 (d, 1H, J=1.5 Hz), 7.2-7.3 (m, 2H), 7.4 (d, 1H, J=8 Hz), 7.9 (m, 1H), 8.4 (s, 1H).

Step 2

3-(5-(Trifluoromethyl)pyridin-2-yloxy)benzaldehyde

To a solution of 2-(3-bromophenoxy)-5-(trifluoromethyl)pyridine (8.0 g, 25.15 mmol) in THF under inert atmosphere at −78° C. was added DMF (3.8 mL, 50.3 mmol) dropwise, followed by n-BuLi (31.4 mL, 50.3 mmol) dropwise. The reaction mixture was stirred for 1 h. The reaction mixture was quenched with saturated $NH_4Cl$ solution and the temperature was allowed to warm to room temperature. The mixture was extracted with ethyl acetate, dried over $Na_2SO_4$, and concentrated to dryness. Purification by column chromatography (EtOAc:Hexane, 40:60) gave the pure title compound (1.6 g). $^1$H NMR (500 MHz, CDCl$_3$): δ 7.1 (d, 1H, J=8.5 Hz), 7.4 (m, 1H), 7.6 (m, 1H), 7.7 (d, 1H, J=7.5 Hz), 7.9 (1H), 8.4 (s, 1H), 10.0 (s, 1H).

Step 3

Diethyl hydroxy(3-(5-(trifluoromethyl)pyridin-2-yloxy)phenyl)methylphosphonate To an ethereal solution of 3-(5-(trifluoromethyl)pyridin-2-yloxy)benzaldehyde (1.6 g, 5.98 mmol) and LiClO$_4$ (5 mL, 5 M solution in diethylether) was added triethyl phosphite (1.24 g, 7.48 mmol) and TMSCl (0.813 g, 7.48 mmol) at 0° C. The reaction mixture was allowed to reach RT and stirred for 10 min. The reaction was quenched by adding distilled water (10 mL), extracted with CH$_2$Cl$_2$, dried and concentrated to dryness. The residue was purified by column chromatography (1:1 EtOAc:Hexane) to afford pure title compound (1.3 g). $^1$H NMR (500 MHz, CDCl$_3$): δ 1.2 (m, 6H), 2.9 (m, 1H), 4.0 (m, 4H), 5.0 (d, 1H, J=11 Hz), 7.0 (d, 1H, J=8.5 Hz), 7.1 (d, 1H, J=7.5 Hz), 7.3 (s, 1H), 7.4 (m, 1H), 7.8 (m, 1H), 8.4 (s, 1H).

Step 4

Diethyl fluoro(3-(5-(trifluoromethyl)pyridin-2-yloxy)phenyl)methylphosphonate To a solution of diethyl hydroxy(3-(5-(trifluoromethyl)pyridin-2-yloxy)phenyl)methylphosphonate (1.3 g, 3.2 mmol) in dry CH$_2$Cl$_2$ at −78° C. was added DAST (0.3 mL, 3.82 mmol) dropwise very slowly. The reaction mixture was allowed to reach RT, and stirred for 2 h. After completion of the reaction, excess DAST was quenched with water at 0° C. The mixture was extracted with CH$_2$Cl$_2$, dried and concentrated to dryness, and the residue was purified by column chromatography to give the pure title compound (940 mg). $^1$H NMR (500 MHz, CDCl$_3$): δ 1.2 (m, 6H), 4.1 (m, 4H), 5.7 (dd, 1H, J=45 Hz, 5 Hz), 7.0 (d, 1H, J=10 Hz), 7.1 (d, 1H, J=5 Hz), 7.2-7.4 (m, 4H), 7.9 (m, 1H), 8.4 (s, 1H).

Step 5 tert-Butyl 4-(fluoro(3-(5-(trifluoromethyl)pyridin-2-yloxy)phenyl)methylene)piperidine-1-carboxylate NaH (166 mg, 6.92 mmol) under a N$_2$ atmosphere was washed with n-pentane and dried blowing N$_2$ gas. THF (5 mL) was added and the mixture was cooled to 0° C. Diethyl fluoro(3-(5-(trifluoromethyl)pyridin-2-yloxy)phenyl)methylphosphonate (940 mg, 2.3 mmol) was added as a solution in THF dropwise and the mixture was stirred for 30 min. tert-Butyl 4-oxopiperidine-1-carboxylate as a solution in THF was added dropwise and the reaction was stirred for 1 h. Excess NaH was quenched with water at 0° C. and the mixture was extracted with ethyl acetate. The organic layer was dried and concentrated to dryness. The residue was purified by column chromatography to give the pure title compound (600 mg). $^1$H NMR (500 MHz, CDCl$_3$): δ 1.4 (s, 9H), 2.0 (m, 2H), 2.4 (m, 2H), 3.4 (m, 2H), 3.5 (m, 2H), 7.0 (d, 1H, J=8.5 Hz), 7.1-7.2 (m, 4H), 7.4 (t, 1H, J=8 Hz), 7.9 (d, 1H, J=8.5 Hz), 8.4 (s, 1H).

Step 6

2-(3-(fluoro(piperidin-4-ylidene)methyl)phenoxy)-5-(trifluoromethyl)pyridine To a solution of tert-butyl 4-(fluoro(3-(5-(trifluoromethyl)pyridin-2-yloxy)phenyl)methylene)piperidine-1-carboxylate (600 mg, 1.32 mmol) in CH$_2$Cl$_2$ (10 mL) was added TFA (0.98 mL, 13.26 mmol) dropwise maintaining ice-cooled conditions. The mixture was stirred for 1 h. The TFA was evaporated and the reaction mixture was partitioned between saturated NaHCO$_3$ solution and CH$_2$Cl$_2$. The organic layer was dried over Na$_2$SO$_4$ and concentrated under reduced pressure to give the title compound (340 mg). $^1$H NMR (500 MHz, CDCl$_3$): δ 2.3 (m, 2H), 2.6 (m, 2H), 2.8 (m, 2H), 2.9 (m, 2H), 7.0 (d, 1H, J=8.5 Hz), 7.1-7.4 (m, 4H), 7.9 (d, 1H, J=2 Hz), 8.4 (s, 1H).

Step 7

To a solution of 2-(3-(fluoro(piperidin-4-ylidene)methyl)phenoxy)-5-(trifluoromethyl)pyridine (110 mg, 0.312 mmol) and phenyl pyridin-3-ylcarbamate (66.8 mg, 0.312 mmol) in DMSO (2 mL) under N$_2$ was added 3 drops of triethyl amine and the reaction mixture was stirred for 12 h. The reaction mixture was diluted with water and extracted with EtOAc. The organic layer was washed several times with water to remove the excess DMSO. The title compound was crystallized from CH$_2$Cl$_2$ and hexane to give the pure title compound (110 mg). $^1$H NMR (500 MHz, CDCl$_3$): δ 2.5 (brs, 2H), 2.6 (brs, 2H), 3.7 (brs, 2H), 3.8 (brs, 2H), 7.0 (d, 1H, J=8.5 Hz), 7.1-7.3 (m, 3H), 7.4 (t, 1H, J=8.5), 7.7 (d, 1H, J=5.5 Hz), 7.9 (d, 1H, J=8 Hz), 8.0 (s, 1H), 8.4 (s, 1H), 9.2 (d, 1H, J=8.5 Hz), 9.6 (brs, 1H), 9.8 (brs, 1H); $^{13}$CNMR (125 MHz, CDCl$_3$): 11.4, 14.3, 22.6, 25.5, 27.7, 31.5, 40.8, 44.1, 44.4, 53.4, 111.6, 114.0, 115.5, 119.8, 121.3, 121.4, 121.7, 122.5, 123.8, 125.3, 128.2, 129.6, 133.5, 133.8, 136.8, 140.5, 142.8, 145.3, 151.8, 153.0, 154.7, 156.7, 165.4; m/z (473.3 M$^+$ H$^+$); HPLC: 94.2%.

Example 70

Synthesis of 4-(fluoro(3-(5-(trifluoromethyl)pyridin-2-yloxy)phenyl)methylene)-N-(6-methylpyridin-3-yl)piperidine-1-carboxamide To a solution of 2-(3-(fluoro(piperidin-4-ylidene)methyl)phenoxy)-5-(trifluoromethyl)pyridine (110 mg, 0.312 mmol) and phenyl 6-methylpyridin-3-ylcarbamate (71.2 mg, 0.312 mmol) in DMSO (5 mL) under a N$_2$ atmosphere was added 5 drops of triethyl amine and the reaction mixture was stirred for 12 h. The reaction mixture was diluted with water and extracted with EtOAc. The organic layer was washed with water several times to remove the excess DMSO. The title compound was crystallized from hexane and diethyl ether to give the pure title compound (90 mg). $^1$H NMR (500 MHz, CDCl$_3$): δ 2.5 (brs, 2H), 2.6 (brs, 2H), 2.8 (s, 3H), 3.7 (brs, 2H), 3.8 (brs, 2H), 7.0 (d, 1H, J=7.5 Hz), 7.1-7.3 (m, 3H), 7.4 (m, 2H), 7.9 (d, 1H, J=7.5 Hz), 8.4 (s, 1H), 9.0 (d, 1H, J=8.5 Hz), 9.4 (s, 1H), 9.8 (s, 1H); $^{13}$C NMR (125 MHz, CDCl$_3$): 22.6, 25.6, 27.8, 44.2, 44.4, 53.4, 111.6, 114.1, 114.3, 121.4, 122.0, 123.8, 125.3, 129.7, 130.0, 133.8, 134.7, 136.9, 138.7, 145.4, 151.8, 153.0, 154.6, 165.4; m/z (487.4 M$^+$ H$^+$); HPLC: 98.9%; MP: 158-160° C.

Example 71

Synthesis of 4-(fluoro(3-(5-(trifluoromethyl)pyridin-2-yloxy)phenyl)methylene)-N-(6-methoxypyridin-3-yl)piperidine-1-carboxamide To a solution of 2-(3-(fluoro(piperidin-4-ylidene)methyl)phenoxy)-5-(trifluoromethyl)pyridine (110 mg, 0.312 mmol) and phenyl 6-methoxypyridin-3-ylcarbamate (76.2 mg, 0.312 mmol) in DMSO (5 mL) under a N$_2$ atmosphere was added 5 drops of triethyl amine and the reaction mixture was stirred for 12 h. The reaction mixture was diluted with water and extracted with EtOAc. The organic layer was washed with water several times to remove the excess DMSO. The title compound was crystallized from hexane and diethyl ether to give the pure title compound (70 mg). $^1$H NMR (500 MHz, CDCl$_3$): δ 2.5 (brs, 2H), 2.6 (brs, 2H), 3.5 (brs, 2H), 3.6 (brs, 2H), 4.0 (s, 3H), 6.7 (d, 1H, J=9 Hz), 7.0 (d, 1H, J=8.5 Hz), 7.1-7.3 (m, 3H), 7.4 (t, 1H, J=8.5 Hz), 7.9 (m, 1H), 8.1 (s, 1H), 8.4 (s, 1H); $^{13}$CNMR (125 MHz, CDCl$_3$): 25.5, 27.7, 29.7, 44.0, 44.3, 53.8, 60.4, 110.3, 111.6, 114.2, 114.3, 121.3, 121.4, 121.7, 122.0, 122.5, 124.7, 125.3, 129.6, 129.9, 133.6, 133.8, 134.1, 136.8, 138.5, 145.3, 145.4, 149.9, 151.8, 153.0, 155.2, 160.3, 165.4; m/z (503.3 M$^+$ H$^+$); HPLC: 97.6%.

Example 72

Synthesis of 4-{3-[(4-methylpyridin-2-yl)oxy]benzylidene}-N-pyridin-3-ylpiperidine-1-carboxamide Step 1
[3-(4-Methyl-pyridin-2-yloxy)-phenyl]-methanol 3-Hydroxymethyl-phenol (3.69 g, 29.7 mmol), 2-fluoro-3-methyl-pyridine (3.00 g, 27 mmol,) and cesium carbonate (9.68 g, 29.7 mmol) were suspended in dimethylsulfoxide (25 mL) and heated to 110° C. After stirring for 16 h, reaction partitioned between water (250 mL) and ethyl acetate (250 mL). The organic layer was separated and the aqueous was extracted again with ethyl acetate. The combined organic layer was dried over sodium sulfate, filtered and concentrated to give a residue. The residue was purified by silica gel chromatography (10-75%, EtOAc:heptane) to afford the desired product (4.75 g, 81%) as a thick oil.

Step 2
2-(3-Chloromethyl-phenoxy)-4-methyl-pyridine

[3-(4-Methyl-pyridin-2-yloxy)-phenyl]-methanol from Step 1 (4.75 g, 22.1 mmol), in dichloromethane (50 mL), was cooled to 0° C., and treated dropwise with thionyl chloride (1.93 mL, 26.5 mmol). The reaction mixture was allowed to warm to ambient temperature and was stirred for 3 h. Saturated aqueous sodium bicarbonate (20 mL) was added and the mixture was stirred at rt for 5 min. The organic layer was separated, dried over sodium sulfate, filtered and concentrated by evaporation to afford the desired product (5.16 g, 99% yield) as an oil.

Step 3
[3-(4-Methyl-pyridin-2-yloxy)-benzyl]-phosphonic acid diethyl ester 2-(3-Chloromethyl-phenoxy)-4-methyl-pyridine (5.16 g, 22 mmol) from Step 2 was treated neat with triethylphosphite (4.68 mL, 27.3 mmol) and heated to 150° C. After 16 h, the reaction mixture was cooled to room temperature and partioned between water and ethyl acetate. The organic layer was separated and the aqueous was extracted again with ethyl acetate. The combined organic layer was dried over sodium sulfate, filtered and concentrated to give a residue. The residue was purified by silica gel chromatography (30-60%, EtOAc:DCM) to afford the desired product (2.9 g, 40% yield) as a thick oil.

Step 4 4-[3-(4-Methyl-Pyridin-2-yloxy)-benzylidene]-piperidine-1-carboxylic acid tert-butyl ester

[3-(4-Methyl-pyridin-2-yloxy)-benzyl]-phosphonic acid diethyl ester (2.9 g, 8.6 mmol) from Step 3 and 1,4,7,10,13-pentaoxacyclopentadecane (15-Crown-5, 0.03 mL, 0.17 mmol) were combined in THF (10 mL). Sodium hydride (381 mg, 60% dispersion in mineral oil, 9.51 mmol) was added. The reaction was stirred for 30 minutes and then a solution of 4-oxo-piperidine-1-carboxylic acid tert-butyl ester (1.90 g, 9.51 mmol) in THF (10 mL) was added. After 16 hours, water was added and the layers were separated. The aqueous layer was extracted with EtOAc (2×200 mL) and the combined organic layer was dried over anhydrous sodium sulfate, filtered and concentrated. The residue was purified by silica gel chromatography (10-30%, EtOAc:heptane) to afford the desired product (1.15 g, 35% yield) as a thick oil.

Step 5 4-Methyl-2-(3-piperidin-4-ylidenemethyl-phenoxy)-pyridine hydrochloride

4-[3-(4-Methyl-pyridin-2-yloxy)-benzylidene]-piperidine-1-carboxylic acid tert-butyl ester (1.15 g, 2.9 mmol) from Step 4 was dissolved in DCM (10 mL) and treated with HCl in dioxane (4.34 mL, 4.0 M, 17.3 mmol). After 16 hours the reaction was concentrated in vacuo to provide the title compound as a white solid (1.6 g).

Step 6 4-{3-[(4-methylpyridin-2-yl)oxy]benzylidene}-N-pyridin-3-ylpiperidine-1-carboxamide 4-Methyl-2-(3-piperidin-4-ylidenemethyl-phenoxy)-pyridine hydrochloride (530 mg, 1.5 mmol, from Step 5), pyridin-3-yl-carbamic acid phenyl ester (402 mg, 1.88 mmol, prepared according to the procedure described in *Synthesis*, 1997, 1189-1194 from 3-aminopyridine) and triethylamine (0.836 mL, 6.0 mmol) were combined in acetonitrile (10 mL) and stirred at room temperature. After 16 hours, the reaction was concentrated forming a residue and the residue was partitioned between EtOAc and water. The organic layer was separated, dried over anhydrous sodium sulfate, filtered and concentrated. The residue was purified by silica gel chromatography (0-5%, (8:1 EtOH:conc. NH$_4$OH):DCM) to afford the desired product (429 mg) as a foamy white solid. MS (APCI 10V) AP+ 401.4, 281.2 1H NMR (400 MHz, METHANOL-d$_4$) δ ppm 2.35 (s, 3H) 2.45 (td, J=5.82, 0.99 Hz, 2H) 2.57 (td, J=5.81, 1.11 Hz, 2H) 3.51-3.57 (m, 2H) 3.61-3.67 (m, 2H) 6.44 (s, 1H) 6.73-6.80 (m, 1H) 6.90-6.95 (m, 2H) 6.97 (dt, J=5.18, 0.61 Hz, 1H) 7.08 (d, J=8.02 Hz, 1H) 7.30-7.42 (m, 2H) 7.91 (ddd, J=8.38, 2.58, 1.45 Hz, 1H) 7.98 (d, J=5.24 Hz, 1H) 8.16 (dd, J=4.81, 1.40 Hz, 1H) 8.58 (d, J=2.51 Hz, 1H)

Example 73

Synthesis of 4-{3-[(4-methylpyridin-2-yl)oxy]benzylidene}-N-pyridazin-3-ylpiperidine-1-carboxamide 4-Methyl-2-(3-piperidin-4-ylidenemethyl-phenoxy)-pyridine hydrochloride (530 mg, 1.5 mmol, from Example 72, Step 5), pyridazin-3-yl-carbamic acid phenyl ester (404 mg, 1.88 mmol, prepared according to the procedure described in *Synthesis*, 1997, 1189-1194 from 3-aminopyridazine) and triethylamine (0.79 mL, 5.66 mmol) were combined in acetonitrile (10 mL) and stirred at room temperature. After 16 hours, the reaction was concentrated forming a residue and the residue was partitioned between EtOAc and water. The organic layer was separated, dried over anhydrous sodium sulfate, filtered and concentrated. The residue was purified by silica gel chromatography (60-100% EtOAc/DCM) to afford the desired product (289 mg) as a white foam. MS (APCI 10V) AP+ 402.0, 281.1 1H NMR (400 MHz, METHANOL-d$_4$) δ ppm 2.34 (s, 3H) 2.45 (td, J=5.72, 1.18 Hz, 2H) 2.57 (td, J=5.68, 1.17 Hz, 2H) 3.53-3.61 (m, 2H) 3.62-3.74 (m, 2H) 6.44 (s, 1H) 6.76 (dt, J=1.40, 0.76 Hz, 1H) 6.87-6.95 (m, 2H) 6.96 (ddd, J=5.28, 1.40, 0.63 Hz, 1H) 7.07 (d, J=7.55 Hz, 1H) 7.36 (dd, J=8.78, 7.71 Hz, 1H) 7.58 (dd, J=9.05, 4.67 Hz, 1H) 7.97 (d, J=5.51 Hz, 1H) 8.11 (d, J=8.77 Hz, 1H) 8.78 (d, J=4.73 Hz, 1H)

Examples 74-84

Step 1

4-(3-(5-(trifluoromethyl)pyridin-2-yloxy)benzylidene)piperidine-1-carbonyl chloride A 100 mL round-bottomed flask was fitted with a stirring bar and dropping funnel. To the reaction flask was added dichloromethane (30 mL) and the vessel was set to chill in an ice/water bath. To the flask was added 19% v/v phosgene in toluene (6 mL). 2-(3-piperidin-4-ylidenemethyl-phenoxy)-5-trifluoromethyl-pyridine hydrochloride (3.34 g, 9 mmol, from Example 1a, Step 5) was dissolved in a 15% v/v solution of diisopropylethylamine in dichloromethane and added to the chilled reaction flask slowly using the dropping funnel. Upon addition, the solution was stirred at 0° C. for 1 h. Upon completion of the reaction, the solvent and excess phosgene were removed in vacuo. A 0.2 M stock solution of the residue in dichloroethane was prepared for use in the next step (45 mL).

Step 2

A 0.02 M solution of 4-dimethylaminopyridine in 10% diisopropylamine in dichloroethane (0.5 mL, 0.1 equiv 4-dimethylaminopyridine) was added to the appropriate arylamine (0.1 mmol) followed by acetonitrile (0.5 mL). The vials were capped and shaken vigorously to effect dissolution. Upon dissolution, the solution of 4-(3-(5-(trifluoromethyl)pyridin-2-yloxy)benzylidene)piperidine-1-carbonyl chloride in dichloroethane (0.2 M, 0.5 mL, 0.1 mmol, 1 equiv; from Step 1) was added. The vials were capped and heated to 70° C. for 16 h. The reactions were concentrated in vacuo. The residues were reconstituted in DMSO and purified by preparative reverse-phase HPLC (acetonitrile/water/0.05% trifluoroacetic acid) to afford Examples 74-84.

| Ex. | Name | Characterization |
|---|---|---|
| 74 | 4-(3-ethoxy-5-{[5-(trifluoromethyl)pyridin-2-yl]oxy}benzylidene)-N-pyridin-3-ylpiperidine-1-carboxamide trifluoroacetate | LCMS (ELSD) MH$^+$ = 444.4; $^1$H NMR (400 MHz, DMSO-d$_6$) δ ppm 2.40-2.48 (m, 2H) 2.52 (m, 2H) 3.72 (m, 2H) 3.81 (m, 2H) 5.72 (d, J = 4 Hz 1H) 6.41 (s, 1H) 7.07 (bs, 2H) 7.15 (d, J = 8 Hz, 1H) 7.25 (d, J = 8 Hz, 1H) 7.40-7.44 (m, 1H) 7.86 (d, J = 4 Hz, 1H) 8.23 (dd, J = 10 Hz, 4 Hz, 1H) 8.58 (s, 1H) |
| 75 | N-isoxazol-4-yl-4-(3-{[5-(trifluoromethyl)pyridin-2-yl]oxy}benzylidene)piperidine-1-carboxamide | LCMS (ELSD) MH$^+$ 445.0; 1H NMR (400 MHz, DMSO-d$_6$) δ ppm 2.35 (m, 2H) 2.46 (m, 2H) 3.45 (m, 2H) 3.52 (m, 2H) 6.41 (s, 1H) 7.06 (s, 1H) 7.07 (bs, 2H) 7.13 (d, J = 4 Hz, 1H) 7.25 (d, J = 2.5 Hz, 1H) 7.40-7.44 (m, 1H) 8.23 (dd, J = 8 Hz, 4 Hz, 1H) 8.54 (s, 1H) 8.58 (s, 1H) 8.91 (s, 1H). |
| 76 | N-pyridin-4-yl-4-(3-{[5-(trifluoromethyl)pyridin-2-yl]oxy}benzylidene)piperidine-1-carboxamide trifluoroacetate | LCMS (ELSD) MH$^+$ 458.1; 1H NMR (400 MHz, DMSO-d$_6$) δ ppm 2.43 (m, 2H) 2.53 (m, 2H) 3.56 (m, 2H) 3.63 (m, 2H) 6.44 (s, 1H) 6.88 (m, 1H) 7.07 (m, 2H) 7.17 (d, J = 8 Hz, 1H) 7.25 (d, J = 8 Hz, 1H) 7.43 (m, 1H) 7.79 (m, 2H) 8.22 (d, J = 8 Hz, 1H) 8.47 (m, 2H), 8.76 (m, 1H) 10.05 (s, 1H). |
| 77 | N-(1-methyl-1H-pyrazol-3-yl)-4-(3-{[5-(trifluoromethyl)pyridin-2-yl]oxy}benzylidene)piperidine-1-carboxamide | LCMS (ELSD) MH$^+$ 458.1; 1H NMR (400 MHz, DMSO-d$_6$) δ ppm δ ppm 2.31 (m, 2H) 2.45 (m, 2H) 3.44 (m, 2H) 3.52 (m, 2H) 3.70 (s, 3H) 6.38 (s, 1H) 7.06 (m, 2H) 7.14 (d, J = 8 Hz, 1H) 7.24 (d, J = 8 Hz, 1H) 7.42 (m, 1H) 7.45 (s, 1H) 8.25 (d, J = 4 Hz, 1H) 8.57 (bs, 1H) 8.94 (s, 1H). |
| 78 | N-(2-methyl-2H-1,2,3-triazol-4-yl)-4-(3-{[5-(trifluoromethyl)pyridin-2-yl]oxy}benzylidene)piperidine-1-carboxamide | LCMS (ELSD) MH$^+$ 459.4; 1H NMR (400 MHz, DMSO-d$_6$) δ ppm 2.32 (m, 2H) 2.44 (m, 2H) 3.47 (m, 2H) 3.54 (m, 2H) 4.01 (s, 3H) 6.39 (s, 1H) 7.06 (m, 2H) 7.15 (d, J = 8 Hz, 1H) 7.25 (d, J = 8 Hz, 1H) 7.42 (t, 1H) 7.45 (s, 1H) 8.24 (dd, J = 8 Hz, 4 Hz, 1H) 8.57 (bs, 1H) 8.94 (s, 1H). |
| 79 | N-(3-hydroxypyridin-2-yl)-4-(3-{[5-(trifluoromethyl)pyridin-2-yl]oxy}benzylidene)piperidine-1-carboxamide trifluoroacetate | LCMS (ELSD) MH$^+$ 471.4; 1H NMR (400 MHz, DMSO-d$_6$) δ ppm 2.43 (m, 2H) 2.60 (m, 2H) 3.53 (m, 2H) 3.66 (m, 2H) 6.5 (s, 1H) 6.79 (t, J = 8 Hz, 8 Hz, 2H) 7.07 (m, 2H) 7.22 (d, J = 8 Hz, 1H) 7.25 (d, J = 8 Hz, 1H) 7.44 (t, J = 8 Hz, 8 Hz, 1H) 7.77 (d, J = 4 Hz, 1H) 8.24 (dd, J = 8 Hz, 2 Hz, 1H) 8.57 (s, 1H). |
| 80 | N-(3-ethyl-1H-pyrazol-5-yl)-4-(3-{[5-(trifluoromethyl)pyridin-2- | LCMS (ELSD) MH$^+$ 472.4; 1H NMR (400 MHz, DMSO-d$_6$) δ ppm 1.11 (t, J = 7.69 Hz, 3H) |

-continued

| Ex. | Name | Characterization |
|---|---|---|
| | yl]oxy}benzylidene)piperidine-1-carboxamide trifluoroacetate | 2.36 2.44 (m, 4H) 2.56 (m, 2H) 3.68 (m, 4H) 5.84 (br. s., 2H) 6.41 (s, 1H) 7.03-7.07 (m, 2H) 7.16 (d, J = 8 Hz, 1H) 7.23 (d, J = 8 Hz, 1H) 7.42 (t, J = 8 Hz, 1H) 8.22 (dd, J = 8 Hz, 4 Hz, 1H) 8.56 (s, 1H). |
| 81 | N-(1-ethyl-1H-1,2,4-triazol-5-yl)-4-(3-{[5-(trifluoromethyl)pyridin-2-yl]oxy}benzylidene)piperidine-1-carboxamide trifluoroacetate | LCMS (ELSD) MH+ 473.0; 1H NMR (400 MHz, DMSO-$d_6$) δ ppm 1.3 (m, 3H) 2.4 (m, 2H) 2.6 (m, 2H) 3.2 (m, 2H) 3.5 (m, 2H) 3.89 (m, 2H) 6.45 (m, 1H) 7.08 (m, 2H) 7.18 (m, 1H) 7.25 (m, 2H) 7.44 (m, 1H) 8.22 (d, J = 8 1H) 8.57 (s, 1H). |
| 82 | N-[3-(hydroxymethyl)phenyl]-4-(3-{[5-(trifluoromethyl)pyridin-2-yl]oxy}benzylidene)piperidine-1-carboxamide | LCMS (ELSD) MH+ 484.4; 1H NMR (400 MHz, DMSO-$d_6$) δ ppm 2.36 (m, 2H) 2.37 (m, 2H) 3.48 (m, 2H) 3.54 (m, 2H) 4.44 (d, J = 5 Hz, 2H) 5.07 (t, J = 5 Hz, 1H) 6.41 (s, 1H) 6.88 (d, J = 8 Hz, 1H) 7.10 (bs, 2H) 7.16 (m, 2H) 7.25 (d, J = 8 Hz, 1H) 7.34 (d, J = 8 Hz, 1H) 7.38-7.47 (m, 2H) 8.23 (dd, J = 8 Hz, 4 Hz, 1H) 8.50 (s, 1H). |
| 83 | N-[4-(hydroxymethyl)pyridin-2-yl]-4-(3-{[5-(trifluoromethyl)pyridin-2-yl]oxy}benzylidene)piperidine-1-carboxamide trifluoroacetate | LCMS (ELSD) MH+ 485.0; 1H NMR (400 MHz, DMSO-$d_6$) δ ppm 2.42 (m, 4H) 3.54 (m, 2H) 3.64 (m, 2H) 4.56 (m, 2H) 6.42 (s, 1H) 7.06 (m, 3H) 7.23 (d, J = 8 Hz, 1H) 7.25 (d, J = 8 Hz, 1H) 7.42 (m, 1H) 7.73 (m, 1H) 8.18 (d, J = 4 Hz, 1H) 8.20 (d, J = 8 Hz, 1H) 8.41 (d, J = 8 Hz, 1H) 8.57 (s, 1H). |
| 84 | N-(6-chloropyridazin-3-yl)-4-(3-{[5-(trifluoromethyl)pyridin-2-yl]oxy}benzylidene)piperidine-1-carboxamide | LCMS (ELSD) MH+ 490.1; 1H NMR (400 MHz, DMSO-$d_6$) δ ppm 2.38 (m, 2H) 2.42 (m, 2H) 3.52 (m, 2H) 3.61 (m, 2H) 6.41 (s, 1H) 7.06 (m, 2H) 7.18 (d, J = 8 Hz, 1H) 7.26 (d, J = 8 Hz, 1H) 7.42 (m, 1H) 7.75 (d, J = 10 Hz, 1H) 8.09 (d, J = 12 Hz, 1H) 8.24 (dd, J = 8 Hz, 4 Hz, 1H) 8.58 (s, 1H)10.15 (bs, 1H). |

Example 85

Synthesis of 4-(3-(5-(pyrrolidin-1-yl)pyridin-2-yloxy)benzylidene)-N-(pyridazin-3-yl)piperidine-1-carboxamide

Step 1 tert-Butyl 4-(3-(5-(pyrrolidin-1-yl)pyridin-2-yloxy)benzylidene)piperidine-1-carboxylate To a mixture of sodium-tert-butoxide (0.18 g, 1.87 mmol) in toluene (2 mL) cooled to 0° C. was added tert-butyl 4-(3-(5-bromopyridin-2-yloxy)benzylidene)piperidine-1-carboxylate (0.6 g, 1.34 mmol). The mixture was degassed for 20 min. Palladium acetate (0.02 g, 0.089 mmol) and (2-biphenyl) di-tert-butylphosphine (0.06 g, 0.2 mmol) was added and the mixture was degassed for 10 min. Pyrrolidine (0.114 g, 1.6 mmol) was added and the mixture was heated at 85° C. for 15 h. The reaction was cooled and then partitioned between ethyl acetate and water. The organic layer was washed with brine, dried over sodium sulfate and evaporated to dryness. The residue was purified by silica gel column chromatography (5% ethyl acetate/hexane) to give the title compound (0.21 g, 35.8%). 1H NMR (500 MHz, DMSO-$d_6$): δ 7.61 (s, 1H), 7.28 (s, 1H), 6.99 (m, 1H), 6.91 (d, J=7.25 Hz, 1H), 6.83 (m, 3H), 6.31 (s, 1H), 3.48 (m, 2H), 3.38 (m, 2H), 3.28 (m, 4H), 2.44 (m, 2H), 2.29 (m, 2H), 2.04 (m, 4H), 1.47 (s, 9H); m/z (436.2, MH+).

Step 2

2-(3-(Piperidin-4-ylidenemethyl)phenoxy)-5-(pyrrolidin-1-yl)pyridine

To a solution of tert-butyl 4-(3-(5-(pyrrolidin-1-yl)pyridin-2-yloxy)benzylidene)piperidine-1-carboxylate (0.335 g, 0.769 mmol) in CH$_2$Cl$_2$ (5 mL) cooled to 0° C. under a N$_2$ atmosphere was added TFA (0.88 mL, 11.49 mmol). The resulting mixture was stirred for 1 h at RT. The solution was concentrated and then quenched with saturated NaHCO$_3$ solution. The mixture was extracted with CH$_2$Cl$_2$. The organic layer was dried over Na$_2$SO$_4$ and concentrated under reduced pressure to give the title compound (0.224 g, 86.8%). 1H NMR (500 MHz, DMSO-$d_6$): δ 7.59 (s, 1H), 7.23 (m, 1H), 6.95 (m, 1H), 6.89 (d, J=7.5 Hz, 1H), 6.82 (m, 3H), 6.25 (s, 1H), 3.27 (m, 4H), 2.98 (m, 2H), 2.86 (m, 2H), 2.49 (m, 2H), 2.34 (m, 2H), 2.02 (m, 4H); m/z (336.2, MH+).

Step 3

To a solution of 2-(3-(piperidin-4-ylidenemethyl)phenoxy)-5-(pyrrolidin-1-yl)pyridine (0.118 g, 0.352 mmol) in DMSO (2 mL) was added phenyl pyridazin-3-ylcarbamate (0.076 g, 0.352 mmol) followed by triethylamine (0.048 mL, 0.352 mmol). The resulting mixture was stirred at RT for 12 h. The reaction mixture was diluted with water and extracted with EtOAc. The organic layer was dried over Na$_2$SO$_4$ and concentrated under reduced pressure to give the crude compound. The residue was purified by silica gel column chromatography (28% acetone/hexane) to give the title compound (0.125 g, 78% yield). 1H NMR (500 MHz, CDCl$_3$): δ 8.78 (s, 1H), 8.39 (s, 1H), 7.59 (d, J=2.5 Hz, 1H), 7.45 (d, J=4.6 Hz, 1H), 7.27 (m, 2H), 6.95 (m, 1H), 6.92 (m, 2H), 6.84 (m, 2H), 6.38 (s, 1H), 3.69 (m, 2H), 3.58 (m, 2H), 3.27 (m, 4H), 2.59 (m, 2H), 2.45 (m, 2H), 2.03 (m, 4H); 13C NMR (125 MHz, CDCl$_3$): δ 156.56, 153.78, 147.15, 141.50, 138.54, 137.14, 130.50, 129.31, 128.31, 125.21, 123.64, 122.70, 119.41, 117.31, 113.03, 47.85, 45.70, 44.70, 35.76, 29.12, 25.39; m/z (457.1, MH+); HPLC: 97.3%.

Example 86

Synthesis of 4-(3-(5-(pyrrolidin-1-yl)pyridin-2-yloxy)benzylidene)-N-(pyridin-3-yl)piperidine-1-carboxamide To a solution of 2-(3-(piperidin-4-ylidenemethyl)phenoxy)-5-(pyrrolidin-1-yl)pyridine (0.119 g, 0.354 mmol) in DMSO (2 mL) was added phenyl pyridin-3-ylcarbamate (0.076 g, 0.354 mmol) followed by triethylamine (0.049 mL, 0.354 mmol). The resulting mixture was stirred at RT for 12 h. The reaction mixture was diluted with water and extracted with EtOAc. The organic layer was dried over $Na_2SO_4$ and concentrated under reduced pressure to give the crude compound. The residue was purified by silica gel column chromatography (32% acetone/hexane) to give the title compound (0.11 g, 68.8% yield). $^1$H NMR (500 MHz, $CDCl_3$): δ 8.56 (s, 1H), 8.24 (s, 1H), 8.12 (d, J=7.3 Hz, 1H), 7.58 (s, 1H), 7.28 (m, 1H), 6.83 (m, 6H), 6.37 (s, 1H), 3.62 (m, 2H), 3.51 (m, 2H), 3.27 (m, 4H), 2.58 (m, 2H), 2.44 (m, 2H), 2.02 (m, 4H); $^{13}$C NMR (125 MHz, $CDCl_3$): δ 156.57, 154.53, 153.74, 143.38, 141.54, 140.80, 138.66, 137.47, 136.49, 130.41, 129.30, 127.70, 124.96, 123.66, 122.73, 119.38, 117.18, 113.11, 47.83, 45.70, 44.75, 41.01, 35.74, 29.71, 29.15, 25.39; m/z (456.2, MH$^+$); HPLC: 97.0%.

Example 87

Synthesis of 4-(3-(5-(azetidin-1-yl)pyridin-2-yloxy)benzylidene)-N-(pyridazin-3-yl)piperidine-1-carboxamide

Step 1 tert-Butyl 4-(3-(5-(azetidin-1-yl)pyridin-2-yloxy)benzylidene)piperidine-1-carboxylate To a mixture of sodium-tert-butoxide (0.18 g, 1.87 mmol) in toluene (2 mL) cooled to 0° C. under an inert atmosphere was added tert-butyl 4-(3-(5-bromopyridin-2-yloxy)benzylidene)piperidine-1-carboxylate (0.6 g, 1.34 mmol). The mixture was degassed for 20 min. Palladium acetate (0.02 g, 0.089 mmol) and (2-biphenyl)di-tert-butylphosphine (0.06 g, 0.2 mmol) was added and the mixture was degassed for 10 min. Azetidine (0.092 g, 1.6 mmol) was added and the reaction was heated at 85° C. for 15 h. The reaction was cooled and then partitioned between ethyl acetate and water. The organic layer was washed with brine, dried over sodium sulfate and evaporated to dryness. The residue was purified by silica gel column chromatography (5% ethyl acetate/hexane) to give the title compound (0.135 g, 23.7%). $^1$H NMR (500 MHz, DMSO-$d_6$): δ 7.49 (s, 1H), 6.92 (d, J=7.7 Hz, 1H), 6.81 (m, 3H), 6.80 (d, J=8.65 Hz, 1H), 6.31 (s, 1H), 3.88 (t, J=7.15 Hz, 4H), 3.48 (m, 2H), 3.38 (m, 2H), 2.40 (m, 4H), 2.30 (m, 2H), 1.47 (s, 9H).

Step 2

5-(Azetidin-1-yl)-2-(3-(piperidin-4-ylidenemethyl)phenoxy)pyridine

To a solution of tert-butyl 4-(3-(5-(azetidin-1-yl)pyridin-2-yloxy)benzylidene)piperidine-1-carboxylate (0.135 g, 0.32 mmol) in $CH_2Cl_2$ (5 mL) cooled to 0° C. under a $N_2$ atmosphere was added TFA (0.24 mL, 3.2 mmol). The resulting mixture was stirred for 1 h at RT. The solution was concentrated and then quenched with saturated $NaHCO_3$ solution. The mixture was extracted with $CH_2Cl_2$. The organic layer was dried over $Na_2SO_4$ and concentrated under reduced pressure to give the title compound (0.98 g, 96%). $^1$H NMR (500 MHz, DMSO-$d_6$): δ 7.46 (s, 1H), 7.28 (s, 1H), 6.91 (d, J=7.5 Hz, 1H), 6.85 (m, 4H), 6.28 (s, 1H), 3.87 (t, J=7 Hz, 4H), 3.02 (m, 2H), 2.90 (m, 2H), 2.53 (m, 2H), 2.39 (m, 4H).

Step 3

To a solution of 5-(azetidin-1-yl)-2-(3-(piperidin-4-ylidenemethyl)phenoxy)pyridine (0.045 g, 0.139 mmol) in DMSO (2 mL) was added phenyl pyridazin-3-ylcarbamate (0.03 g, 0.139 mmol) followed by triethylamine (0.048 mL, 0.352 mmol). The resulting mixture was stirred at RT for 12 h. The reaction mixture was diluted with water and extracted with EtOAc. The organic layer was dried over $Na_2SO_4$ and concentrated under reduced pressure. The residue was purified by silica gel column chromatography (28% acetone/hexane) to give the title compound (0.04 g, 64.5% yield). $^1$H NMR (500 MHz, $CDCl_3$): δ 8.76 (s, 1H), 8.52 (s, 1H), 7.52 (s, 1H), 7.47 (d, J=2 Hz, 1H), 7.27 (m, 2H), 6.93 (d, J=7.5 Hz, 1H), 6.90 (d, J=8.5 Hz, 1H), 6.86 (m, 2H), 6.80 (m, 1H), 6.39 (s, 1H), 3.88 (t, J=7 Hz, 4H), 3.72 (m, 2H), 3.61 (m, 2H), 2.60 (d, J=6 Hz, 2H), 2.47 (m, 2H), 2.38 (m, 2H); $^{13}$C NMR (125 MHz, $CDCl_3$): δ 156.44, 156.01, 155.45, 145.21, 138.58, 137.18, 130.97, 129.35, 125.16, 123.98, 123.06, 119.87, 117.73, 112.55, 53.11, 45.73, 44.73, 35.76, 29.70, 29.12, 17.53; m/z (443.2, MH$^+$); HPLC: 95.0%.

Example 88

Synthesis of 4-(3-(5-(azetidin-1-yl)pyridin-2-yloxy)benzylidene)-N-(pyridin-3-yl)piperidine-1-carboxamide To a solution of 5-(azetidin-1-yl)-2-(3-(piperidin-4-ylidenemethyl)phenoxy)pyridine (0.098 g, 0.304 mmol) in DMSO (2 mL) was added phenyl pyridin-3-ylcarbamate (0.065 g, 0.304 mmol) followed by triethylamine (0.049 mL, 0.354 mmol). The resulting mixture was stirred at RT for 12 h. The reaction mixture was diluted with water and extracted with EtOAc. The organic layer was dried over $Na_2SO_4$ and concentrated under reduced pressure. The residue was purified by silica gel column chromatography (32% acetone/hexane) to give the title compound (0.099 g, 73.8% yield). $^1$H NMR (500 MHz, $CDCl_3$): δ 8.62 (s, 1H), 8.23 (s, 1H), 8.17 (d, J=7.8 Hz, 1H), 7.45 (s, 1H), 7.28 (m, 2H), 7.09 (s, 1H), 6.93 (d, J=7.55 Hz, 1H), 6.88 (m, 3H), 6.80 (m, 1H), 6.37 (s, 1H), 3.87 (t, J=7.05 Hz, 4H), 3.62 (m, 2H), 3.51 (m, 2H), 2.57 (m, 2H), 2.39 (m, 4H); $^{13}$C NMR (125 MHz, $CDCl_3$): δ 156.02, 155.42, 154.56, 145.26, 143.28, 140.75, 138.71, 137.58, 136.56, 130.88, 129.34, 127.80, 124.88, 124.01, 123.70, 123.09, 119.85, 117.62, 112.61, 53.85, 53.09, 45.71, 44.75, 35.75, 31.74, 29.71, 29.29, 29.16, 17.52; m/z (442.2, MH$^+$); HPLC: 97.8%.

Example 89

Synthesis of 4-(3-(5-(pent-4-ynyloxy)pyridin-2-yloxy)benzylidene)-N-(pyridin-3-yl)piperidine-1-carboxamide

Step 1 tert-Butyl 4-(3-(5-(5-(trimethylsilyl)pent-4-ynyloxy)pyridin-2-yloxy)benzylidene)piperidine-1-carboxylate To a solution of tert-butyl 4-(3-(5-hydroxypyridin-2-yloxy)benzylidene)piperidine-1-carboxylate (0.8 g, 2.09 mmol, from Example 47, step 2) in DMF (5 mL) was added 5-trimethylsilyl-4-pentyn-1-iodide (0.696 g, 2.6 mmol), K$_2$CO$_3$ (0.57 g, 4.18 mmol) and 18-crown-6 (0.87 g, 4.18 mmol) at RT. The reaction mixture was stirred at RT overnight. The mixture was diluted with water (10 mL) and extracted with ethyl acetate. The organic layer was washed with water and brine solution, dried over Na$_2$SO$_4$ and concentrated to dryness under reduced pressure. The residue was purified by silica gel column chromatography (acetone:hexane, 1:4) to give the title compound (0.7 g, 64%). $^1$H NMR (500 MHz, CDCl$_3$): δ 7.88 (d, J=2.5 Hz, 1H), 7.29 (d, J=8.1 Hz, 2H), 6.97 (d, J=7.8 Hz, 1H), 6.91 (d, J=9.6 Hz, 2H), 6.85 (d, J=8.8 Hz, 1H), 6.32 (s, 1H), 4.06 (t, J=6 Hz, 2H), 3.49 (s, 2H), 3.39 (s, 2H), 2.43 (t, J=6.9 Hz, 4H), 2.31 (s, 2H), 1.97 (t, J=6.4 Hz, 2H), 1.47 (s, 9H), 0.14 (s, 9H).

Step 2 tert-Butyl 4-(3-(5-(pent-4-ynyloxy)pyridin-2-yloxy) benzylidene)piperidine-1-carboxylate To a solution of tert-butyl 4-(3-(5-(5-(trimethylsilyl)pent-4-ynyloxy)pyridin-2-yloxy)benzylidene)piperidine-1-carboxylate (0.7 g, 1.34 mmol) in dry THF (4 mL) was added TBAF (3.8 mL, 13.4 mmol) dropwise maintaining ice-cooled conditions. The mixture was stirred for 30 min. The reaction was concentrated and then partitioned between saturated NaHCO$_3$ solution and CH$_2$Cl$_2$. The organic layer was dried over Na$_2$SO$_4$ and concentrated under reduced pressure to give the title compound (0.6 g, 98% yield).

Step 3

5-(Pent-4-ynyloxy)-2-(3-(piperidin-4-ylidenemethyl) phenoxy)pyridine

To a solution of tert-butyl 4-(3-(5-(pent-4-ynyloxy)pyridin-2-yloxy)benzylidene)piperidine-1-carboxylate (0.68 g, 1.33 mmol) in dry CH$_2$Cl$_2$ (3 mL) cooled to 0° C. was added TFA (1 mL, 13.3 mmol) dropwise. The mixture was stirred for 30 min. The reaction was concentrated and then partitioned between saturated NaHCO$_3$ solution and CH$_2$Cl$_2$. The organic layer was dried over Na$_2$SO$_4$ and concentrated under reduced pressure to give the title compound (0.53 g, 99%). m/z (421.2, MH$^+$).

Step 4

5-(Pent-4-ynyloxy)-2-(3-(piperidin-4-ylidenemethyl)phenoxy)pyridine (0.26 g, 0.746 mmol) and phenyl pyridin-3-ylcarbamate (0.159 g, 0.746 mmol) were dissolved in DMSO (3 mL) and triethylamine (0.3 mL) was added dropwise. The reaction was stirred for 12 h at RT. The reaction mixture was diluted with water and extracted with EtOAc. The organic layer was washed with water, dried over sodium sulfate and evaporated to dryness. The residue was purified by silica gel column chromatography (acetone:hexane, 2:5) to give the title compound (0.23 g, 65%). $^1$H NMR (500 MHz, CDCl$_3$): δ 8.60 (s, 1H), 8.24 (s, 1H), 8.16 (d, J=7.5 Hz, 1H), 7.88 (s, 1H), 7.29 (m, 3H), 6.98 (d, J=7.5 Hz 2H), 6.93 (d, J=11 Hz, 2H), 6.86 (d, J=9 Hz, 1H), 6.38 (s, 1H), 4.07 (t, J=6 Hz, 2H), 3.64 (m, 2H), 3.53 (m, 2H), 2.59 (m, 2H), 2.46 (m, 2H), 2.40 (d, J=7 Hz, 2H), 1.98 (t, J=7 Hz, 3H); $^{13}$C NMR (125 MHz, CDCl$_3$): δ 157.51, 155.22, 154.49, 151.84, 143.19, 140.58, 138.81, 137.68, 136.57, 133.71, 129.44, 127.90, 126.87, 124.84, 124.63, 123.78, 120.59, 118.35, 112.56, 83.15, 69.15, 67.28, 45.74, 44.74, 35.76, 29.17, 28.09, 15.08; m/z (469.2, MH$^+$); HPLC: 97.8%.

Example 90

Synthesis of 4-(3-(5-(pent-4-ynyloxy)pyridin-2-yloxy)benzylidene)-N-(Pyridazin-3-yl)piperidine-1-carboxamide 5-(Pent-4-ynyloxy)-2-(3-(piperidin-4-ylidenemethyl)phenoxy)pyridine (0.26 g, 0.746 mmol) and phenyl pyridazin-3-ylcarbamate (0.16 g, 0.746 mmol) were dissolved in DMSO (3 mL) and triethylamine (0.3 mL) was added dropwise. The reaction was stirred for 12 h at RT. The reaction mixture was diluted with water and extracted with EtOAc. The organic layer was washed with water, dried over sodium sulfate and evaporated to dryness. The residue was purified by silica gel column chromatography (acetone:hexane, 2:5) to give the title compound (0.225 g, 64%). $^1$H NMR (500 MHz, CDCl$_3$): δ 8.77 (s, 1H), 8.40 (s, 1H), 7.89 (s, 1H), 7.46 (t, J=4.5 Hz, 1H), 7.29 (m, 2H), 6.98 (d, J=7.5 Hz, 1H), 6.92 (m, 2H), 6.87 (d, J=8.75 Hz, 1H), 6.40 (s, 1H), 4.08 (t, J=5.75 Hz, 2H), 3.70 (m, 2H), 3.59 (m, 2H), 2.60 (d, J=5.2 Hz, 2H), 2.47 (m, 2H), 2.40 (t, J=6.6 Hz, 2H), 1.99 (m, 3H); $^{13}$C NMR (125 MHz, CDCl$_3$): δ157.48, 156.60, 155.19, 151.80, 138.72, 137.46, 133.67, 129.42, 128.15, 126.84, 124.96, 124.59, 120.58, 118.38, 112.52, 83.14, 69.12, 67.25, 45.66, 44.64, 35.76, 29.13, 28.08, 15.06; m/z (470.2 MH$^+$); HPLC: 97.8%.

Example 91

Synthesis of 4-((6-phenoxypyridin-2-yl)methylene)-N-(pyridazin-3-yl)piperidine-1-carboxamide Step 1 tert-Butyl-4-(3-(pyridine-2-yloxy)benzylidene)piperidine-1-carboxylate

A mixture of tert-butyl 4-(3-hydroxybenzylidene)piperidine-1-carboxylate (0.300 g, Example 57, Step 3), 2-bromopyridine (0.253 mL, 1.50 equiv), cesium carbonate (1.13 g, 2.01 equiv), and tetrakis(acetonitrile)copper(I) hexafluorophosphate (0.048 g, 0.075 equiv) in toluene (9 mL, 0.2 M) was heated to reflux for 12 hours. Additional tetrakis(acetonitrile)copper(I) hexafluorophosphate (0.02 g) and 2-bromopyridine (0.1 mL) were added, and the reaction was heated an additional 6 hours. After cooling to room temperature, the reaction was filtered through Celite, washing the Celite with dichloromethane. The filtrate was concentrated and purified on 60 g silica gel using a gradient eluent consisting of 0-10% ethyl acetate/dichloromethane over 60 minutes to give the title compound as a white solid. 0.483 g, 76% yield. $^1$H NMR (400 MHz, CDCl$_3$) δ ppm 1.45 (9H, s), 2.29 (2H, br. S.), 2.45 (2H, t, J=5.5 Hz), 3.37 (2H, t, J=5.4 Hz), 3.47 (2H, t, J=5.7 Hz), 6.32 (1H, s), 6.76-7.13 (5H, m), 7.32 (1H, t, J=7.7 Hz), 7.67 (1H, t, J=6.5 Hz), 8.18 (1H, br. s.).

Step 2

2-(3-(Piperidin-4-ylidenemethyl)phenoxy)pyridine trifluoroacetate

A solution of tert-butyl-4-(3-(pyridin-2-yloxy)benzylidene)piperidine-1-carboxylate (0.483 g) in dichloromethane (2.5 mL, 0.53 M) was treated with trifluoroacetic acid (2.5 mL). The reaction was allowed to stir for 3 hours, then concentrated to give an oil. The oil was used without purification. 0.652 g, quantitative yield.

Step 3

4-((6-phenoxypyridin-2-yl)methylene)-N-(pyridazin-3-yl)piperidine-1-carboxamide

A solution of 2-(3-(piperidin-4-ylidenemethyl)phenoxy) pyridine trifluoroacetate (0.300 g), phenyl pyridazin-3-ylcarbamate (0.183 g, 1.40 equiv; Example 39, Step 2), and triethylamine (0.423 mL, 5.00 equiv) in dimethyl sulfoxide (2.0 mL, 0.30 M) was heated to 65° C. for 2 h. The reaction was cooled to room temperature. Water was added and then the solution was extracted with ethyl acetate (3×). The organic extracts were combined and washed with water, dried over magnesium sulfate, filtered, and concentrated. The residue was purified on a 12 g silica gel column using 20-50% ethyl acetate/dichloromethane over 60 minutes as the eluent. Combined product fractions and concentrated to give the title compound as a yellow foam. 0.071 g, 30% yield. $^1$H NMR (400 MHz, CDCl$_3$) δ ppm 2.45 (2H, t, J=5.5 Hz), 2.59 (2H, t, J=5.5 Hz), 3.60 (2H, t, J=5.8 Hz), 3.70 (2H, t, J=5.8 Hz), 6.39 (1H, s), 6.90 (1H, d, J=8.2 Hz), 6.93-7.05 (4H, m), 7.34 (1H, t, J=8.0 Hz), 7.47 (1H, dd, J=9.4, 4.7 Hz), 7.63-7.72 (1H, m), 8.18 (1H, dd, J=1.9, 0.8 Hz), 8.45 (1H, d, J=9.0 Hz), 8.74 (1H, d, J=3.9 Hz).

Example 92

Synthesis of 4-((6-phenoxypyridin-2-yl)methylene)-N-(pyridin-3-yl)piperidine-1-carboxamide To a solution of 2-(3-(piperidin-4-ylidenemethyl)phenoxy)pyridine trifluoroacetate (127.97 mg, 0.480 mmol; Example 91, Step 2) in DMSO (2 mL) was added phenyl pyridin-3-ylcarbamate (102.88 mg, 0.480 mmol) and triethylamine (1.33 mL, 9.6 mmol). The resulting mixture was stirred at room temperature for 12 h. The reaction mixture was diluted with water and extracted with ethyl acetate. The organic extract was dried over sodium sulphate and concentrated. The crude compound was purified by silica gel column chromatography (30% acetone/hexane) to give the title compound (180 mg, 97% yield). $^1$H NMR (500 MHz, CDCl$_3$) δ ppm 8.59 (s, 1H), 8.24-8.14 (m, 3H), 7.70 (t, J=7 Hz, 1H), 7.37 (m, 1H), 7.04-6.98 (m, 5H), 6.93 (d, J=8.5 Hz, 1H), 6.40 (s, 1H), 3.65 (t, J=5.5 Hz, 2H), 3.54 (t, J=5.5 Hz, 2H), 2.61 (t, J=5 Hz, 2H), 2.47 (t, J=5.5 Hz, 2H); $^{13}$C NMR (125 MHz, CDCl$_3$) δ ppm 163.64, 154.54, 154.13, 147.75, 140.67, 139.52, 138.86, 137.78, 129.47, 127.82, 125.20, 124.74, 121.46, 119.21, 118.62, 111.71, 45.72, 44.72, 35.76, 29.16; m/z (387.1 MH$^+$); HPLC: 97.66%.

Example 93

4-{3-[(5-fluoropyridin-2-yl)oxy]benzylidene}-N-pyridazin-3-ylpiperidine-1-carboxamide Step 1 tert-Butyl-4-(3-(5-fluoropyridin-2-yloxy)benzylidene)piperidine-1-carboxylate

A mixture of tert-butyl-4-(3-hydroxybenzylidene)piperidine-1-carboxylate (0.500 g; Example 57, Step 3), 2-bromo5-fluoropyridine (0.456 g, 1.50 equiv), cesium carbonate (1.13 g, 2.01 equiv), and tetrakis(acetonitrile)copper(I) hexafluorophosphate (0.058 g, 0.090 equiv) in toluene (9 mL, 0.2 M) was heated to 100° C. in a Biotage Personal microwave for 10 minutes. The reaction mixture was filtered through Celite, and the Celite was washed with dichloromethane. The filtrate was concentrated and purified on 60 g silica gel using a gradient eluent consisting of 0-10% ethyl acetate/dichloromethane over 60 minutes to give the title compound as a white solid. 0.274 g, 41% yield. $^1$H NMR (400 MHz, CDCl$_3$) δ ppm 1.46 (9H, s), 2.31 (2H, t, J=5.8 Hz), 2.45 (2H, t, J=5.4 Hz), 3.39 (2H, t, J=5.9 Hz), 3.49 (2H, t, J=5.9), 6.33 (1H, s), 6.85-6.98 (3H, m), 7.02 (1H, d, J=7.6 Hz), 7.33 (1H, t, J=7.8 Hz), 7.40-7.47 (1H, m), 8.03 (1H, d, J=3.1 Hz).

Step 2

5-Fluoro-2-(3-(piperidin-4-ylidenemethyl)phenoxy) pyridine trifluoroacetate

A solution of tert-butyl-4-(3-(5-fluoropyridin-2-yloxy) benzylidene)piperidine-1-carboxylate (0.274 g) in dichloromethane (2.5 mL, 0.28 M) was treated with trifluoroacetic acid (2.5 mL). The reaction was allowed to stir for 3 hours, then concentrated to an oil. The oil was used without purification. 0.466 g, quantitative yield.

Step 3

4-{3-[(5-fluoropyridin-2-yl)oxy]benzylidene}-N-pyridazin-3-ylpiperidine-1-carboxamide A solution of 5-fluoro-2-(3-(piperidin-4-ylidenemethyl) phenoxy)pyridine trifluoroacetate (0.466 g), phenyl pyridazin-3-ylcarbamate (0.274 g, 1.40 equiv), and triethylamine (0.634 mL, 5.00 equiv) in dimethyl sulfoxide (2.0 mL, 0.30 M) was heated to 65° C. for 2 h. The reaction was cooled to room temperature. Water was added and then the solution was extracted with ethyl acetate (3 times). The organic extracts were combined and washed with water, dried over magnesium sulfate, filtered, and concentrated. The residue was purified on a 12 g silica gel column using 20-50% ethyl acetate/dichloromethane over 60 minutes as the eluent to give the title compound as a yellow foam. 0.155 g, 42% yield. $^1$H NMR (400 MHz, CDCl$_3$) δ ppm 2.46 (2H, t, J=5.5 Hz), 2.59 (2H, t, J=5.5 Hz), 3.61 (2H, t, J=5.8 Hz), 3.71 (2H, t, J=5.8 Hz), 6.39 (1H, s), 6.84-6.99 (3H, m), 7.02 (1H, d, J=7.8 Hz), 7.34 (1H, t, J=7.8 Hz), 7.39-7.54 (2H, m), 8.02 (1H, d, J=3.1 Hz), 8.47 (1H, d, J=8.6 Hz), 8.74 (1H, d, J=3.5 Hz).

Example 94

N-(5-ethyl-1,3,4-thiadiazol-2-yl)-4-(3-{[5-(trifluoromethyl)pyridin-2-yl]oxy}benzylidene)piperidine-1-carboxamide A solution of 2-(3-(piperidin-4-ylidenemethyl)phenoxy)-5-(trifluoromethyl)pyridine hydrochloride (0.100 g; Example 1a, Step 5), phenyl 5-ethyl-1,3,4-thiadiazol-2-ylcarbamate (0.081 g, 1.2 equiv), and triethylamine (0.045 mL, 1.2 equiv) in dimethyl sulfoxide (1 mL, 0.3 M) was heated to 65° C. for 2 h. The reaction was cooled to room temperature. Water was added and then the solution was extracted with ethyl acetate (2×). The organic extracts were dried over magnesium sulfate, filtered, and concentrated. The residue was purified on a 12 g silica gel column using 10-30% ethyl acetate/dichloromethane over 30 minutes as the eluent to give the title compound as a white foam. 0.056 g, 42% yield. $^1$H NMR (400

MHz, CDCl$_3$) δ ppm 1.36 (3H, t, J=7.6 Hz), 2.46 (2H, t, J=5.7 Hz), 2.61 (2H, t, J=5.7 Hz), 2.95 (2H, q, J=7.8 Hz), 3.67 (2H, t, J=5.8 Hz), 3.77 (2H, t, J=5.8 Hz), 6.40 (1H, s), 6.96-7.05 (3H, m), 7.08 (1H, d, J=7.8 Hz), 7.37 (1H, t, J=8.0 Hz), 7.89 (1H, dd, J=8.8, 2.5 Hz), 8.43 (1H, s).

Example 95

N-(5-cyclopropyl-1,3,4-thiadiazol-2-yl)-4-(3-{[5-(trifluoromethyl)pyridin-2-yl]oxy}benzylidene)piperidine-1-carboxamide A solution of 2-(3-(piperidin-4-ylidenemethyl)phenoxy)-5-(trifluoromethyl)pyridine hydrochloride (0.100 g; Example 1a, Step 5), phenyl 5-cyclopropyl-1,3,4-thiadiazol-2-ylcarbamate (0.085 g, 1.2 equiv), and triethylamine (0.045 mL, 1.2 equiv) in dimethyl sulfoxide (1 mL, 0.3 M) was heated to 65° C. for 2 h. The reaction was cooled to room temperature. Water was added and then the solution was extracted with ethyl acetate (2×). The organic extracts were dried over magnesium sulfate, filtered, and concentrated. The residue was purified on a 12 g silica gel column using 10-30% ethyl acetate/dichloromethane over 30 minutes as the eluent to give the title compound as a white foam. 0.057 g, 42% yield. $^1$H NMR (400 MHz, CDCl$_3$) δ ppm 0.98-1.07 (2H, m), 1.09-1.18 (2H, m), 2.15-2.25 (1H, m), 2.46 (2H, t, J=5.5 Hz), 2.60 (2H, t, J=5.5 Hz), 3.66 (2H, t, J=5.8 Hz), 3.76 (2H, t, J=5.9 Hz), 6.40 (1H, s), 6.95-7.04 (3H, m), 7.09 (1H, d, J=7.8 Hz), 7.37 (1H, t, J=7.8 Hz), 7.89 (1H, dd, J=8.6, 2.7 Hz), 8.43 (1H, dd, J=1.6, 0.8 Hz).

Example 96

N-(5-acetyl-4-methyl-1,3-thiazol-2-yl)-4-(3-{[5-(trifluoromethyl)pyridin-2-yl]oxy}benzylidene)piperidine-1-carboxamide A solution of 2-(3-(piperidin-4-ylidenemethyl)phenoxy)-5-(trifluoromethyl)pyridine hydrochloride (0.100 g; Example 1a, Step 5), phenyl 5-acetyl-4-methylthiazol-2-ylcarbamate (0.089 g, 1.2 equiv), and triethylamine (0.045 mL, 1.2 equiv) in dimethyl sulfoxide (1 mL, 0.3 M) was heated to 65° C. for 2 h. The reaction was cooled to room temperature. Water was added and then the solution was extracted with ethyl acetate (2×). The organic extracts were dried over magnesium sulfate, filtered, and concentrated. The residue was purified on a 12 g silica gel column using 10-30% ethyl acetate/dichloromethane over 20 minutes as the eluent to give the title compound as a light yellow foam. 0.065 g, 47% yield. $^1$H NMR (400 MHz, CDCl$_3$) δ ppm 2.44-2.54 (5H, m), 2.61 (2H, t, J=5.7 Hz), 2.66 (3H, s), 3.63 (2H, t, J=5.8 Hz), 3.73 (2H, t, J=5.9 Hz), 6.42 (1H, s), 6.92-7.04 (3H, m), 7.07 (1H, d, J=7.8 Hz), 7.38 (1H, t, J=8.0 Hz), 7.89 (1H, dd, J=8.6, 2.7 Hz), 8.43 (1H, s).

Example 97

4-{3-[(6-methoxy-2-methylpyridin-3-yl)oxy]benzylidene}-N-pyridazin-3-ylpiperidine-1-carboxamide Step 1 tert-butyl 4-(3-((6-methoxy-2-methylpyridin-3-yl)methyl)benzylidene)piperidine-1-carboxylate A mixture of tert-Butyl 4-(3-hydroxybenzylidene)piperidine-1-carboxylate (1 g, 3 mmol; Example 57, Step 3), 6-methoxy-2-methylpyridin-3-ylboronic acid (1.15 g, 6 mmol), copper acetate (0.627 g, 3 mmol), 4 Å molecular sieves, and triethylamine (2.40 mL, 15 mmol) in dichloromethane (5 mL) was stirred at r.t for 48 hours. The reaction mixture was filtered through a celite bed, and the filtrate was concentrated under reduced pressure and purified by column chromatography (3.5% ethyl acetate/hexane) to give the title compound (0.42 g, 30% yield). $^1$HNMR (500 MHz, CDCl$_3$): δ ppm 7.20 (m, 2H), 6.86 (d, J=7.45 Hz, 1H), 6.68 (m, 2H), 6.59 (d, J=8.6 Hz, 1H), 6.28 (s, 1H), 3.94 (s, 1H), 3.49 (s, 2H), 3.38 (s, 2H), 2.42 (s, 2H), 2.36 (s, 3H), 2.31 (d, J=5.45 Hz, 2H), 1.47 (s, 9H).

Step 2 3-(3-(piperidin-4-ylidenemethyl)benzyl)-6-methoxy-2-methylpyridine trifluoroacetate A 0° C. solution of tert-butyl 4-(3-((6-methoxy-2-methylpyridin-3-yl)methyl)benzylidene)piperidine-1-carboxylate (0.186 g, 0.487 mmol) dichloromethane (3 mL) was treated with trifluoroacetic acid (0.693 mL, 9.74 mmol). The resulting mixture was stirred for 1 h at room temperature. The solution was concentrated under reduced pressure to give the crude title compound (0.15 g).

Step 3 A solution of 3-(3-(piperidin-4-ylidenemethyl)benzyl)-6-methoxy-2-methylpyridine trifluoroacetate (0.14 g, 0.453 mmol) in DMSO (2 mL) was treated with phenyl pyridazin-3-ylcarbamate (97.47 mg, 0.453 mmol) followed by triethylamine (1.26 mL, 9.06 mmol). The resulting mixture was stirred at room temperature for 12 h. The reaction mixture was diluted with water and extracted with ethyl acetate. The organic extract was dried over Na$_2$SO$_4$, concentrated under reduced pressure, and purified by column chromatography (30% acetone/hexane) to give the title compound (0.15 g, 76.9% yield). $^1$HNMR (500 MHz, CDCl$_3$): δ ppm 8.77 (s, 1H), 8.48 (s, 1H), 7.51 (s, 1H), 7.22 (m, 2H), 6.87 (d, J=7 Hz, 1H), 6.67 (m, 2H), 6.60 (d, J=9 Hz, 1H), 6.36 (s, 1H), 3.95 (m, 3H), 3.71 (s, 2H), 3.61 (s, 2H), 2.57 (s, 2H), 2.47 (d, J=4.5 Hz, 2H), 2.37 (m, 3H). m/z (432.2 MH$^+$); HPLC: 98.01%.

Example 98

4-{3-[(6-methoxy-2-methylpyridin-3-yl)oxy]benzylidene}-N-pyridin-3-ylpiperidine-1-carboxamide A solution of 3-(3-(piperidin-4-ylidenemethyl)benzyl)-6-methoxy-2-methylpyridine trifluoroacetate (0.14 g, 0.453 mmol; Example 97, Step 2) in DMSO (2 mL) was treated with phenyl pyridin-3-ylcarbamate (97.06 mg, 0.453 mmol) followed by triethylamine (1.26 mL, 9.06 mmol). The resulting mixture was stirred at room temperature for 12 h. The reaction mixture was diluted with water and extracted with ethyl acetate. The organic extract was dried over Na$_2$SO$_4$, concentrated under reduced pressure, and purified by column chromatography (30% acetone/hexane) to give the title compound (0.18 g, 92.4% yield). $^1$HNMR (500 MHz, CDCl$_3$): δ ppm 8.54 (s, 1H), 8.26 (s, 1H), 8.12 (d, J=7.85 Hz, 1H), 7.29 (m, 1H), 7.24 (m, 1H), 6.84 (m, 2H), 6.67 (m, 2H), 6.59 (d, J=8.6 Hz, 1H), 6.34 (s, 1H), 3.96 (m, 3H), 3.64 (t, J=5.1 Hz, 2H), 3.54 (t, J=5.3 Hz, 2H), 2.57 (m, 2H), 2.46 (m, 2H), 2.35 (s, 3H). m/z (431.3 MH$^+$); HPLC: 98.90%.

Example 99

N-pyridin-{3-yl-4-3-[4-(2,2,2-trifluoroethoxy)phenoxy]benzylidene}piperidine-1-carboxamide Step 1 tert-butyl 4-(3-(4-methoxyphenoxy)benzylidene)piperidine-1-carboxylate To a mixture of 4-methoxyphenylboronic acid (1.57 g, 10.36 mmole) and tert-butyl 4-(3-hydroxybenzylidene)piperidine-1-carboxylate (2.5 g, 8.6 mmole) in dichloromethane (75 mL) were added copper acetate (1.63 g, 8.6 mmole), triethyl amine (5.219 g, 51.6 mmol) and molecular sieves. The mixture was stirred at room temperature overnight. The reaction mixture was filtered through celite pad. The filtrate was evaporated and purified by column chromatography to give the title compound (1.1 g, 32%). $^1$H NMR (500 MHz, CDCl$_3$): δ ppm 7.26 (t, 1H), 6.99 (d, 2H), 6.89 (t, 3H), 6.79 (t, 2H), 6.29 (s, 1H), 3.80 (s, 3H), 3.48 (s, 2H), 3.38 (s, 2H), 2.42 (s, 2H), 2.29 (s, 2H), 1.47 (s, 9H).

Step 2 4-(3-(piperidin-4-ylidenemethyl)phenoxy)phenol-tert-Butyl 4-(3-(4-methoxyphenoxy)benzylidene)piperidine-1-carboxylate (260 mg, 0.657 mmol) was taken in 10 ml dry dichloromethane and cooled in ice-salt mixture. Boron tribromide (165 mg, 0.657 mmol) dissolved in 2 ml dry dichloromethane was slowly added to the reaction mixture. The reaction mixture stirred for 2 hours. The reaction mixture was quenched by addition of saturated sodium bicarbonate solution until pH 8-9. The organic portion was extracted twice with 1:1 ethyl acetate/tetrahydrofuran. The organic layers were dried over sodium sulfate and evaporated to give the crude title compound (190 mg, quant.). $^1$H-NMR (500 MHz, DMSO): δ ppm 9.35 (s, 1H), 7.28 (t, 1H J=8 Hz), 6.90 (t, J=8.8 Hz, 3H), 6.79 (d, J=8.6 Hz, 2H), 6.74 (d, J=8 Hz, 1H), 5.76 (s, 1H) 2.28 (s, 2H), 2.72 (s, 2H), 2.34 (s, 2H), 2.24 (s, 2H).

Step 3 tert-butyl 4-(3-(4-hydroxyphenoxy)benzylidene)piperidine-1-carboxylate A solution of 4-(3-(piperidin-4-ylidenemethyl)phenoxy)phenol (190 mg, 0.675 mmol) and triethylamine (270 mg, 2.7 mmol) in 10 ml dry dichloromethane was treated with Boc-anhydride (162 mg, 0.742 mmol). After stirring overnight at room temperature, the reaction mixture was washed with water and extracted with ether (2×40 mL). The organic fractions were dried over sodium sulphate, evaporated, and purified by column chromatography (10-20% ethyl acetate/hexanes) to give the title compound (150 mg, 58%).

Step 4 tert-butyl 4-(3-(4-(2,2,2-trifluoroethoxy)phenoxy)benzylidene)piperidine-1-carboxylate A solution of tert-butyl 4-(3-(4-hydroxyphenoxy)benzylidene)piperidine-1-carboxylate (150 mg, 0.393 mmol) in dimethylformamide (5 mL) was treated with potassium carbonate (218 mg, 1.572 mmol), 18-crown ether (210 mg, 0.786 mmol) and 2-iodo-1,1,1 trifluoroethane (105 mg, 0.491 mmol). The mixture was stirred overnight at a temperature below 50° C. The reaction mixture was washed with water and organic part extracted with ether (2×50 mL). The organic fractions were dried over sodium sulfate and evaporated. The crude material was purified by column chromatography (10-20% ethyl acetate/hexanes) to give the title compound (50 mg, 27%). $^1$H-NMR (500 MHz, CDCl$_3$): δ ppm 7.26 (m, 1H), 7.00 (d, J=6 Hz, 2H), 6.94 (m, 3H), 6.80 (m, 2H), 6.29 (s, 1H), 4.36 (m, 2H), 3.49 (s, 2H), 3.38 (s, 2H), 2.42 (s, 2H), 2.30 (s, 2H), 1.47 (s, 9H).

Step 5 4-(3-(4-(2,2,2-trifluoroethoxy)phenoxy)benzylidene)piperidine

A solution of tert-butyl 4-(3-(4-(2,2,2-trifluoroethoxy)phenoxy)benzylidene)piperidine-1-carboxylate (50 mg, 0.107 mmol) in dichloromethane (5 mL) was cooled to 0° C. and treated with trifluoroacetic acid (123 mg, 1.07 mmol) dropwise. The reaction mixture was then allowed to warm to room temperature and stirred at that temperature overnight. The reaction was concentrated, and the residue was dissolved in water (5 mL). The aqueous layer basified up to pH ~8 with 1M sodium hydroxide solution. The aqueous layer was extracted with dichloromethane (3×20 mL), and organic layers were washed with water (2×10 mL), dried over sodium sulfate, and concentrated to give the crude title compound (40 mg, quant.)

Step 6 A mixture of 4-(3-(4-(2,2,2-trifluoroethoxy)phenoxy)benzylidene)piperidine (40 mg, 0.110 mmol), phenyl pyridin-3-ylcarbamate (24 mg, 0.110 mmol), and triethyl amine (55 mg, 0.55 mmol) in DMSO (2.5 mL) was stirred at room temperature for overnight. The reaction was quenched with water, extracted with EtOAc, dried over sodium sulfate, concentrated, and purified by column chromatography (50% acetone/hexane) to yield the title compound (35 mg, 60%). $^1$H-NMR (500 MHz, CDCl$_3$): δ ppm 9.76 (s, 1H), 9.63 (s, 1H), 9.25 (d, J=9 Hz, 1H), 8.09 (s, 1H), 7.72 (s, 1H), 7.00 (m, 2H), 6.95 (m, 3H), 6.80 (d, J=9 Hz, 2H), 6.33 (s, 1H), 4.35 (m, 2H), 3.80 (s, 2H), 3.69 (s, 2H), 2.58 (s, 2H), 2.46 (s, 2H), m/z (484.1 MH$^+$); HPLC: 99.36%.

Example 100

N-pyridazin-3-yl-4-{3-[4-(2,2,2-trifluoroethoxy)phenoxy]benzylidene}piperidine-1-carboxamide A mixture of 4-(3-(4-(2,2,2-trifluoroethoxy)phenoxy)benzylidene)piperidine (40 mg, 0.110 mmol; Example 99, Step 5), phenyl pyridazin-3-ylcarbamate (24 mg, 0.110 mmol), and triethyl amine (55 mg, 0.55 mmol) in DMSO (2.5 mL) was stirred at room temperature for overnight. The reaction was quenched with water, extracted with EtOAc, dried over sodium sulfate, concentrated, and purified by column chromatography (50% acetone/hexane) to yield the title compound. (45 mg, 80%). $^1$H NMR (500 MHz, CDCl$_3$): δ ppm 8.76 (s, 1H), 7.52 (s, 1H), 7.02 (m, 2H), 6.95 (m, 2H), 6.83 (m, 2H), 6.78 (s, 1H), 6.37 (s, 1H), 4.37 (m, 2H), 3.72 (s, 2H), 3.63 (s, 2H), 2.63 (s, 2H), 2.58 (s, 2H), m/z (485.1 MH$^+$); HPLC: 98.33%.

Examples 101-113

Step 1: Reaction of tert-Butyl 4-(3-hydroxybenzylidene)piperidine-1-carboxylate with heteroaryl chlorides 1.00 g of tert-butyl 4-(3-hydroxybenzylidene)piperidine-1-carboxylate (Example 57, Step 3) was dissolved in 16.0 mL anhydrous 1,4-dioxane to give a 0.216 M solution. 0.400 mL of this solution (0.086 mmol, 1 equiv) was added to the appropriate heteroaryl chloride (0.100 mmol, 1.16 equiv) and cesium carbonate (56 mg, 0.172 mmol, 2 equiv) in 1 dram vials. The vials were capped and stirred at 90° C. for 6 h. The reaction mixtures were cooled to room temp, diluted with 0.4 mL methylene chloride and filtered through a 0.2 micron PTFE syringe filter into another 1 dram vial, rinsing with 0.4 mL methylene chloride to give a solution of the crude piperidine tert-butyl carbamate derivatives.

Step 2: Deprotection of the Piperidine Tert-Butyl Carbamate Derivatives

The solutions of the crude piperidine tert-butyl carbamate derivatives were treated with 4 N HCl in dioxane (0.6 mL) and stirred at room temp for 1.5 h. The mixtures were concentrated under a stream of nitrogen at 30 to 40° C. to give the crude piperidine hydrochloride derivatives.

Step 3: Reaction of phenyl pyridazin-3-ylcarbamate with piperidine hydrochloride derivatives Phenyl pyridazin-3-ylcarbamate (861 mg) and diisopropylethylamine (2.4 mL) were suspended in 17.6 mL anhydrous acetonitrile to give a 0.2 M suspension of phenyl pyridazin-3-ylcarbamate. 0.5 mL of this suspension (0.100 mmol of phenyl pyridazin-3-ylcarbamate, 1.16 equiv; 0.344 mmol of diisopropylethylamine, 4 equiv) was added to the crude HCl salts, and the vials were stirred at room temperature overnight. The reactions were concentrated under a stream of nitrogen. The residues were dissolved in 1 mL DMSO and purified by reverse phase HPLC (acetonitrile/water/0.1% formic acid) to give Examples 101-113.

| Ex. | Name | Characterization |
|---|---|---|
| 101 | 4-{3-[(8-methoxyquinazolin-2-yl)oxy]benzylidene}-N-pyridazin-3-ylpiperidine-1-carboxamide | 15.7 mg. LCMS 469.2197 (MH$^+$). $^1$H NMR (400 MHz, DMSO-d$_6$) δ ppm 9.83 (br. s., 1H), 9.49 (s, 1H), 8.82 (d, J = 4.4 Hz, 1H), 7.99 (d, J = 10.2 Hz, 1H), 7.66 (d, J = 8.1 Hz, 1H), 7.49-7.58 (m, 2H), 7.39-7.47 (m, 2H), 7.10-7.16 (m, 3H), 6.43 (s, 1H), 3.91 (s, 3H), 3.61 (t, J = 5.9 Hz, 2H), 3.52 (t, J = 5.9 Hz, 2H), 2.51-2.57 (m, 2H), 2.38 (t, J = 5.5 Hz, 2H) |
| 102 | N-pyridazin-3-yl-4-[3-(pyrido[2,3-d]pyrimidin-2-yloxy)benzylidene]piperidine-1-carboxamide | 15.8 mg. LCMS 440.1939 (MH$^+$). |
| 103 | N-pyridazin-3-yl-4-[3-(pyrimidin-2-yloxy)benzylidene]piperidine-1-carboxamide | 17.4 mg. LCMS 389.1702 (MH$^+$). |
| 104 | 4-(3-{[5-(4-methoxyphenyl)pyrimidin-2-yl]oxy}benzylidene)-N-pyridazin-3-ylpiperidine-1-carboxamide | 7.6 mg. LCMS 495.2208 (MH$^+$). |
| 105 | N-pyridazin-3-yl-4-[3-(quinazolin-2-yloxy)benzylidene]piperidine-1-carboxamide | 12.0 mg. LCMS 439.1970 (MH$^+$). |
| 106 | 4-{3-[(5-cyclopropylpyrimidin-2-yl)oxy]benzylidene}-N-pyridazin-3-ylpiperidine-1-carboxamide | 12.1 mg. LCMS 429.2122 (MH$^+$). $^1$H NMR (400 MHz, DMSO-d$_6$) δ ppm 9.82 (br. s., 1H), 8.83 (d, J = 3.7 Hz, 1H), 8.41 (s, 2H), 8.00 (d, J = 10.2 Hz, 1H), 7.56 (dd, J = 8.8, 4.4 Hz, 1H), 7.38 (t, J = 8.1 Hz, 1H), 7.11 (d, J = 8.1 Hz, 1H), 6.98-7.04 (m, 2H), 6.40 (s, 1H), 3.61 (t, J = 5.9 Hz, 2H), 3.54 (t, J = 5.5 Hz, 2H), 2.45-2.49 (m, 2H), 2.38 (t, J = 5.5 Hz, 2H), 1.87-1.96 (m, 1H), 0.93-1.02 (m, 2H), 0.73-0.80 (m, 2H) |
| 107 | 4-{3-[(5-ethylpyrimidin-2-yl)oxy]benzylidene}-N-pyridazin-3-ylpiperidine-1-carboxamide | 15.4 mg. LCMS 417.1989 (MH$^+$). |
| 108 | 4-{3-[(5-fluoropyrimidin-2-yl)oxy]benzylidene}-N-pyridazin-3-ylpiperidine-1-carboxamide | 13.0 mg. LCMS 407.1574 (MH$^+$). $^1$H NMR (400 MHz, DMSO-d$_6$) δ ppm 9.82 (br. s., 1H), 8.83 (d, J = 4.4 Hz, 1H), 8.73 (s, 2H), 8.00 (d, J = 10.2 Hz, 1H), 7.56 (dd, J = 9.1, 4.8 Hz, 1H), 7.36-7.45 (m, 1H), 7.13 (d, J = 7.3 Hz, 1H), 7.02-7.09 (m, 2H), 6.41 (s, 1H), 3.61 (t, J = 5.9 Hz, 2H), 3.54 (t, J = 5.9 Hz, 2H), 2.45-2.49 (m, 2H), 2.38 (t, J = 5.9 Hz, 2H) |
| 109 | 4-{3-[(5-methylpyrimidin-2-yl)oxy]benzylidene}-N-pyridazin-3-ylpiperidine-1-carboxamide | 15.9 mg. LCMS 403.1815 (MH$^+$). |
| 110 | 4-(3-{[5-(3-chlorophenyl)pyrimidin-2-yl]oxy}benzylidene)-N-pyridazin-3-ylpiperidine-1-carboxamide | 20.8 mg. LCMS 499.1789 (MH$^+$). |

-continued

| Ex. | Name | Characterization |
|---|---|---|
| 111 | 4-{3-[(5-propylpyrimidin-2-yl)oxy]benzylidene}-N-pyridazin-3-ylpiperidine-1-carboxamide | 15.9 mg. LCMS 431.2283 (MH+). |
| 112 | 4-{3-[(4-isopropyl-5-methylpyrimidin-2-yl)oxy]benzylidene}-N-pyridazin-3-ylpiperidine-1-carboxamide | 14.1 mg. LCMS 445.2414 (MH+). |
| 113 | N-pyridazin-3-yl-4-(3-{[4-(trifluoromethyl)pyrimidin-2-yl]oxy}benzylidene)piperidine-1-carboxamide | 19.0 mg. LCMS 457.1733 (MH+). $^1$H NMR (400 MHz, DMSO-d$_6$) δ ppm 9.83 (br. s., 1H), 9.00 (d, J = 5.1 Hz, 1H), 8.82 (d, J = 3.7 Hz, 1H), 8.00 (d, J = 8.8 Hz, 1H), 7.77 (d, J = 4.4 Hz, 1H), 7.55 (dd, J = 9.1, 4.8 Hz, 1H), 7.44 (t, J = 7.7 Hz, 1H), 7.10-7.20 (m, 3H), 6.42 (s, 1H), 3.61 (t, J = 5.5 Hz, 2H), 3.53 (t, J = 5.5 Hz, 2H), 2.44-2.50 (m, 2H), 2.38 (t, J = 5.9 Hz, 2H) |

Examples 114-125

Step 1: Reaction of tert-Butyl 4-(3-hydroxybenzylidene)piperidine-1-carboxylate with heteroaryl chlorides 0.45 g of tert-butyl 4-(3-hydroxybenzylidene)piperidine-1-carboxylate (Example 57, Step 3) was dissolved in 8.0 mL anhydrous 1,4-dioxane to give a 0.194 M solution. 0.400 mL of this solution (0.0777 mmol, 1 equiv) was added to the appropriate heteroaryl chloride (0.100 mmol, 1.3 equiv) and cesium carbonate (51 mg, 0.155 mmol, 2 equiv) in 1 dram vials. The vials were capped and stirred at 90° C. The reactions were monitored by HPLC. Upon completion (2 to 24 hours), the reaction mixtures were cooled to room temp, diluted with 0.4 mL methylene chloride and filtered through a 0.2 micron PTFE syringe filter into another 1 dram vial, rinsing with 0.4 mL methylene chloride to give a solution of the crude piperidine tert-butyl carbamate derivatives.

Step 2: Deprotection of the Piperidine tert-butyl Carbamate Derivatives

The solutions of the crude piperidine tert-butyl carbamate derivatives were treated with 4 N HCl in dioxane (0.6 mL) and stirred at room temp for 1.5 h. The mixtures were concentrated under a stream of nitrogen at 35° C. to give the crude piperidine hydrochloride derivatives.

Step 3: Reaction of phenyl pyridazin-3-ylcarbamate with piperidine hydrochloride derivatives Diisopropylethylamine (1.2 mL) were dissolved in 8.8 mL anhydrous acetonitrile to give a 0.689 M solution. 0.5 mL of this solution (0.344 mmol of diisopropylethylamine, 4.4 equiv) was added to the crude HCl salts and phenyl pyridazin-3-ylcarbamate (20.0 mg, 0.093 mmol, 1.2 equiv), and the vials were stirred at room temperature for 3 h. The reactions were concentrated under a stream of nitrogen. The residues were dissolved in 1 mL DMSO and purified by reverse phase HPLC (acetonitrile/water/0.1% formic acid) to give Examples 114-125.

| Ex. | Name | Characterization |
|---|---|---|
| 114 | 4-{3-[(2,7-dimethyl-5,6,7,8-tetrahydropyrido[3,4-d]pyrimidin-4-yl)oxy]benzylidene}-N-pyridazin-3-ylpiperidine-1-carboxamide | 15.6 mg. LCMS 472.2447 (MH+). |
| 115 | 4-(3-{[6-ethyl-2-(trifluoromethyl)pyrimidin-4-yl]oxy}benzylidene)-N-pyridazin-3-ylpiperidine-1-carboxamide | 15.5 mg. LCMS 485.2048 (MH+). $^1$H NMR (400 MHz, DMSO-d$_6$) δ ppm 9.94 (s, 1H), 8.85 (d, J = 3.7 Hz, 1H), 8.01 (d, J = 8.1 Hz, 1H), 7.58 (dd, J = 9.2, 4.8 Hz, 1H), 7.48 (t, J = 7.7 Hz, 1H), 7.29 (s, 1H), 7.13-7.24 (m, 3H), 6.45 (s, 1H), 3.63 (t, J = 5.5 Hz, 2H), 3.53 (t, J = 5.5 Hz, 2H), 2.85 (q, J = 7.8 Hz, 2H), 2.47-2.51 (m, 2H), 2.40 (t, J = 5.5 Hz, 2H), 1.26 (t, J = 7.7 Hz, 3H) |
| 116 | 4-(3-{[6-methyl-4-(trifluoromethyl)pyridin-2-yl]oxy}benzylidene)-N-pyridazin-3-ylpiperidine-1-carboxamide | 7.9 mg. LCMS 470.2043 (MH+). |

-continued

| Ex. | Name | Characterization |
|---|---|---|
| 117 | 4-(3-{[5-(morpholin-4-ylcarbonyl)pyridin-2-yl]oxy}benzylidene)-N-pyridazin-3-ylpiperidine-1-carboxamide | 18.6 mg. LCMS 501.236 (MH+). |
| 118 | 4-{3-[(3-methylpyrazin-2-yl)oxy]benzylidene}-N-pyridazin-3-ylpiperidine-1-carboxamide | 6.2 mg. LCMS 403.1898 (MH+). |
| 119 | 4-{3-[(4-methylphthalazin-1-yl)oxy]benzylidene}-N-pyridazin-3-ylpiperidine-1-carboxamide | 10.9 mg. LCMS 453.2372 (MH+). |
| 120 | 4-{3-[(4,6-dimethylpyrimidin-2-yl)oxy]benzylidene}-N-pyridazin-3-ylpiperidine-1-carboxamide | 16.9 mg. LCMS 417.2032 (MH+). |
| 121 | 4-{3-[(6-methoxypyrimidin-4-yl)oxy]benzylidene}-N-pyridazin-3-ylpiperidine-1-carboxamide | 8.0 mg. LCMS 419.1631 (MH+). |
| 122 | N-pyridazin-3-yl-4-[3-(quinoxalin-2-yloxy)benzylidene]piperidine-1-carboxamide | 11.5 mg. LCMS 439.1987 (MH+). |
| 123 | 4-[3-(pyrazin-2-yloxy)benzylidene]-N-pyridazin-3-ylpiperidine-1-carboxamide | 13 mg. LCMS 389.1789 (MH+). $^1$H NMR (400 MHz, DMSO-$d_6$) δ ppm 9.92 (s, 1H), 8.85 (d, J = 3.7 Hz, 1H), 8.57 (s, 1H), 8.40 (d, J = 2.9 Hz, 1H), 8.24 (s, 1H), 8.01 (d, J = 10.3 Hz, 1H), 7.58 (dd, J = 9.2, 4.8 Hz, 1H), 7.44 (t, J = 8.4 Hz, 1H), 7.16 (d, J = 7.3 Hz, 1H), 7.05-7.13 (m, 2H), 6.43 (s, 1H), 3.62 (t, J = 5.5 Hz, 2H), 3.55 (t, J = 5.5 Hz, 2H), 2.47-2.51 (m, 2H), 2.39 (t, J = 5.5 Hz, 2H) |
| 124 | 4-[3-(1,3-benzothiazol-2-yloxy)benzylidene]-N-pyridazin-3-ylpiperidine-1-carboxamide | 17.9 mg. LCMS 444.1548 (MH+). $^1$H NMR (400 MHz, DMSO-$d_6$) δ ppm 9.94 (s, 1H), 8.85 (d, J = 4.4 Hz, 1H), 8.02 (d, J = 8.1 Hz, 1H), 7.96 (d, J = 8.1 Hz, 1H), 7.72 (d, J = 8.1 Hz, 1H), 7.58 (dd, J = 8.8, 4.4 Hz, 1H), 7.48-7.55 (m, 1H), 7.42-7.48 (m, 1H), 7.32-7.38 (m, 3H), 7.27 (d, J = 8.1 Hz, 1H), 6.47 (s, 1H), 3.63 (t, J = 5.5 Hz, 2H), 3.57 (t, J = 5.9 Hz, 2H), 2.53-2.57 (m, 2H), 2.41 (t, J = 5.1 Hz, 2H) |
| 125 | 4-{3-[(3-phenyl-1,2,4-thiadiazol-5-yl)oxy]benzylidene}-N-pyridazin-3-ylpiperidine-1-carboxamide | 16.6 mg. LCMS 471.1988 (MH+). $^1$H NMR (400 MHz, DMSO-$d_6$) δ ppm 9.94 (br. s., 1H), 8.85 (d, J = 4.4 Hz, 1H), 8.12 (dd, J = 6.6, 2.9 Hz, 2H), 8.02 (d, J = 9.5 Hz, 1H), 7.51-7.62 (m, 5H), 7.43-7.50 (m, 2H), 7.35 (d, J = 8.1 Hz, 1H), 6.48 (s, 1H), 3.64 (t, J = 5.5 Hz, 2H), 3.58 (t, J = 5.9 Hz, 2H), 2.50-2.57 (m, 2H), 2.42 (t, J = 5.5 Hz, 2H) |

Examples 126-143

A 0.02 M solution of 4-dimethylaminopyridine (DMAP, 244 mg) in 10% diisopropylamine (10 mL) in dichloroethane (90 mL) was prepared. An aliquot (1.0 mL, 0.1 equiv DMAP) was added to each of the 8 mL vials containing the amine monomer (0.200 mmol). To each of the vials was added acetonitrile (1.0 mL). The vials were capped and stirred vigorously to effect dissolution. Upon dissolution, to each of the vials was added an aliquot of a 0.2 M solution of 4-(3-(5-(trifluoromethyl)pyridin-2-yloxy)benzylidene)piperidine-1-carbonyl chloride in dichloroethane (1.0 mL, 1 equiv 0.2 mmol; from Example 74, Step 1). The vials were capped and heated to 70° C. overnight. The reactions were concentrated under reduced pressure. The residues were reconstituted in DMSO and purified by reverse phase HPLC (acetonitrile/water/0.1% formic acid) to afford the Examples 126-143.

| Ex. | Name | Characterization |
|---|---|---|
| 126 | N-[6-(trifluoromethyl)pyridin-3-yl]-4-(3-{[5-(trifluoromethyl)pyridin-2-yl]oxy}benzylidene)piperidine-1-carboxamide | 6.9 mg. LCMS 523.2006 (MH+). $^1$H NMR (400 MHz, DMSO-$d_6$) δ ppm 2.35-2.44 (m, 2H) 2.49 (br. s., 1H) 2.52 (br. s., 1H) 3.31 (br. s., 1H) 3.49-3.55 (m, 2H) 3.60 (dd, J = 6.96, 4.76 Hz, 2H) 6.42 (s, 1H) 7.02-7.09 (m, 2H) 7.16 (d, J = 7.69 Hz, 1H) 7.25 (d, J = 8.79 Hz, 1H) 7.43 (t, J = 8.24 Hz, 1H) 7.77 (d, J = 8.79 Hz, 1H) 8.16 (dd, J = 8.60, 2.75 Hz, 1H) 8.20-8.26 (m, 1H) 8.55-8.59 (m, 1H) 8.82 (d, J = 2.93 Hz, 1H) 9.19 (s, 1H). |

-continued

| Ex. | Name | Characterization |
|---|---|---|
| 127 | N-(2,6-dimethoxypyridin-3-yl)-4-(3-{[5-(trifluoromethyl)pyridin-2-yl]oxy}benzylidene)piperidine-1-carboxamide | 14.2 mg. LCMS 515.1832 (MH$^+$). |
| 128 | N-[6-(pyridin-3-yloxy)pyridin-3-yl]-4-(3-{[5-(trifluoromethyl)pyridin-2-yl]oxy}benzylidene)piperidine-1-carboxamide | 9.9 mg. LCMS 548.1926 (MH$^+$). |
| 129 | N-(2-methoxypyridin-3-yl)-4-(3-{[5-(trifluoromethyl)pyridin-2-yl]oxy}benzylidene)piperidine-1-carboxamide | 16.3 mg. LCMS 485.1965 (MH$^+$). $^1$H NMR (400 MHz, DMSO-d$_6$) δ ppm 2.32-2.42 (m, 2H) 2.43-2.49 (m, 2H) 3.31 (br. s., 1H) 3.44-3.56 (m, 4H) 3.89 (s, 3H) 6.41 (s, 1H) 6.93 (dd, J = 7.69, 4.76 Hz, 1H) 7.01-7.09 (m, 2H) 7.16 (d, J = 8.05 Hz, 1H) 7.24 (d, J = 8.79 Hz, 1H) 7.38-7.45 (m, 1H) 7.78-7.85 (m, 2H) 7.95 (dd, J = 7.69, 1.83 Hz, 1H) 8.20-8.26 (m, 1H) 8.55-8.59 (m, 1H) |
| 130 | N-(5-methoxypyridin-3-yl)-4-(3-{[5-(trifluoromethyl)pyridin-2-yl]oxy}benzylidene)piperidine-1-carboxamide | 3.8 mg. LCMS 485.1953 (MH$^+$). |
| 131 | N-(5,6-dimethylpyridin-3-yl)-4-(3-{[5-(trifluoromethyl)pyridin-2-yl]oxy}benzylidene)piperidine-1-carboxamide | 8.1 mg. LCMS 483.1976 (MH$^+$). |
| 132 | N-[5-bromo-3-(hydroxymethyl)pyridin-2-yl]-4-(3-{[5-(trifluoromethyl)pyridin-2-yl]oxy}benzylidene)piperidine-1-carboxamide | 20 mg. LCMS 563.0987 (MH$^+$). |
| 133 | N-(3,5-dimethylisoxazol-4-yl)-4-(3-{[5-(trifluoromethyl)pyridin-2-yl]oxy}benzylidene)piperidine-1-carboxamide | 8.8 mg. LCMS 473.1876 (MH$^+$). $^1$H NMR (400 MHz, DMSO-d$_6$) δ ppm 2.00-2.10 (m, 3H) 2.22 (s, 3H) 2.34 (dd, J = 6.59, 4.76 Hz, 2H) 2.42-2.49 (m, 2H) 3.31 (br. s., 1H) 3.41-3.46 (m, 2H) 3.51 (dd, J = 6.95, 4.76 Hz, 2H) 6.41 (s, 1H) 7.02-7.09 (m, 2H) 7.15 (d, J = 7.69 Hz, 1H) 7.24 (d, J = 8.79 Hz, 1H) 7.38-7.45 (m, 1H) 7.97 (s, 1H) 8.23 (dd, J = 8.79, 2.56 Hz, 1H) 8.55-8.59 (m, 1H) |
| 134 | 4-(3-{[5-(trifluoromethyl)pyridin-2-yl]oxy}benzylidene)-N-(1,3,5-trimethyl-1H-pyrazol-4-yl)piperidine-1-carboxamide | 21.7 mg. LCMS 486.2156 (MH$^+$). |
| 135 | N-(4-methylpyridin-2-yl)-4-(3-{[5-(trifluoromethyl)pyridin-2-yl]oxy}benzylidene)piperidine-1-carboxamide | 4.5 mg. LCMS 469.1941 (MH$^+$). |
| 136 | N-(5-methylisoxazol-4-yl)-4-(3-{[5-(trifluoromethyl)pyridin-2-yl]oxy}benzylidene)piperidine-1-carboxamide | 8.7 mg. LCMS 459.1739 (MH$^+$). |
| 137 | N-(1-methyl-1H-pyrazol-4-yl)-4-(3-{[5-(trifluoromethyl)pyridin-2-yl]oxy}benzylidene)piperidine-1-carboxamide | 25.8 mg. LCMS 458.177 (MH$^+$). |
| 138 | N-1H-pyrazol-4-yl-4-(3-{[5-(trifluoromethyl)pyridin-2-yl]oxy}benzylidene)piperidine-1-carboxamide | 17.1 mg. LCMS 444.1647 (MH$^+$). |
| 139 | N-(5-methyl-1H-pyrazol-3-yl)-4-(3-{[5-(trifluoromethyl)pyridin-2-yl]oxy}benzylidene)piperidine-1-carboxamide | 19.7 mg. LCMS 458.1977 (MH$^+$). |
| 140 | N-(6-methoxy-2-methylpyridin-3-yl)-4-(3-{[5-(trifluoromethyl)pyridin-2- | 9.6 mg. LCMS 499.1924 (MH$^+$). |

| Ex. | Name | Characterization |
|---|---|---|
| | yl]oxy}benzylidene)piperidine-1-carboxamide | |
| 141 | N-(4-ethylpyridin-2-yl)-4-(3-{[5-(trifluoromethyl)pyridin-2-yl]oxy}benzylidene)piperidine-1-carboxamide | 5.6 mg. LCMS 483.2046 (MH+). |
| 142 | N-(6-hydroxypyridin-3-yl)-4-(3-{[5-(trifluoromethyl)pyridin-2-yl]oxy}benzylidene)piperidine-1-carboxamide | 13.1 mg. LCMS 471.1675 (MH+). |
| 143 | N-(5-hydroxy-1H-pyrazol-3-yl)-4-(3-{[5-(trifluoromethyl)pyridin-2-yl]oxy}benzylidene)piperidine-1-carboxamide | 11.2 mg. LCMS 460.1695 (MH+). |

The biological activities of compounds described in the above examples were determined using the following assay.

FAAH Assay

The FAAH assay was carried out in 384-well clear polystyrene plates in a total volume of 50 µl per well. All percents are by volume. To each well, was placed the reaction mixture (40 µl) containing 1-4 nM FAAH, 50 mM NaP$_i$, pH 7.4, 3 mM α-ketoglutarate, 0.15 mM NADH, 7.5 U/ml glutamate dehydrogenase, 2 mM ADP, 1 mM EDTA, and 0.1% Triton X-100 (The concentration shown for each component is the final concentration in the assay). To this mixture, was added 5 µl of a compound of Examples 1 to 20 at various concentrations prepared in 50% DMSO (or 5 µl 50% DMSO for controls). This was immediately followed by the addition of 5 µl oleamide (500 µM) dissolved in 75% EtOH/25% DMSO and the reaction mixture was mixed for 1.5 min. The final concentrations of DMSO and EtOH in the assay were each 7.5%. The reactions were incubated at 30° C. and the absorbance at 340 nm was collected over a period of 90 min with readings taken in 30-second intervals using SpectraMax Plus$^{384}$ Microplate Spectrophotometer (Molecular Devices, Sunnyvale, Calif.). Human FAAH used in the assay was prepared as described in the patent application WO 2006/067613. The purity of the enzyme was greater than 98% based on an analysis by SDS-polyacrylamide gel electrophoresis followed by Coomassie Blue staining.

Kinetic Data Analyses

Initial velocity data (V) were obtained from the slopes of the initial progressive curves. They were plotted as a function of substrate concentration and fit to the Michaelis-Menten equation (1) using Prism (GraphPad Software, Inc., San Diego, Calif.) software to obtain K$_m$ and V$_{max}$ values.

$$V = \frac{V_{max}[S]}{K_m + [S]} \quad (1)$$

To obtain potencies of irreversible inhibitors, progressive curves consistent with first order inhibition kinetics (two-step irreversible inhibition mechanism) were fit to equation (2) by nonlinear least squares regressions to determine k$_{obs}$ values at each inhibitor concentration, where [P]$_t$ is the absorbance at time t, V$_0$ is a constant related to the steady state rate of the uninhibited reaction, and k$_{obs}$ is the first order rate constant for enzyme inactivation. The inhibitor dissociation constant (K$_i$) and the first order rate $$[P]_t = V_o \frac{(1 - e^{-k_{obs}t})}{k_{obs}} \quad (2)$$

constant of enzyme inactivation at infinite inhibitor concentration (k$_{inact}$) were then obtained by fitting the k$_{obs}$ vs. [I] curves to equation (3).

$$k_{obs} = \frac{k_{inact}[I]}{[I] + K_i\left(1 + \frac{[S]}{K_m}\right)} \quad (3)$$

TABLE 2 k$_{inact}$/K$_i$ data for Examples 1-143

| Ex. | hFAAH k$_{inact}$/K$_i$ (M$^{-1}$s$^{-1}$) |
|---|---|
| 1 | 13300 |
| 2 | 5050 |
| 3 | 7800 |
| 4 | 25800 |
| 5 | 24700 |
| 6 | 2510 |
| 7 | 2880 |
| 8 | 10100 |
| 9 | 3660 |
| 10 | 3070 |
| 11 | 4040 |
| 12 | 10800 |
| 13 | 3870 |
| 14 | 3190 |
| 15 | 12900 |
| 16 | 2150 |
| 17 | 1620 |
| 18 | 2730 |
| 19 | 3450 |
| 20 | 2380 |
| 21 | 1850 |
| 22 | 12000 |
| 23 | 2910 |
| 24 | 2410 |
| 25 | 12100 |
| 26 | 11000 |
| 27 | 3900 |
| 28 | 6190 |
| 29 | 3370 |
| 30 | 3540 |
| 31 | 931 |

TABLE 2-continued $k_{inact}/K_i$ data for Examples 1-143

| Ex. | hFAAH $k_{inact}/K_i$ (M$^{-1}$s$^{-1}$) |
|---|---|
| 32 | 973 |
| 33 | 26300 |
| 34 | 50900 |
| 35 | 3670 |
| 36 | 5070 |
| 37 | 15100 |
| 38 | 9180 |
| 39 | 18200 |
| 40 | 554 |
| 41 | 687 |
| 42 | 834 |
| 43 | 1410 |
| 44 | 9480 |
| 45 | 12800 |
| 46 | 3700 |
| 47 | 4490 |
| 48 | 5830 |
| 49 | 6560 |
| 50 | 5670 |
| 51 | 4330 |
| 52 | 4090 |
| 53 | 4520 |
| 54 | 12000 |
| 55 | 1610 |
| 56 | 3580 |
| 57 | 16800 |
| 58 | 322 |
| 59 | 260 |
| 60 | 1580 |
| 61 | 2130 |
| 62 | 1370 |
| 63 | 2530 |
| 64 | 417 |
| 65 | 6710 |
| 66 | 1560 |
| 67 | 5980 |
| 68 | 206 |
| 69 | 2300 |
| 70 | 4590 |
| 71 | 777 |
| 72 | 681 |
| 73 | 963 |
| 74 | 9870 |
| 75 | 3620 |
| 76 | 2390 |
| 77 | 339 |
| 78 | 2100 |
| 79 | 4880 |
| 80 | 353 |
| 81 | 1010 |
| 82 | 979 |
| 83 | 356 |
| 84 | 5590 |
| 85 | 1540 |
| 86 | 856 |
| 87 | 1840 |
| 88 | 3580 |
| 89 | 6450 |
| 90 | 7600 |
| 91 | 636 |
| 92 | 894 |
| 97 | 394 |
| 99 | 1130 |
| 100 | 2000 |
| 101 | 209 |
| 102 | 1390 |
| 103 | 162 |
| 104 | 105 |
| 105 | 2530 |
| 106 | 3330 |
| 107 | 6220 |
| 108 | 1120 |
| 109 | 1240 |
| 110 | 1020 |
| 111 | 4240 |
| 112 | 861 |
| 113 | 584 |
| 114 | <10 |
| 115 | <11.2 |
| 116 | 40.8 |
| 117 | <12.4 |
| 118 | 191 |
| 119 | 77.7 |
| 120 | <14.5 |
| 121 | 896 |
| 122 | 909 |
| 123 | 203 |
| 124 | 7400 |
| 125 | 140 |
| 126 | 405 |
| 127 | 675 |
| 128 | 1300 |
| 129 | 1730 |
| 130 | 944 |
| 131 | 1110 |
| 132 | 105 |
| 133 | 36.8 |
| 134 | <10 |
| 135 | 173 |
| 137 | 1070 |
| 138 | 4300 |
| 139 | 306 |
| 140 | 837 |
| 141 | 117 |
| 142 | 246 |
| 143 | 412 |

The disclosures of all documents, including patents, patent applications and other publications, are herein incorporated by reference in their entireties.

What is claimed is:

1. A compound of Formula I

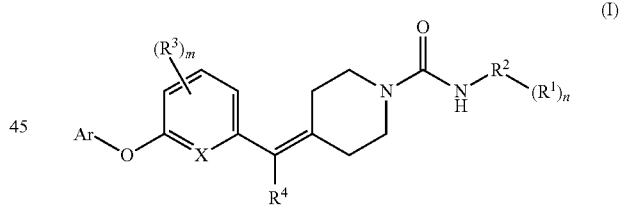

wherein:
each $R^1$ is independently hydrogen, —OH, halogen, haloalkyl, —$C_1$-$C_6$alkyl, —O—$C_1$-$C_6$alkyl, —S—$C_1$-$C_6$alkyl, aryl, heteroaryl, —O-aryl, —O-heteroaryl, —$NH_2$, —NHC(O)$C_1$-$C_6$alkyl, —(CH$_2$)$_{0-3}$—$C_3$-$C_6$cycloalkyl, —NHC(O)$C_3$-$C_6$cycloalkyl, —NHC$_1$-$C_6$alkyl, CN, —C(O)NR'R" or —C(O)$C_1$-$C_6$alkyl; with each $R^1$—$C_1$-$C_6$alkyl group being optionally substituted by an —O—$C_1$-$C_6$alkyl group or from 1 to 3 —OH substituents;
R' and R" are independently selected from H or $C_1$-$C_6$alkyl;
$R^2$ is pyridazine;
each $R^3$ is independently hydrogen, halogen, haloalkyl, —$C_1$-$C_6$alkyl, —O—$C_1$-$C_6$alkyl, —S—$C_1$-$C_6$alkyl, —(CH$_2$)$_{0-3}$—$C_3$-$C_6$ cycloalkyl, —S—$C_3$-$C_6$cycloalkyl and —O—$C_3$-$C_6$cycloalkyl; said $R^3$—$C_1$-$C_6$alkyl, —O—$C_1$-$C_6$alkyl, —S—$C_1$-$C_6$alkyl, —(CH$_2$)$_{0-3}$—$C_3$-

$C_6$ cycloalkyl, —S—$C_3$-$C_6$cycloalkyl and —O—$C_3$-$C_6$cycloalkyl, groups are optionally substituted with from 1 to 4 halogen, haloalkyl, —O-haloalkyl, —$C_1$-$C_6$alkyl, or —O($C_1$-$C_6$alkyl) substituents;

$R^4$ is hydrogen, —$C_1$-$C_6$alkyl, phenyl, —$(CH_2)_{0-3}$—$C_3$-$C_6$ cycloalkyl or halogen; said $R^4$—$C_1$-$C_6$alkyl, phenyl, and —$(CH_2)_{0-3}$—$C_3$-$C_6$ cycloalkyl groups being optionally substituted with from 1 to 4 halogen, —$C_1$-$C_6$alkyl, or —O($C_1$-$C_6$alkyl) substituents;

X is N or CH;

m is 0, 1, 2, 3, or 4;

n is 0, 1, 2, 3 or 4; and

Ar is aryl, —$CH_2$-aryl, or heteroaryl, with said aryl, —$CH_2$-aryl and heteroaryl groups being optionally independently substituted with from 1 to 4 substituents selected from hydrogen, —$C_1$-$C_6$alkyl, —$C_2$-$C_6$alkenyl, —$C_2$-$C_6$alkynyl, —$(CH_2)_{0-3}$—$C_3$-$C_6$ cycloalkyl, halogen, haloalkyl, —O-haloalkyl, —C(O)$C_1$-$C_6$alkyl, —O—$C_1$-$C_6$alkyl, —S—$C_1$-$C_6$alkyl, —O—$C_2$-$C_6$alkenyl, —O—$C_2$-$C_6$alkynyl, CN, aryl, heterocyclyl or heteroaryl; said —$C_1$-$C_6$alkyl, —$(CH_2)_{0-3}$—$C_3$-$C_6$cycloalkyl, —C(O)$C_1$-$C_6$alkyl, —O($C_1$-$C_6$alkyl), —S—$C_1$-$C_6$alkyl, aryl, —$CH_2$-aryl, heterocyclyl and heteroaryl substituents on Ar are optionally independently substituted with from 1 to 4 —$C_1$-$C_6$alkyl, —$C_1$-$C_6$alkoxy, —OH, or halogen substituents;

or a pharmaceutically acceptable salt thereof.

2. A compound according to claim 1 wherein Ar is phenyl, pyrimidinyl, pyridyl, benzothiazolyl; and $R^2$ is pyridazinyl; m is 0, 1 or 2; n is 0 to 2; and X is C or CH; or a pharmaceutically acceptable salt thereof.

3. A compound according to claim 1 having Formula III:

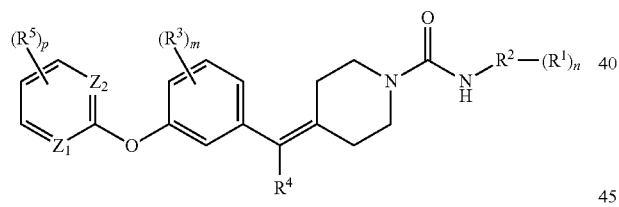

III wherein:
each $R^1$ is independently hydrogen, —$C_1$-$C_6$alkyl, or —O($C_1$-$C_6$alkyl);

$R^2$ is a pyridazine;

each $R^3$ is independently hydrogen, halogen, —$C_1$-$C_6$alkyl, —$(CH_2)_{0-3}$—$C_3$-$C_6$ cycloalkyl, or —O—$C_1$-$C_6$alkyl;

$R^4$ is hydrogen, —$C_1$-$C_6$alkyl, phenyl, or halogen;

each $R^5$ is independently hydrogen, halogen, haloalkyl, —O-haloalkyl, —$C_1$-$C_6$alkyl, —C(O)$C_1$-$C_6$alkyl, —O—$C_1$-$C_6$alkyl, —S—$C_1$-$C_6$alkyl, —$(CH_2)_{0-3}$—$C_3$-$C_6$cycloalkyl, CN, aryl, and heteroaryl; said —$C_1$-$C_6$alkyl, —O($C_1$-$C_6$alkyl), —$(CH_2)_{0-3}$—$C_3$-$C_6$cycloalkyl, aryl, and heteroaryl groups are optionally independently substituted with from 1 to 4-$C_1$-$C_6$alkyl, —OH, or halogen substituents;

m is 0, 1, 2, 3, or 4;

n is 0, 1, 2, 3 or 4;

p is 0, 1, 2, 3, or 4 and $Z_1$ and $Z_2$ are independently selected from N, or CH; or a pharmaceutically acceptable salt thereof.

4. A compound according to claim 3 wherein $Z_1$ is N; $Z_2$ is CH; p is 1; $R^5$ is $CF_3$; and $R^1$ is hydrogen.

5. A compound according to claim 1, or a pharmaceutically acceptable salt thereof, which is:

N-pyridazin-3-yl-4-(3-{[5-(trifluoromethyl)pyridin-2-yl]oxy}benzylidene)piperidine-1-carboxamide;

N-(pyridazin-4-yl)-4-(3-{[5-(trifluoromethyl)pyridin-2-yl]oxy}benzylidene)piperidine-1-carboxamide;

N-(6-methoxypyridazin-3-yl)-4-(3-{[5-(trifluoromethyl)pyridin-2-yl]oxy}benzylidene)piperidine-1-carboxamide;

N-(pyridazin-3-yl)-4-(3-{[phenyl]oxy}benzylidene)piperidine-1-carboxamide;

4-(3-(5-bromopyridin-2-yloxy)benzylidene)-N-(pyridazin-3-yl)piperidine-1-carboxamide;

4-(3-(5-bromopyrimidin-2-yloxy)benzylidene)-N-(pyridazin-3-yl)piperidine-1-carboxamide;

4-(3-(5-cyclopropylpyridin-2-yloxy)benzylidene)-N-(pyridazin-3-yl)piperidine-1-carboxamide;

4-(3-(6-methylpyridin-2-yloxy)benzylidene)-N-(pyridazin-3-yl)piperidine-1-carboxamide;

4-(3-(3-methylpyridin-2-yloxy)benzylidene)-N-(pyridazin-3-yl)piperidine-1-carboxamide;

4-(3-(5-methylpyridin-2-yloxy)benzylidene)-N-(pyridazin-3-yl)piperidine-1-carboxamide;

4-(3-(5-ethoxypyridin-2-yloxy)benzylidene)-N-(pyridazin-3-yl)piperidine-1-carboxamide;

4-(3-(5-(2,2,2-trifluoroethoxy)pyridin-2-yloxy)benzylidene)-N-(pyridazin-3-yl)piperidine-1-carboxamide;

4-(3-(5-isopropoxypyridin-2-yloxy)benzylidene)-N-(pyridazin-3-yl)piperidine-1-carboxamide;

4-(3-(4-(trifluoromethyl)phenoxy)benzylidene)-N-(pyridazin-3-yl)piperidine-1-carboxamide;

4-(3-(6-(trifluoromethyl)pyridin-3-yloxy)benzylidene)-N-(pyridazin-3-yl)piperidine-1-carboxamide;

4-(3-bromo-5-(5-(trifluoromethyl)pyridin-2-yloxy)benzylidene)-N-(pyridazin-3-yl)piperidine-1-carboxamide;

4-(3-cyclopropyl-5-(5-(trifluoromethyl)pyridin-2-yloxy)benzylidene)-N-(pyridazin-3-yl)piperidine-1-carboxamide;

4-{3-[(4-methylpyridin-2-yl)oxy]benzylidene}-N-pyridazin-3-ylpiperidine-1-carboxamide;

N-(6-chloropyridazin-3-yl)-4-(3-{[5-(trifluoromethyl)pyridin-2-yl]oxy}benzylidene)piperidine-1-carboxamide;

4-(3-(5-(pyrrolidin-1-yl)pyridin-2-yloxy)benzylidene)-N-(pyridazin-3-yl)piperidine-1-carboxamide;

4-(3-(5-(azetidin-1-yl)pyridin-2-yloxy)benzylidene)-N-(pyridazin-3-yl)piperidine-1-carboxamide;

4-(3-(5-(pent-4-ynyloxy)pyridin-2-yloxy)benzylidene)-N-(pyridazin-3-yl)piperidine-1-carboxamide;

4-((6-phenoxypyridin-2-yl)methylene)-N-(pyridazin-3-yl)piperidine-1-carboxamide;

4-{3-[(5-fluoropyridin-2-yl)oxy]benzylidene}-N-pyridazin-3-ylpiperidine-1-carboxamide;

4-{3-[(6-methoxy-2-methylpyridin-3-yl)oxy]benzylidene}-N-pyridazin-3-ylpiperidine-1-carboxamide;

N-pyridazin-3-yl-4-{3-[4-(2,2,2-trifluoroethoxy)phenoxy]benzylidene}piperidine-1-carboxamide;

4-{3-[(8-methoxyquinazolin-2-yl)oxy]benzylidene}-N-pyridazin-3-ylpiperidine-1-carboxamide;

N-pyridazin-3-yl-4-[3-(pyrido[2,3-d]pyrimidin-2-yloxy)benzylidene]piperidine-1-carboxamide;

N-pyridazin-3-yl-4-[3-(pyrimidin-2-yloxy)benzylidene]piperidine-1-carboxamide;

4-(3-{[5-(4-methoxyphenyl)pyrimidin-2-yl]oxy}benzylidene)-N-pyridazin-3-ylpiperidine-1-carboxamide;

N-pyridazin-3-yl-4-[3-(quinazolin-2-yloxy)benzylidene]piperidine-1-carboxamide;

4-{3-[(5-cyclopropylpyrimidin-2-yl)oxy]benzylidene}-N-pyridazin-3-ylpiperidine-1-carboxamide;

4-{3-[(5-ethylpyrimidin-2-yl)oxy]benzylidene}-N-pyridazin-3-ylpiperidine-1-carboxamide;

4-{3-[(5-fluoropyrimidin-2-yl)oxy]benzylidene}-N-pyridazin-3-ylpiperidine-1-carboxamide;

4-{3-[(5-methylpyrimidin-2-yl)oxy]benzylidene}-N-pyridazin-3-ylpiperidine-1-carboxamide;

4-(3-{[5-(3-chlorophenyl)pyrimidin-2-yl]oxy}benzylidene)-N-pyridazin-3-ylpiperidine-1-carboxamide;

4-{3-[(5-propylpyrimidin-2-yl)oxy]benzylidene}-N-pyridazin-3-ylpiperidine-1-carboxamide;

4-{3-[(4-isopropyl-5-methylpyrimidin-2-yl)oxy]benzylidene}-N-pyridazin-3-ylpiperidine-1-carboxamide;

N-pyridazin-3-yl-4-(3-{[4-(trifluoromethyl)pyrimidin-2-yl]oxy}benzylidene)piperidine-1-carboxamide;

4-{3-[(2,7-dimethyl-5,6,7,8-tetrahydropyrido[3,4-d]pyrimidin-4-yl)oxy]benzylidene}-N-pyridazin-3-ylpiperidine-1-carboxamide;

4-(3-{[6-ethyl-2-(trifluoromethyl)pyrimidin-4-yl]oxy}benzylidene)-N-pyridazin-3-ylpiperidine-1-carboxamide;

4-(3-{[6-methyl-4-(trifluoromethyl)pyridin-2-yl]oxy}benzylidene)-N-pyridazin-3-ylpiperidine-1-carboxamide;

4-(3-{[5-(morpholin-4-ylcarbonyl)pyridin-2-yl]oxy}benzylidene)-N-pyridazin-3-ylpiperidine-1-carboxamide;

4-{3-[(3-methylpyrazin-2-yl)oxy]benzylidene}-N-pyridazin-3-ylpiperidine-1-carboxamide;

4-{3-[(4-methylphthalazin-1-yl)oxy]benzylidene}-N-pyridazin-3-ylpiperidine-1-carboxamide;

4-{3-[(4,6-dimethylpyrimidin-2-yl)oxy]benzylidene}-N-pyridazin-3-ylpiperidine-1-carboxamide;

4-{3-[(6-methoxypyrimidin-4-yl)oxy]benzylidene}-N-pyridazin-3-ylpiperidine-1-carboxamide;

N-pyridazin-3-yl-4-[3-(quinoxalin-2-yloxy)benzylidene]piperidine-1-carboxamide;

4-[3-(pyrazin-2-yloxy)benzylidene]-N-pyridazin-3-ylpiperidine-1-carboxamide;

4-[3-(1,3-benzothiazol-2-yloxy)benzylidene]-N-pyridazin-3-ylpiperidine-1-carboxamide;

4-{3-[(3-phenyl-1,2,4-thiadiazol-5-yl)oxy]benzylidene}-N-pyridazin-3-ylpiperidine-1-carboxamide;

or a pharmaceutically acceptable salt thereof.

6. A pharmaceutical composition comprising a compound of claim 1, and a pharmaceutically acceptable excipient.

7. The compound N-pyridazin-3-yl-4-(3-{[5-(trifluoromethyl)pyridin-2-yl]oxy}benzylidene)piperidine-1-carboxamide or a pharmaceutically acceptable salt thereof.

8. A pharmaceutical composition comprising N-pyridazin-3-yl-4-(3-{[5-(trifluoromethyl)pyridin-2-yl]oxy}benzylidene)piperidine-1-carboxamide or a pharmaceutically acceptable salt thereof and a pharmaceutically acceptable excipient.

9. A compound according to claim 1 having Formula IV:

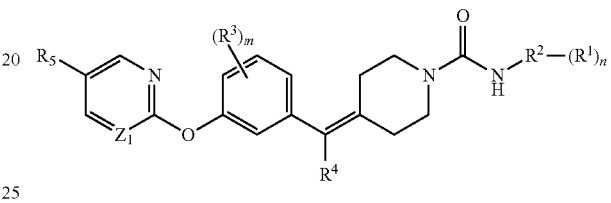

IV wherein:

each $R^1$ is independently hydrogen, —$C_1$-$C_6$alkyl, or —O($C_1$-$C_6$alkyl);

$R^2$ is pyridazinyl;

each $R^3$ is independently hydrogen, halogen, —$C_1$-$C_6$alkyl, —(CH$_2$)$_{0-3}$—$C_3$-$C_6$ cycloalkyl, or —O—$C_1$-$C_6$alkyl;

$R^4$ is hydrogen, —$C_1$-$C_6$alkyl, phenyl, or halogen;

$R^5$ is hydrogen, halogen, haloalkyl, —$C_1$-$C_6$alkyl, or —(CH$_2$)$_{0-3}$—$C_3$-$C_6$cycloalkyl; and said —$C_1$-$C_6$alkyl is optionally substituted with from 1 to 4 —OH substituents and —(CH$_2$)$_{0-3}$—$C_3$-$C_6$cycloalkyl is optionally substituted by from 1 to 4 halogen or —OH substituents;

m is 0, 1 or 2;

n is 0, 1, 2, 3 or 4;

$Z_1$ is selected from N or CH;

or a pharmaceutically acceptable salt thereof.

10. A compound of claim 9 wherein $R^5$ is selected from hydrogen, halogen, —$C_1$-$C_6$alkyl, —$CF_3$ or —$C_3$-$C_6$ cycloalkyl; or a pharmaceutically acceptable salt thereof.

* * * * *